United States Patent
Lee et al.

(10) Patent No.: US 12,310,235 B2
(45) Date of Patent: May 20, 2025

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hyo-Jung Lee, Gyeonggi-do (KR); So-Young Jung, Gyeonggi-do (KR); Sang-Hee Cho, Gyeonggi-do (KR); Jin-Ri Hong, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 756 days.

(21) Appl. No.: 17/405,739

(22) Filed: Aug. 18, 2021

(65) Prior Publication Data

US 2022/0059777 A1    Feb. 24, 2022

(30) Foreign Application Priority Data

Aug. 20, 2020  (KR) ................. 10-2020-0104439

(51) Int. Cl.
*H01L 51/50*    (2006.01)
*H10K 85/60*    (2023.01)
*H10K 50/11*    (2023.01)
*H10K 101/00*   (2023.01)

(52) U.S. Cl.
CPC ....... *H10K 85/6572* (2023.02); *H10K 85/622* (2023.02); *H10K 85/626* (2023.02); *H10K 85/633* (2023.02); *H10K 85/636* (2023.02); *H10K 85/654* (2023.02); *H10K 85/6574* (2023.02); *H10K 85/6576* (2023.02); *H10K 50/11* (2023.02); *H10K 2101/90* (2023.02)

(58) Field of Classification Search
None
See application file for complete search history.

(56) References Cited

U.S. PATENT DOCUMENTS

2021/0151693 A1    5/2021    Lee et al.

FOREIGN PATENT DOCUMENTS

| CN | 110467630 A |   | 11/2019 |           |
|----|-------------|---|---------|-----------|
| CN | 110903300 A |   | 3/2020  |           |
| CN | 110903301 A | * | 3/2020  | H01L 51/50 |
| CN | 110903305 A |   | 3/2020  |           |
| CN | 112409371 A |   | 2/2021  |           |

OTHER PUBLICATIONS

Search Report from China National Intellectual Property Administration for China Patent Application No. 202110911173.9; Application Date: Aug. 9, 2021.

* cited by examiner

*Primary Examiner* — Gregory D Clark
(74) *Attorney, Agent, or Firm* — G. Creston Campbell

(57) ABSTRACT

The present disclosure relates to a plurality of host materials comprising a first host material comprising a compound represented by formula 1 and a second host material comprising a compound represented by formula 2 and an organic electroluminescent device comprising the same. By comprising the host materials according to the present disclosure, an organic electroluminescent device having low driving voltage and/or high luminous efficiency and/or long lifespan can be provided.

12 Claims, No Drawings

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

An organic electroluminescent device (OLED) was first developed by Eastman Kodak in 1987, by using small aromatic diamine molecules and aluminum complexes as materials for forming a light-emitting layer [Appl. Phys. Lett. 51, 913, 1987].

An OLED changes electric energy into light by applying electricity to an organic electroluminescent material, and commonly comprises an anode, a cathode, and an organic layer formed between the two electrodes.

The most important factor determining luminous efficiency in an OLED is light-emitting materials. The light-emitting material is classified into a host material and a dopant material in a functional aspect. A light-emitting material can be used as a combination of a host and a dopant to improve color purity, luminous efficiency, and stability. Generally, a device having excellent electroluminescent (EL) characteristics has a structure comprising a light-emitting layer formed by doping a dopant to a host. When using such a dopant/host material system as a light-emitting material, their selection is important since host materials greatly influence the efficiency and lifespan of the EL device.

Recently, an urgent task is the development of an OLED having high efficiency and long lifespan. In particular, the development of highly excellent light-emitting material over conventional light-emitting materials is urgently required, considering the EL properties necessary for medium and large-sized OLED panels.

CN 110467630 A and CN 110903301 A disclose an organic light-emitting device comprising a compound having the same skeleton as the host material of the present disclosure in the light-emitting layer. However, said references do not specifically disclose a specific combination of host materials as described in the present disclosure. In addition, there is continuous need to develop a light-emitting material having improved performances such as improved driving voltage, luminous efficiency, power efficiency and/or lifespan properties, compared to the conventional specific combination of compounds.

DISCLOSURE OF THE INVENTION

Problems to be Solved

The object of the present disclosure is firstly, to provide a plurality of host materials which is able to produce an organic electroluminescent device having low driving voltage and/or high luminous efficiency and/or long lifespan, and secondly, to provide an organic electroluminescent device comprising the host materials.

Solution to Problems

As a result of intensive studies to solve the technical problem above, the present inventors found that the aforementioned objective can be achieved by a plurality of host materials comprising a first host material comprising a compound represented by the following formula 1 and a second host material comprising a compound represented by the following formula 2, so that the present invention was completed.

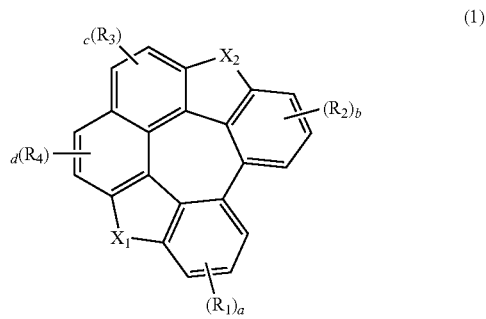

(1)

In formula 1, $X_1$ and $X_2$ each independently represent $NR_5$, $CR_6R_7$, O, or S;

$R_1$ to $R_4$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30) alkenylamino, a substituted or unsubstituted mono- or di- (C6-C30)arylamino, a substituted or unsubstituted (C1-C30)alkyl(C6-C30)arylamino, a substituted or unsubstituted mono- or di- (3- to 30-membered)heteroarylamino, a substituted or unsubstituted (C1-C30) alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, or a substituted or unsubstituted (C6-C30)aryl(3- to 30-membered)heteroarylamino;

$R_5$ to $R_7$ each independently represent a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di- (C6-C30) arylamino, a substituted or unsubstituted (C1-C30) alkyl(C6-C30)arylamino, a substituted or unsubstituted mono- or di- (3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

a and b each independently represent an integer of 1 to 3, and c and d each independently represent an integer of 1 or 2; and when a to d each independently are an integer of 2 or more, each of $R_1$, each of $R_2$, each of $R_3$, and each of $R_4$ may be the same or different;

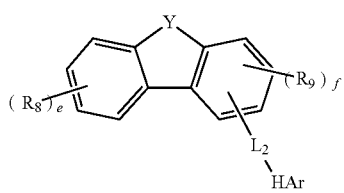

(2)

in formula 2,

Y represents —O— or —S—;

HAr represents a substituted or unsubstituted (3- to 30-membered)heteroaryl containing one or more nitrogen atoms;

$L_2$ represents a single bond, a substituted or unsubstituted (C6-C30)arylene, or a substituted or unsubstituted (3- to 30-membered)heteroarylene;

$R_8$ and $R_9$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30)alkenylamino, a substituted or unsubstituted mono- or di- (C6-C30)arylamino, a substituted or unsubstituted (C1-C30)alkyl(C6-C30)arylamino, a substituted or unsubstituted mono- or di- (3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or may be linked to the adjacent substituents to form a ring(s);

e represents an integer of 1 to 4, and f represents an integer of 1 to 3; and when e and f each independently are an integer of 2 or more, each of $R_5$ and each of $R_9$ may be the same or different.

Advantageous Effects of Invention

By using the plurality of host materials according to the present disclosure, an organic electroluminescent device having low driving voltage and/or high luminous efficiency and/or long lifespan can be prepared.

EMBODIMENTS OF THE INVENTION

Hereinafter, the present disclosure will be described in detail. However, the following description is intended to explain the invention, and is not meant in any way to restrict the scope of the invention.

The present disclosure relates to a plurality of host materials comprising at least one first host material represented by formula 1 and at least one second host material represented by the formula 2, and an organic electroluminescent device comprising the host materials.

In addition, the present disclosure relates to an organic electroluminescent compound represented by formula 1-1-1, and an organic electroluminescent device comprising the same.

The term "organic electroluminescent compound" in the present disclosure means a compound that may be used in an organic electroluminescent device, and may be comprised in any material layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (containing host and dopant materials), an electron buffer material, a hole blocking material, an electron transport material, or an electron injection material, etc.

The term "a plurality of organic electroluminescent materials" in the present disclosure means an organic electroluminescent material comprising a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. Such at least two compounds may be comprised in the same layer or different layers, and may be mixture-evaporated or co-evaporated, or may be individually evaporated.

The term "a plurality of host materials" in the present disclosure means an organic electroluminescent material comprising a combination of at least two host materials. It may mean both a material before being comprised in an organic electroluminescent device (e.g., before vapor deposition) and a material after being comprised in an organic electroluminescent device (e.g., after vapor deposition). A plurality of host materials of the present disclosure may be comprised in any light-emitting layer constituting an organic electroluminescent device. The at least two compounds comprised in a plurality of host materials may be comprised together in one light-emitting layer, or may each be comprised in separate light-emitting layers. When at least two host materials are comprised in one layer, the at least two host materials may be mixture-evaporated to form a layer or may be individually and simultaneously co-evaporated to form a layer.

The term "(C1-C30)alkyl" in the present disclosure is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, ter-butyl, sec-butyl, etc. The term "(3-C30)cycloalkyl" in the present disclosure is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(C6-C30)aryl(ene)" in the present disclosure is a monocyclic or fused ring radical derived from an aromatic hydrocarbon having 6 to 30 ring backbone carbon atoms, in which the number of the ring backbone carbon atoms is preferably 6 to 20, more preferably 6 to 15, and may be partially saturated. The aryl may comprise a spiro structure. Examples of the aryl specifically include phenyl, biphenyl, terphenyl, quaterphenyl, naphthyl, binaphthyl, phenylnaphthyl, naphthylphenyl, fluorenyl, phenylfluorenyl, dimethylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cumenyl, spiro[fluorene-fluorene]yl, spiro[fluorene-benzofluorene]yl, azulenyl, tetramethyl-dihydrophenanthrenyl, etc. More specifically, the aryl may be o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4-methylbiphenyl, 4"-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 1111-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc. The term "(3- to 30-membered)heteroaryl(ene)" in the present disclosure is an aryl having 3 to 30 ring backbone atoms including at least one, preferably 1 to 4 heteroatoms selected from the group consisting of B, N, O, S, Si, P. Se, and Ge, in which the number of ring backbone atoms is preferably 3 to 30, more preferably 5 to 20. The above heteroaryl may be a monocyclic ring, or a fused ring condensed with at least one benzene ring; and may be partially saturated. Also, the above heteroaryl or heteroarylene in the present disclosure may be one formed by linking at least one heteroaryl or aryl group to a heteroaryl group via a single bond(s) and may comprise a spiro structure. Examples of the heteroaryl specifically may include a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, dibenzoselenophenyl, benzofuroquinolinyl, benzofuroquinazolinyl, benzofuronaphthiridinyl, benzofuropyrimidinyl, naphthofuropyrimidinyl, benzothienoquinolinyl, benzothienoquinazolinyl, benzothienonaphthiridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzoimidazolyl, benzothiazolyl, benzoisothiazolyl, benzoisoxazolyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazolyl, benzocarbazolyl, dibenzocarbazolyl, phenoxazinyl, phenanthridinyl, benzodioxolyl, indolizidinyl, acridinyl, silafluorenyl, germafluorenyl, benzotriazolyl, phenazinyl, imidazopyridinyl, chromenoquinazolinyl, thiochromenoquinazolinyl, dimethylbenzopyrimidinyl, indolocarbazolyl, indenocarbazolyl, etc. More specifically, the heteroaryl may be 1-pyrrolyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyridinyl, 3-imidazopyridinyl, 5-imidazopyridinyl, 6-imidazopyridinyl, 7-imidazopyridinyl, 8-imidazopyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazol-1-yl, azacarbazol-2-yl, azacarbazol-3-yl, azacarbazol-4-yl, azacarbazol-5-yl, azacarbazol-6-yl, azacarbazol-7-yl, azacarbazol-8-yl, azacarbazol-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl–1-indolyl, 4-methyl–1-indolyl, 2-methyl-3-indolyl, 4-methyl-3-indolyl, 2-t-butyl-1-indolyl, 4-t-butyl–1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. The term "a fused ring of (C3-C30) aliphatic ring and (C6-C30) aromatic ring" in the present disclosure means a ring formed by fusing at least one aliphatic ring having 3 to 30 ring backbone carbon atoms in which the number of the carbon atoms is preferably 3 to 25, more preferably 3 to 18, and at least one aromatic ring having 6 to 30 ring backbone carbon atoms in which the number of the carbon atoms is preferably 6 to 25, more preferably 6 to 18. For example, the fused ring may be a fused ring of at least one benzene and at least one cyclohexane, or a fused ring of at least one naphthalene and at least one cyclopentane, etc. Herein, the carbon atoms in the fused ring of (C3-C30) aliphatic ring and (C6-C30) aromatic ring may be replaced with at least one heteroatoms selected from B, N, O, S, Si and P, preferably at least one heteroatoms selected from N, O and S. The term "Halogen" in the present disclosure includes F, Cl, Br, and I.

In addition, "ortho (o)," "meta (m)," and "para (p)" in the present disclosure are meant to signify the substitution position of all substituents. Ortho position is a compound with substituents, which are adjacent to each other, i.e., at the 1 and 2 positions on benzene. Meta position is the next substitution position of the immediately adjacent substitution position, i.e., a compound with substituents at the 1 and 3 positions on benzene. Para position is the next substitution position of the meta position, i.e., a compound with substituents at the 1 and 4 positions on benzene.

The term "a ring formed in linking to an adjacent substituent" in the present disclosure means a substituted or unsubstituted (3- to 30-membered) mono- or polycyclic, alicyclic, aromatic ring, or a combination thereof, formed by linking or fusing two or more adjacent substituents, preferably, may be a substituted or unsubstituted (5- to 25-membered) mono- or polycyclic, alicyclic, aromatic ring, or a combination thereof. Further, the formed ring may include at least one heteroatom selected from the group consisting of B, N, O, S, Si and P, preferably at least one heteroatom selected from N, O and S. According to one embodiment of the present disclosure, the number of atoms in the ring skeleton is 5 to 20; according to another embodiment of the present disclosure, the number of atoms in the ring skeleton is 5 to 15. In one embodiment, the fused ring may be, for example, a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzofluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, a substituted or unsubstituted carbazole ring, etc.

In addition, "substituted" in the expression "substituted or unsubstituted" means that a hydrogen atom in a certain functional group is replaced with another atom or functional group, i.e., a substituent, and substituted with a group to which two or more substituents are connected among the substituents. For example, "a substituent to which two or more substituents are connected" may be pyridine-triazine. That is, pyridine-triazine may be heteroaryl or may be interpreted as a substituent in which two heteroaryls are connected. Preferably, the substituents of the substituted alkyl, the substituted aryl(ene), the substituted heteroaryl (ene), the substituted cycloalkyl, the substituted alkoxy, the substituted trialkylsilyl, the substituted dialkylarylsilyl, the substituted alkyldiarylsilyl, the substituted triarylsilyl, the substituted fused ring of aliphatic ring and aromatic ring, the substituted mono- or di-alkylamino, the substituted mono- or di- alkenylamino, the substituted alkylalkenylamino, the substituted mono- or di- arylamino, the substituted alkylarylamino, the substituted mono- or di- heteroarylamino, the substituted alkylheteroarylamino, the substituted alkenylarylamino, the substituted alkenylheteroarylamino, and the substituted arylheteroarylamino in the formulas of the present disclosure, each independently are at least one selected from the group consisting of deuterium, halogen, cyano, carboxyl, nitro, hydroxy, phosphine oxide, (C1-C30) alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered) heterocycloalkyl, (C6-C30)aryloxy, (C6-C30)arylthio, (5- to 30-membered)heteroaryl unsubstituted or substituted with (C6-C30)aryl, (C6-C30)aryl unsubstituted or substituted with (5- to 30-membered)heteroaryl, tri(C1-C30)alkylsilyl, tri(C6-C30)arylsilyl, di(C1-C30)alkyl(C6-C30)arylsilyl, (C1-C30)alkyldi(C6-C30)arylsilyl, a fused ring of (C3-C30) aliphatic ring and (C6-C30) aromatic ring, amino, mono- or di- (C1-C30)alkylamino, mono- or di- (C2-C30)alkenylamino, (C1-C30)alkyl(C2-C30)alkenylamino, a substituted or unsubstituted mono- or di- (C6-C30)arylamino, (C1-C30)alkyl(C6-C30)arylamino, mono- or di- (3- to 30-membered)heteroarylamino, (C1-C30)alkyl(3- to 30-membered)heteroarylamino, (C2-C30)alkenyl(C6-C30) arylamino, (C2-C30)alkenyl(3- to 30-membered)heteroarylamino, (C6-C30)aryl(3- to 30-membered)heteroarylamino, (C1-C30)alkylcarbonyl, (C1-C30)alkoxycarbonyl, (C6-C30)arylcarbonyl, (C6-C30)arylphosphinyl, di(C6-C30) arylboronyl, di(C1-C30)alkylboronyl, (C1-C30)alkyl(C6-C30)arylboronyl, (C6-C30)ar(C1-C30)alkyl, and (C1-C30) alkyl(C6-C30)aryl. For example, the substituent may be methyl, amino, phenyl, naphthyl, triazinyl, carbazolyl, quinoxalinyl, dibenzofuranyl, or dibenzothiophenyl, etc.

Hereinafter, the host materials according to one embodiment will be described.

The plurality of host materials according to one embodiment comprise a first host material comprising a compound represented by formula 1 above and a second host material comprising a compound represented by formula 2 above; and the plurality of host materials may be contained in a light-emitting layer of an organic electroluminescent device according to one embodiment.

The first host material as the host material according to one embodiment may comprise a compound represented by the following formula 1.

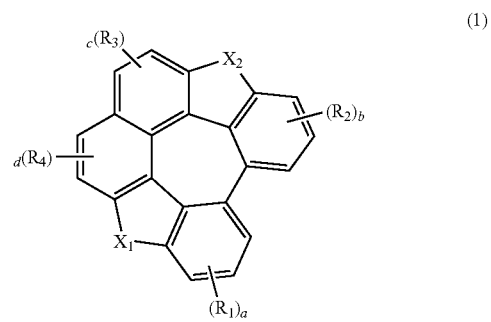

(1)

In formula 1,
X$_1$ and X$_2$ each independently represent NR$_5$, CR$_6$R$_7$, O, or S;
R$_1$ to R$_4$ each independently represent hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-030) aromatic ring, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30) alkenylamino, a substituted or unsubstituted mono- or di- (C6-C30)arylamino, a substituted or unsubstituted (C1-C30)alkyl(C6-C30)arylamino, a substituted or unsubstituted mono- or di- (3- to 30-membered)heteroarylamino, a substituted or unsubstituted (C1-C30) alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, or a substituted or unsubstituted (C6-C30)aryl(3- to 30-membered)heteroarylamino;
R$_5$ to R$_7$ each independently represent a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di- (C6-C30) arylamino, a substituted or unsubstituted (C1-C30) alkyl(C6-C30)arylamino, a substituted or unsubstituted mono- or di- (3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

a and b each independently represent an integer of 1 to 3, and c and d each independently represent an integer of 1 or 2; and when a to d each independently are an integer of 2 or more, each of $R_1$, each of $R_2$, each of $R_3$, and each of $R_4$ may be the same or different.

In one embodiment, $X_1$ and $X_2$ each independently may be O, S, $NR_5$, or $CR_6R_7$, wherein $R_5$ to $R_7$ each independently may be a substituted or unsubstituted (C1-C30)alkyl, a substituted or unsubstituted (C6-C30)aryl, a substituted or unsubstituted (3- to 30-membered)heteroaryl, a substituted or unsubstituted mono- or di- (C6-C30)arylamino, a substituted or unsubstituted mono- or di- (3- to 30-membered) heteroarylamino, or a substituted or unsubstituted (C6-C30) aryl(3- to 30-membered)heteroarylamino, preferably, a substituted or unsubstituted (C1-C10)alkyl, a substituted or unsubstituted (C6-C25)aryl, a substituted or unsubstituted (5- to 25-membered)heteroaryl, a substituted or unsubstituted mono- or di- (C6-C25)arylamino, a substituted or unsubstituted mono- or di- (5- to 25-membered)heteroarylamino, or a substituted or unsubstituted (C6-C25)aryl(5- to 25-membered)heteroarylamino, more preferably, a substituted or unsubstituted (C1-C4)alkyl, (C6-C18)aryl unsubstituted or substituted with at least one of (5- to 30-membered)heteroaryl; di(C6-C30)arylamino; di(5- to 30-membered)heteroarylamino; and (C6-C30)aryl(5- to 30-membered)heteroarylamino, or (5- to 18-membered)heteroaryl unsubstituted or substituted with (C6-C30)aryl. For example, $R_5$ may be substituted or unsubstituted phenyl, a substituted or unsubstituted m-biphenyl, a substituted or unsubstituted o-terphenyl, a substituted or unsubstituted m-terphenyl, a substituted or unsubstituted pyridyl, a substituted or unsubstituted dibenzofuranyl, or a substituted or unsubstituted dibenzothiophenyl. For example, all of $R_6$ and $R_7$ may be methyl.

In one embodiment, $R_1$ to $R_4$ each independently may be hydrogen, deuterium, a substituted or unsubstituted (C6-C30)aryl, a substituted or unsubstituted (3- to 30-membered) heteroaryl, a substituted or unsubstituted mono- or di- (C6-C30)arylamino, a substituted or unsubstituted mono- or di- (3- to 30-membered)heteroarylamino, or a substituted or unsubstituted (C6-C30)aryl(3- to 30-membered)heteroarylamino, preferably, hydrogen, a substituted or unsubstituted (C6-C25)aryl, a substituted or unsubstituted (5- to 25-membered)heteroaryl, a substituted or unsubstituted mono- or di- (C6-C25)arylamino, a substituted or unsubstituted mono- or di- (5- to 25-membered)heteroarylamino, or a substituted or unsubstituted (C6-C25)aryl(5- to 25-membered)heteroarylamino, more preferably, hydrogen, (C6-C18)aryl unsubstituted or substituted with at least one of (5- to 30-membered) heteroaryl; di(C6-C30)arylamino; di(5- to 30-membered) heteroarylamino; and (C6-C30)aryl(5- to 30-membered) heteroarylamino, (5- to 18-membered)heteroaryl unsubstituted or substituted with (C6-C30)aryl, a substituted or unsubstituted mono- or di- (C6-C18)arylamino, a substituted or unsubstituted mono- or di- (5- to 18-membered) heteroarylamino, or a substituted or unsubstituted (C6-C18) aryl(5- to 18-membered)heteroarylamino. For example, $R_1$ to $R_4$ each independently may be a substituted or unsubstituted phenyl, a substituted or unsubstituted m-biphenyl, a substituted or unsubstituted o-terphenyl, a substituted or unsubstituted m-terphenyl, a substituted or unsubstituted pyridyl, a substituted or unsubstituted dibenzofuranyl, or a substituted or unsubstituted dibenzothiophenyl.

The compound of formula 1 according to one embodiment may be represented by any one of the following formulas 1-1 to 1-6.

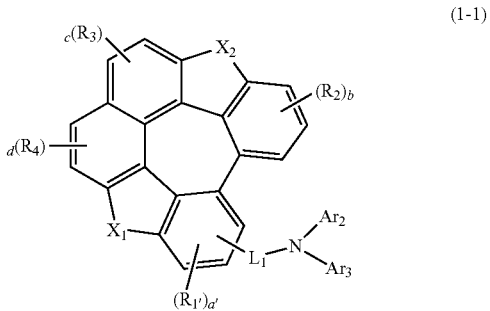

(1-1)

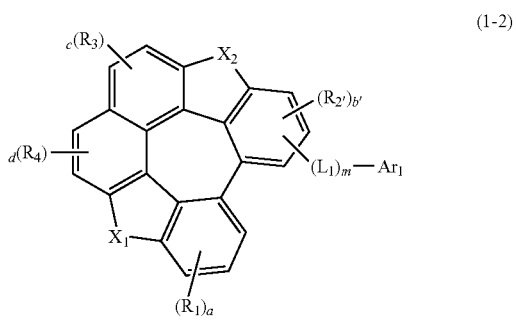

(1-2)

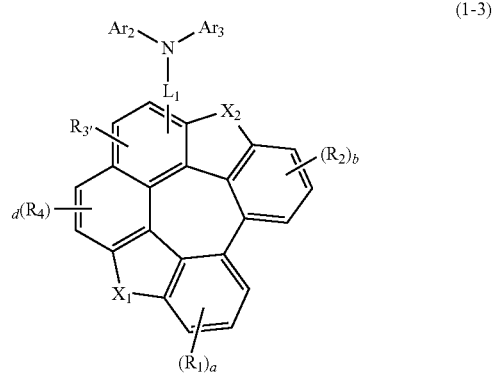

(1-3)

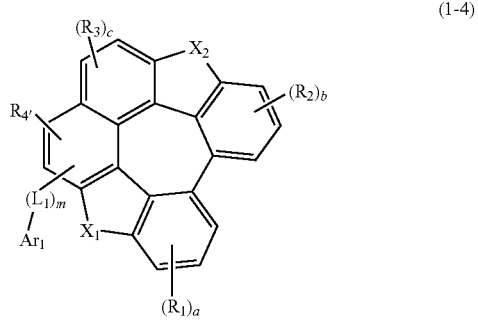

(1-4)

(1-5)

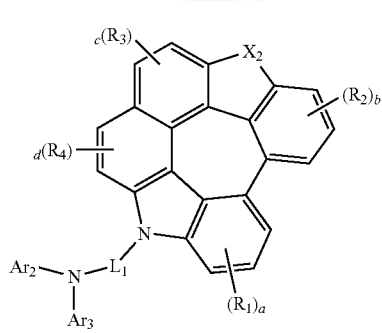

(1-6)

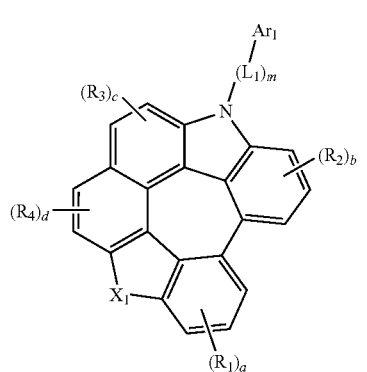

In formulas 1-1 to 1-6, $X_1$, $X_2$, $R_1$ to $R_4$, and a to d are as defined in formula 1;

$R_{1'}$ to $R_{4'}$ are as defined as $R_1$ to $R_4$ in formula 1;

$L_1$ represents a single bond, a substituted or unsubstituted (C6-C30)arylene, a substituted or unsubstituted fused ring of (C3-C30) aliphatic ring and (C6-C30) aromatic ring, or a substituted or unsubstituted (3- to 30-membered)heteroarylene;

$Ar_1$ represents a substituted or unsubstituted (C6-C30) aryl, a substituted or unsubstituted fused ring of (C3-C30) aliphatic ring and (C6-C30) aromatic ring, or a substituted or unsubstituted (3- to 30-membered)heteroaryl;

$Ar_2$ and $Ar_3$ each independently represent a substituted or unsubstituted (C1-C30)alkyl, a substituted or unsubstituted (C2-C30)alkenyl, a substituted or unsubstituted fused ring of (C3-C30) aliphatic ring and (C6-C30) aromatic ring, a substituted or unsubstituted (C6-C30) aryl, or a substituted or unsubstituted (3- to 30-membered)heteroaryl; and a', b', and m each independently represent an integer of 1 or 2;

when a', b', and m each independently are an integer of 2, each of $R_{1'}$, each of $R_{2'}$, and each of $L_1$ may be the same or different.

In one embodiment, $L_1$ may be a substituted or unsubstituted (C6-C30)arylene, for example, $L_1$ may be a substituted or unsubstituted phenylene.

In one embodiment, $Ar_2$ and $Ar_3$ each independently may be a substituted or unsubstituted (C6-C30)aryl or a substituted or unsubstituted (3- to 30-membered)heteroaryl, preferably, a substituted or unsubstituted (C6-C25)aryl or a substituted or unsubstituted (5- to 25-membered)heteroaryl, more preferably, a substituted or unsubstituted (C6-C18)aryl or a substituted or unsubstituted (5- to 18-membered)heteroaryl. For example, $Ar_2$ and $Ar_3$ each independently may be a substituted or unsubstituted phenyl, a substituted or unsubstituted naphthyl, a substituted or unsubstituted m-biphenyl, a substituted or unsubstituted phenanthrenyl, a substituted or unsubstituted dimethylfluorenyl, or a substituted or unsubstituted dibenzofuranyl.

In one embodiment, the first host material represented by formula 1 above may be more specifically illustrated by the following compounds, but is not limited thereto.

C1-1

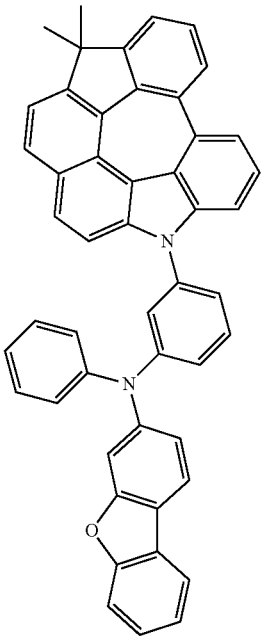

C1-2

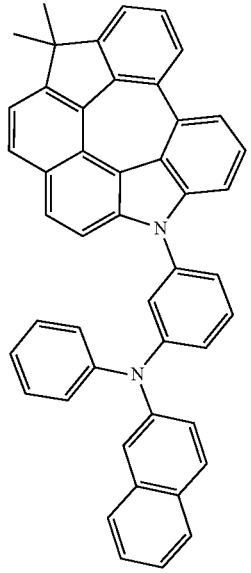

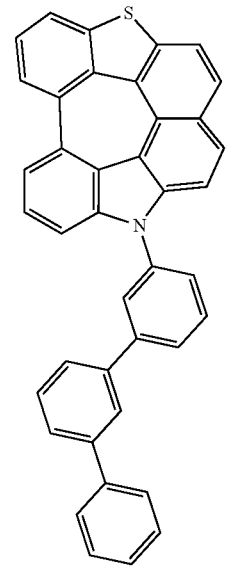
C1-3
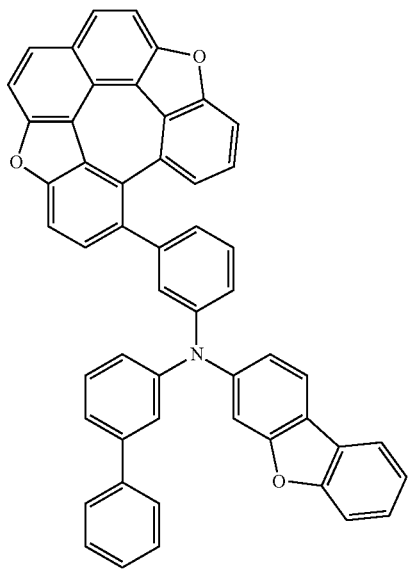
C1-6
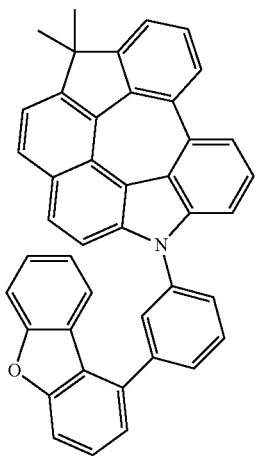
C1-4
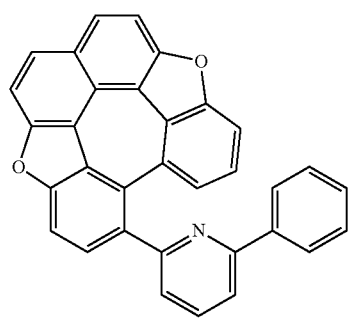
C1-7
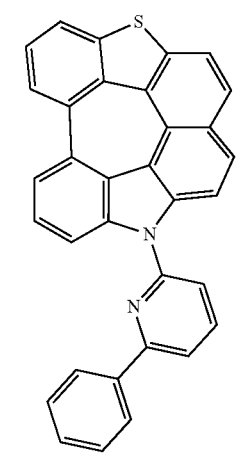
C1-5
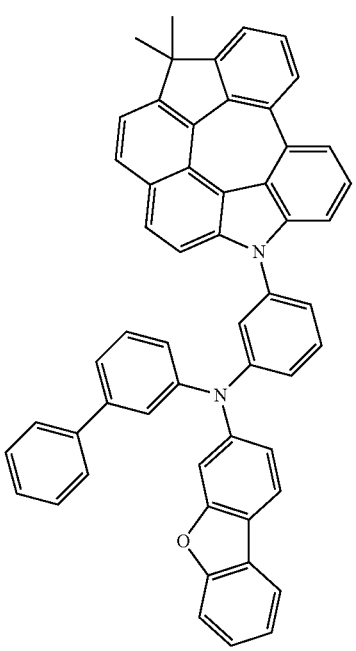
C1-8

C1-9
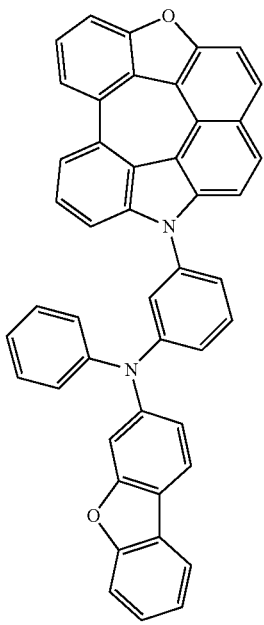
C1-10
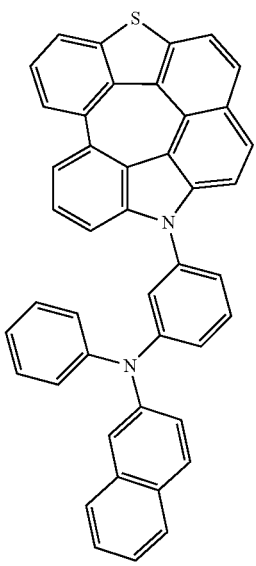
C1-11
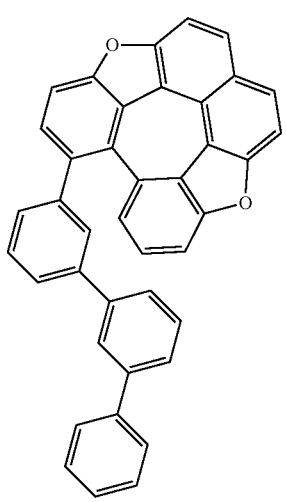
C1-12
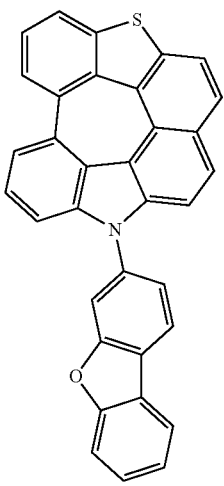
C1-13
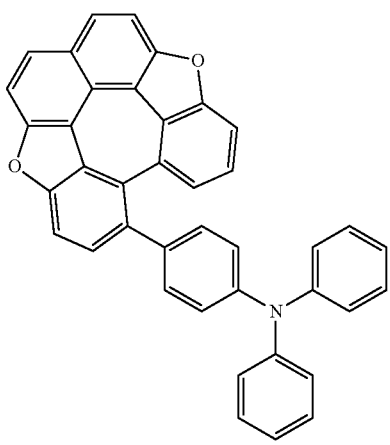
C1-14
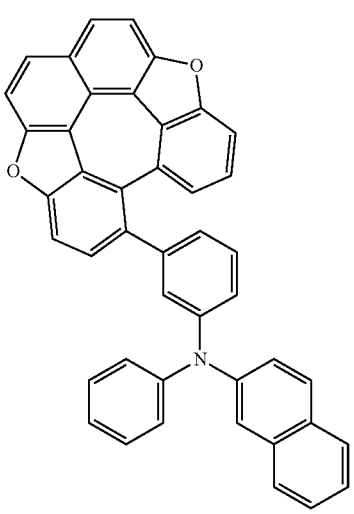

C1-15
C1-16
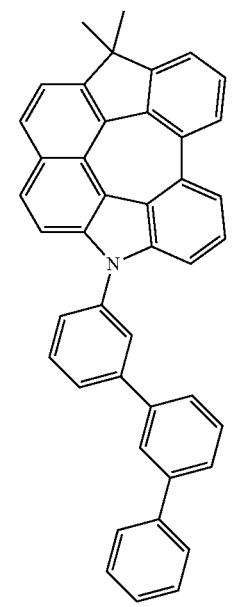
C1-17
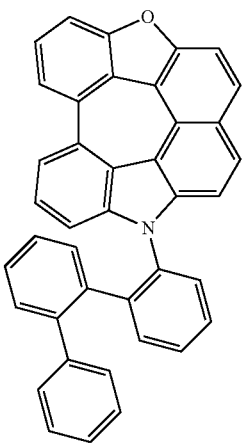
C1-18
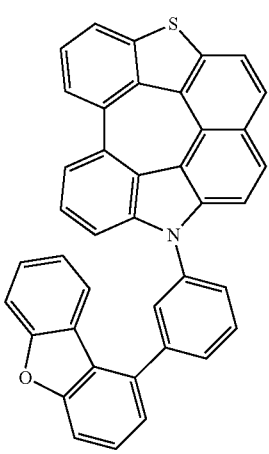
C1-19

C1-20
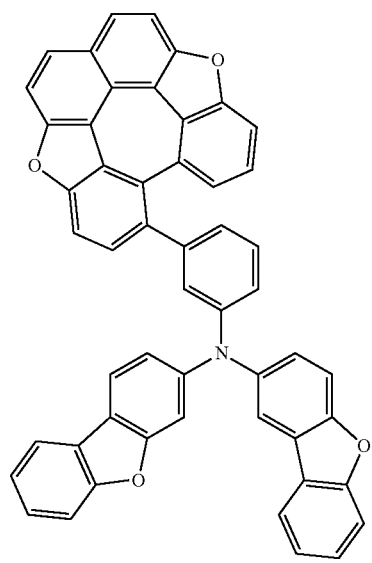
C1-21
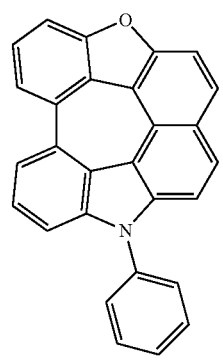
C1-22
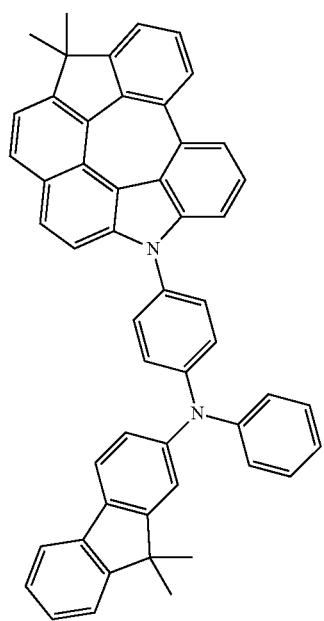
C1-23
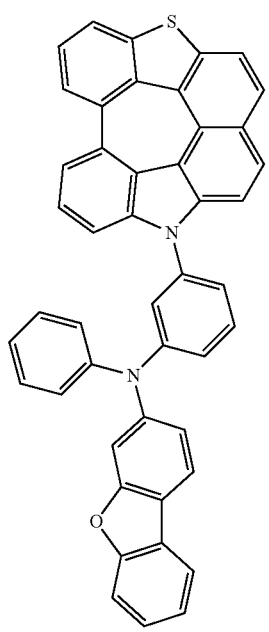
C1-24
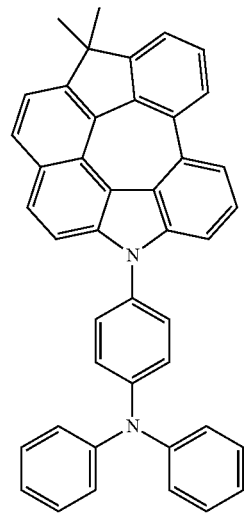
C1-25
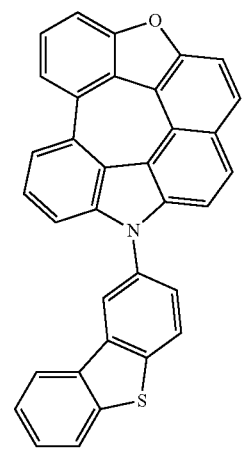

C1-26
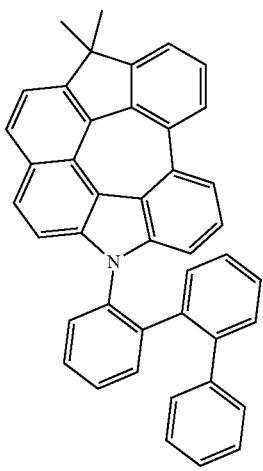
C1-27
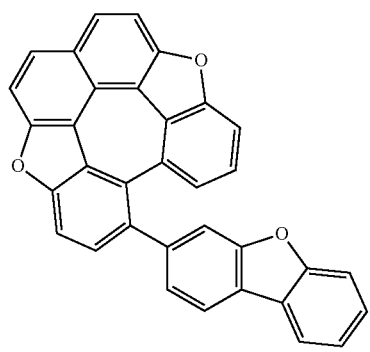
C1-28
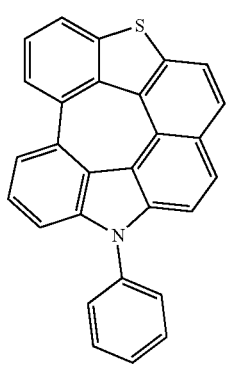
C1-29
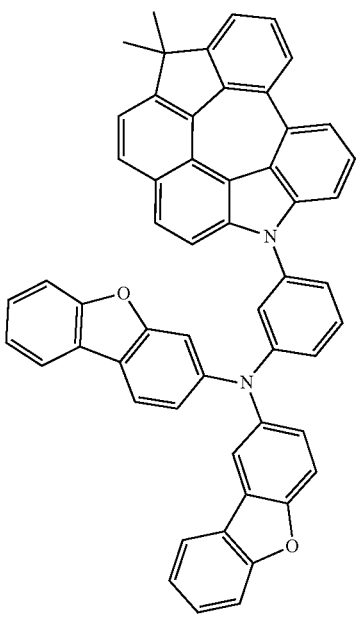
C1-30
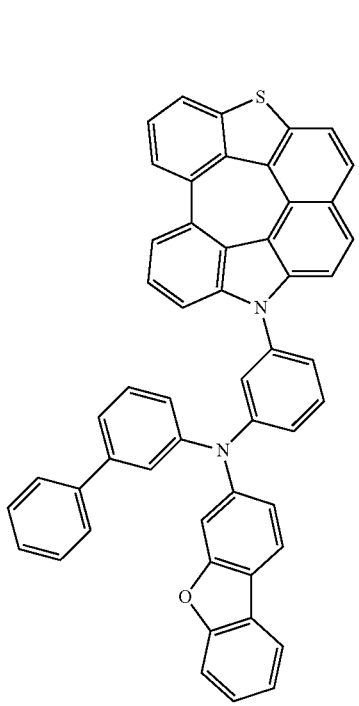

C1-31
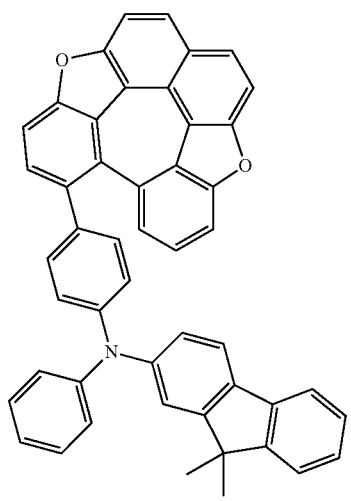
C1-34
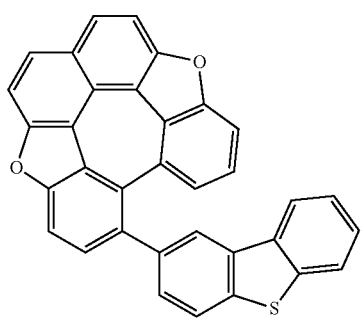
C1-32
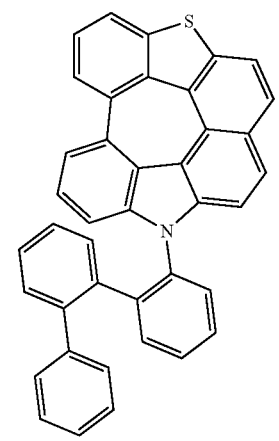
C1-35
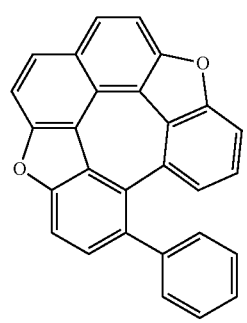
C1-33
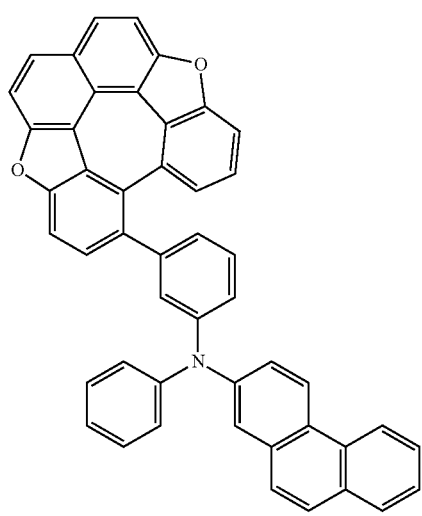
C1-36
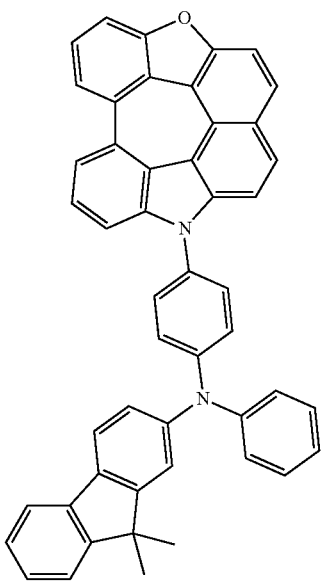

C1-37
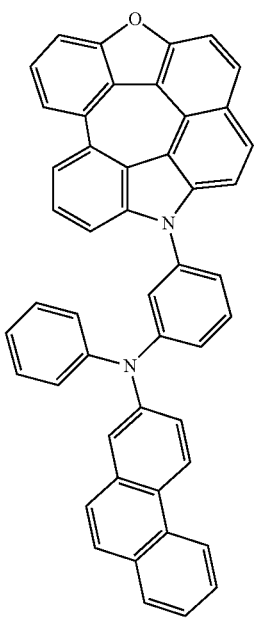
C1-38
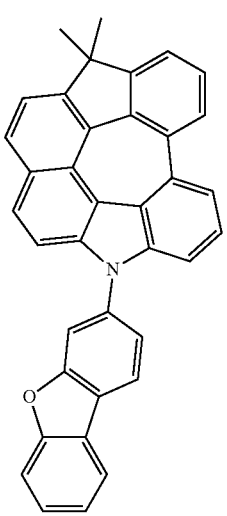
C1-39
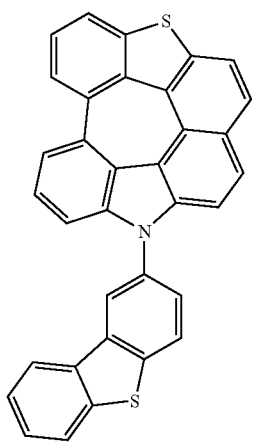
C1-40
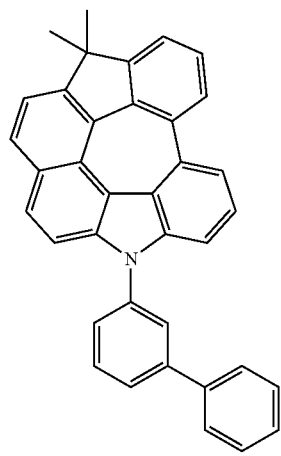
C1-41
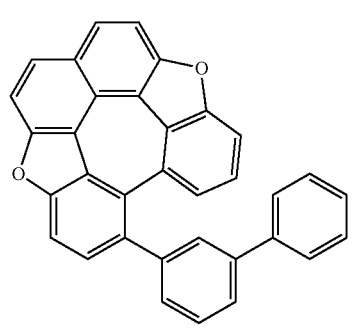
C1-42
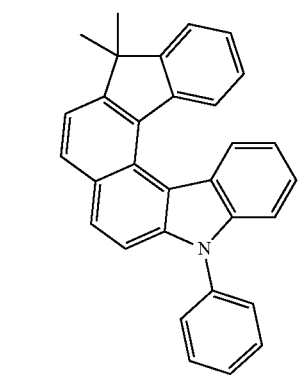
C1-43
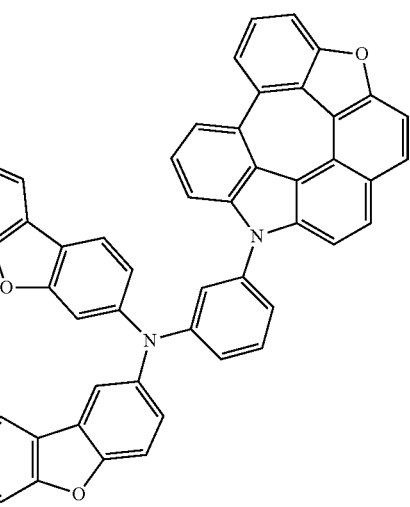

C1-44
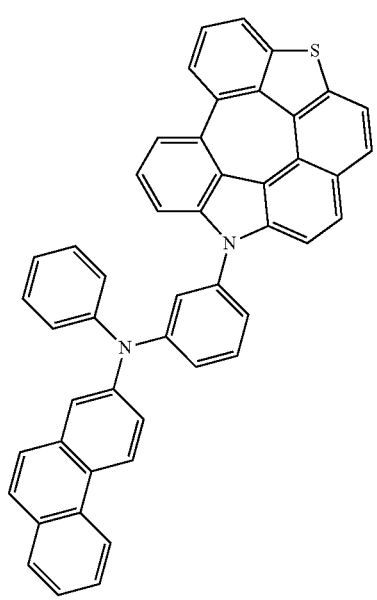
C1-45
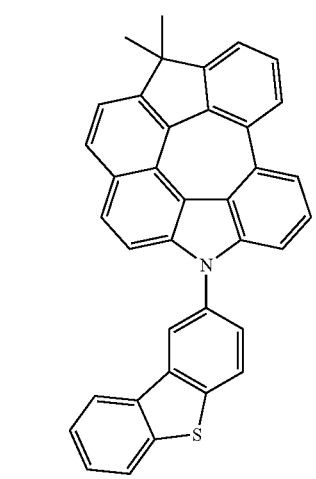
C1-46
C1-47
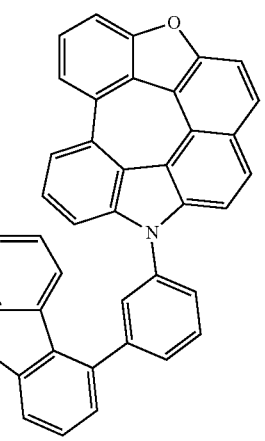
C1-48
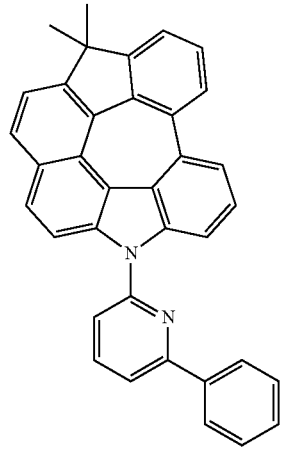
C1-49
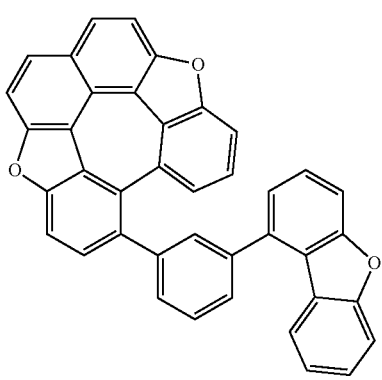

C1-50
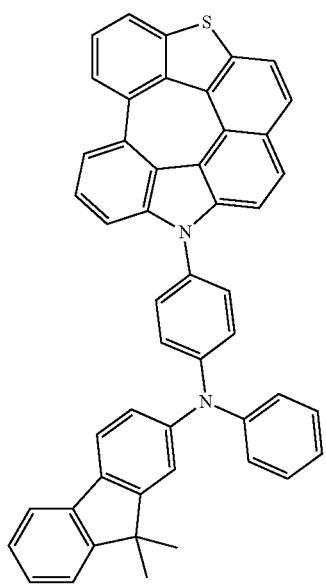
C1-51
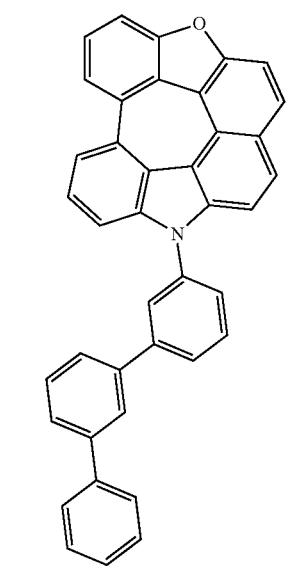
C1-52
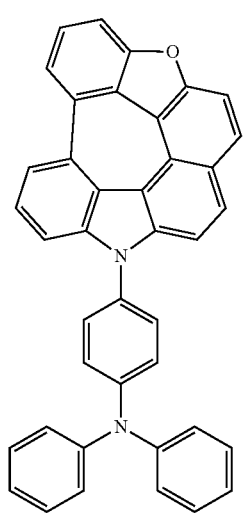
C1-53
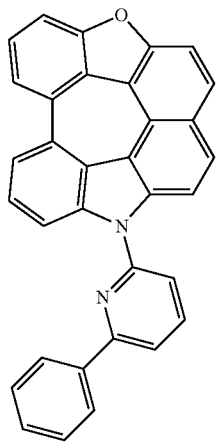
C1-54
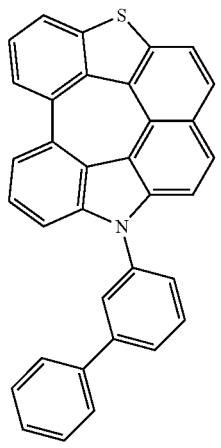
C1-55
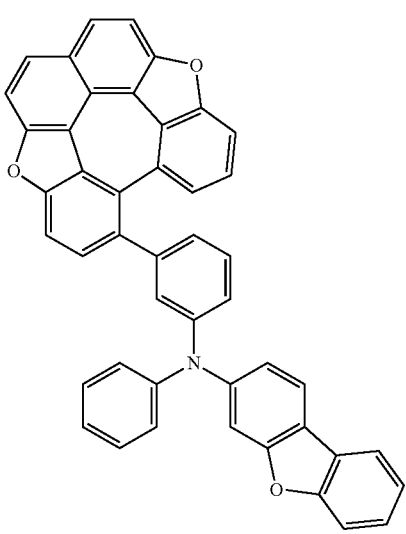

-continued
C1-56
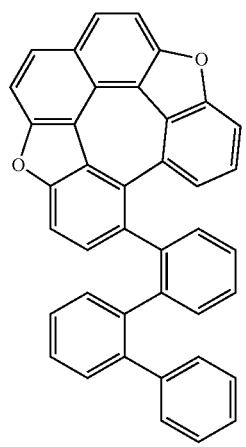
C1-57
C1-58
C1-59
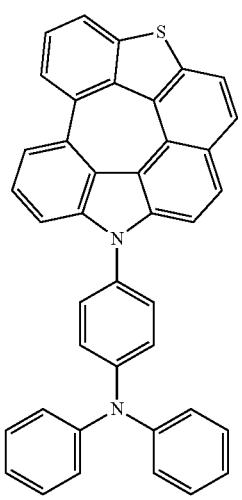
C1-60
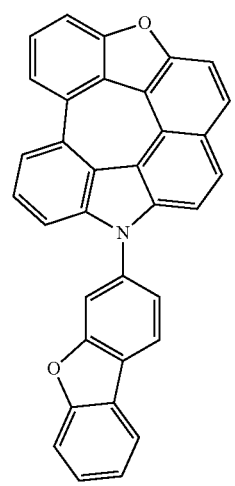
C1-61
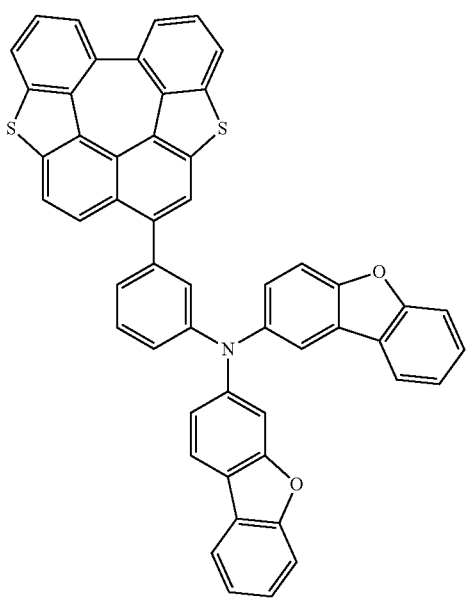

C1-62
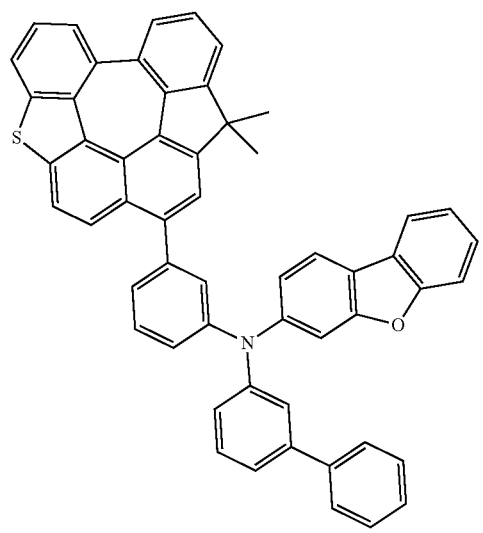
C1-65
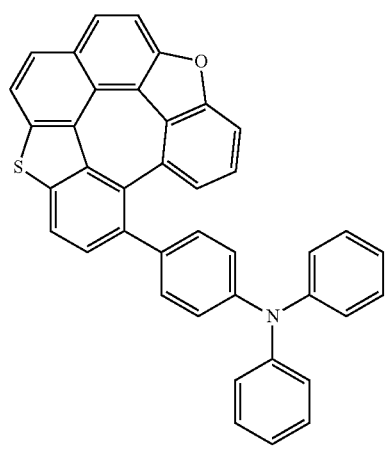
C1-63
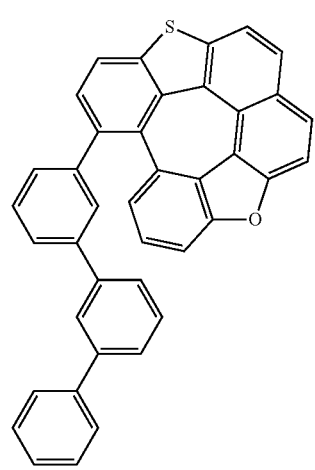
C1-66
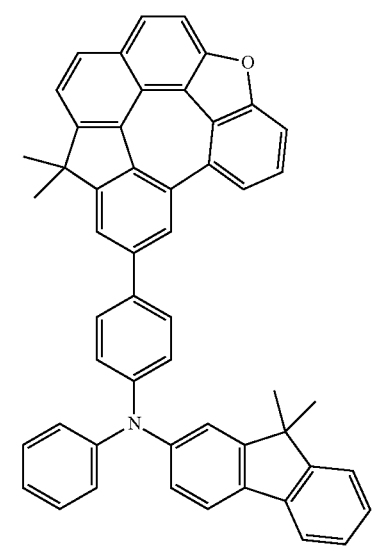
C1-64
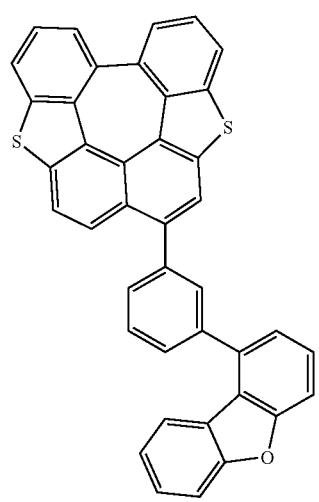
C1-67
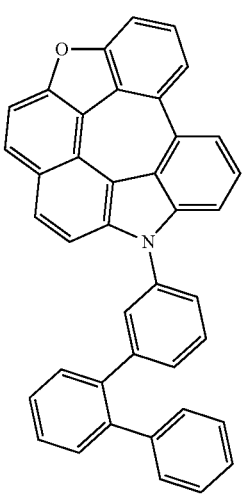

C1-68
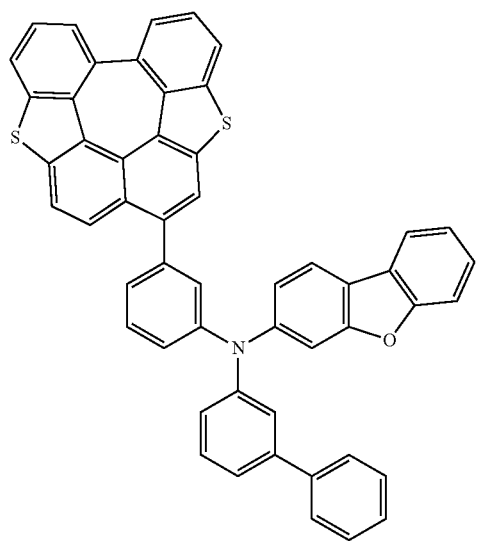
C1-69
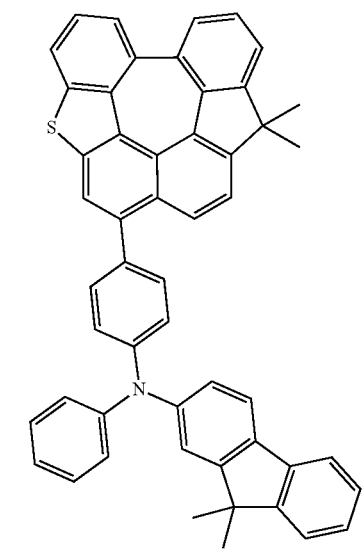
C1-70
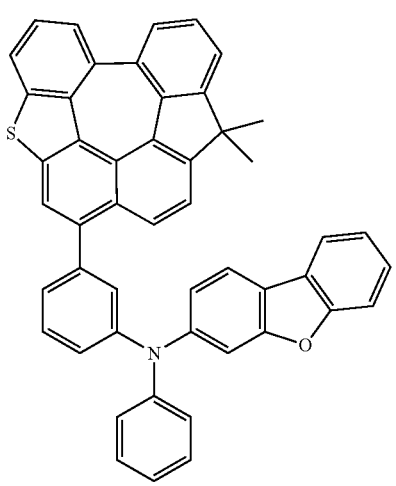
C1-71
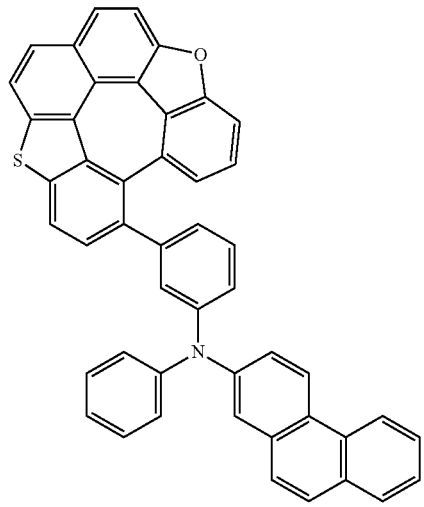
C1-72
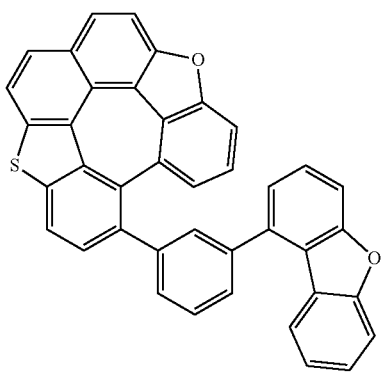
C1-73
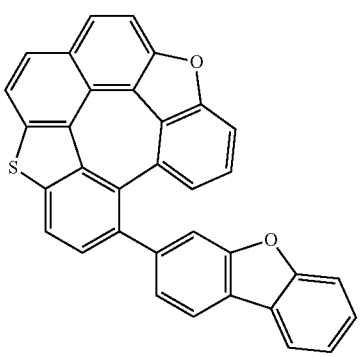

C1-74
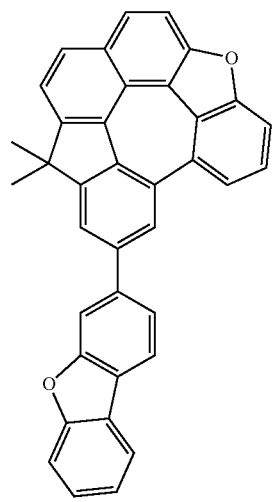
C1-75
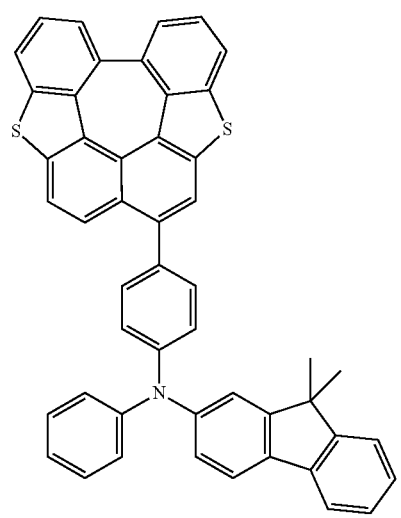
C1-76
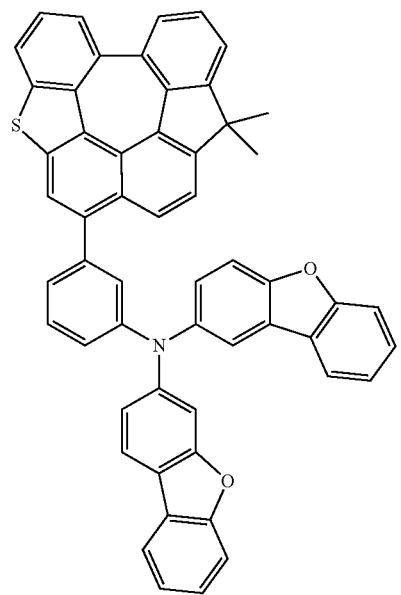
C1-77
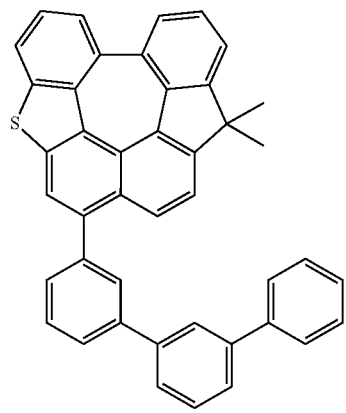
C1-78
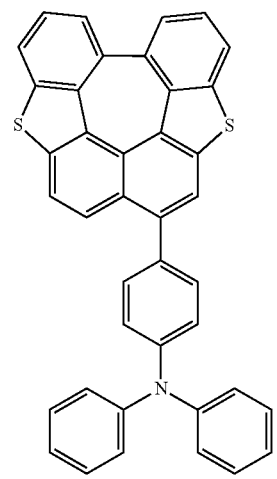
C1-79
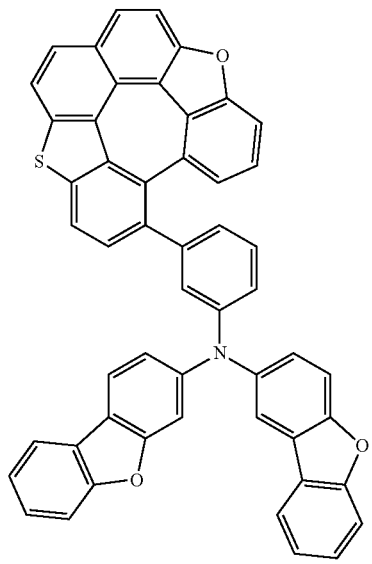

C1-80
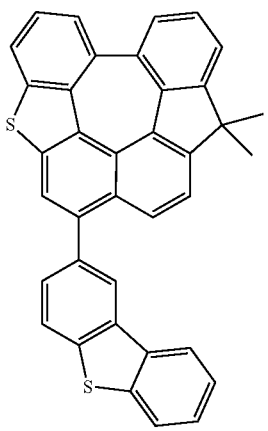
C1-81
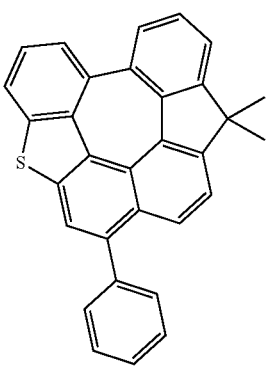
C1-82
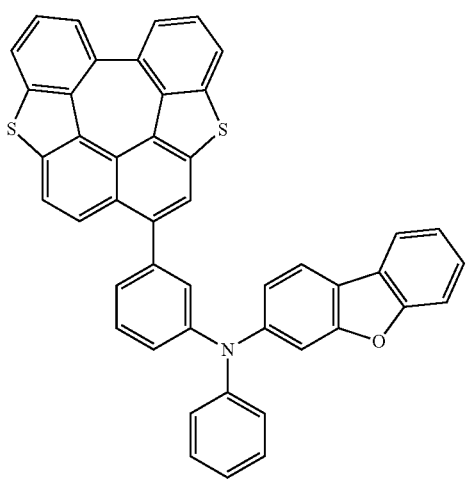
C1-83
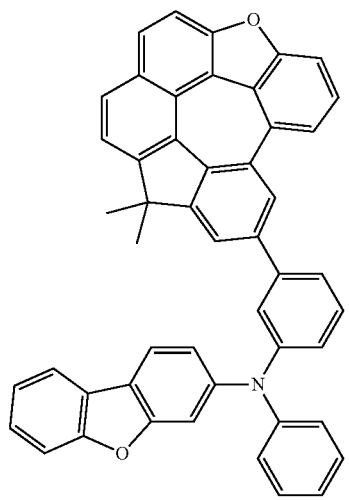
C1-84
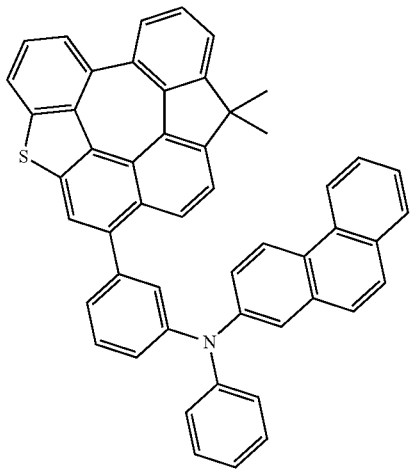
C1-85
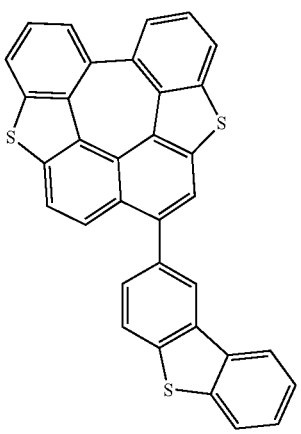

C1-86
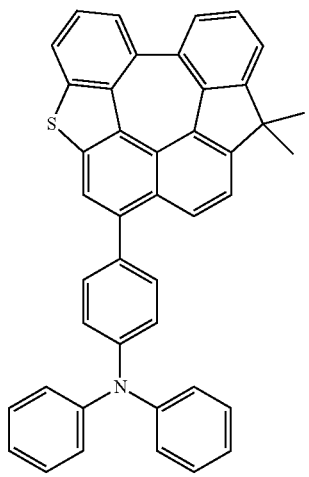
C1-89
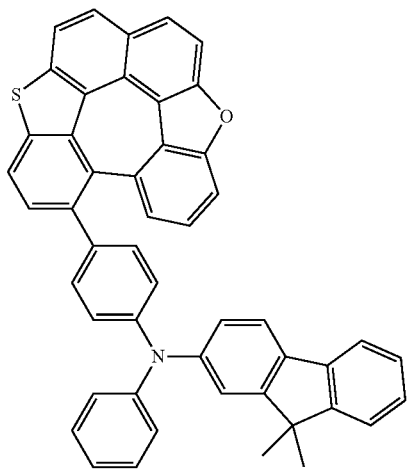
C1-87
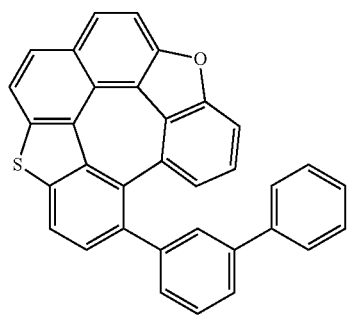
C1-90
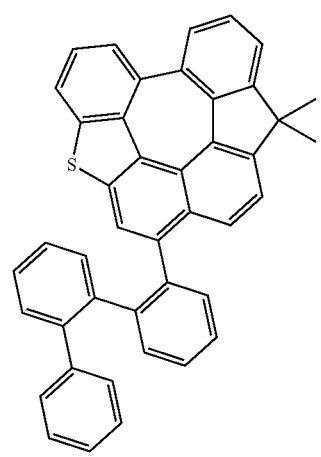
C1-88
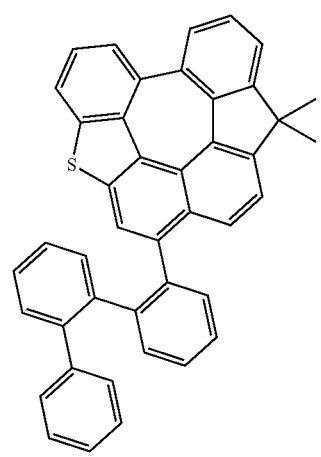
C1-91
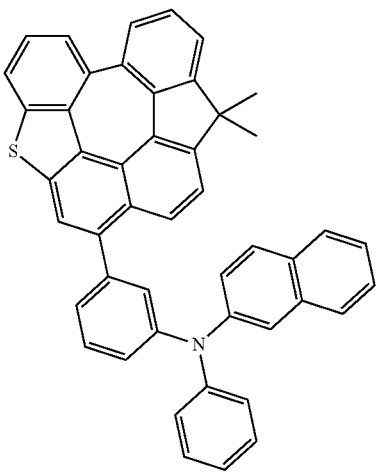

C1-92
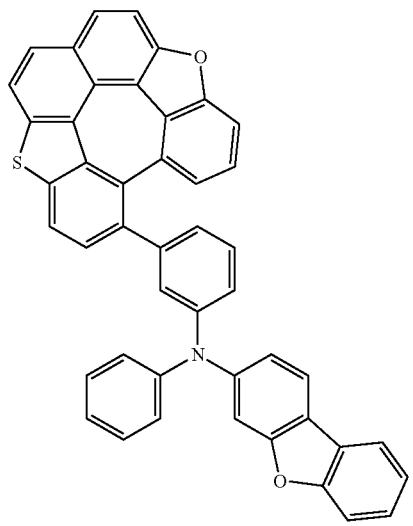
C1-93
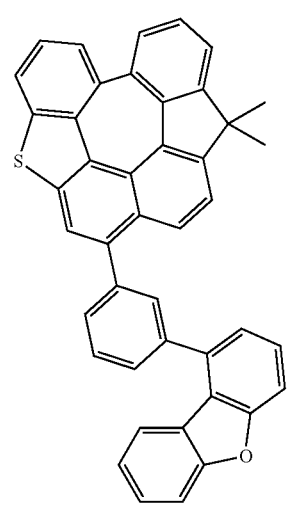
C1-94
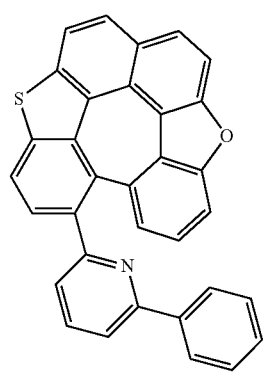
C1-95
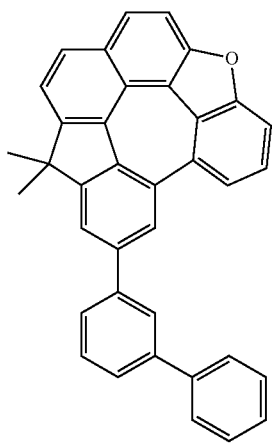
C1-96
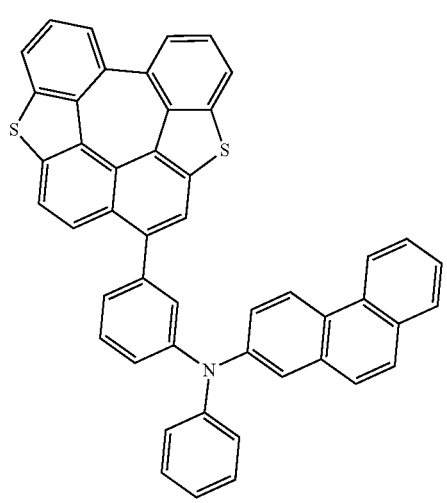
C1-97
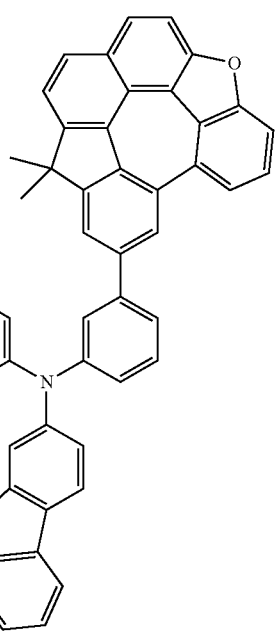

C1-98
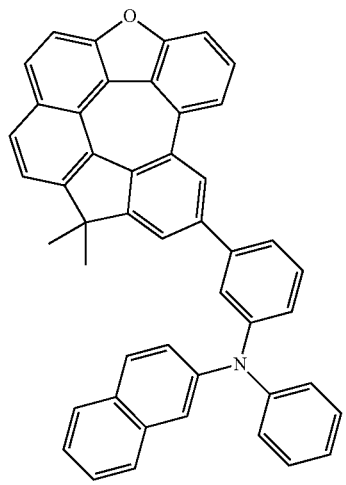
C1-99
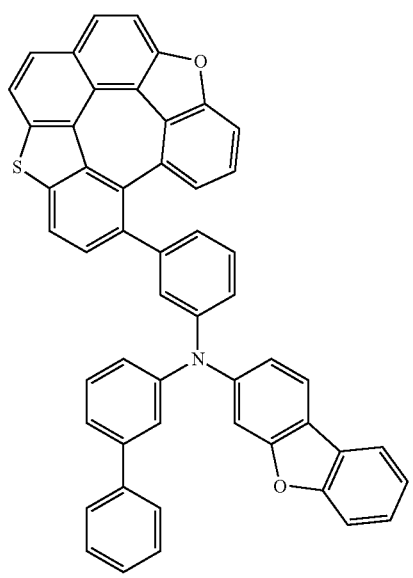
C1-100
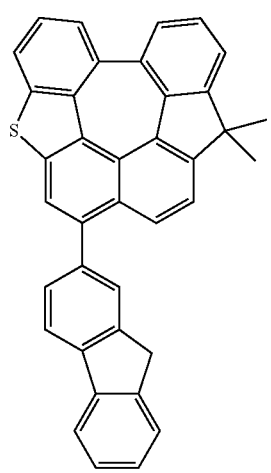
C1-101
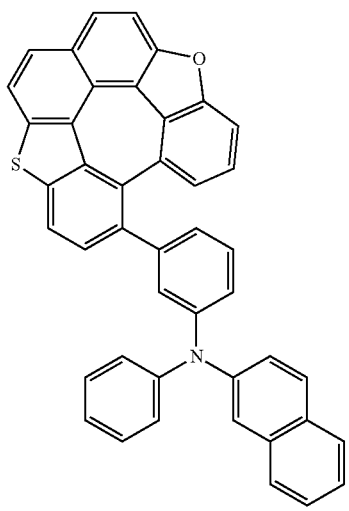
C1-102
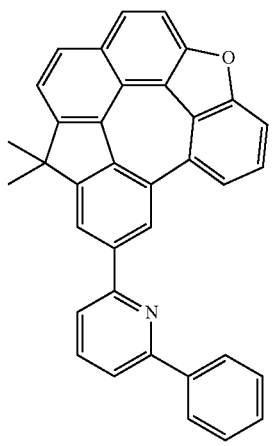
C1-103
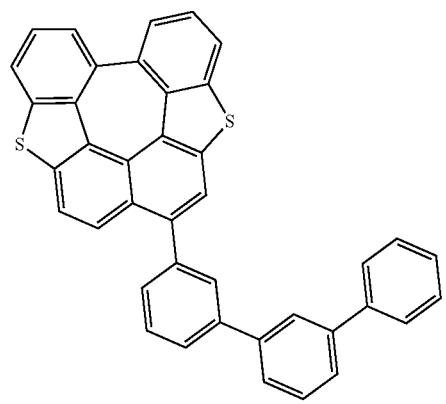

C1-104
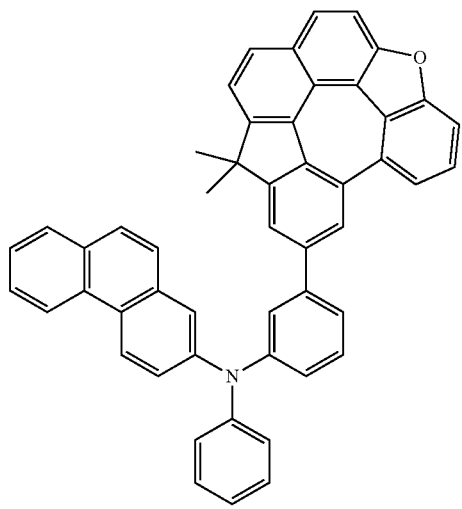
C1-107
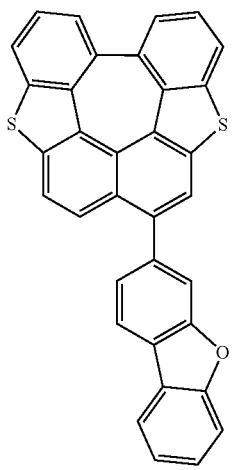
C1-105
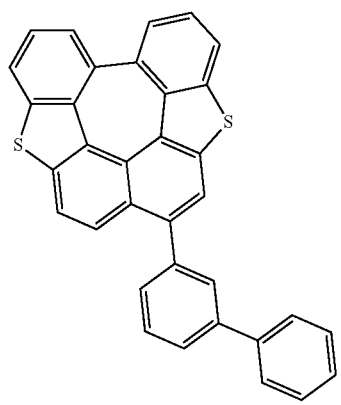
C1-108
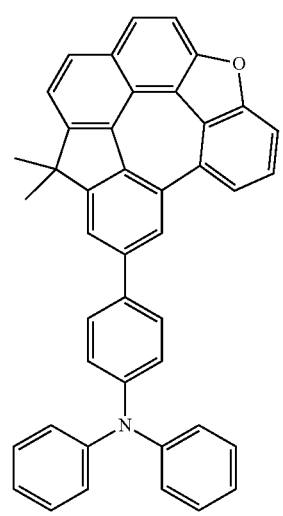
C1-106
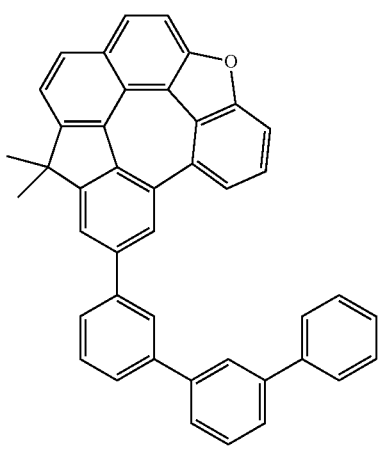
C1-109
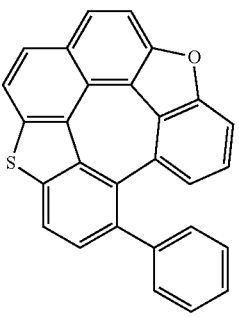

C1-110
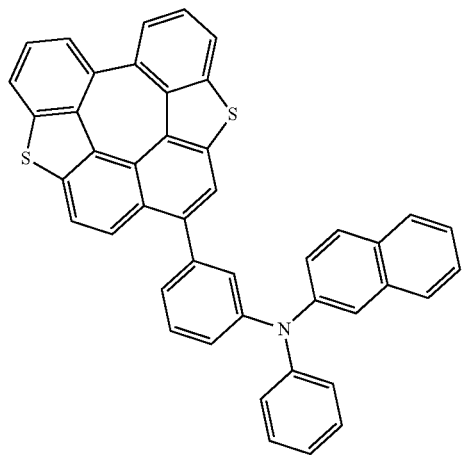
C1-113
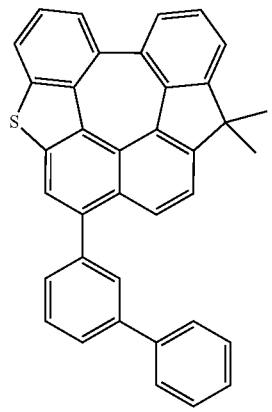
C1-111
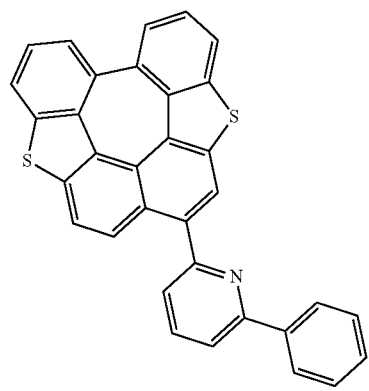
C1-114
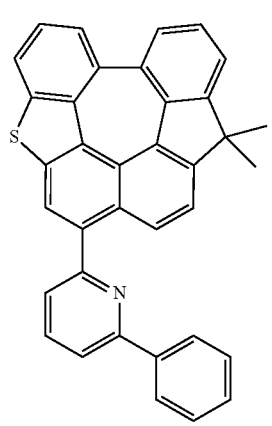
C1-112
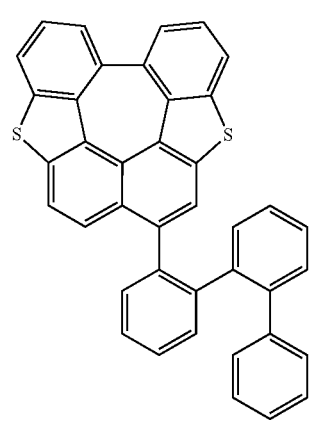
C1-115
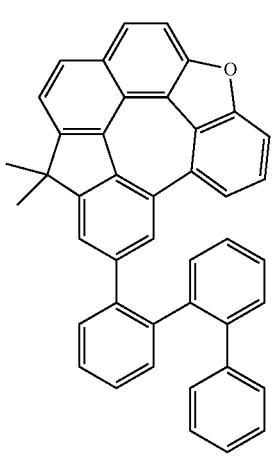

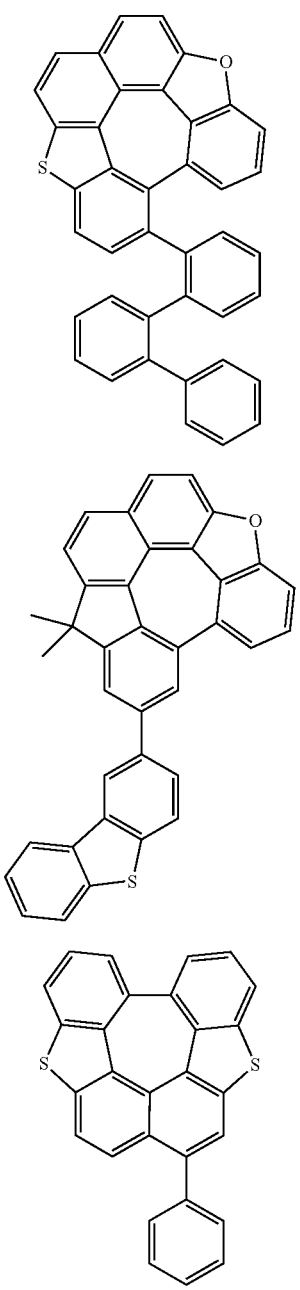
C1-116
C1-117
C1-118
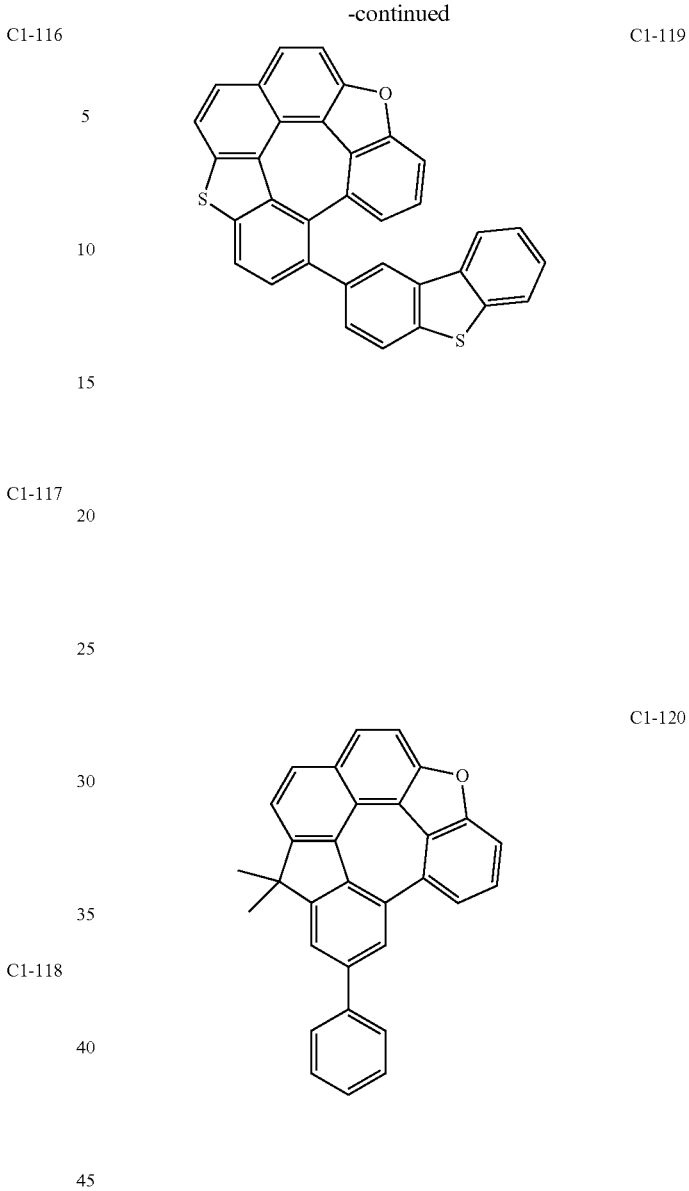
C1-119
C1-120
The compound represented by formula 1 of the present disclosure may be produced by a synthetic method known to a person skilled in the art. For example it may be prepared by referring to the following reaction schemes 1 to 4, but is not limited thereto.
[Reaction Scheme 1]
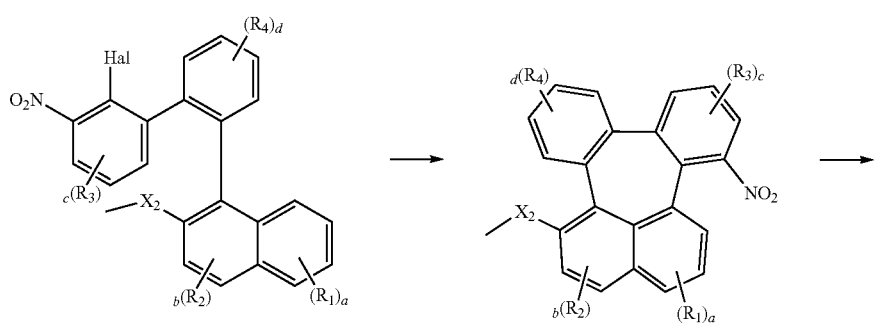

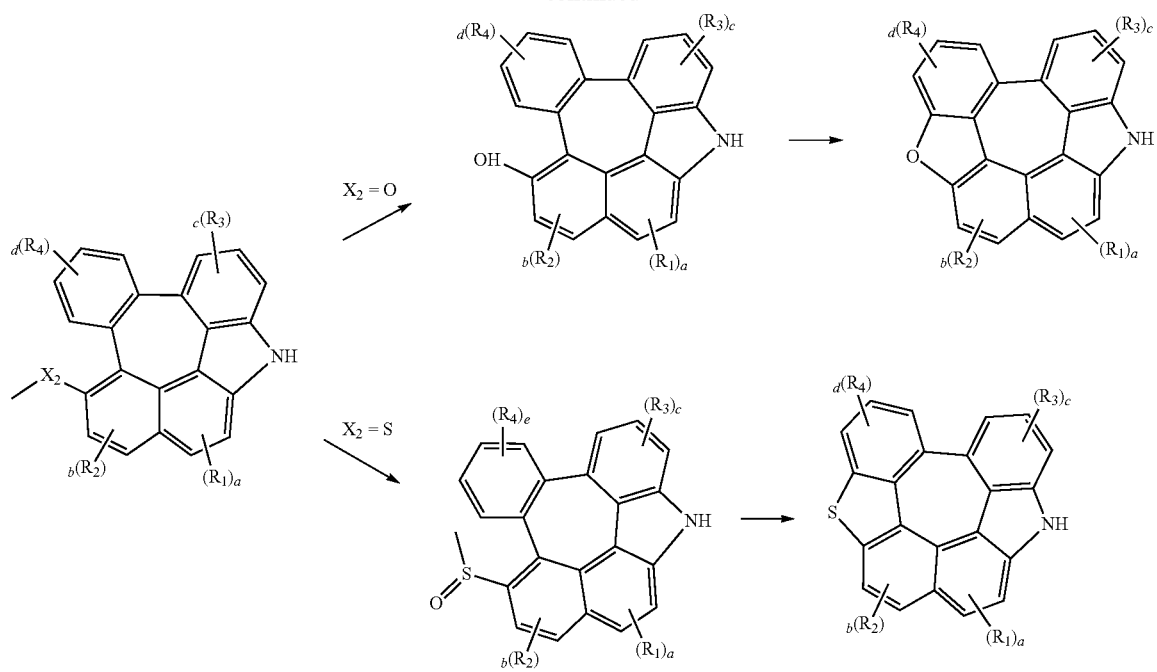
[Reaction Scheme 2]
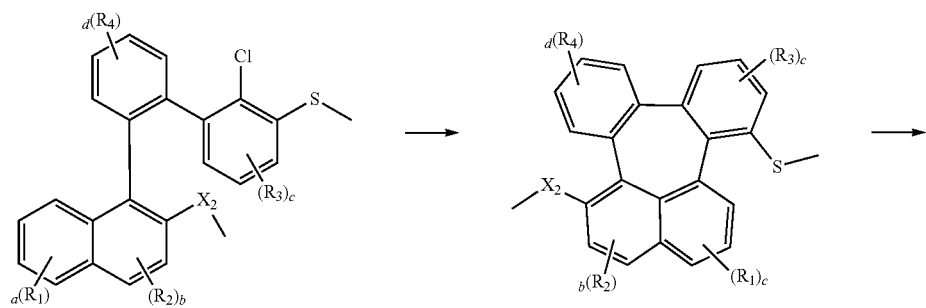
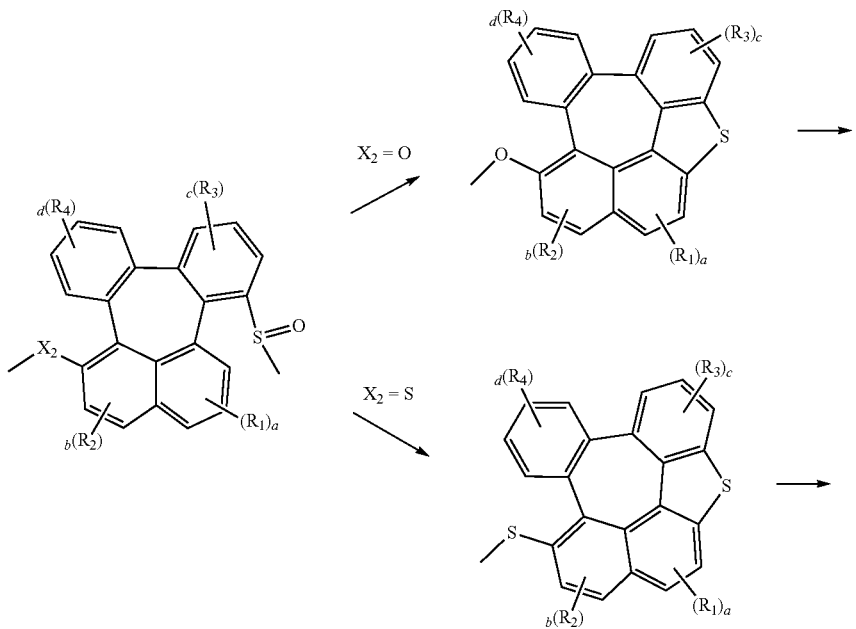

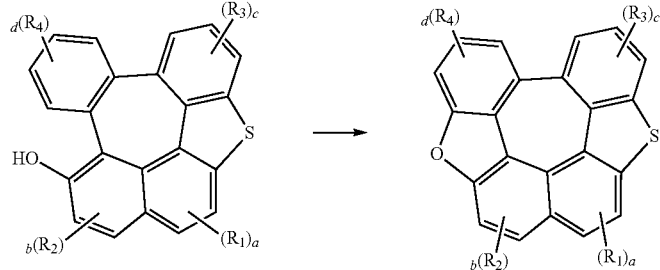
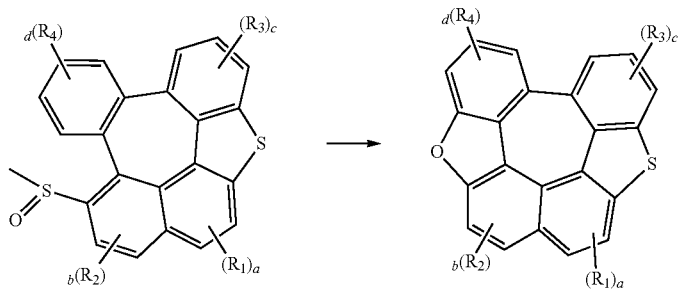
[Reaction Scheme 3]
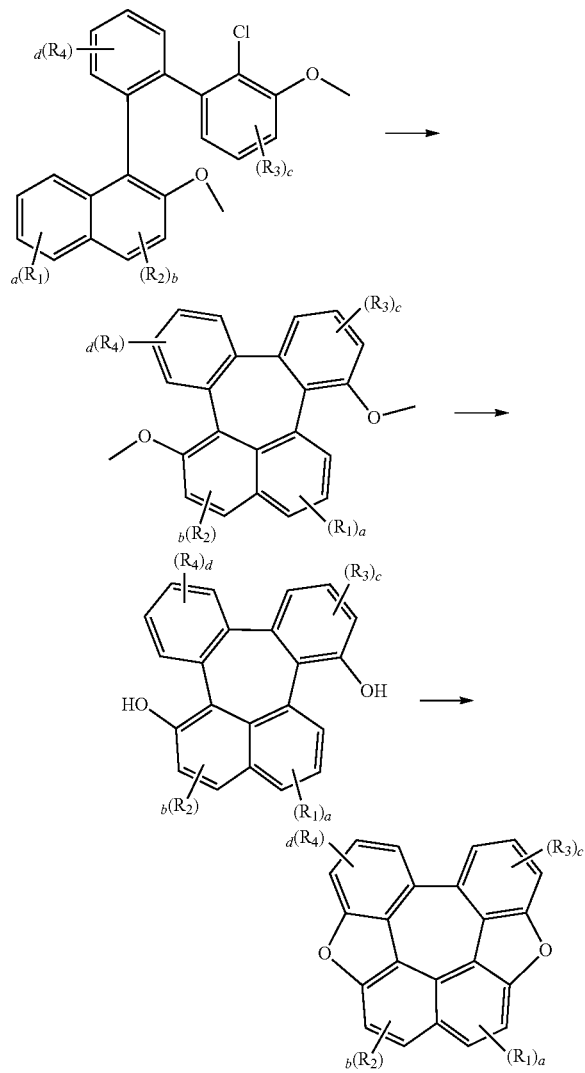

[Reaction Scheme 4]

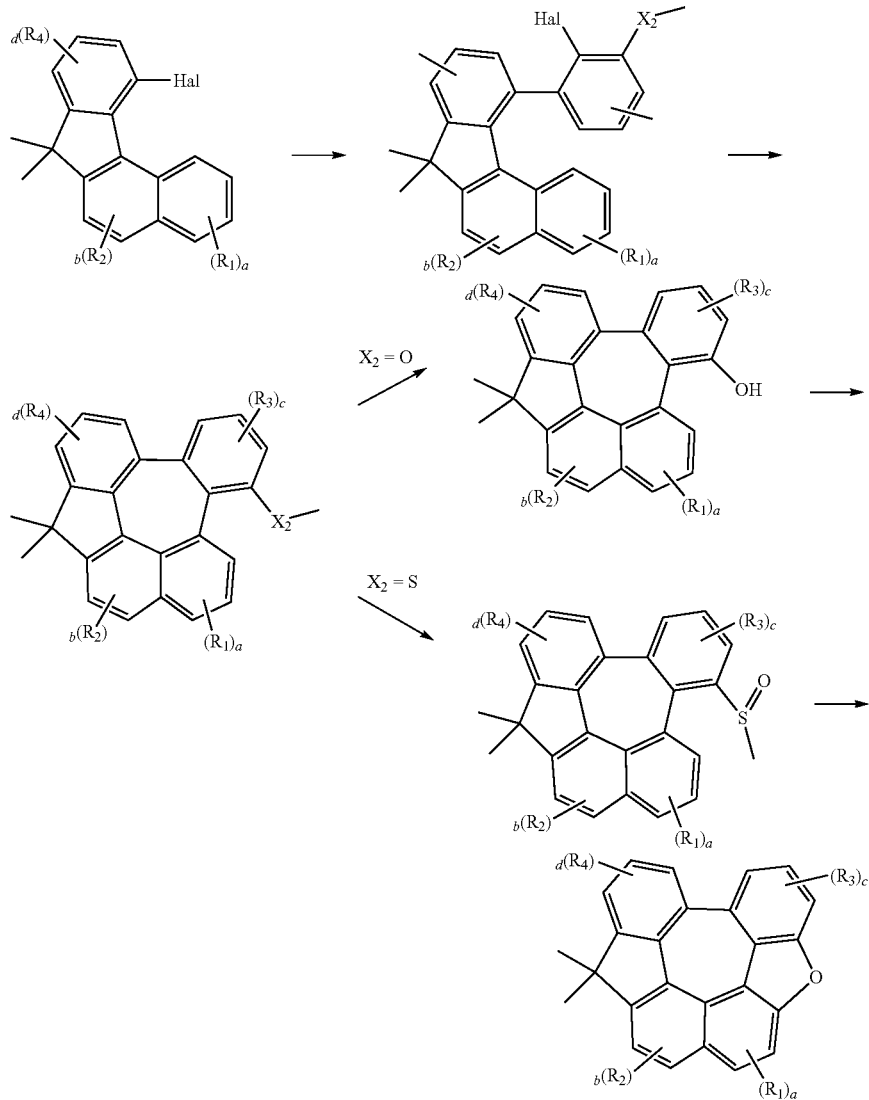

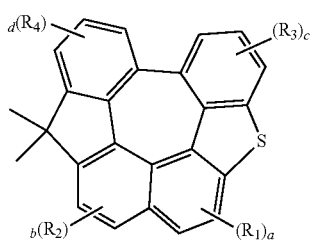

In reaction schemes 1 to 4 above, the definition of each substituent is as defined in formula 1, and Hal means a halogen atom.

As described above, exemplary synthesis examples of the compounds represented by formula 1 according to one embodiment are described, but they are based on Buchwald-Hartwig cross coupling reaction, N-arylation reaction, H-mont-mediated etherification reaction, Miyaura borylation reaction, Suzuki cross-coupling reaction, Intramolecular acid-induced cyclization reaction, Pd(II)-catalyzed oxidative cyclization reaction, Grignard reaction, Heck reaction, Cyclic Dehydration reaction, SN1 substitution reaction, SN2 substitution reaction, and Phosphine-mediated reductive cyclization reaction etc. It will be understood by one skilled in the art that the above reaction proceeds even if other substituents defined in formula 1, other than the substituents described in the specific synthesis examples, are bonded.

The second host material as another host material according to one embodiment may comprise a compound represented by the following formula 2.

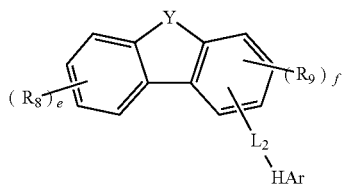
(2)

In formula 2,

Y represents —O— or —S—;

HAr represents a substituted or unsubstituted (3- to 30-membered)heteroaryl containing one or more nitrogen atoms;

L₂ represents a single bond, a substituted or unsubstituted (C6-C30)arylene, or a substituted or unsubstituted (3- to 30-membered)heteroarylene;

R₈ and R₉ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di- (C2-C30)alkenylamino, a substituted or unsubstituted (C1-C30) alkyl(C2-C30)alkenylamino, a substituted or unsubstituted mono- or di- (C6-C30)arylamino, a substituted or unsubstituted (C1-C30)alkyl(C6-C30)arylamino, a substituted or unsubstituted mono- or di- (3- to 30-membered)heteroarylamino, a substituted or unsubstituted (C1-C30)alkyl(3- to 30-membered)heteroarylamino, a substituted or unsubstituted (C2-C30) alkenyl(C6-C30)arylamino, a substituted or unsubstituted (C2-C30)alkenyl(3- to 30-membered) heteroarylamino, or a substituted or unsubstituted (C6-C30)aryl(3- to 30-membered)heteroarylamino; or may be linked to the adjacent substituents to form a ring(s);

e represents an integer of 1 to 4, and f represents an integer of 1 to 3; and when e and f each independently are an integer of 2 or more, each of R₈ and each of R₉ may be the same or different.

In one embodiment, L₂ may be a single bond or a substituted or unsubstituted (C6-C30)arylene, preferably, a single bond or a substituted or unsubstituted (C6-C25) arylene, more preferably, a single bond, or a substituted or unsubstituted (C6-C18)arylene. For example, L₂ may be a single bond, a substituted or unsubstituted phenylene, a substituted or unsubstituted naphthylene, a substituted or unsubstituted naphthylphenylene, a substituted or unsubstituted phenylnaphthylene, or a substituted or unsubstituted m-biphenylene.

In one embodiment, HAr may be a substituted or unsubstituted (5- to 30-membered)heteroaryl containing one or more nitrogen atoms, for example, a substituted or unsubstituted (5- to 25-membered)heteroaryl containing at least two nitrogen atoms, for example, a substituted or unsubstituted (5- to 25-membered)heteroaryl containing at least three nitrogen atoms. For example, HAr may be a substituted or unsubstituted pyridyl, a substituted or unsubstituted pyrimidinyl, a substituted or unsubstituted triazinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted benzofuropyrimidinyl, a substituted or unsubstituted benzothienopyrimidinyl, a substituted or unsubstituted carbazolyl, or a substituted or unsubstituted pyridopyrazinyl, preferably, a substituted or unsubstituted triazinyl, a substituted or unsubstituted quinazolinyl, a substituted or unsubstituted benzoquinazolinyl, a substituted or unsubstituted quinoxalinyl, a substituted or unsubstituted benzoquinoxalinyl, or a substituted or unsubstituted naphthyridinyl.

In one embodiment, R₈ and R₉ each independently may be hydrogen or a substituted or unsubstituted (C6-C30)aryl, preferably, hydrogen or a substituted or unsubstituted (C6-C25)aryl, more preferably, hydrogen or a substituted or unsubstituted (C6-C18)aryl. For example, R₈ and R₉ each independently may be hydrogen or a substituted or unsubstituted phenyl.

The second host material represented by formula 2 above according to one embodiment may be represented by the following formula 2-1 or 2-2.

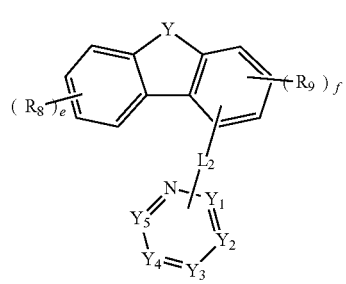
(2-1)

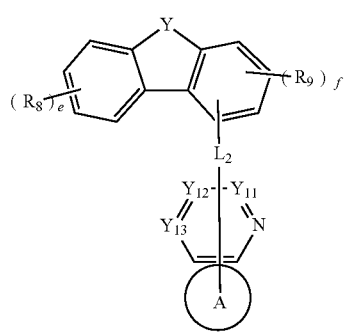
(2-2)

In formula 2-1 and 2-2,

Y, R₈, R₉, L₂, e, and f are as defined in formula 2;

A represents a substituted or unsubstituted (C6-C10) aromatic ring where the carbon atom of the aromatic ring may be replaced with one or more heteroatoms selected from N, O, and S;

$Y_1$ to $Y_5$ and $Y_{11}$ to $Y_{13}$ each independently represent N or $CR_a$; and $R_a$ represents hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30)alkenylamino, a substituted or unsubstituted mono- or di- (C6-C30)arylamino, a substituted or unsubstituted (C1-C30)alkyl(C6-C30)arylamino, a substituted or unsubstituted mono- or di- (3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or the adjacent $R_a$'s may be linked to each other to form a ring(s).

In one embodiment, at least one of $Y_1$ to $Y_5$ may be N. For example, at least two of $Y_1$ to $Y_5$ may be N. As another example, $Y_2$ and $Y_4$ may be N.

In one embodiment, $R_a$ may be hydrogen, a substituted or unsubstituted (C6-C30)aryl, or a substituted or unsubstituted (3- to 30-membered)heteroaryl, preferably, hydrogen, a substituted or unsubstituted (C6-C25)aryl, or a substituted or unsubstituted (5- to 25-membered)heteroaryl, more preferably, hydrogen, (C6-C18)aryl unsubstituted or substituted with at least one of di(C6-C30)arylamino; (C6-C30)aryl; and (3- to 30-membered)heteroaryl, or a substituted or unsubstituted (5- to 18-membered)heteroaryl. For example, $R_a$ may be hydrogen, a substituted or unsubstituted phenyl, a substituted or unsubstituted naphthyl, a substituted or unsubstituted p-biphenyl, a substituted or unsubstituted m-biphenyl, a substituted or unsubstituted o-biphenyl, a substituted or unsubstituted m-terphenyl, a substituted or unsubstituted phenanthrenyl, a substituted or unsubstituted triphenylenyl, a substituted or unsubstituted dimethylfluorenyl, a substituted or unsubstituted dimethylbenzofluorenyl, carbazolyl unsubstituted or substituted with phenyl, a substituted or unsubstituted dibenzofuranyl, or a substituted or unsubstituted dibenzothiophenyl.

In one embodiment, at least one of $Y_{11}$ to $Y_{13}$ may be N. For example, $Y_{11}$ may be N, or $Y_{13}$ may be N.

In one embodiment, A may be a substituted or unsubstituted (C6-C10) aromatic ring, wherein at least one carbon atom of the aromatic ring may be replaced with a nitrogen atom. For example, A may be a substituted or unsubstituted (C6-C10)aryl or a substituted or unsubstituted (C6-C10)heteroaryl containing at least one nitrogen atom.

According to one embodiment, the second host material represented by formula 2 above may be more specifically illustrated by the following compounds, but is not limited thereto.

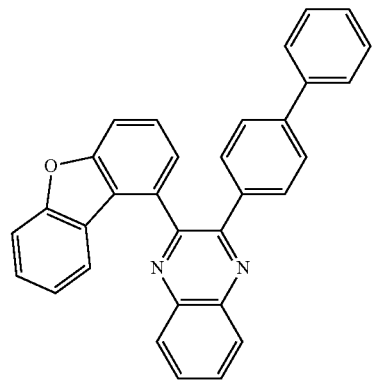

C2-1

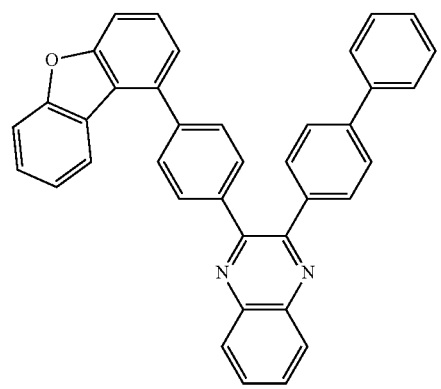

C2-2

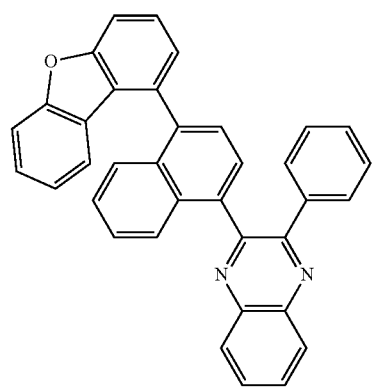

C2-3

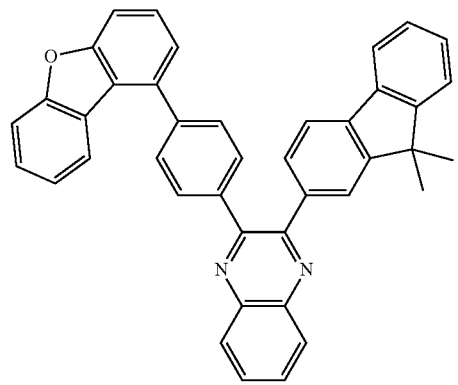

C2-4

C2-5
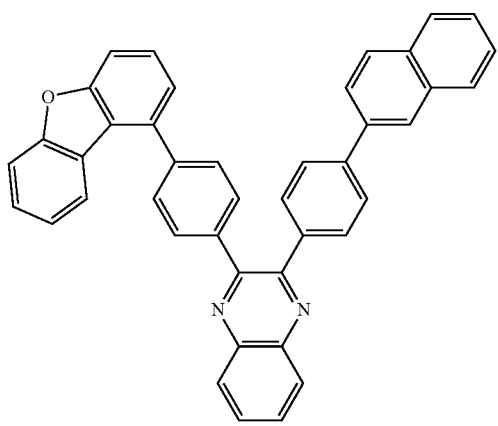
C2-8
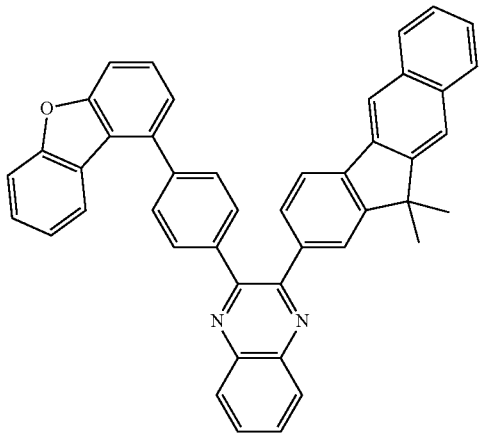
C2-6
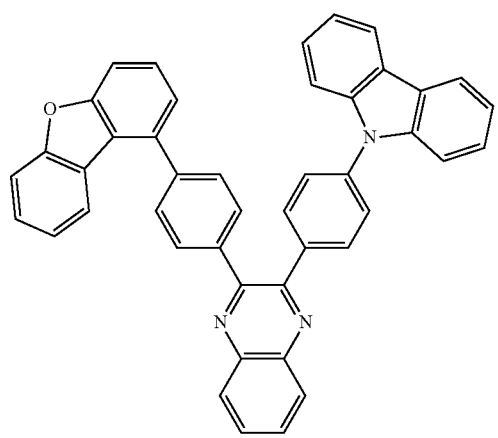
C2-9
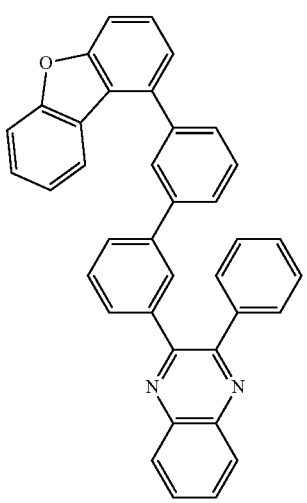
C2-7
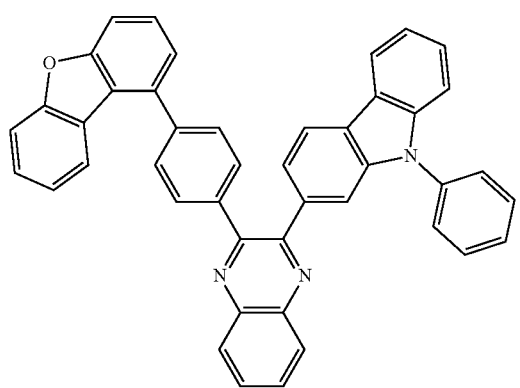
C2-10
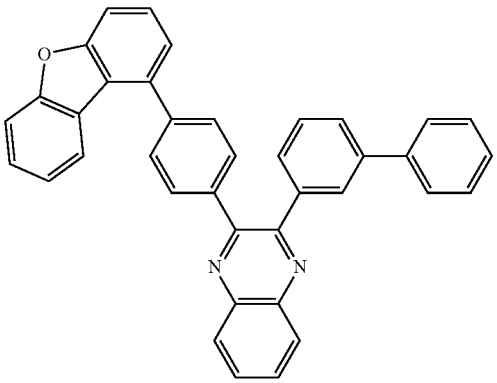

-continued
C2-11
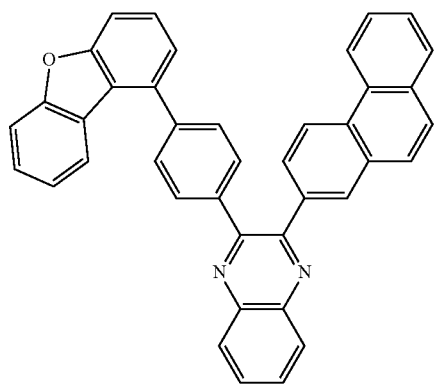
C2-12
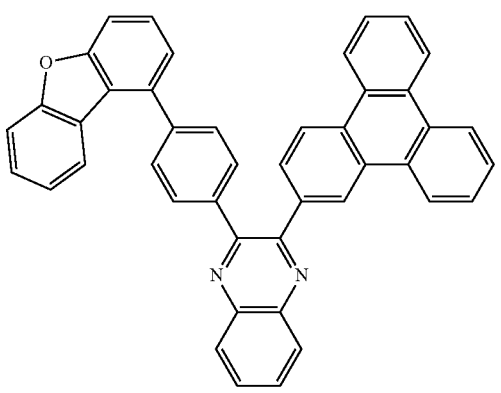
C2-13
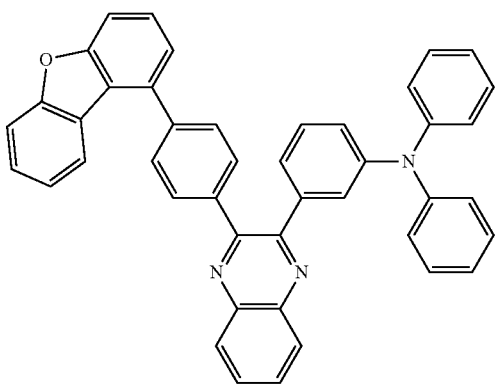
C2-14
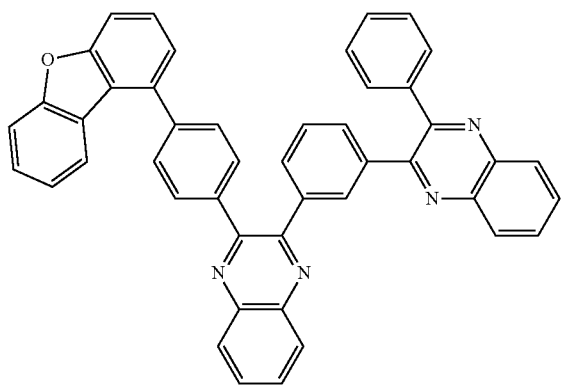
-continued
C2-15
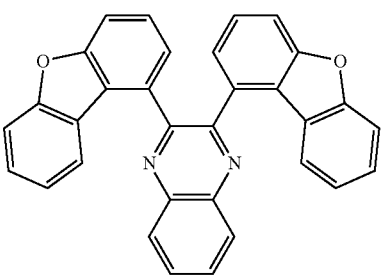
C2-16
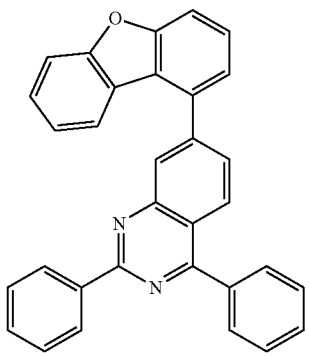
C2-17
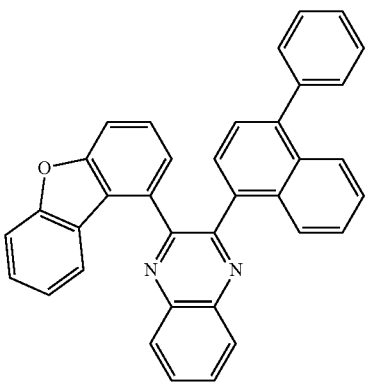
C2-18
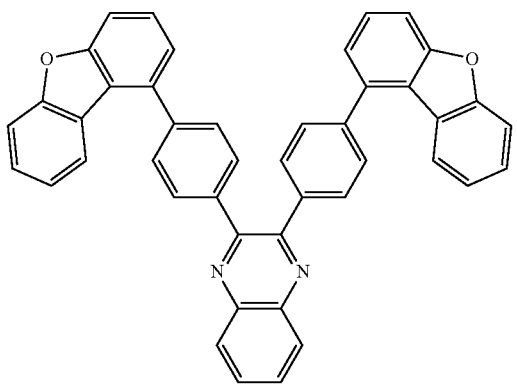

-continued
C2-19
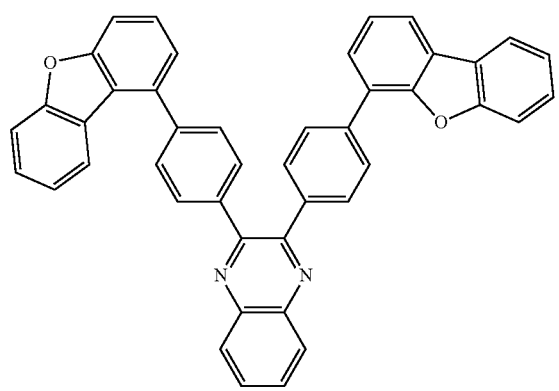
C2-20
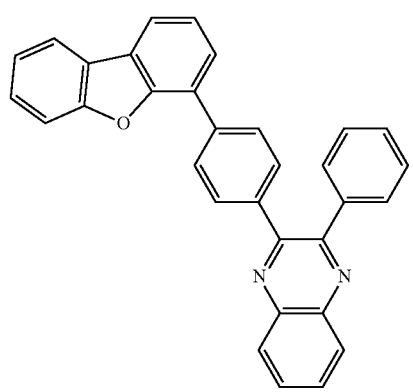
C2-21
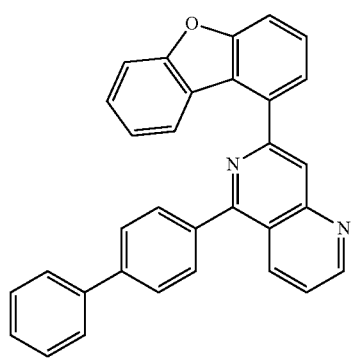
C2-22
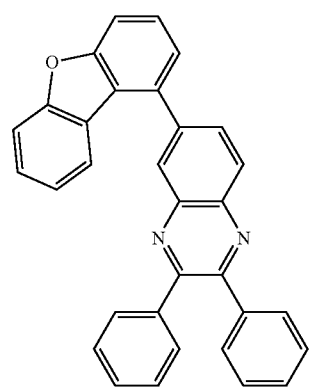
-continued
C2-23
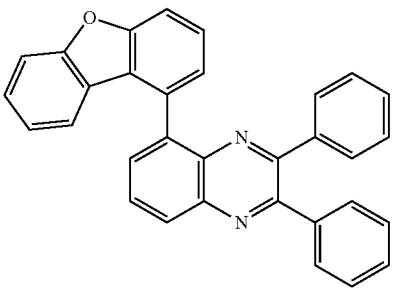
C2-24
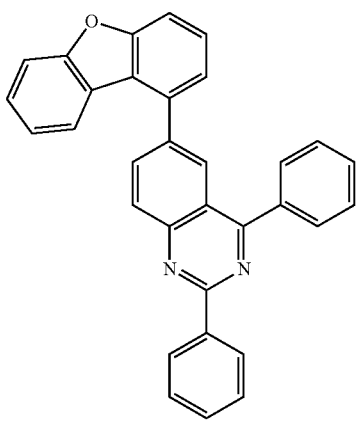
C2-25
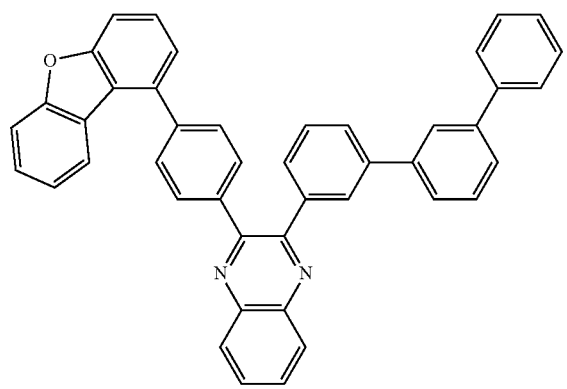
C2-26
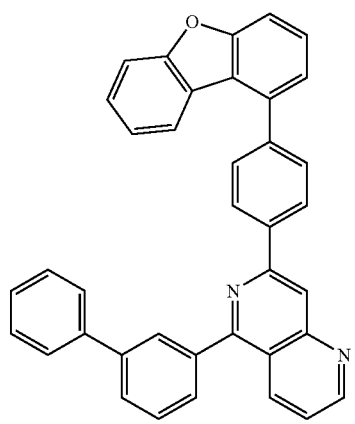

-continued
C2-27
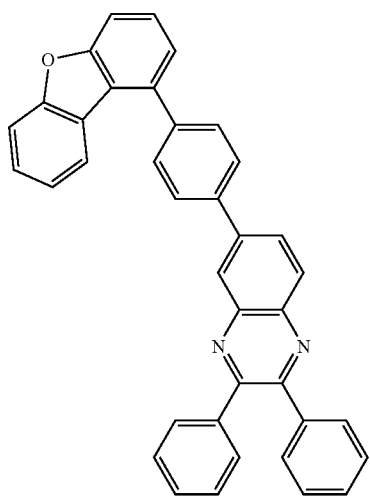
C2-28
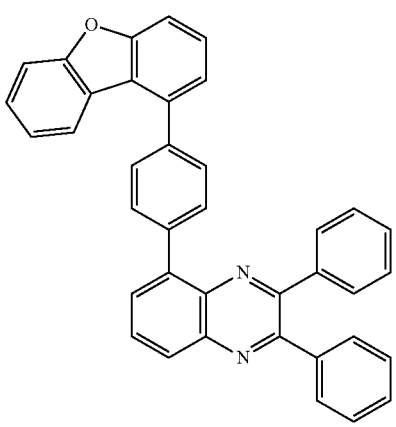
C2-29
-continued
C2-30
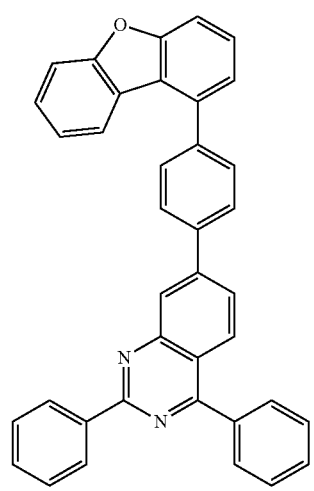
C2-31
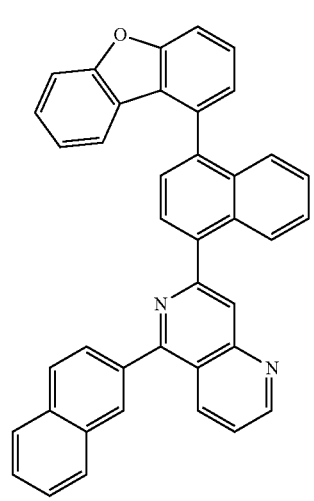
C2-32
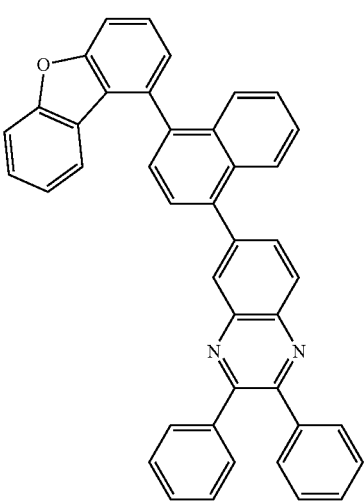

C2-33
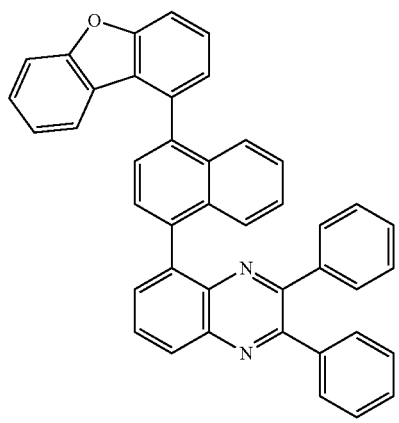
C2-34
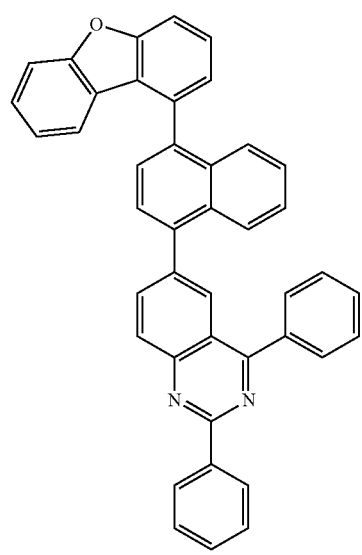
C2-35
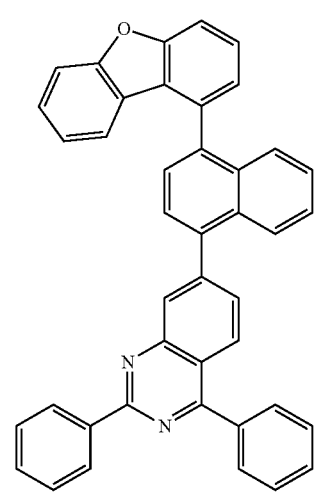
C2-36
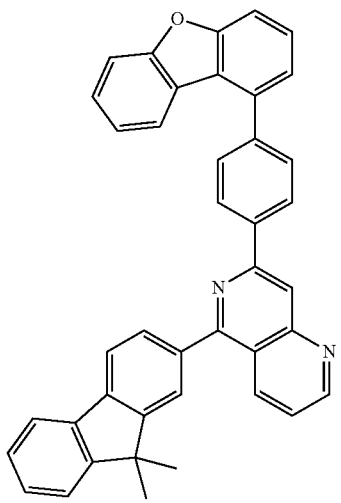
C2-37
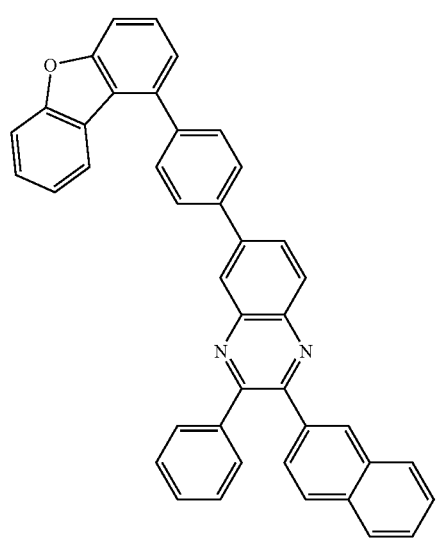
C2-38
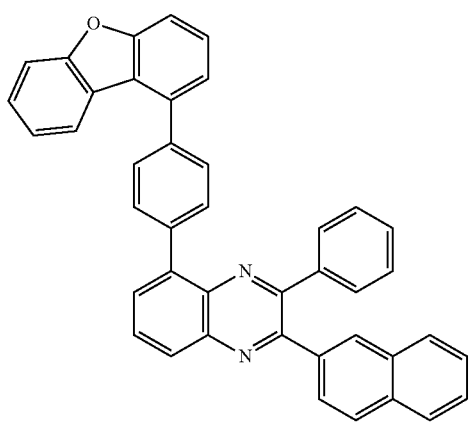

C2-39
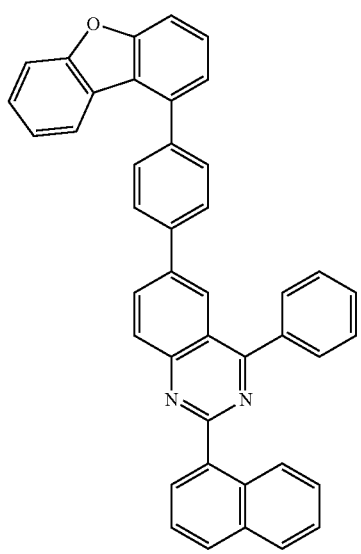
C2-40
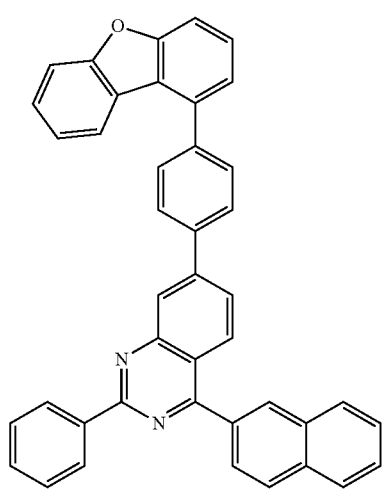
C2-41
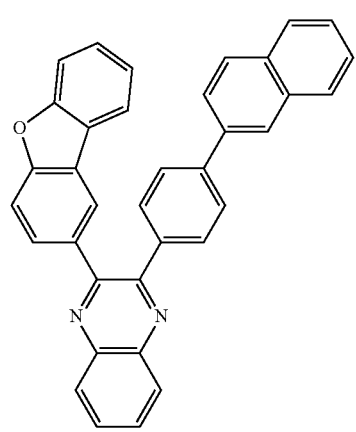
C2-42
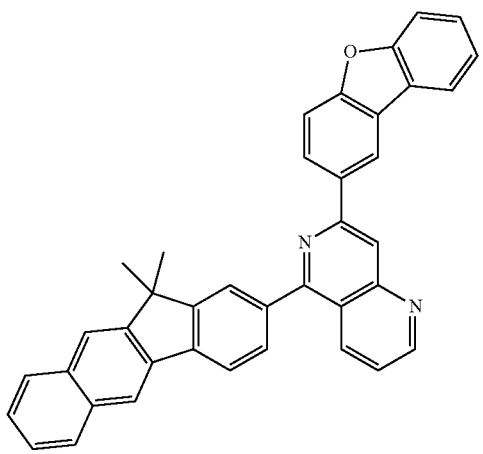
C2-43
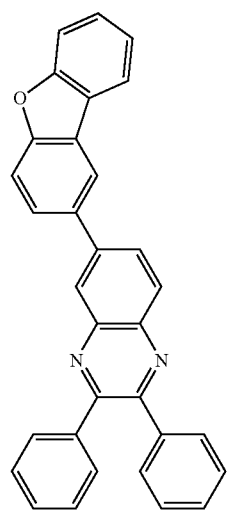
C2-44
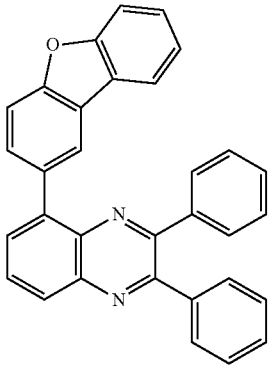

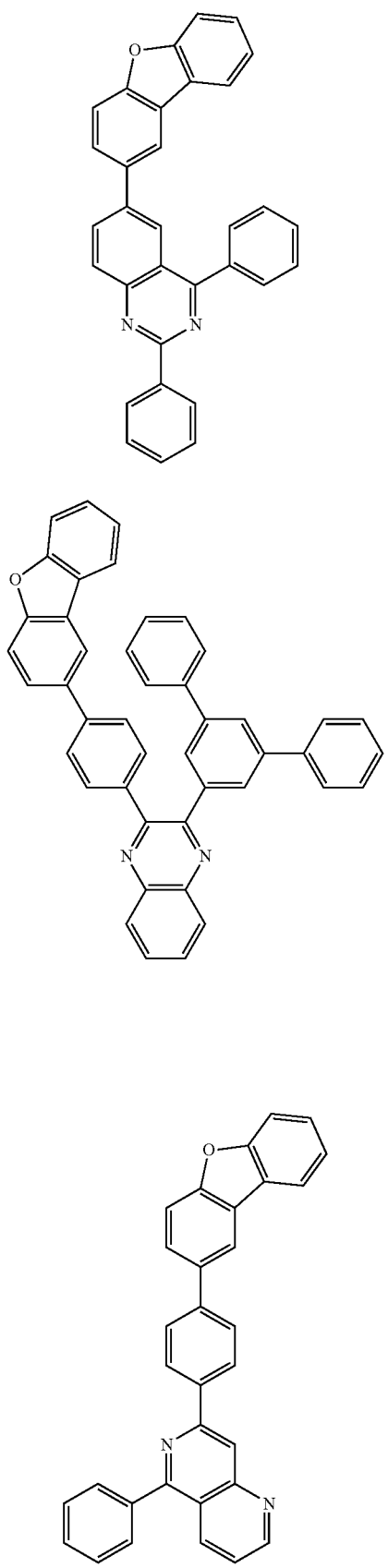
C2-45
C2-46
C2-47
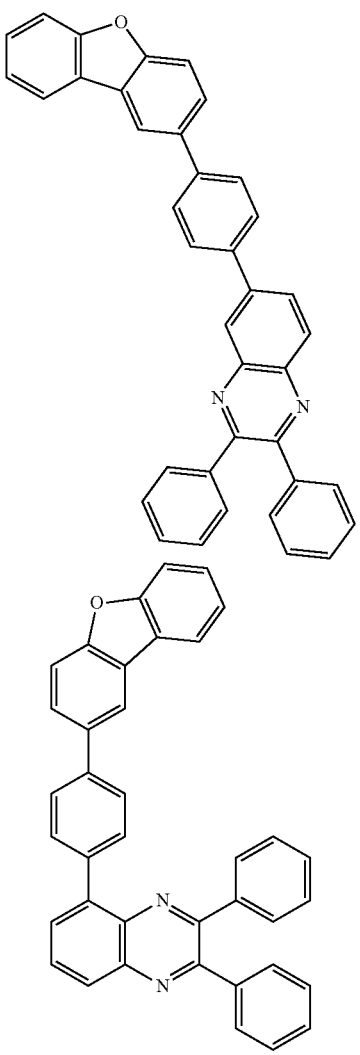
C2-48
C2-49
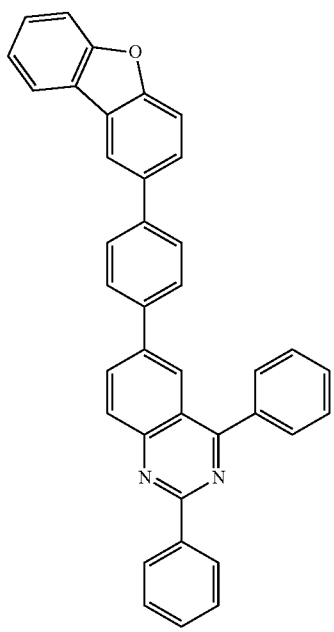
C2-50

-continued
C2-51
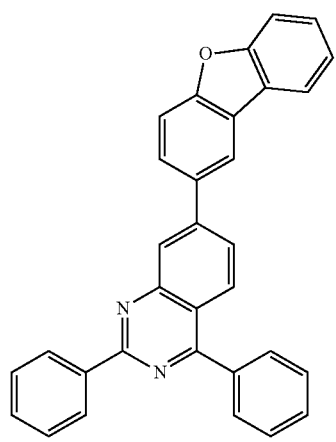
C2-52
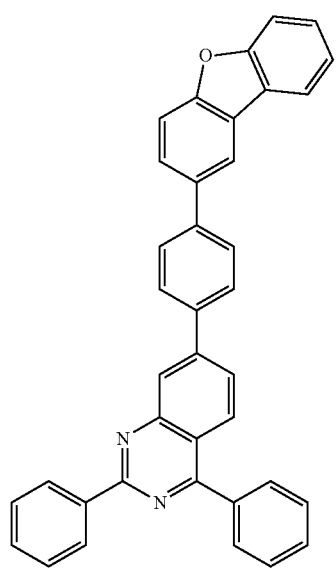
C2-53
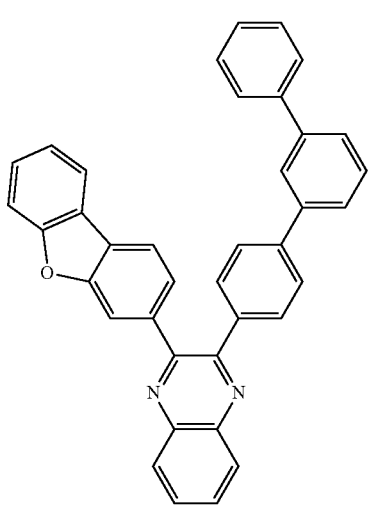
-continued
C2-54
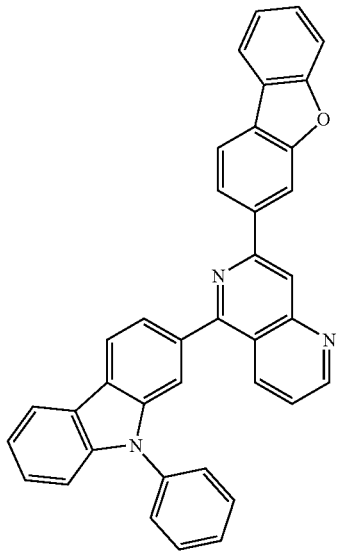
C2-55
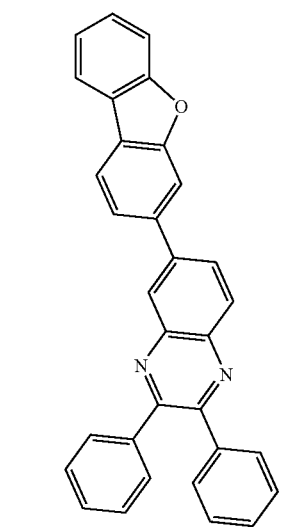
C2-56
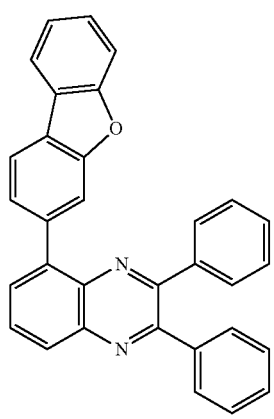

-continued
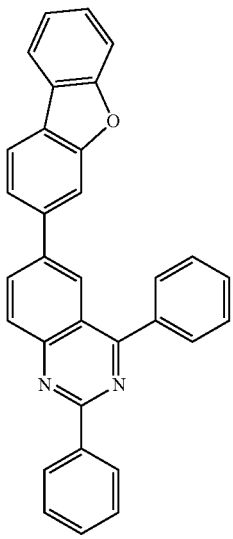
C2-57
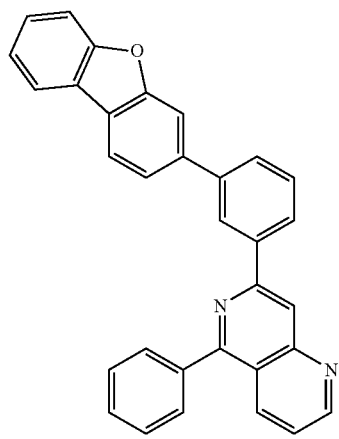
C2-60
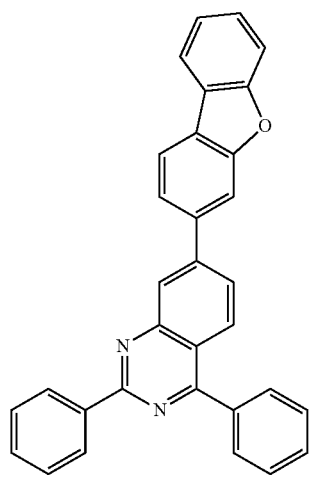
C2-58
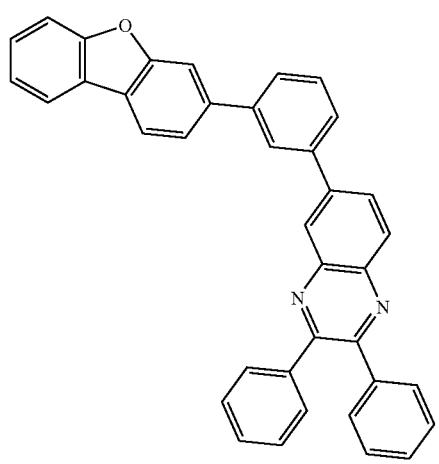
C2-61
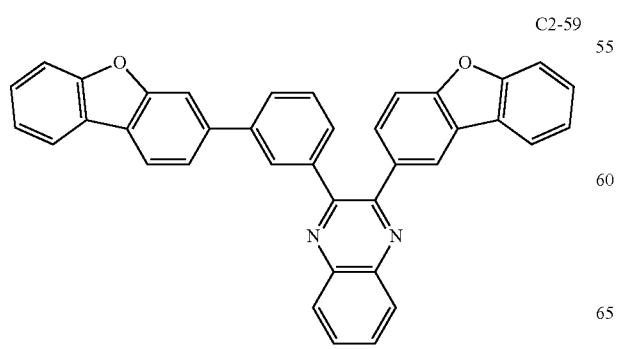
C2-59
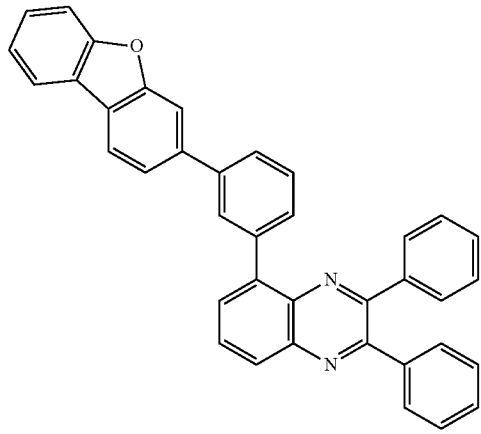
C2-62

C2-63
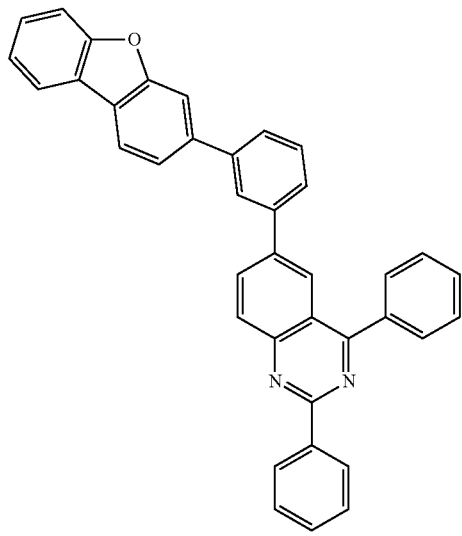
C2-64
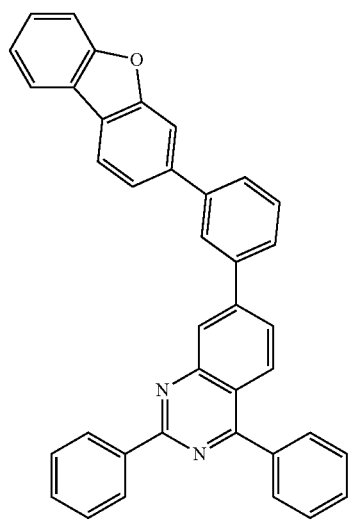
C2-65
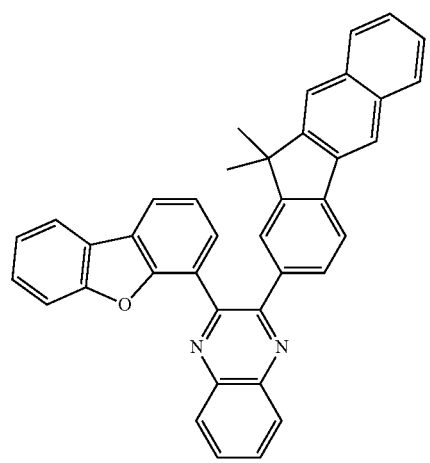
C2-66
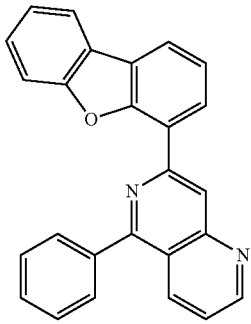
C2-67
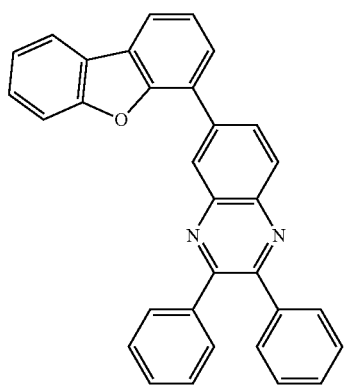
C2-68
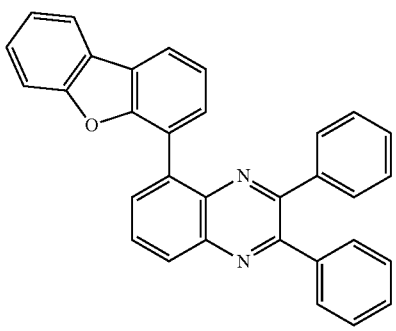
C2-69
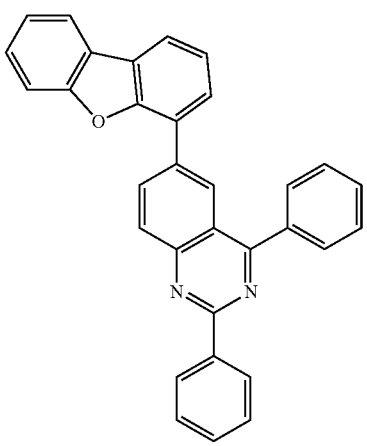

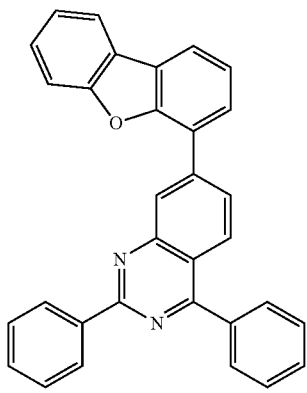
C2-70
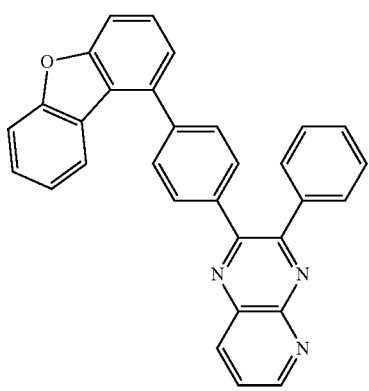
C2-71
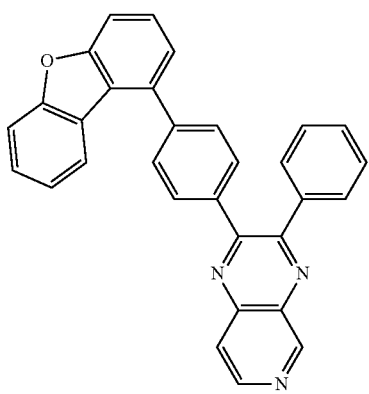
C2-72
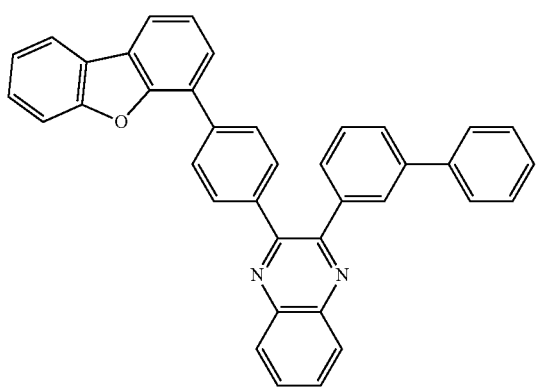
C2-73
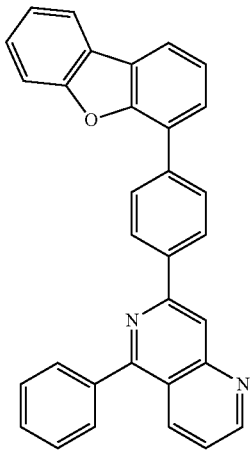
C2-74
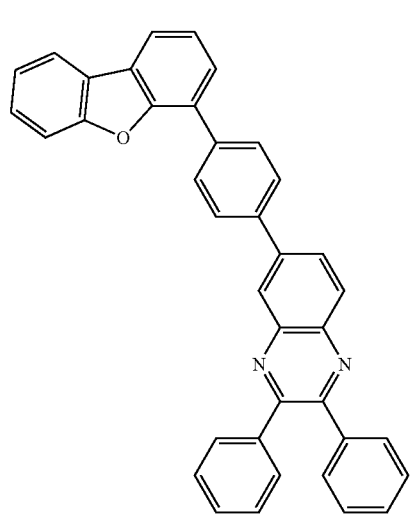
C2-75
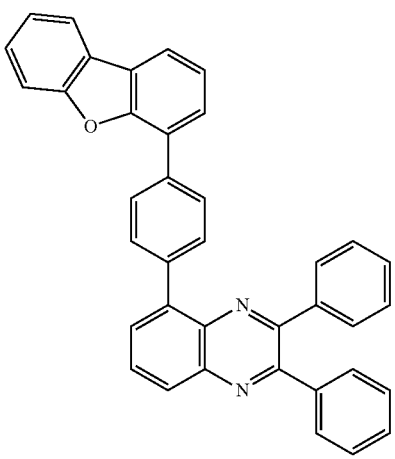
C2-76

C2-77
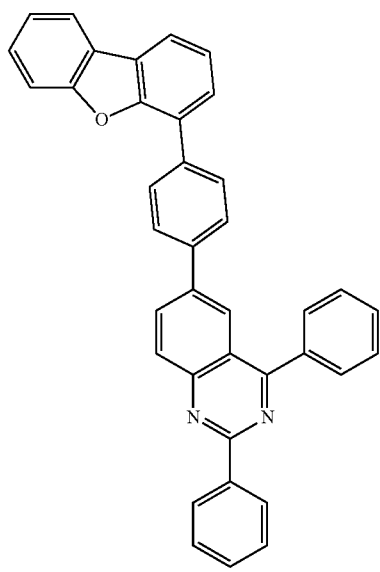
C2-78
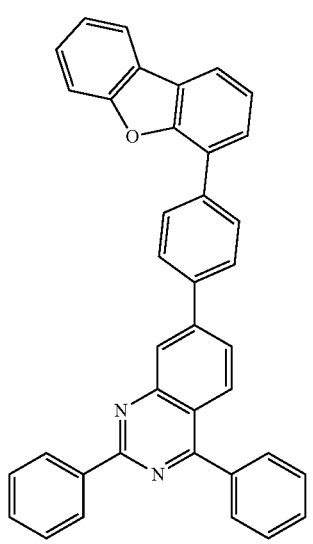
C2-79
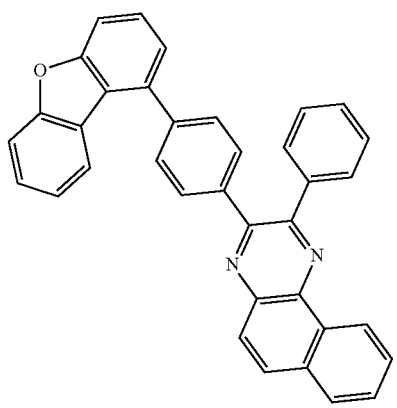
C2-80
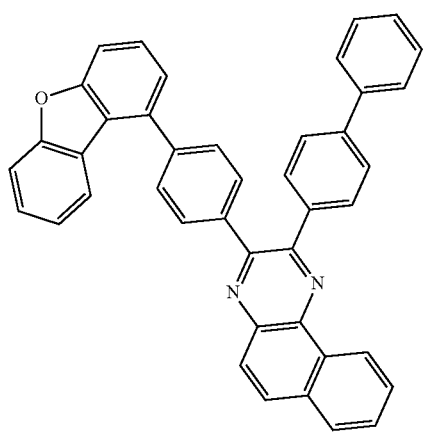
C2-81
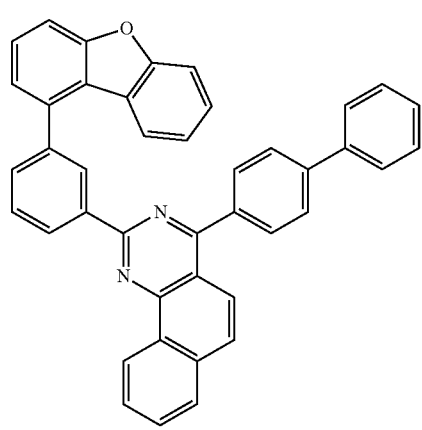
C2-82
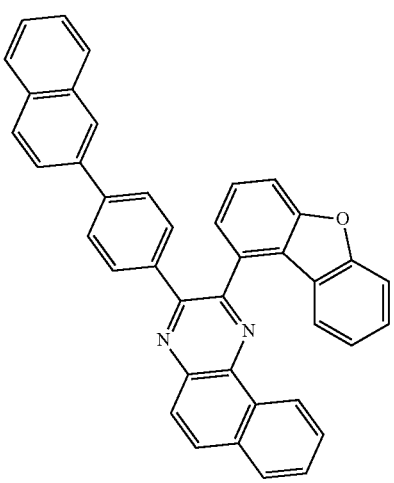

-continued
C2-83
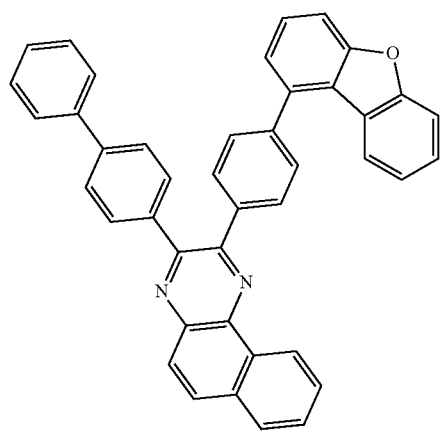
C2-84
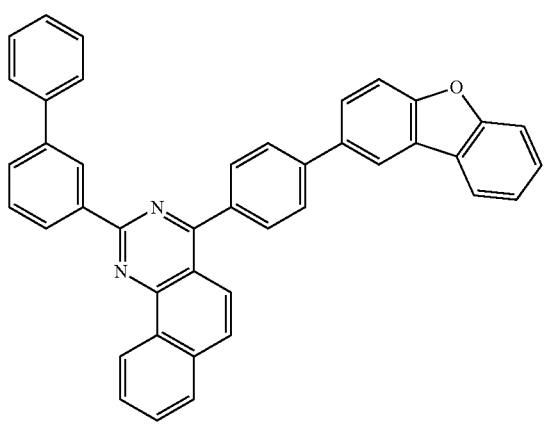
C2-85
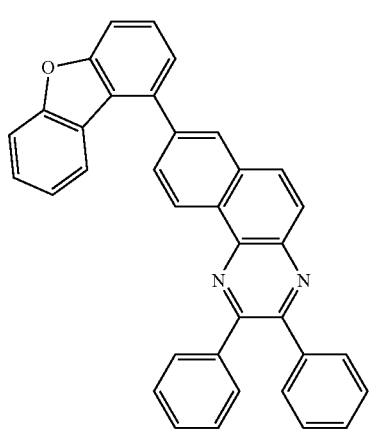
-continued
C2-86
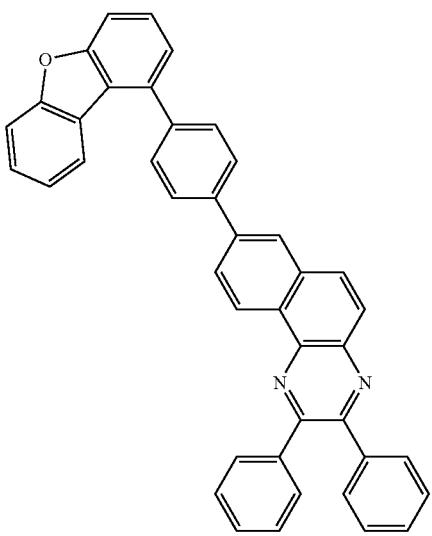
C2-87
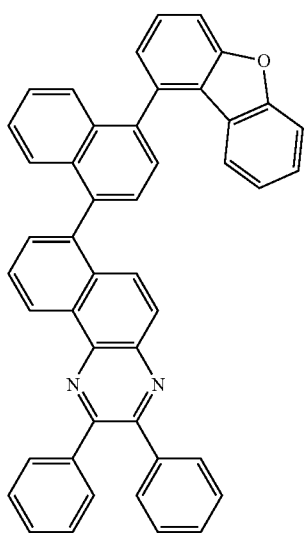
C2-88
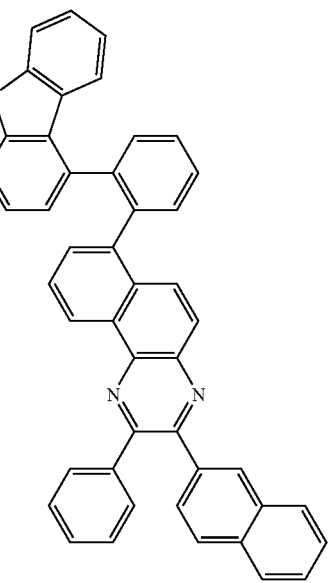

C2-89
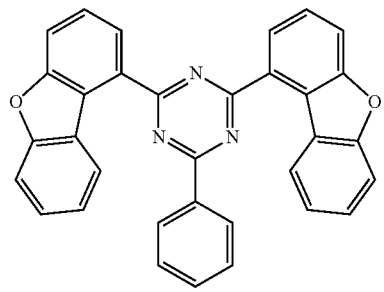
C2-90
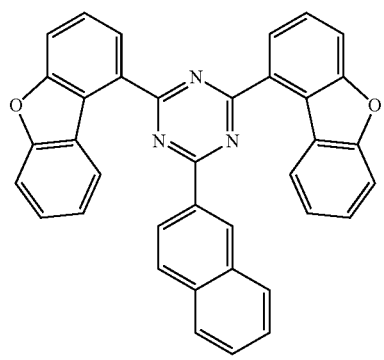
C2-91
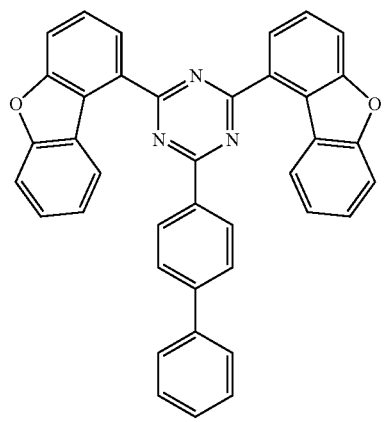
C2-92
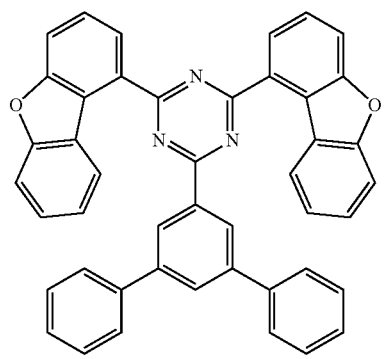
C2-93
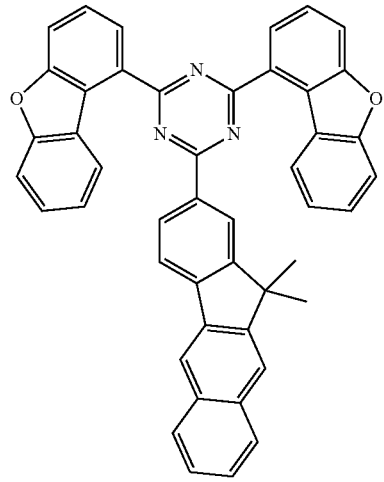
C2-94
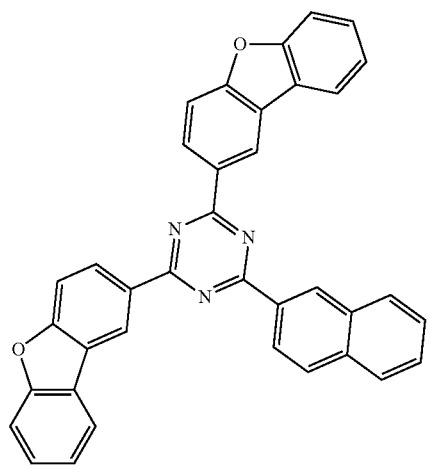
C2-95
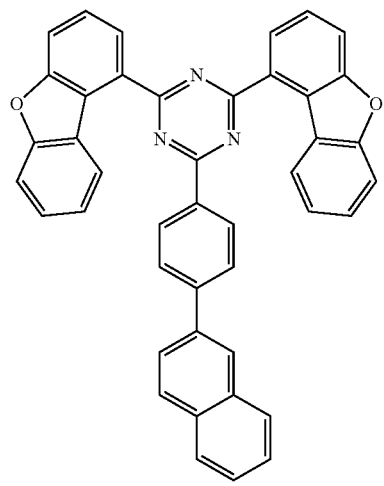

C2-96
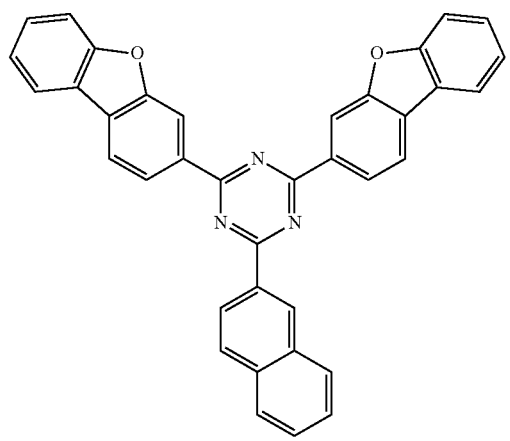
C2-97
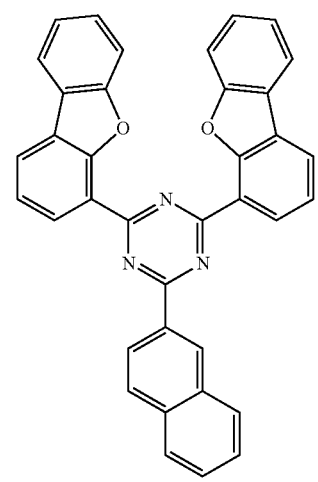
C2-98
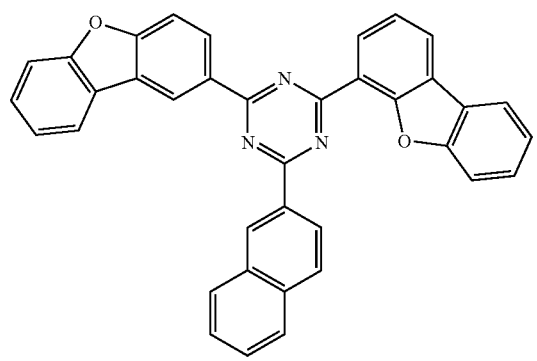
C2-99
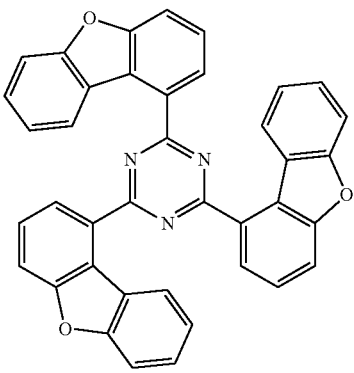
C2-100
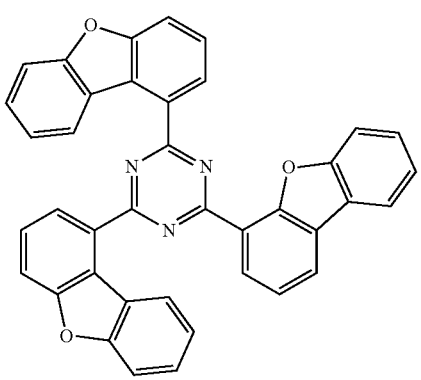
C2-101
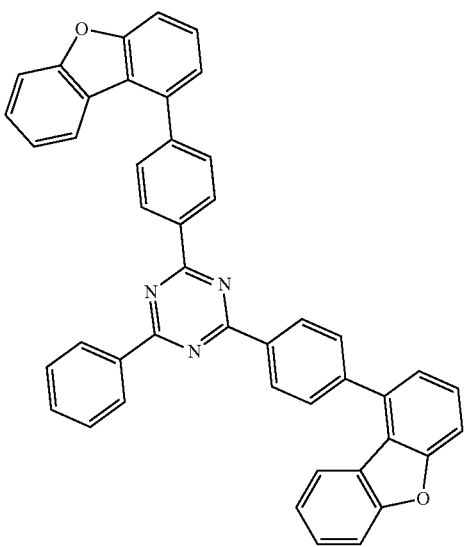

C2-102
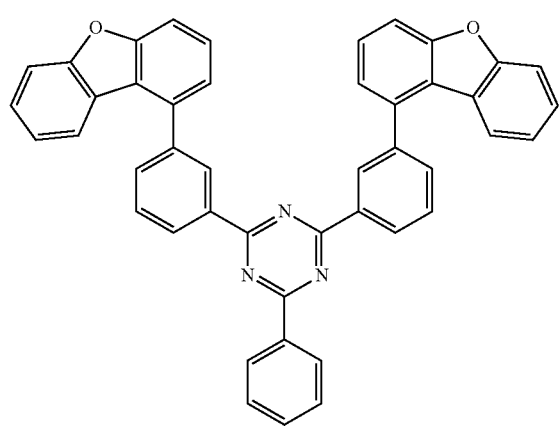
C2-105
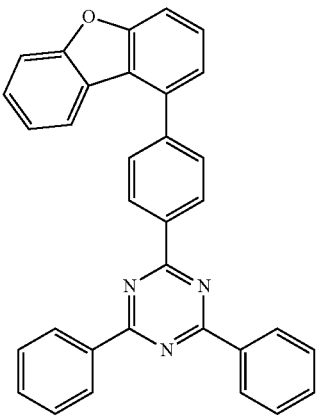
C2-103
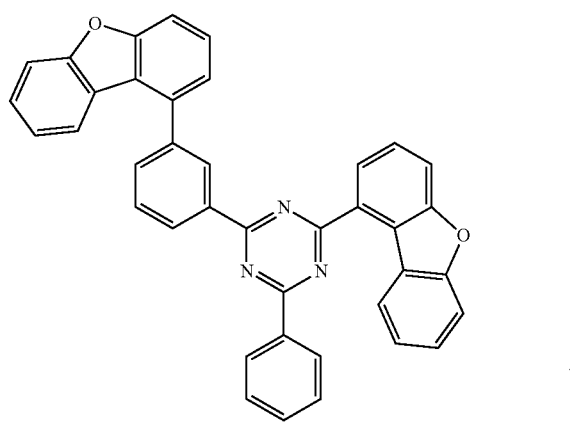
C2-106
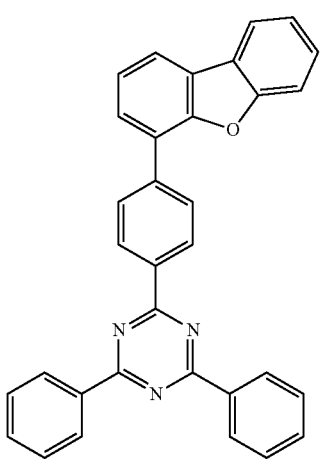
C2-104
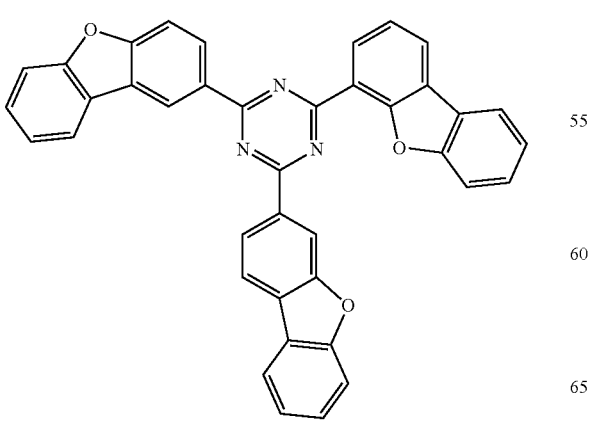
C2-107
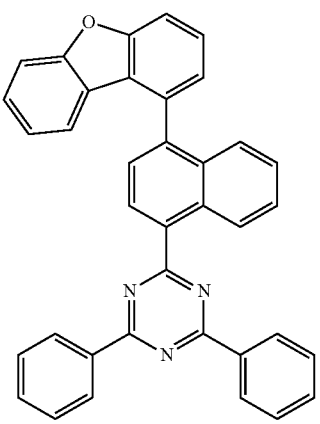

C2-108
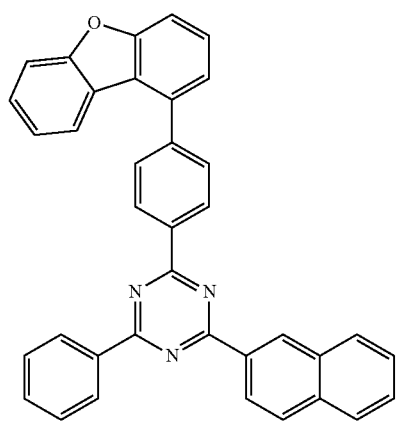
C2-109
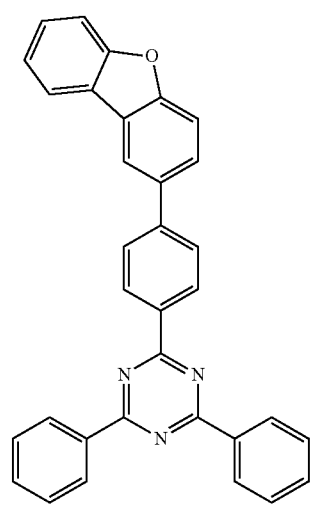
C2-110
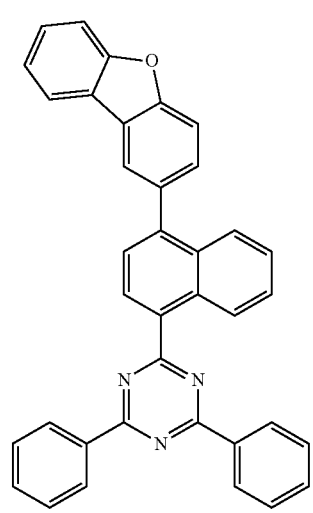
C2-111
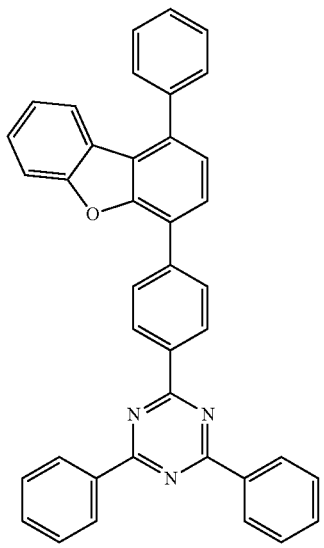
C2-112
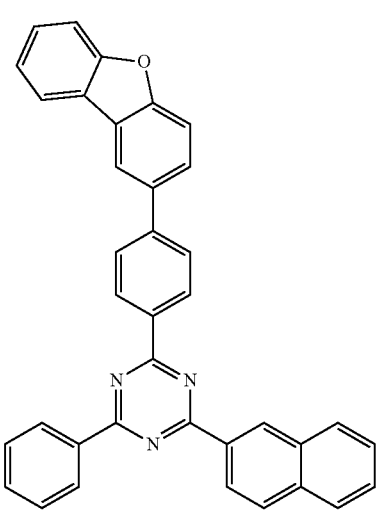
C2-113
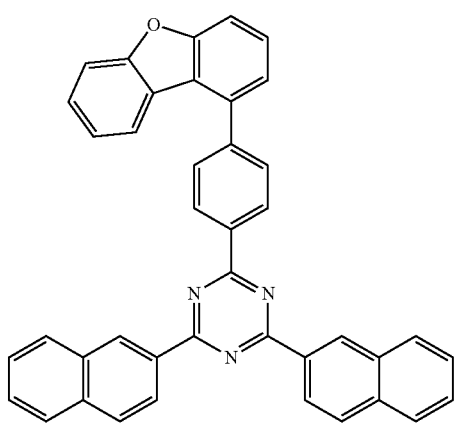

C2-114
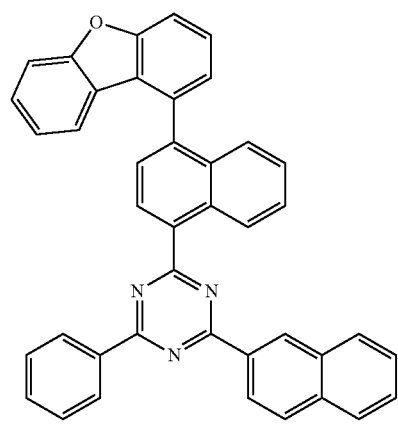
C2-117
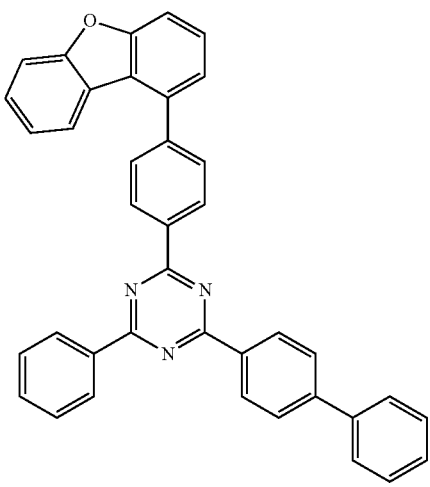
C2-115
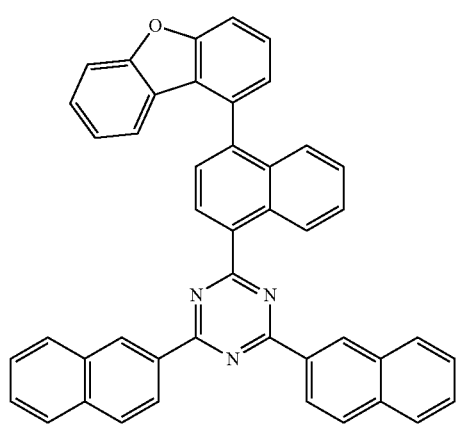
C2-118
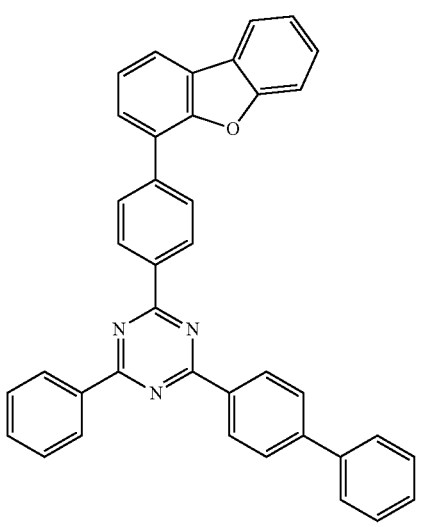
C2-116
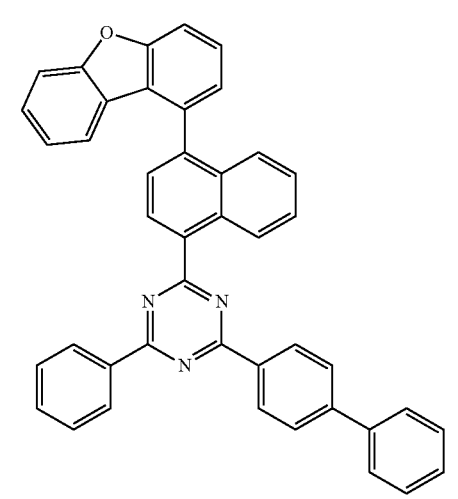
C2-119
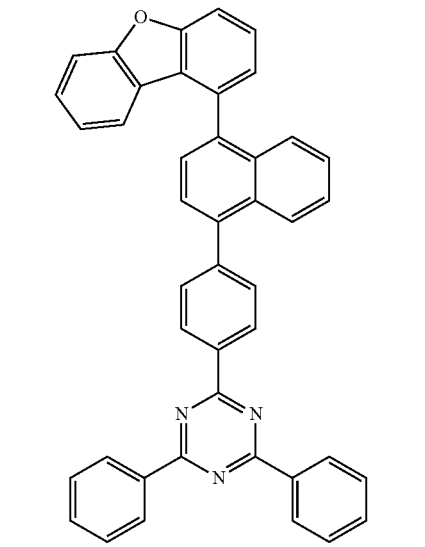

C2-120
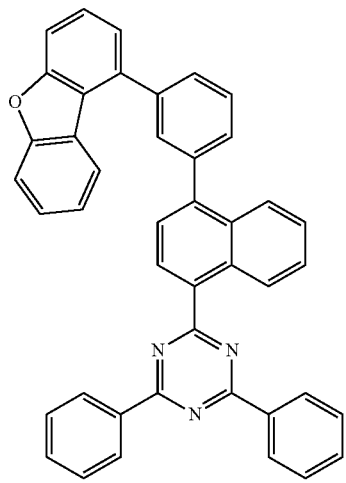
C2-121
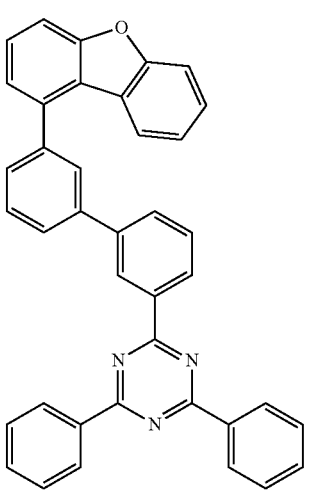
C2-122
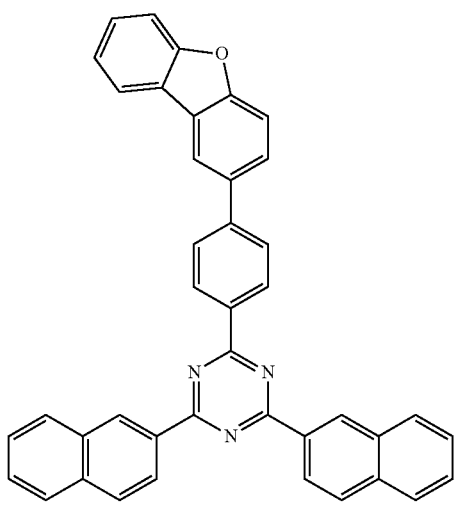
C2-123
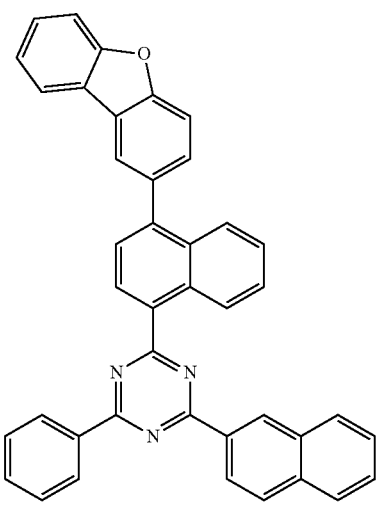
C2-124
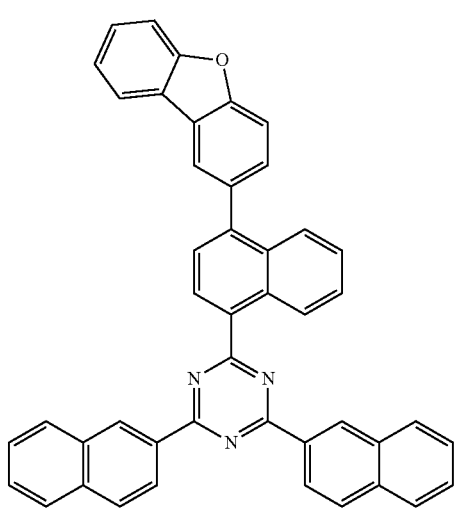
C2-125
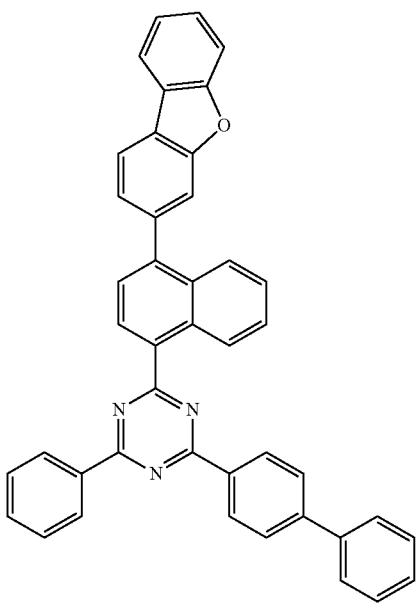

C2-126
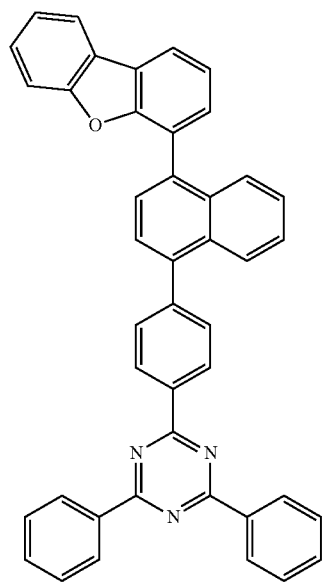
C2-127
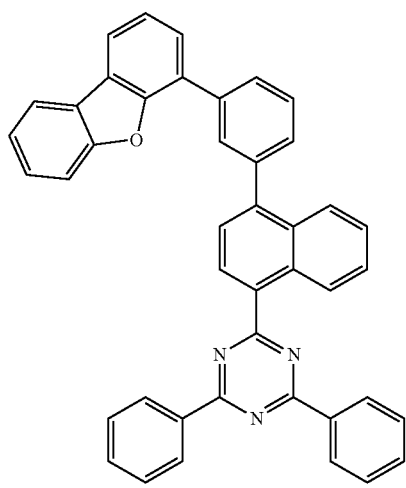
C2-128
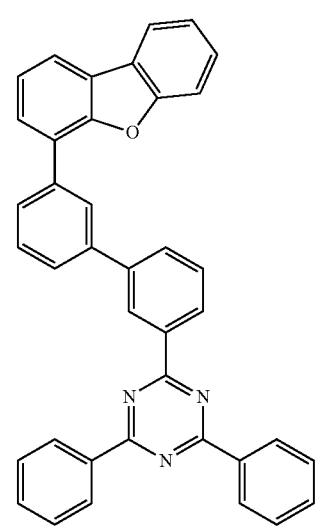
C2-129
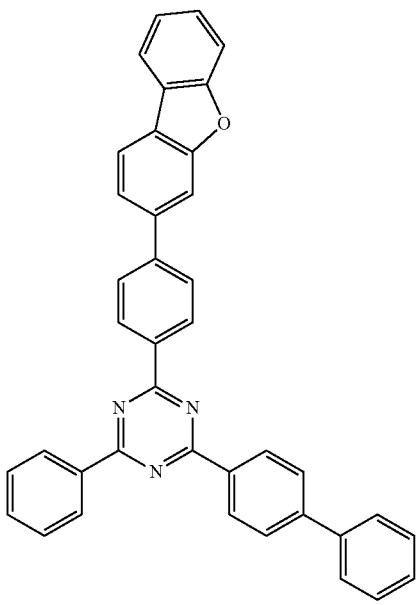
C2-130
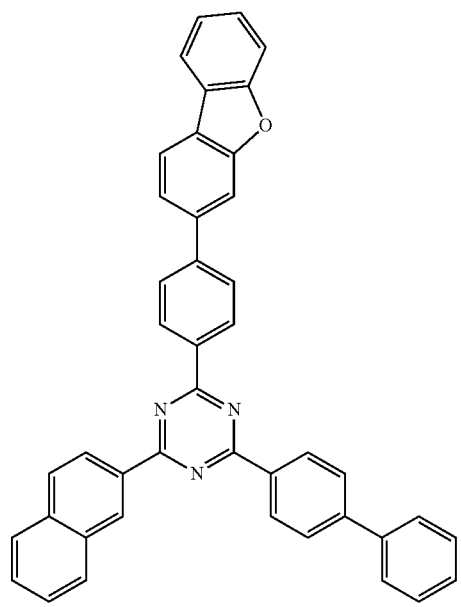
C2-131
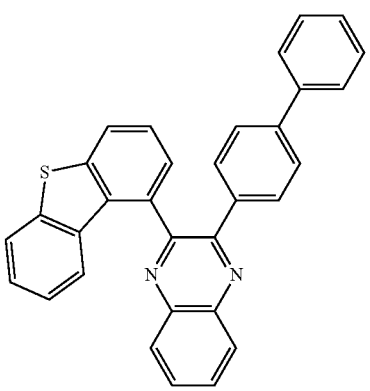

C2-132
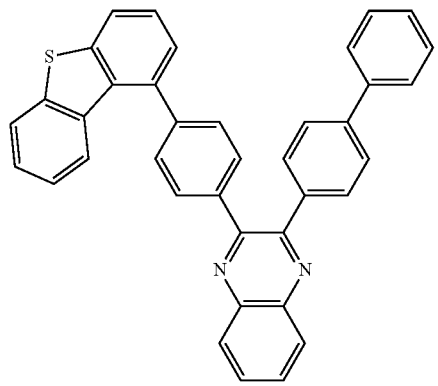
C2-133
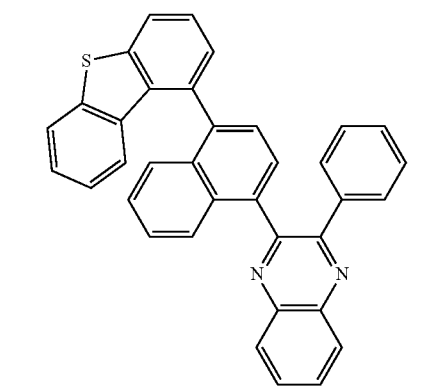
C2-134
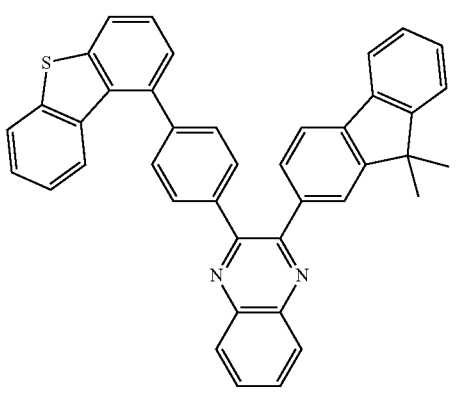
C2-135
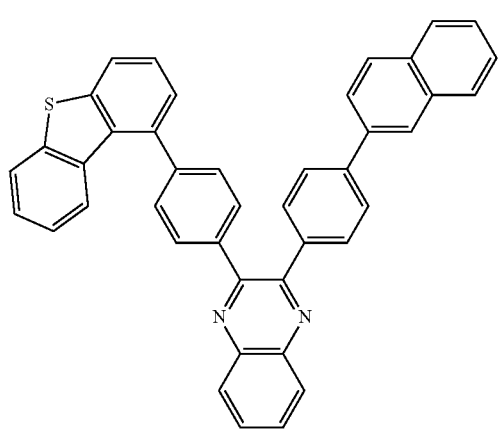
C2-136
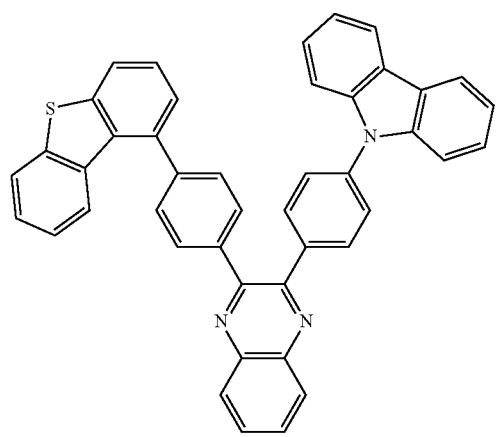
C2-137
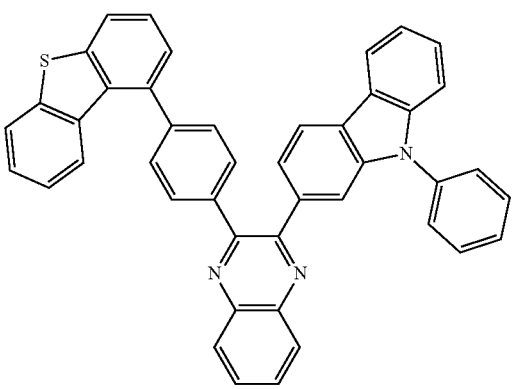
C2-138
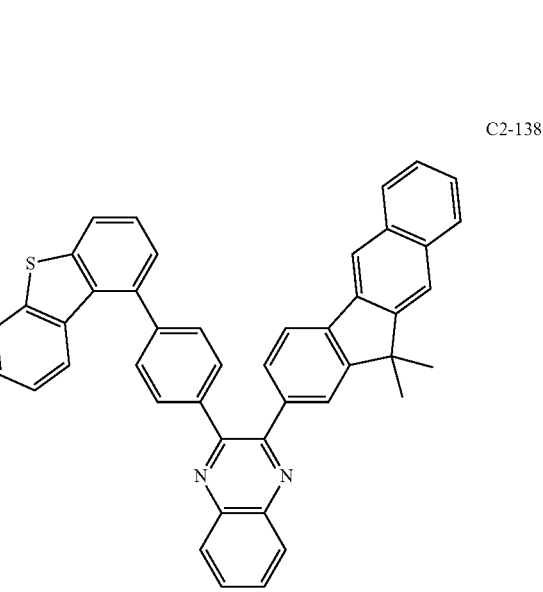

C2-139
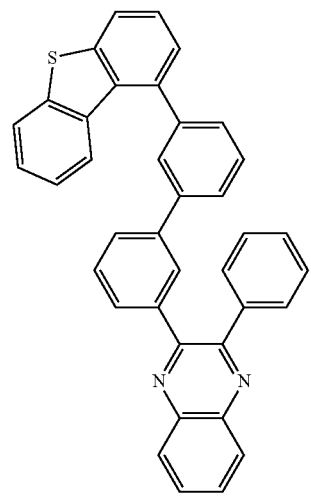
C2-140
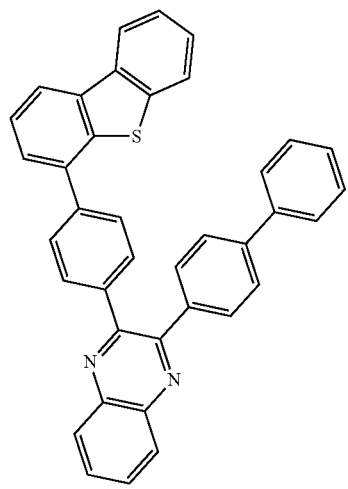
C2-141
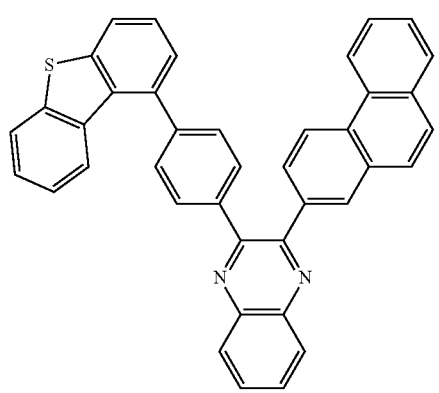
C2-142
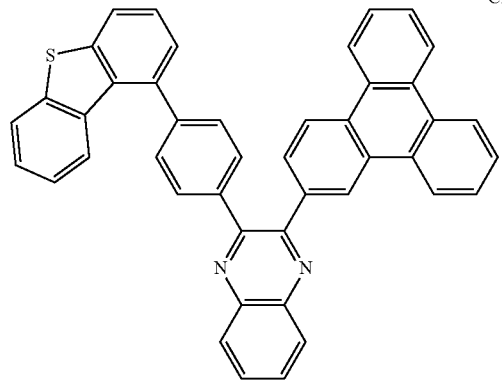
C2-143
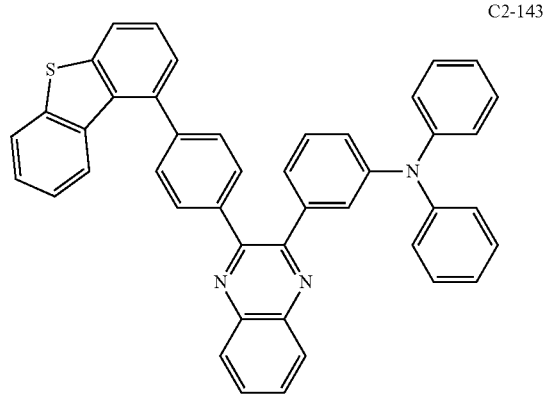
C2-144
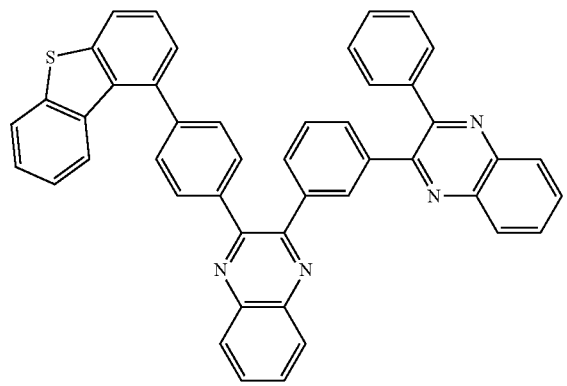
C2-145
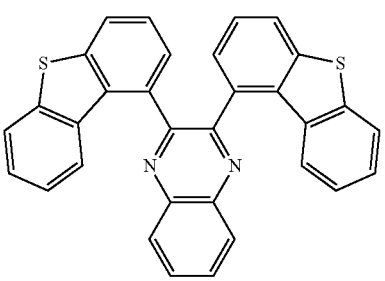

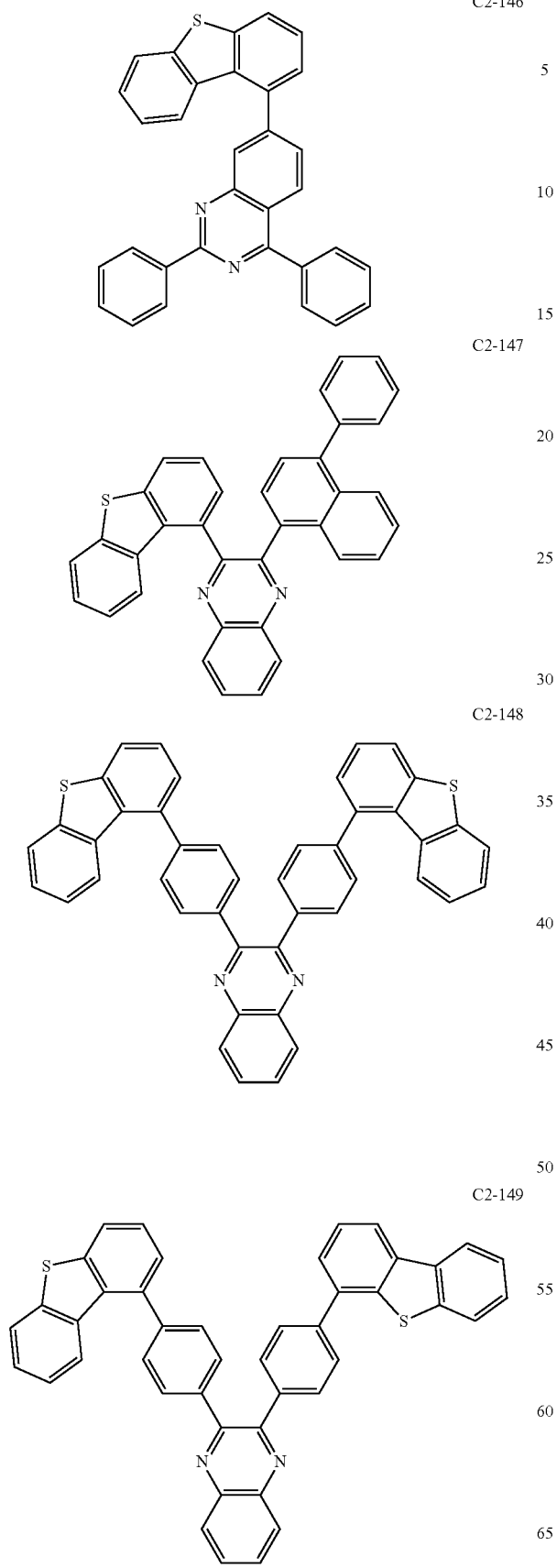
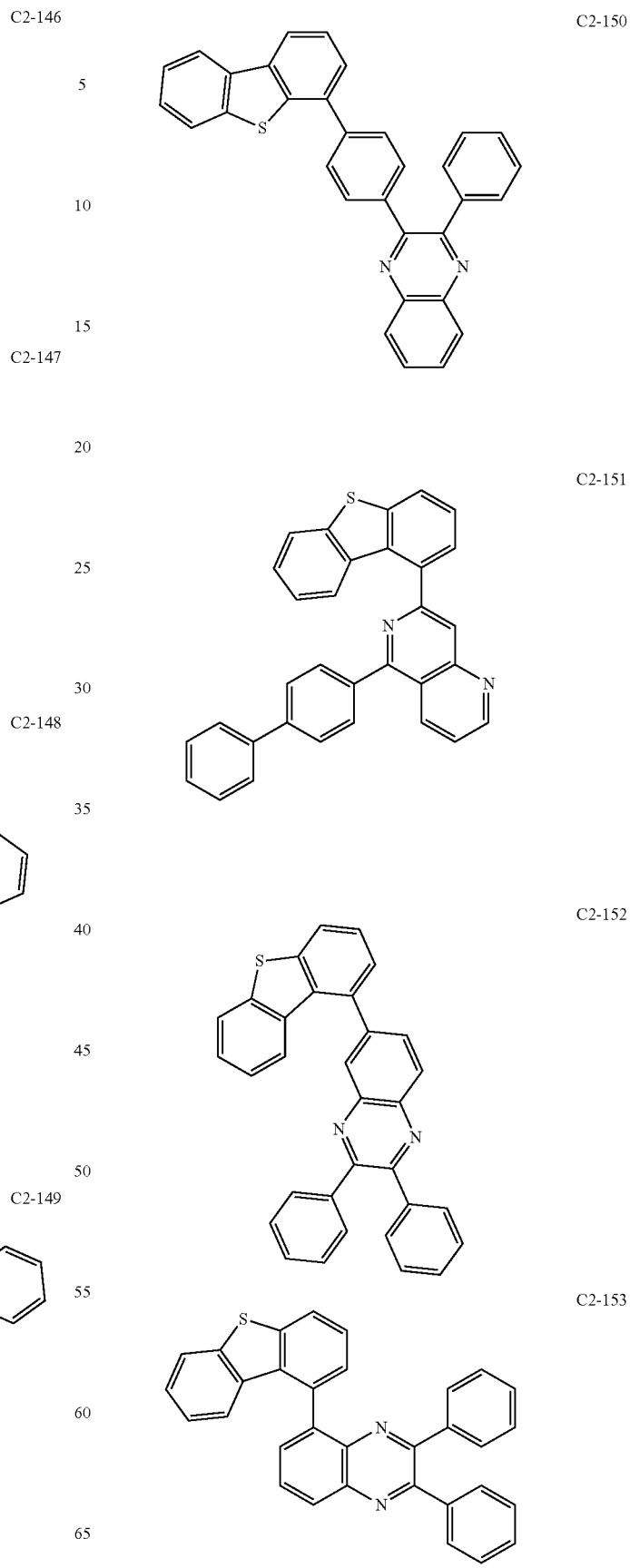

-continued
C2-154
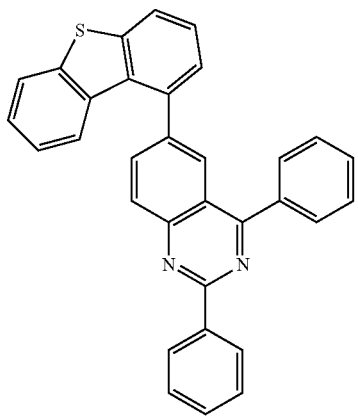
C2-155
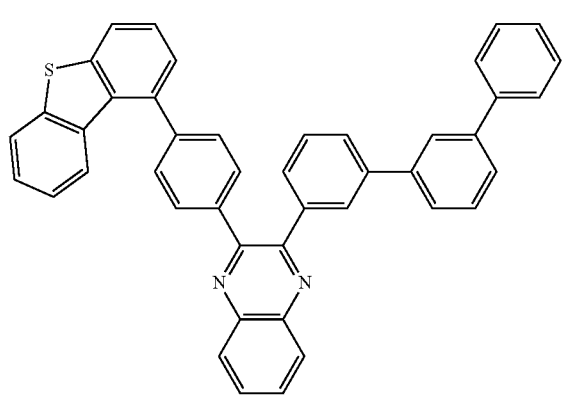
C2-156
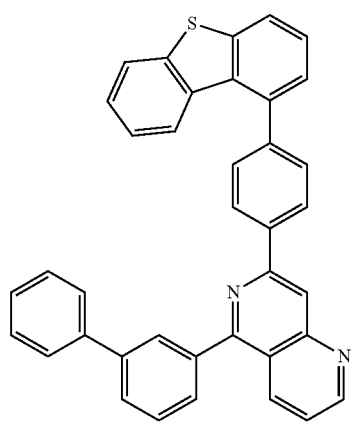
C2-157
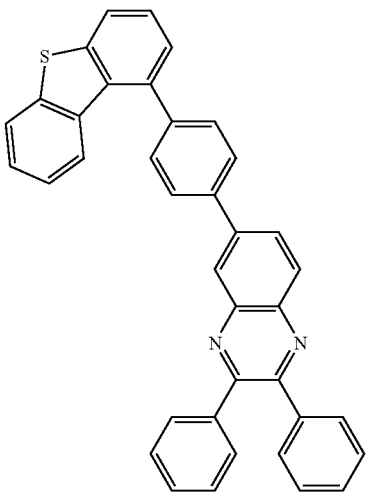
C2-158
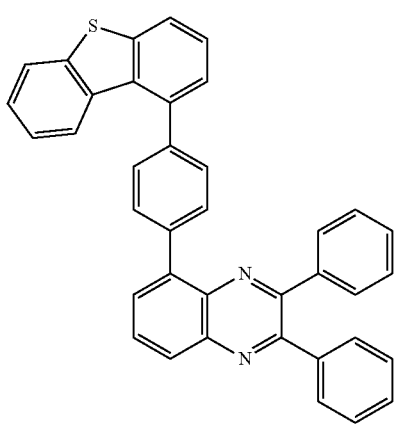
C2-159
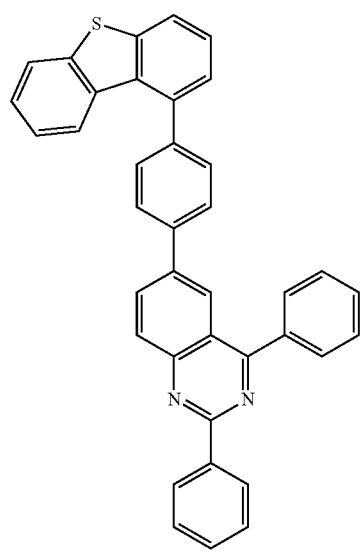

C2-160
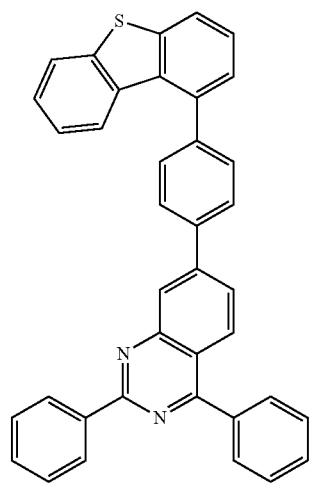
C2-161
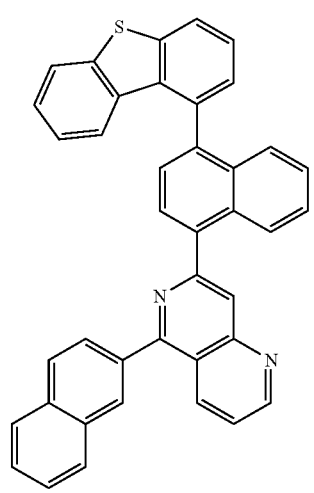
C2-162
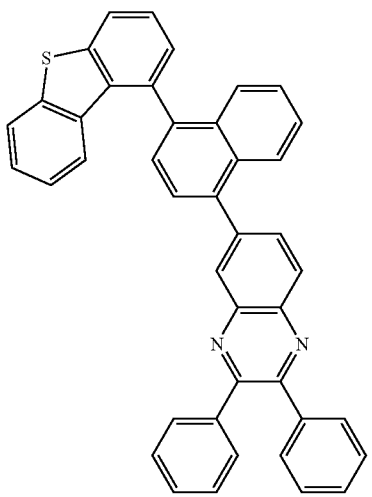
C2-163
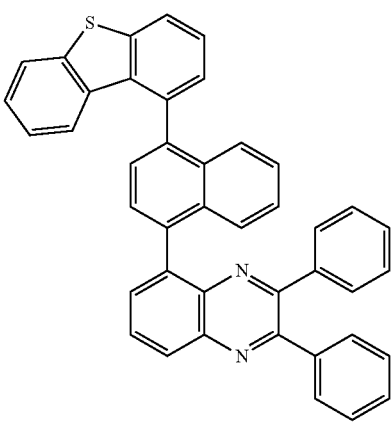
C2-164
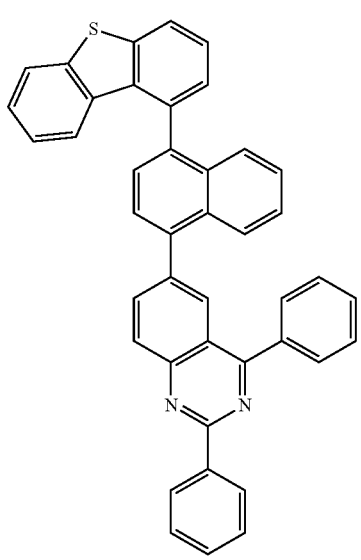
C2-165
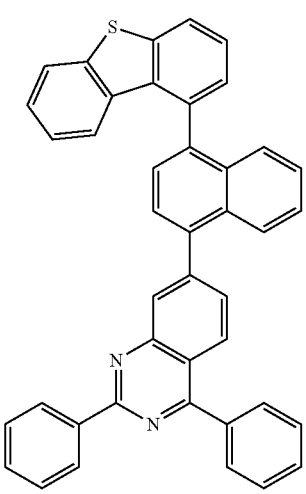

-continued
C2-166
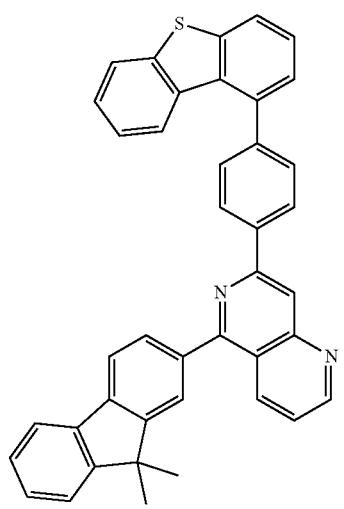
C2-167
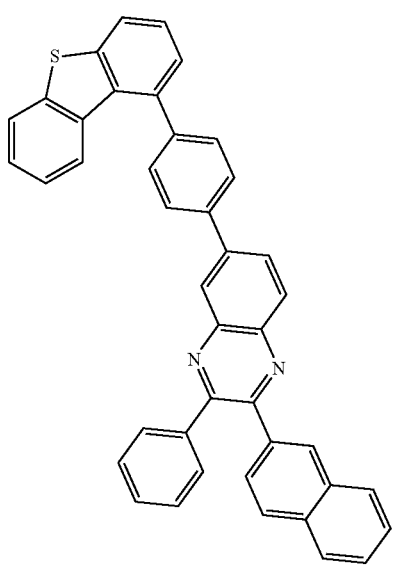
C2-168
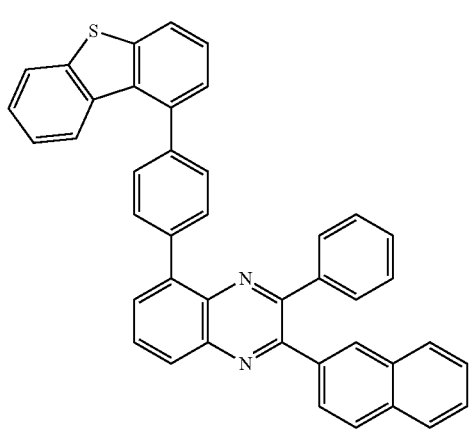
-continued
C2-169
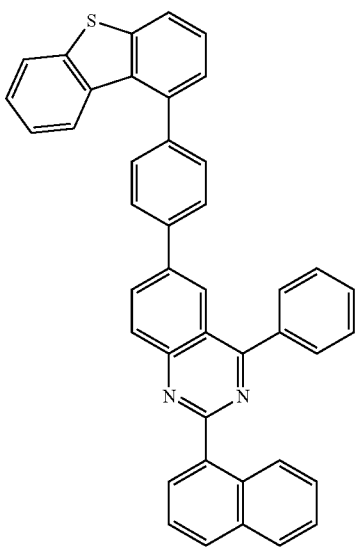
C2-170
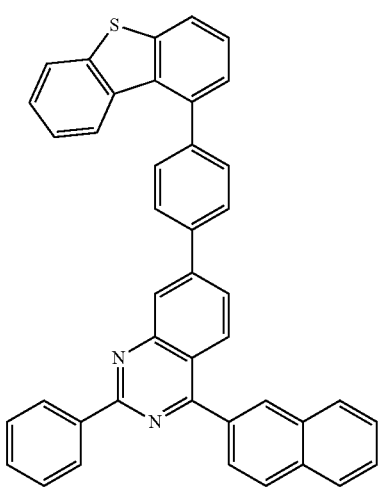
C2-171
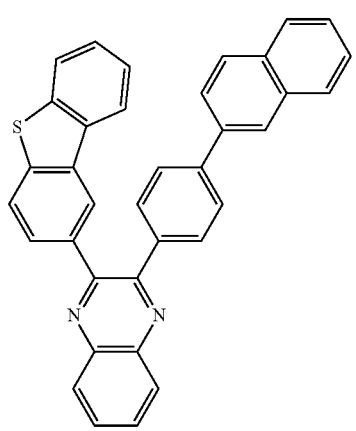

-continued
C2-172
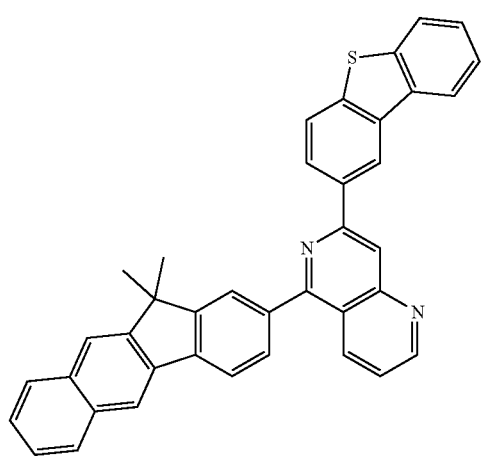
C2-173
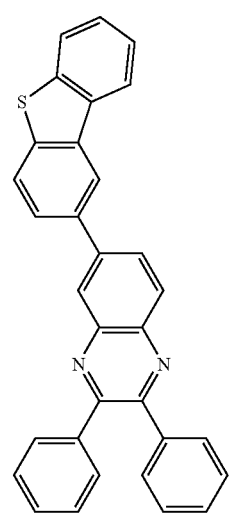
C2-174
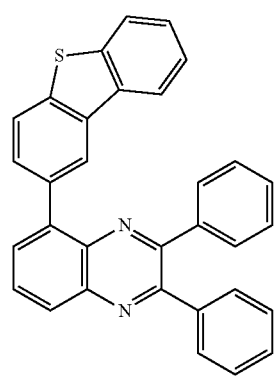
-continued
C2-175
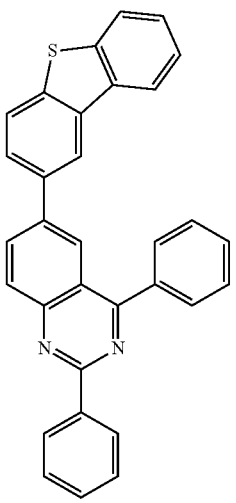
C2-176
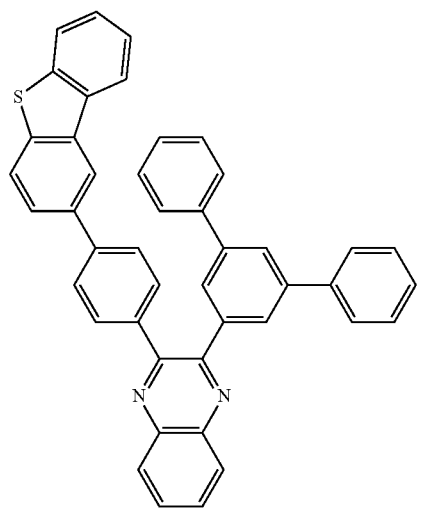
C2-177
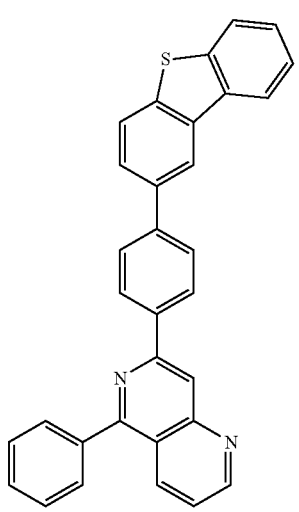

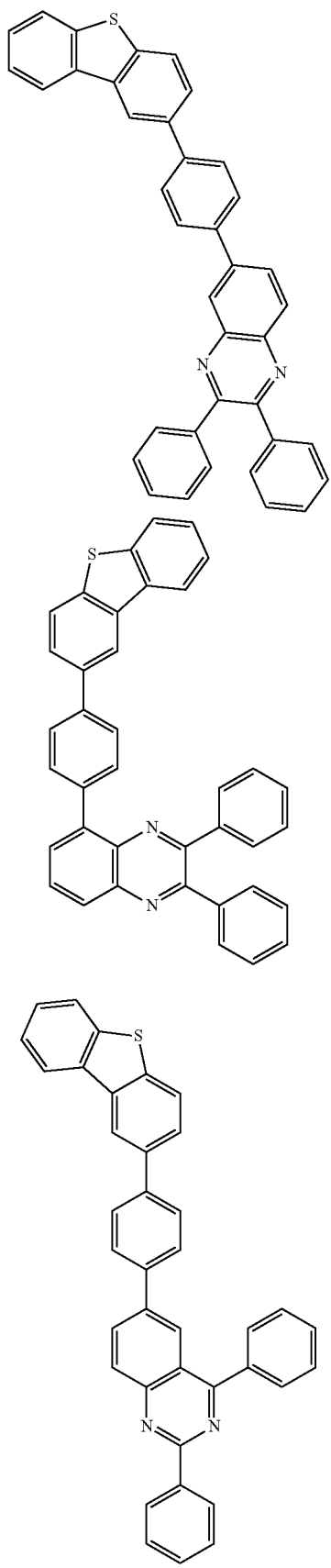
C2-178
C2-179
C2-180
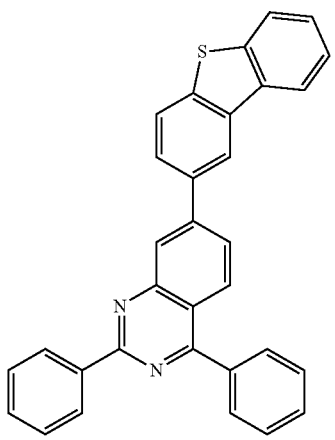
C2-181
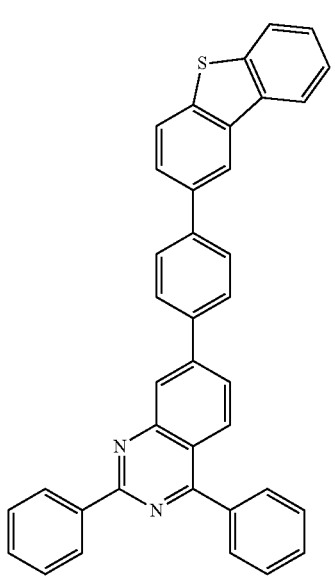
C1-182
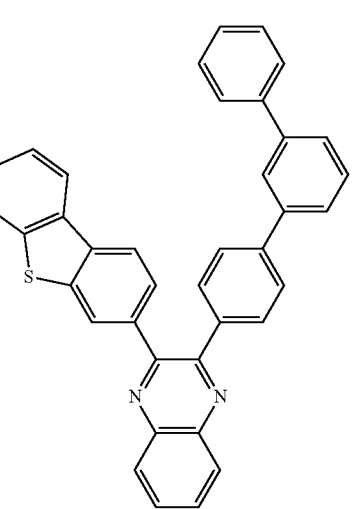
C2-183

C2-184
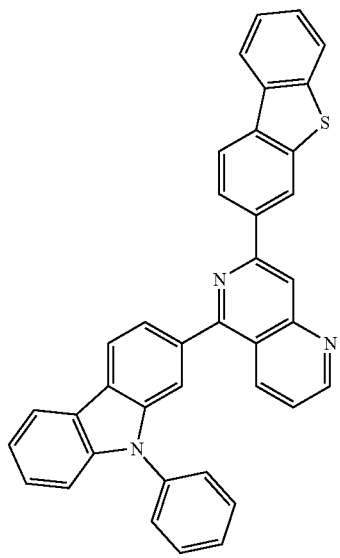
C2-187
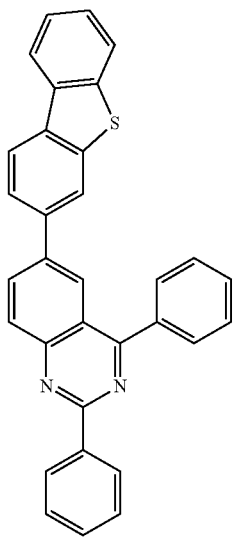
C2-185
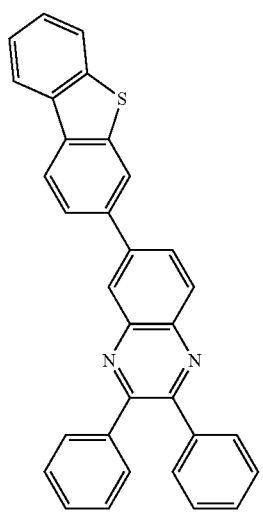
C2-188
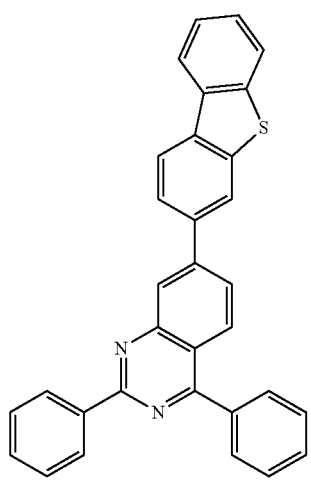
C2-186
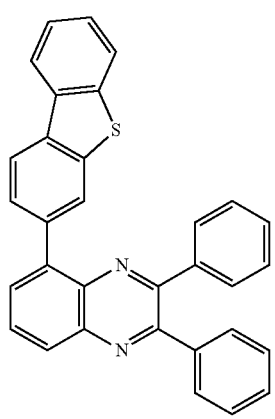
C2-189
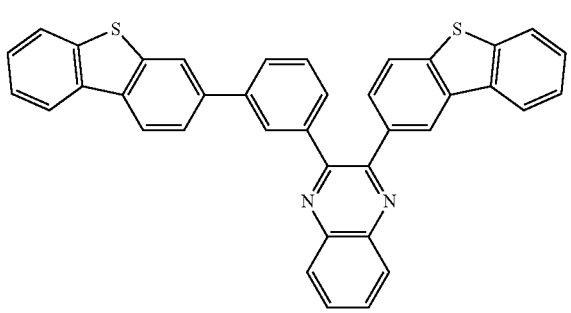

C2-190
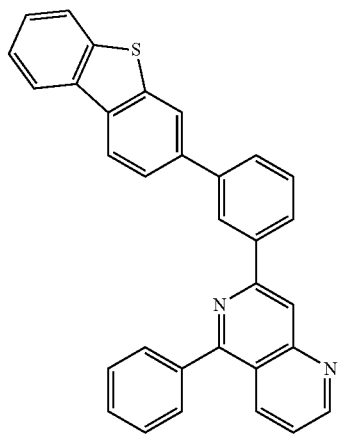
C2-191
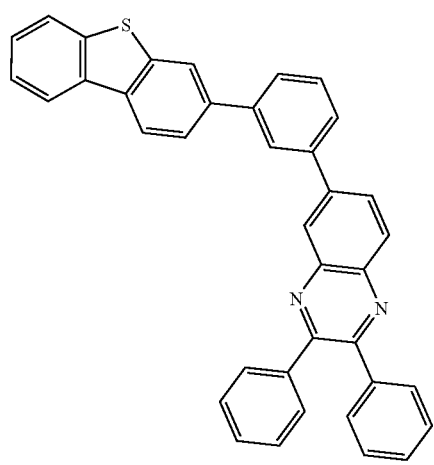
C2-192
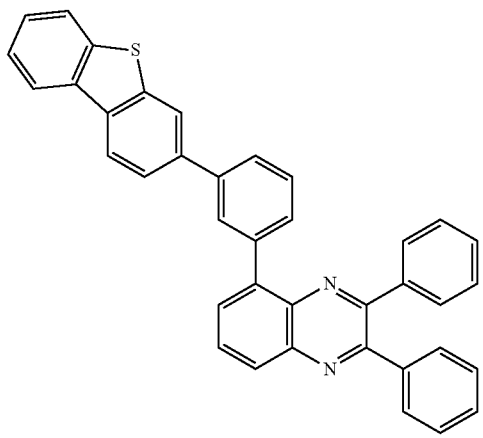
C2-193
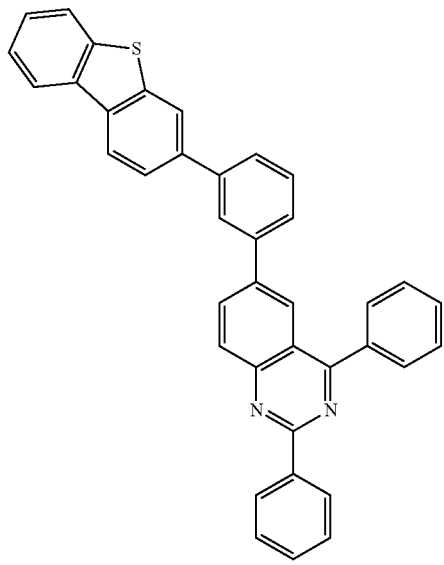
C2-194
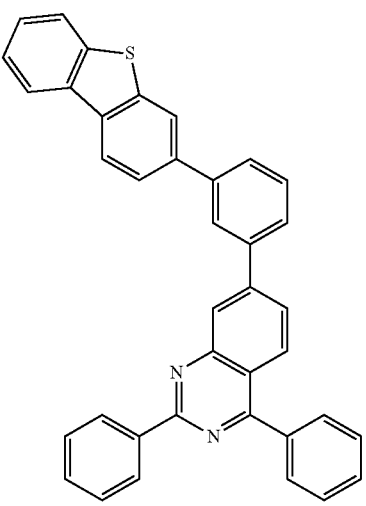
C2-195
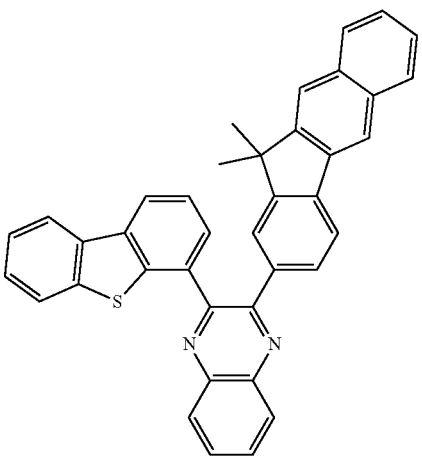

C2-196 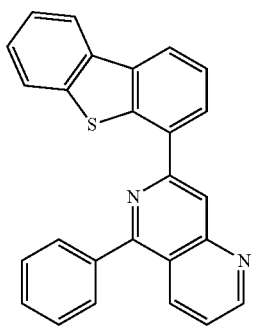
C2-197 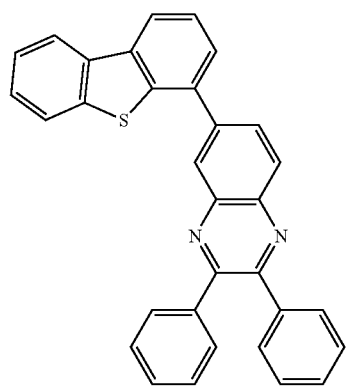
C2-198 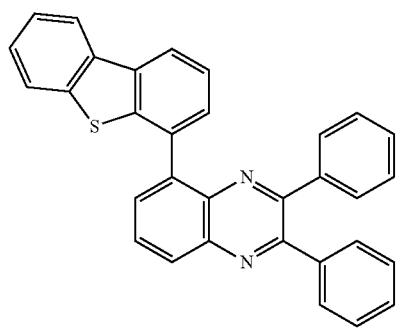
C2-199 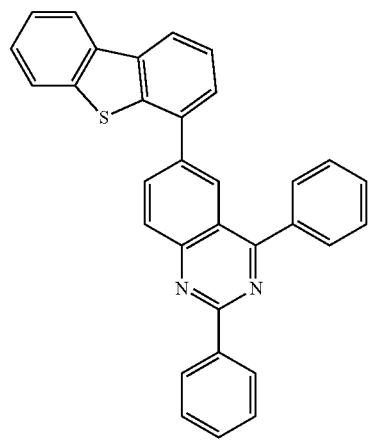
C2-200 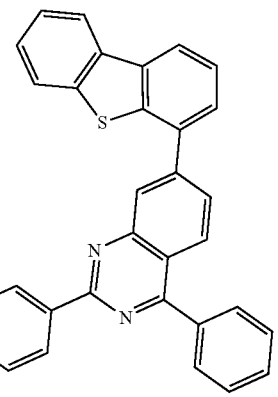
C2-201 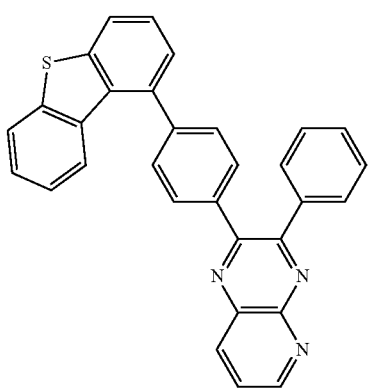
C2-202 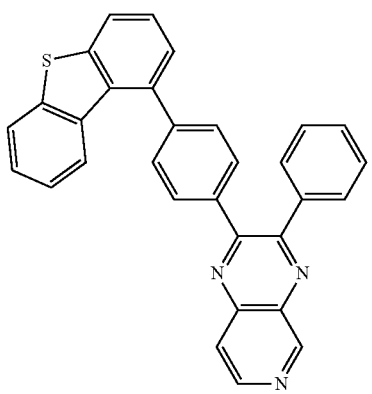
C2-203 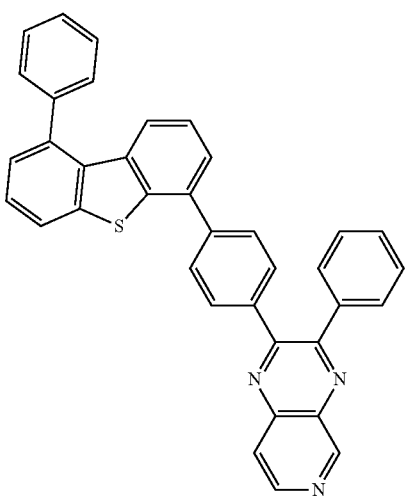

-continued
C2-204
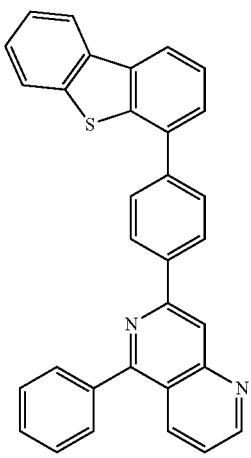
C2-205
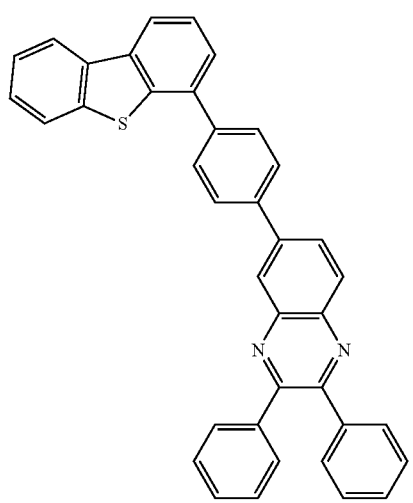
C2-206
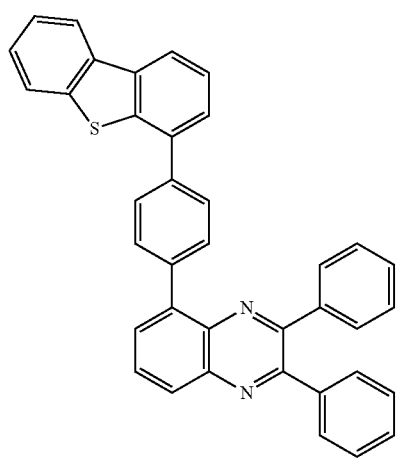
-continued
C2-207
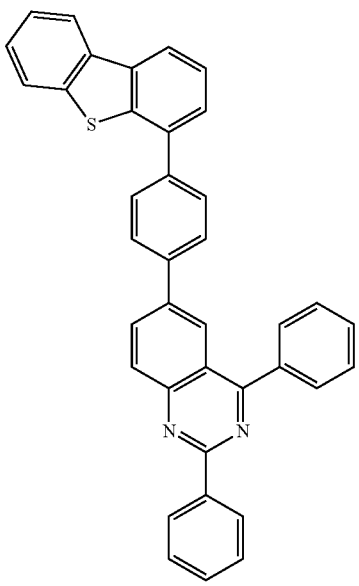
C2-208
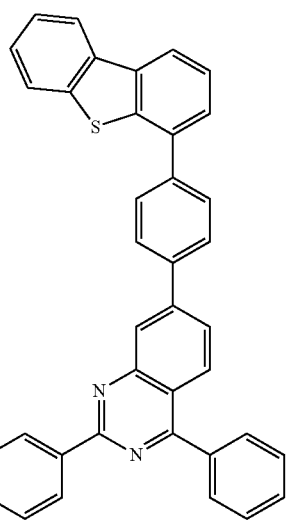
C2-209
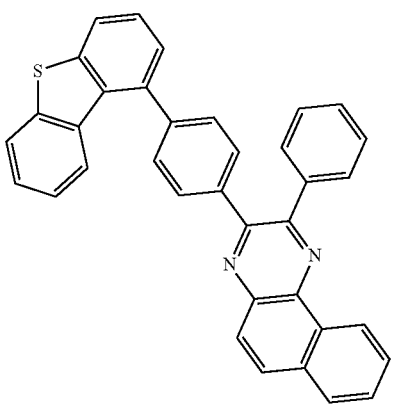

-continued
C2-210
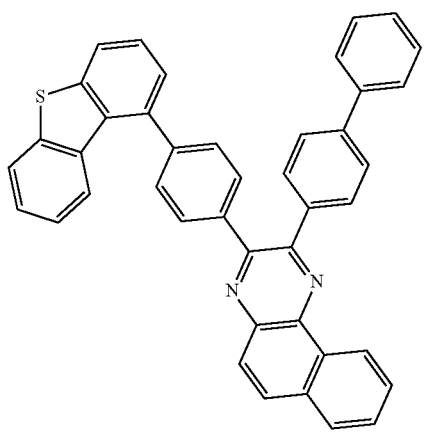
C2-213
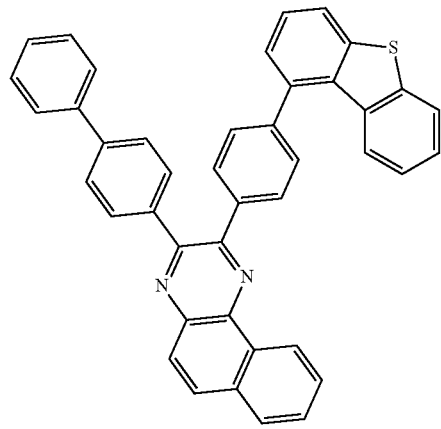
C2-211
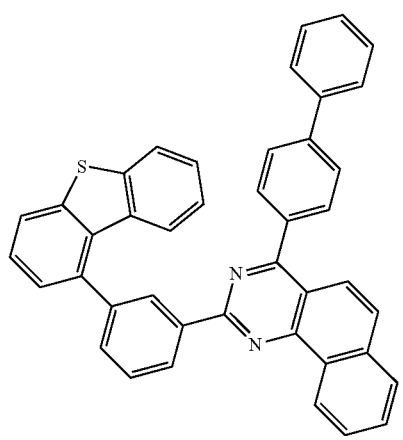
C2-214
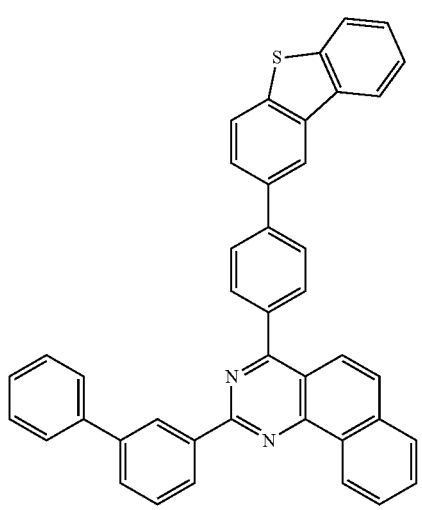
C2-212
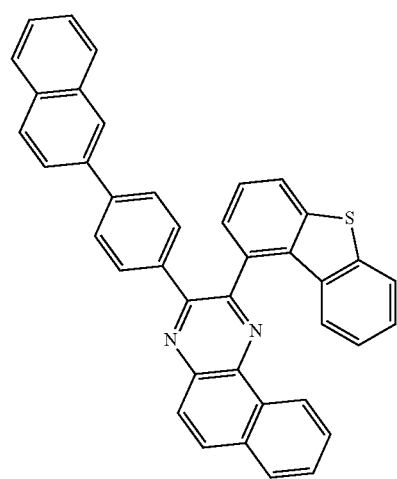
C2-215
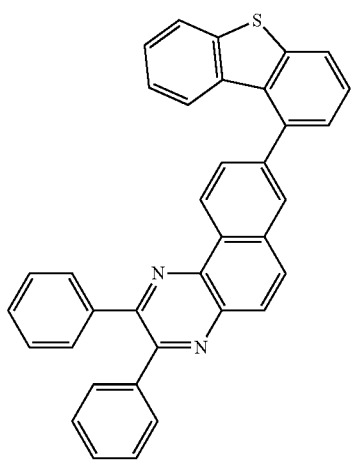

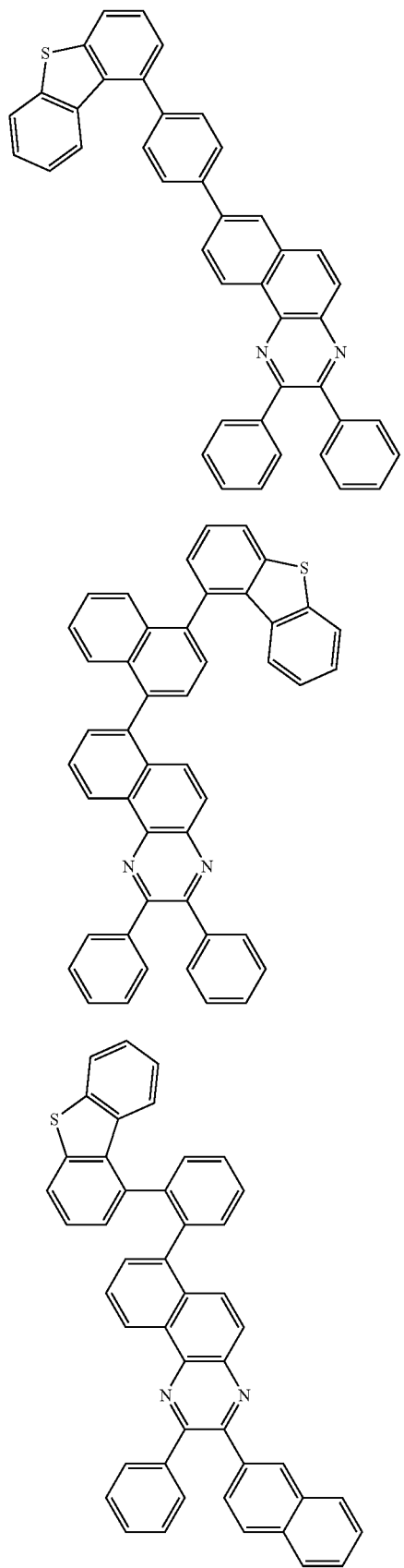
C2-216
C2-217
C2-218
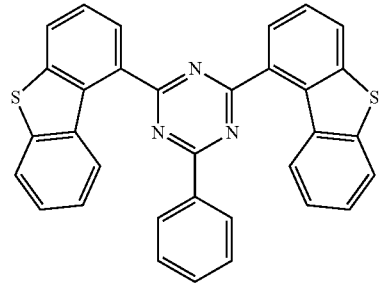
C2-219
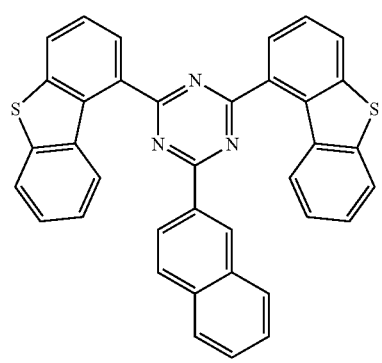
C2-220
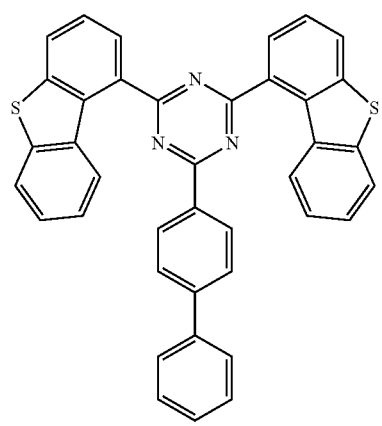
C2-221
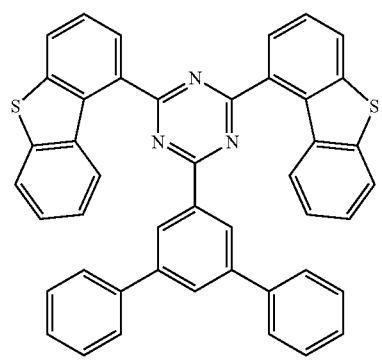
C2-222

C2-223 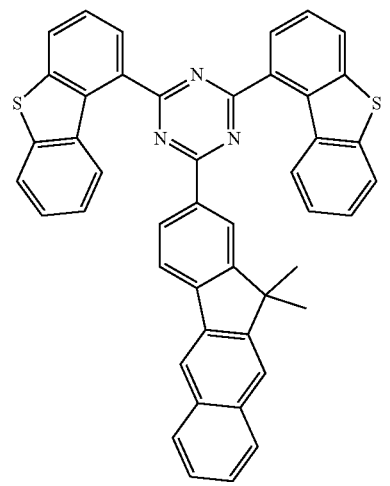
C2-224 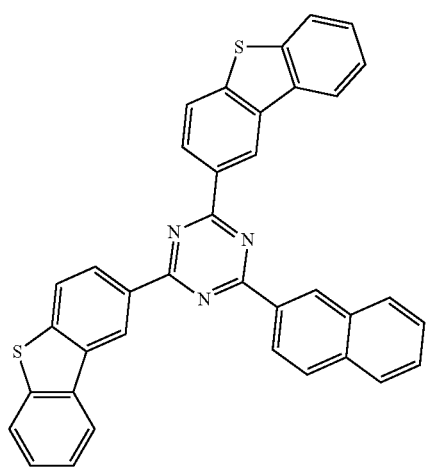
C2-225 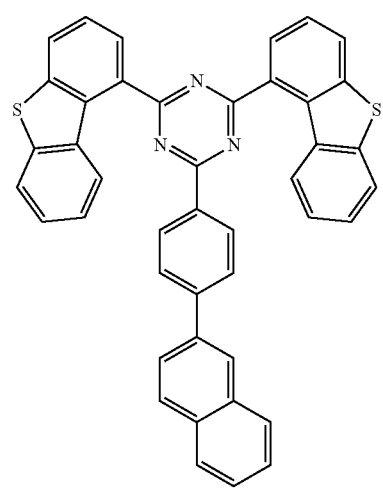
C2-226 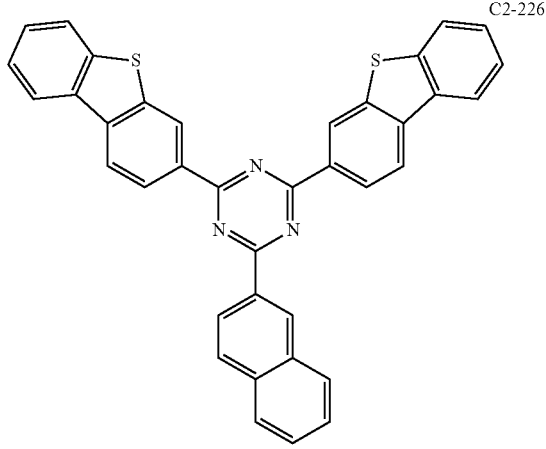
C2-227 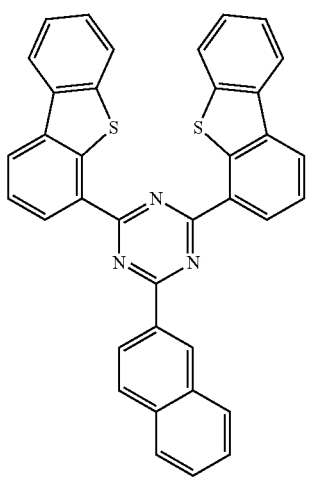
C2-228 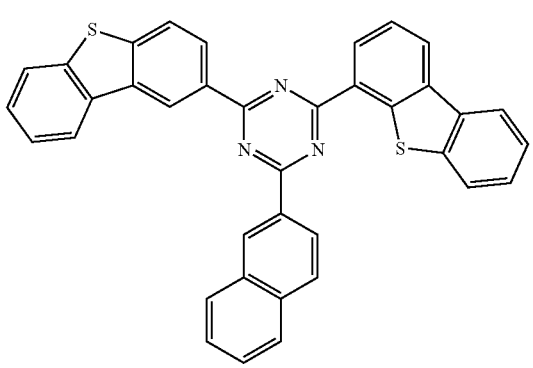
C2-229 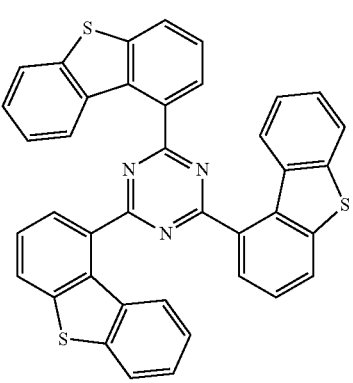

-continued
C2-230
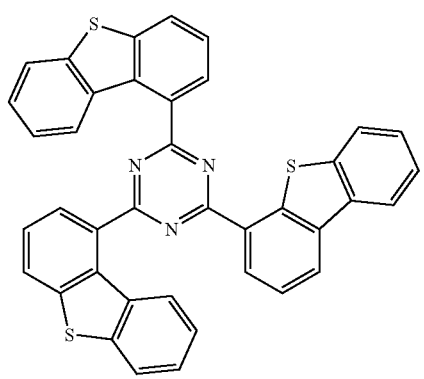
C2-231
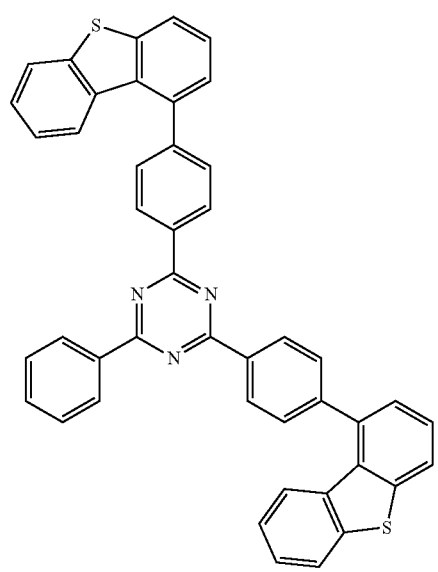
C2-232
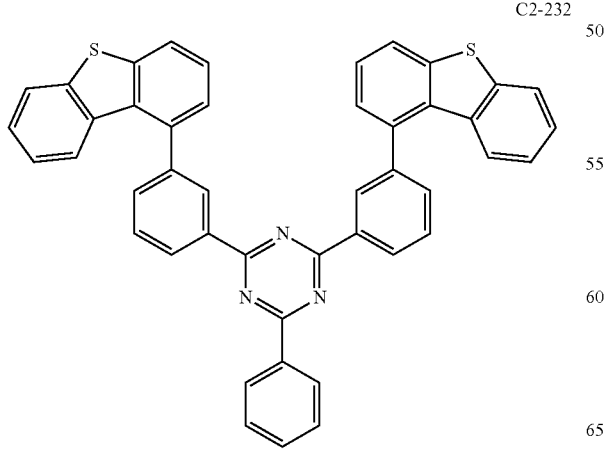
-continued
C2-233
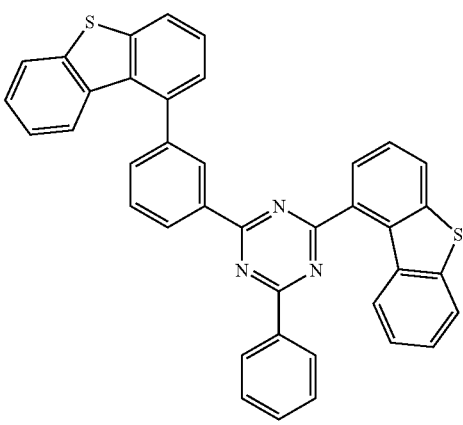
C2-234
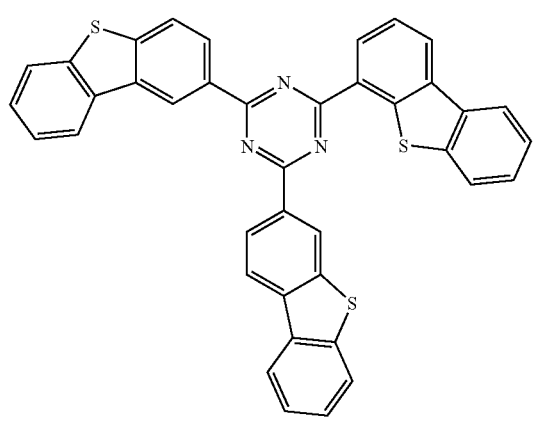
C2-235
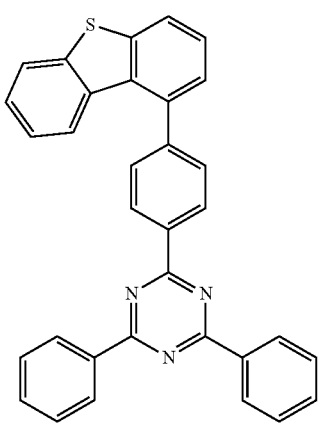

C2-236
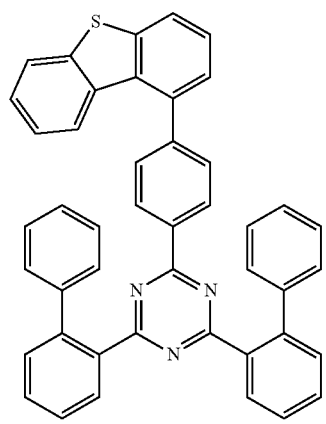
C2-237
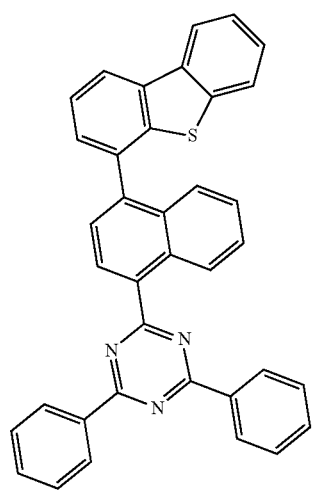
C2-238
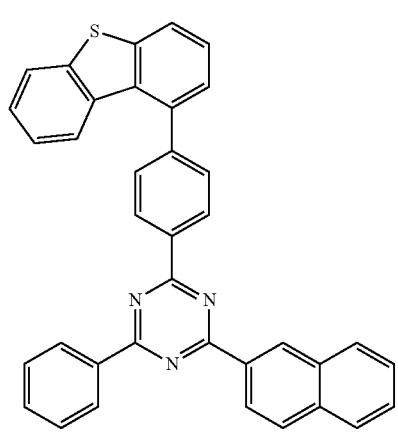
C2-239
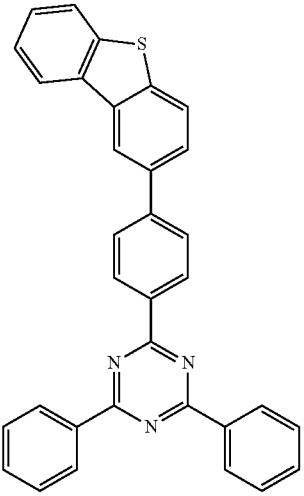
C2-240
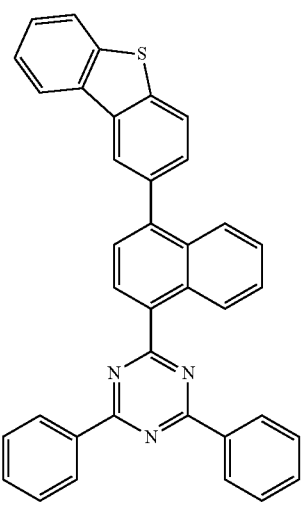
C2-241
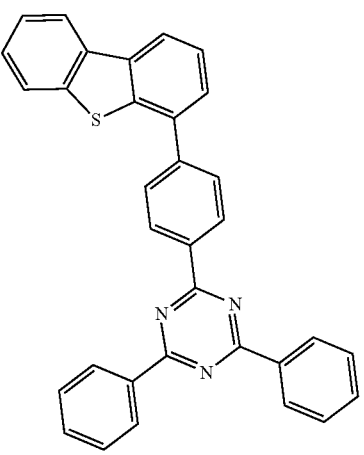

C2-242
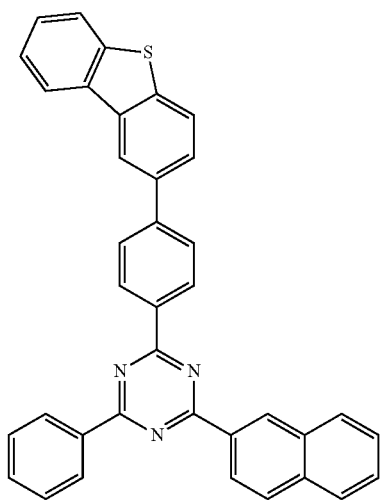
C2-243
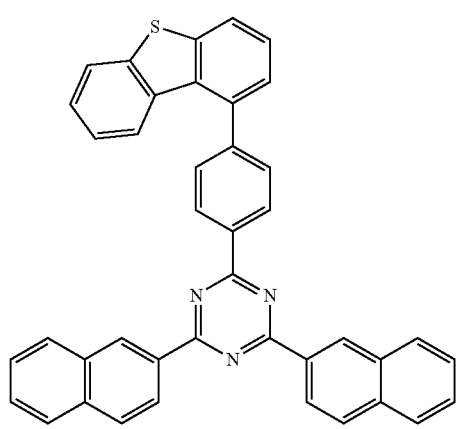
C2-244
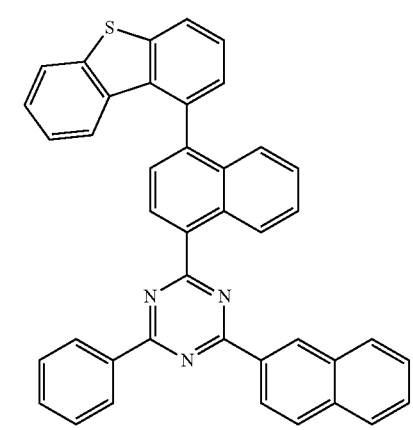
C2-245
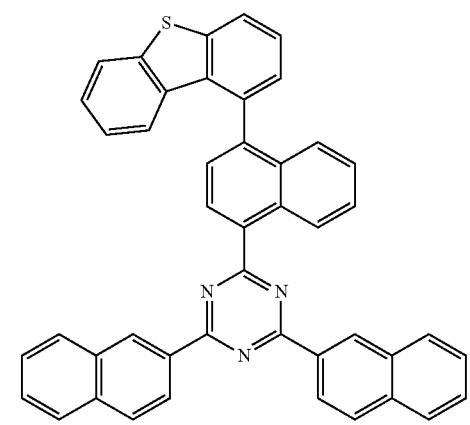
C2-246
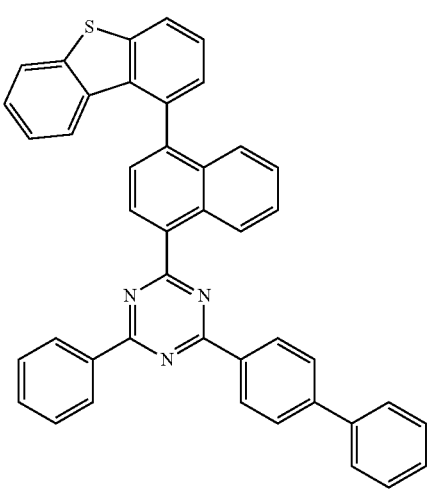
C2-247
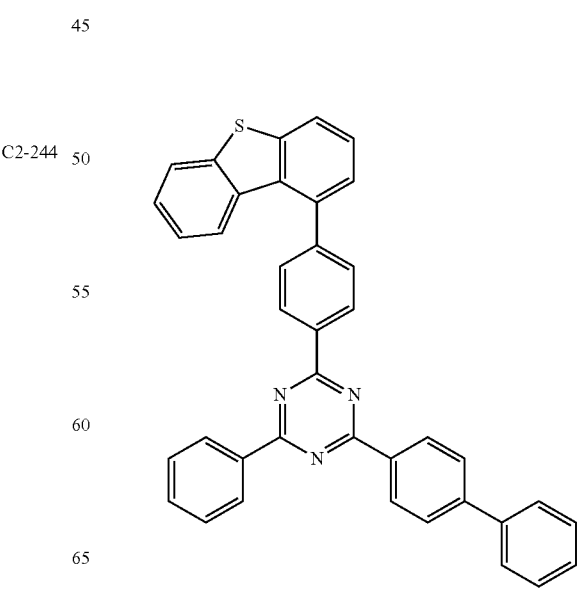

-continued
C2-248
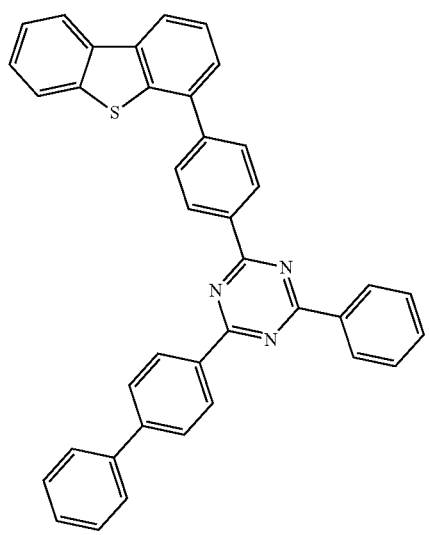
C2-249
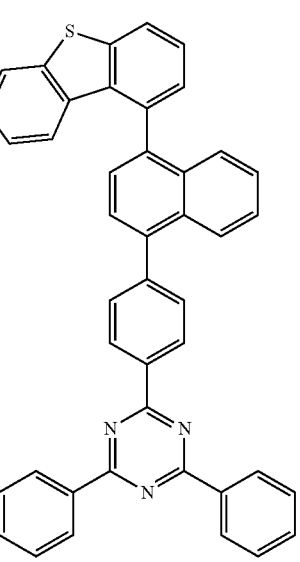
C2-250
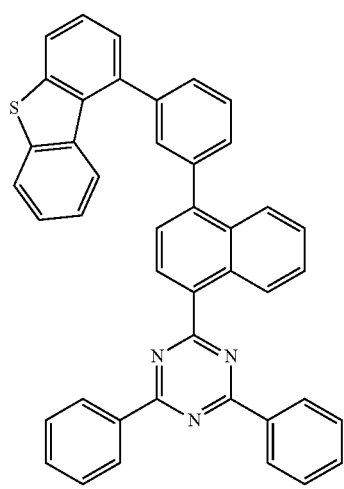
-continued
C2-251
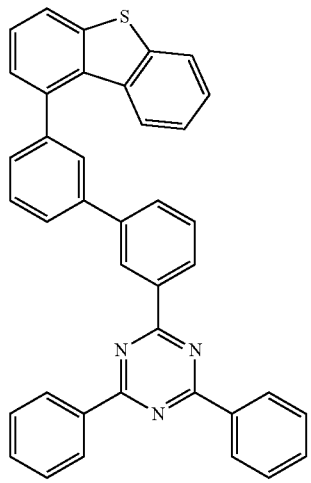
C2-252
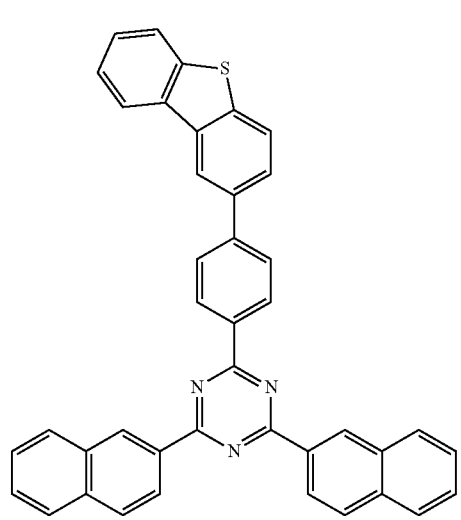
C2-253
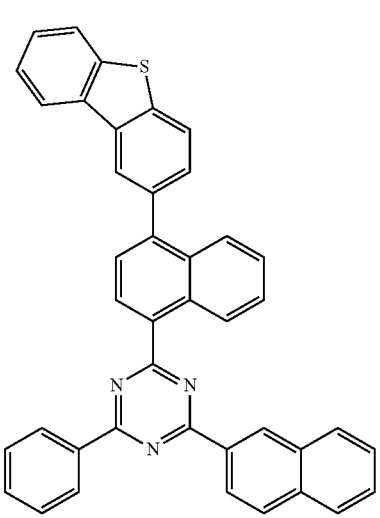

C2-254
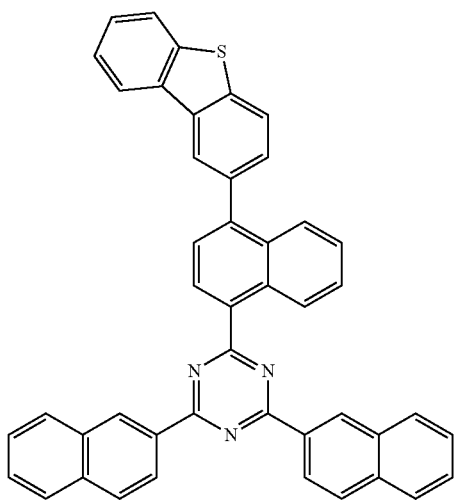
C2-255
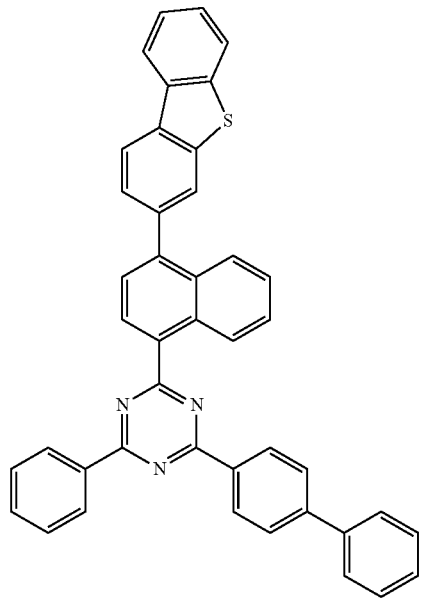
C2-256
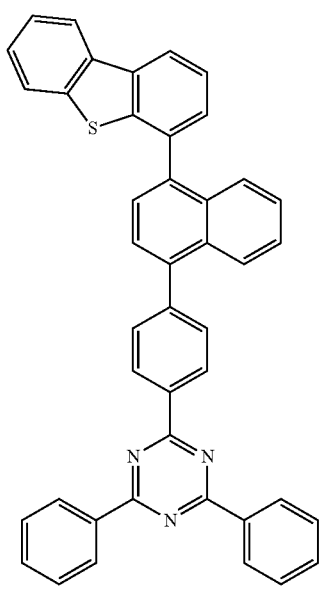
C2-257
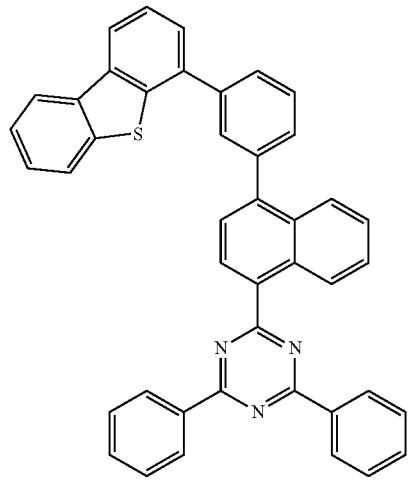
C2-258
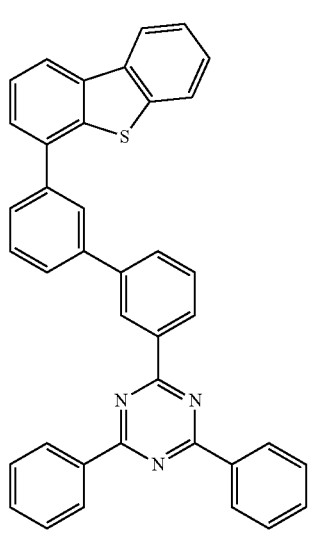
C2-259
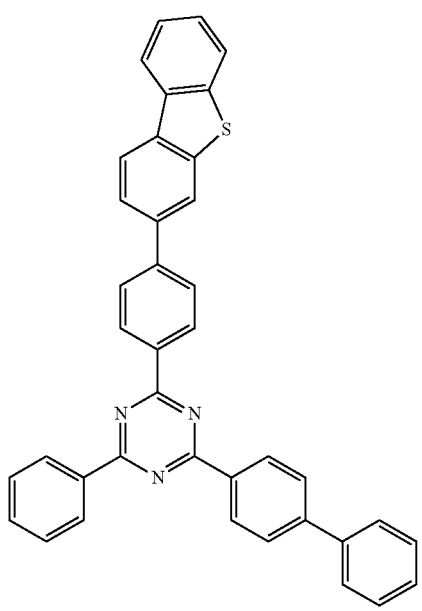

C2-260
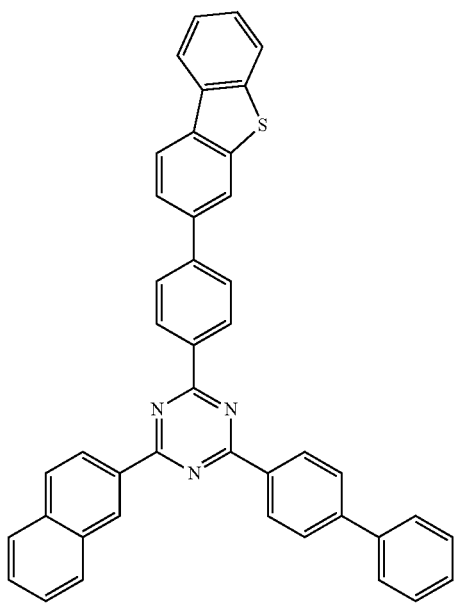
C2-261
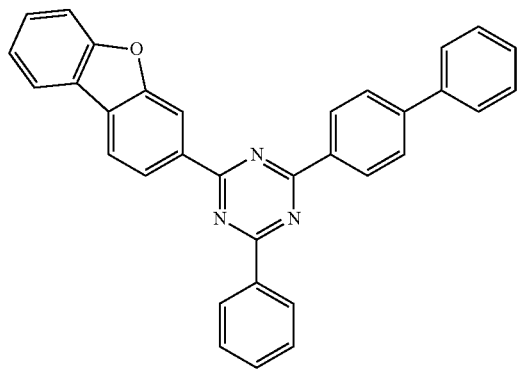
C2-262
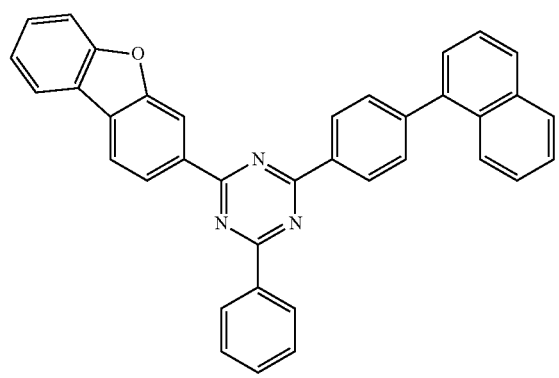
C2-263
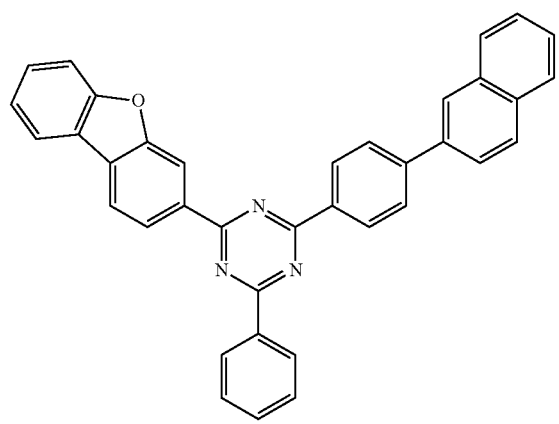
C2-264
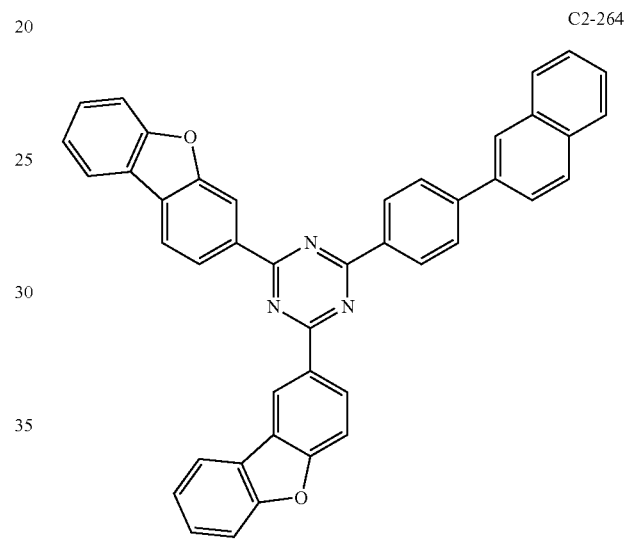
C2-265
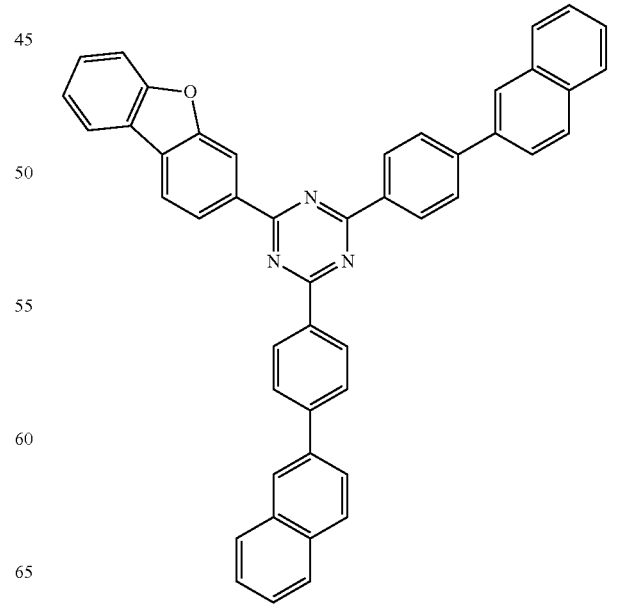

-continued
C2-266
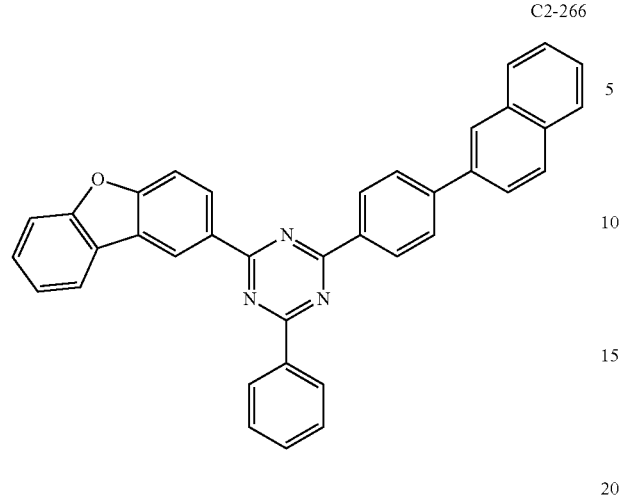
C2-269
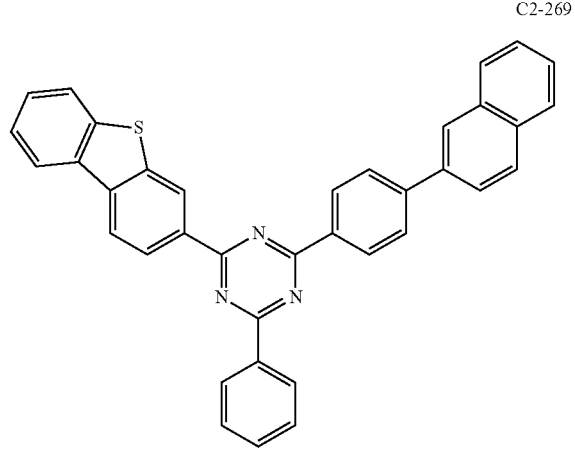
C2-267
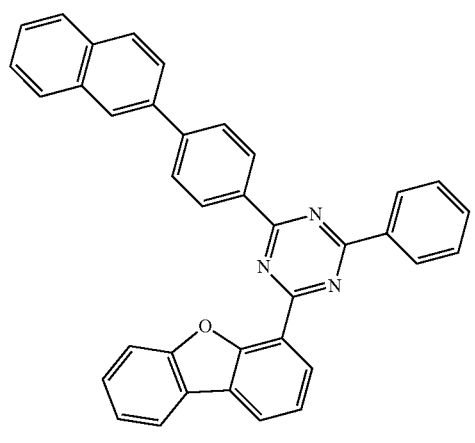
C2-270
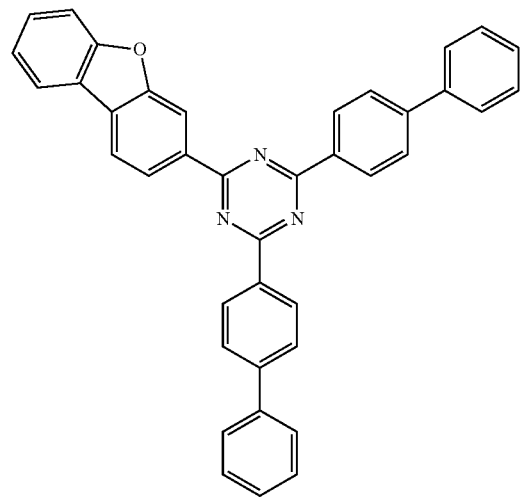
C2-268
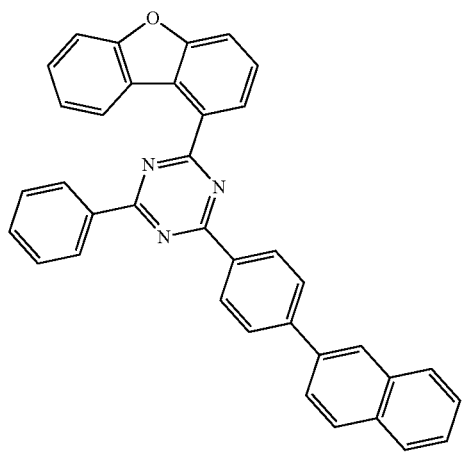
C2-271
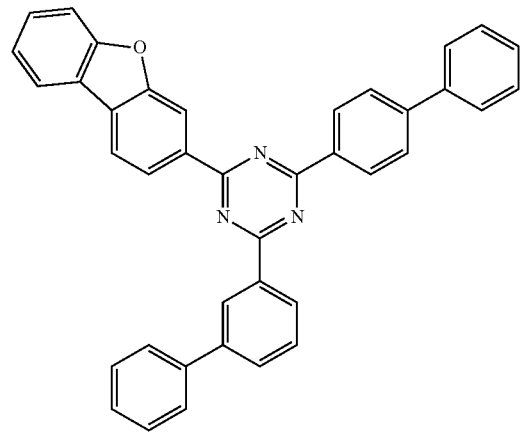

C2-272

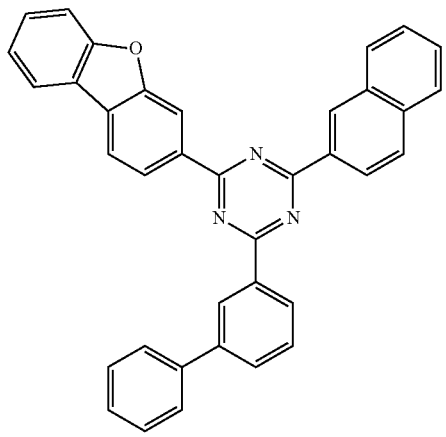

C2-273

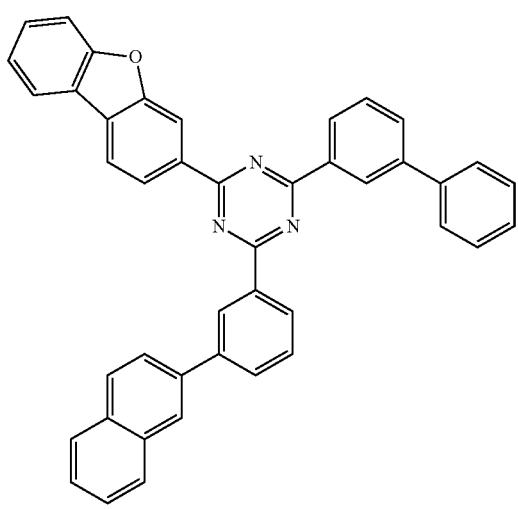

C2-274

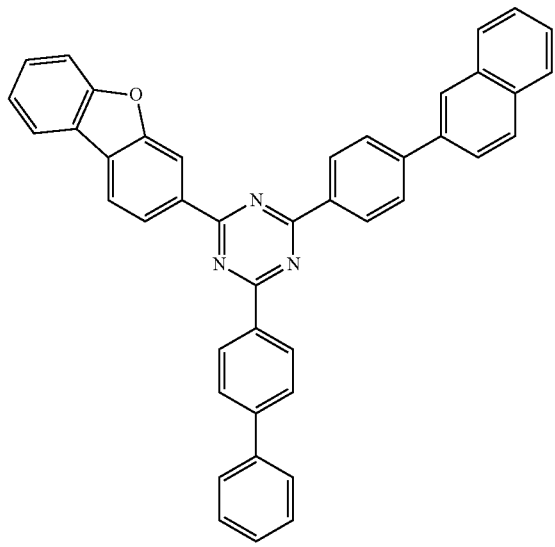

C2-275

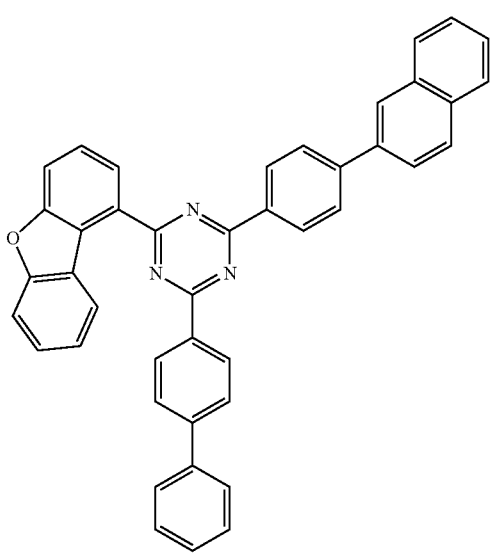

The compound represented by formula 2 according to one embodiment may be prepared by a synthetic method known to a person skilled in the art.

An organic electroluminescent compound according to another embodiment of the present disclosure may be represented by the following formula 1-1-1.

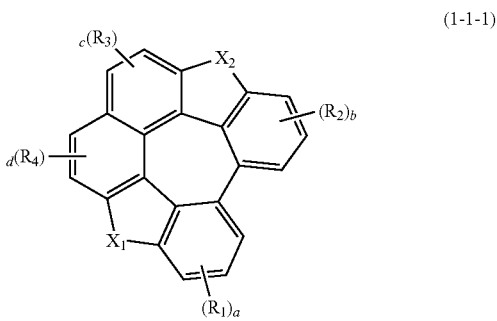

(1-1-1)

In formula 1-1-1
$X_1$ and $X_2$ each independently represent $NR_5$, $CR_6R_7$, C, or S;
$R_1$ to $R_4$ each independently represent hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C3) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30) alkenylamino, a substituted or unsubstituted mono- or di- (C6-C30)arylamino, a substituted or unsubstituted (C1-C30)alkyl(C6-C30)arylamino, a substituted or unsubstituted mono- or di- (3- to 30-membered)heteroarylamino, a substituted or unsubstituted (C1-C30) alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, or a substituted or unsubstituted (C6-C30)aryl(3- to 30-membered)heteroarylamino;

$R_5$ to $R_7$ each independently represent a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted fused ring of (O3-C30) aliphatic ring and (C6-C30) aromatic ring, a substituted or unsubstituted mono- or di- (C1-C30)alkylamino, a substituted or unsubstituted mono- or di-(C2-C30)alkenylamino, a substituted or unsubstituted (C1-C30)alkyl(C2-C30)alkenylamino, a substituted or unsubstituted mono- or di- (C6-C30) arylamino, a substituted or unsubstituted (C1-C30) alkyl(C6-C30)arylamino, a substituted or unsubstituted mono- or di- (3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

provided that at least one of $R_1$ to $R_5$ represents -$(L_1)_m$-$(Ar_1)_n$;

$L_1$ represents a single bond, a substituted or unsubstituted fused ring of (C3-C30) aliphatic ring and (C6-C30) aromatic ring, or a substituted or unsubstituted (C6-C30)arylene;

$Ar_1$ represents a substituted or unsubstituted (C6-C30) aryl, a substituted or unsubstituted (3- to 30-membered) heteroaryl, or —N—$(Ar_2)(Ar_3)$;

$Ar_2$ and $Ar_3$ each independently represent a substituted or unsubstituted (C1-C30)alkyl, a substituted or unsubstituted (C2-C30)alkenyl, a substituted or unsubstituted fused ring of (C3-C30) aliphatic ring and (C6-C30) aromatic ring, a substituted or unsubstituted (C6-C30) aryl, or a substituted or unsubstituted (3- to 30-membered)heteroaryl;

a and b each independently represent an integer of 1 to 3, and c, d, m, and n each independently represent an integer of 1 or 2; and when a to d, m, and n each independently are an integer of 2 or more, each of $R_1$ to $R_4$, each of $L_1$, and each of $Ar_1$ may be the same or different;

provided that, the compound in which $L_1$ represents a single bond and $Ar_1$ excludes all that represents a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted benzofuropyrimidinyl, or a substituted or unsubstituted benzothienopyrimidinyl, is excluded from formula 1-1-1.

In one embodiment, $X_1$ and $X_2$ each independently may be O, S, $NR_5$, or $CR_6R_7$, wherein $R_5$ to $R_7$ each independently may be a substituted or unsubstituted (C1-C30)alkyl, a substituted or unsubstituted (C6-C30)aryl, a substituted or unsubstituted (3- to 30-membered)heteroaryl, a substituted or unsubstituted mono- or di- (C6-C30)arylamino, a substituted or unsubstituted mono- or di- (3- to 30-membered) heteroarylamino, or a substituted or unsubstituted (C6-C30) aryl(3- to 30-membered)heteroarylamino, preferably, a substituted or unsubstituted (C1-C10)alkyl, a substituted or unsubstituted (C6-C25)aryl, a substituted or unsubstituted (5- to 25-membered)heteroaryl, a substituted or unsubstituted mono- or di- (C6-C25)arylamino, a substituted or unsubstituted mono- or di- (5- to 25-membered)heteroarylamino, or a substituted or unsubstituted (C6-C25)aryl(5- to 25-membered)heteroarylamino, more preferably, a substituted or unsubstituted (C1-C4)alkyl, (C6-C13)aryl unsubstituted or substituted with at least one of (5- to 30-membered)heteroaryl; di(C6-C30)arylamino; di(5- to 30-membered)heteroarylamino; and (C6-C30)aryl(5- to 30-membered)heteroarylamino, or (5- to 18-membered)heteroaryl unsubstituted or substituted with (C6-C30)aryl. For example, $R_5$ may be a substituted or unsubstituted phenyl, a substituted or unsubstituted naphthyl, a substituted or unsubstituted m-biphenyl, a substituted or unsubstituted o-terphenyl, a substituted or unsubstituted m-terphenyl, a substituted or unsubstituted pyridyl, a substituted or unsubstituted dibenzofuranyl, or a substituted or unsubstituted dibenzothiophenyl. For example, all of $R_6$ and $R_7$ may be methyl.

In one embodiment, $R_1$ to $R_4$ each independently may be hydrogen, deuterium, a substituted or unsubstituted (C6-C30)aryl, a substituted or unsubstituted (3- to 30-membered) heteroaryl, a substituted or unsubstituted mono- or di- (C6-C30)arylamino, a substituted or unsubstituted mono- or di- (3- to 30-membered)heteroarylamino, or a substituted or unsubstituted (C6-C30)aryl(3- to 30-membered)heteroarylamino, preferably, hydrogen, a substituted or unsubstituted (C6-C25)aryl, a substituted or unsubstituted (5- to 25-membered)heteroaryl, a substituted or unsubstituted mono- or di- (C6-C25)arylamino, a substituted or unsubstituted mono- or di- (5- to 25-membered)heteroarylamino, or a substituted or unsubstituted (C6-C25)aryl(5- to 25-membered)heteroarylamino, more preferably, hydrogen, (C6-C18)aryl unsubstituted or substituted with at least one of (5- to 30-membered) heteroaryl; di(C6-C30)arylamino; di(5- to 30-membered) heteroarylamino; and (C6-C30)aryl(5- to 30-membered) heteroarylamino, (5- to 18-membered)heteroaryl unsubstituted or substituted with (C6-C30)aryl, a substituted or unsubstituted mono- or di- (C6-C18)arylamino, a substituted or unsubstituted mono- or di- (5- to 18-membered) heteroarylamino, or a substituted or unsubstituted (C6-C18) aryl(5- to 18-membered)heteroarylamino. For example, $R_1$ to $R_4$ each independently may be a substituted or unsubstituted phenyl, a substituted or unsubstituted m-biphenyl, a substituted or unsubstituted o-terphenyl, a substituted or unsubstituted m-terphenyl, a substituted or unsubstituted pyridyl, a substituted or unsubstituted triazinyl, a substituted or unsubstituted dibenzofuranyl, or a substituted or unsubstituted dibenzothiophenyl.

In one embodiment, at least one of $R_1$ to $R_5$ in formula 1-1-1 represents -$(L_1)_m$-$(Ar_1)_n$.

In one embodiment, $L_1$ may be a single bond or a substituted or unsubstituted (C6-C30)arylene, preferably, a single bond or a substituted or unsubstituted (C6-C25) arylene, more preferably, a single bond or a substituted or unsubstituted (C6-C18)arylene. For example, $L_1$ may be a single bond, a substituted or unsubstituted phenylene, a substituted or unsubstituted naphthylene, a substituted or unsubstituted o-biphenylene, or a substituted or unsubstituted m-biphenylene.

In one embodiment, $Ar_1$ may be a substituted or unsubstituted (C6-C30)aryl, a substituted or unsubstituted (3- to 30-membered)heteroaryl, or —N—$(Ar_2)(Ar_3)$, preferably, a substituted or unsubstituted (C6-C25)aryl, a substituted or unsubstituted (5- to 25-membered)heteroaryl, or —N—(Ar₂)(Ar₃), more preferably, a substituted or unsubstituted (C6-C18)aryl, a substituted or unsubstituted (5- to 18-membered)heteroaryl, or —N—(Ar₂)(Ar₃). Wherein, Ar₂ and Ar₃ each independently may be a substituted or unsubstituted (C6-C30)aryl or a substituted or unsubstituted (3- to 30-membered)heteroaryl, preferably, a substituted or unsubstituted (C6-C25)aryl or a substituted or unsubstituted (5- to 25-membered)heteroaryl, more preferably, (C6-C18)aryl unsubstituted or substituted with (C6-C30)aryl and/or (5- to 30-membered)heteroaryl, or (5- to 18-membered)heteroaryl unsubstituted or substituted with (C6-C30)aryl and/or (5- to 30-membered)heteroaryl. For example, Ar₁ may be a substituted or unsubstituted phenyl, a substituted or unsubstituted o-biphenyl, a substituted or unsubstituted m-biphenyl, a substituted or unsubstituted m-terphenyl, a substituted or unsubstituted o-terphenyl, a substituted or unsubstituted pyridyl, a substituted or unsubstituted dibenzofuranyl, a substituted or unsubstituted dibenzothiophenyl, for example, Ar₂ and Ar₃ each independently may be a substituted or unsubstituted phenyl, a substituted or unsubstituted naphthyl, a substituted or unsubstituted m-biphenyl, a substituted or unsubstituted phenanthrenyl, a substituted or unsubstituted dimethylfluorenyl, or a substituted or unsubstituted dibenzofuranyl.

The compound represented by form Lila 1-1-1 above may be more specifically illustrated by the following compounds, but is not limited thereto.

C1-1

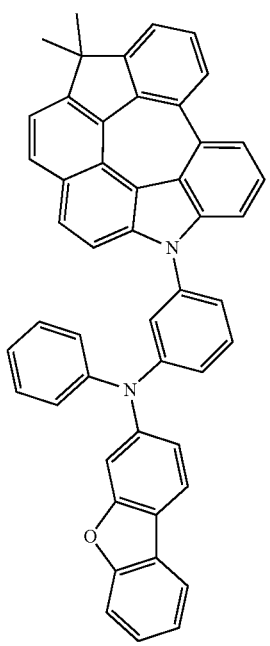

C1-2

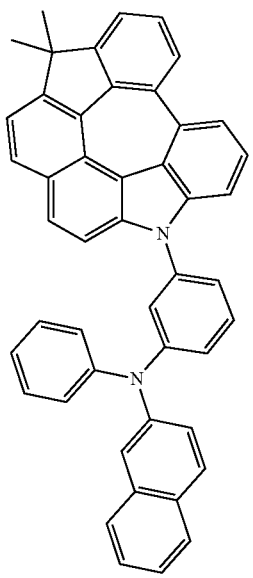

C1-3

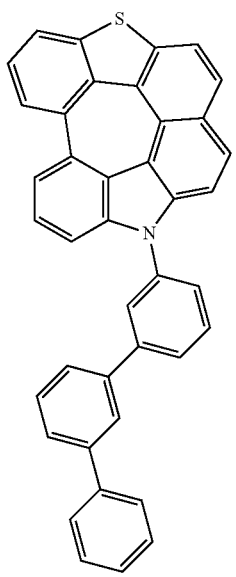

C1-4

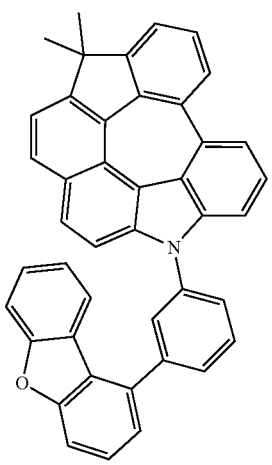

C1-5
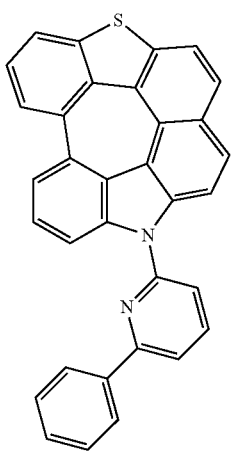
C1-6
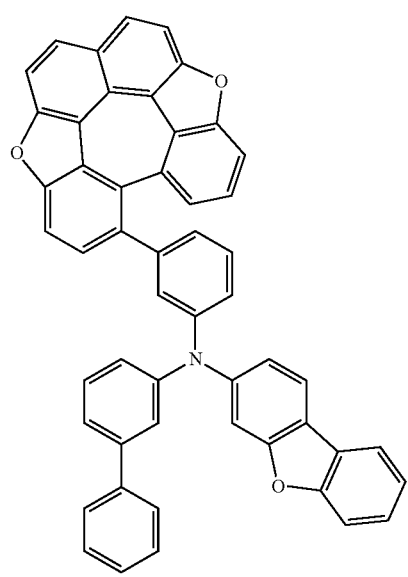
C1-7
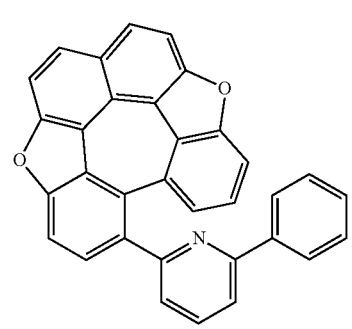
C1-8
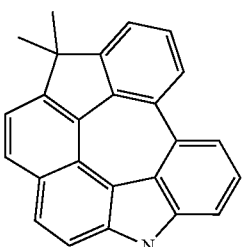
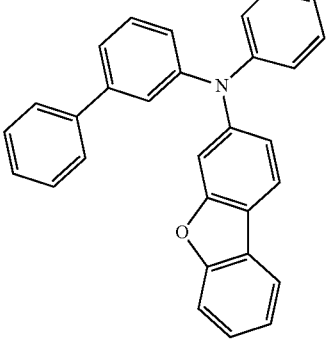
C1-9
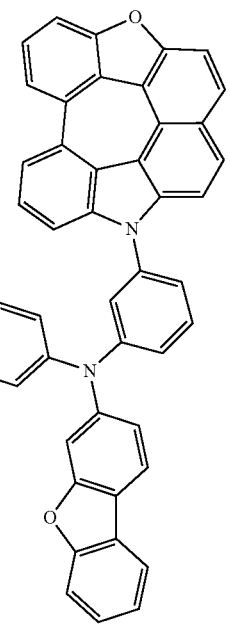

C1-10
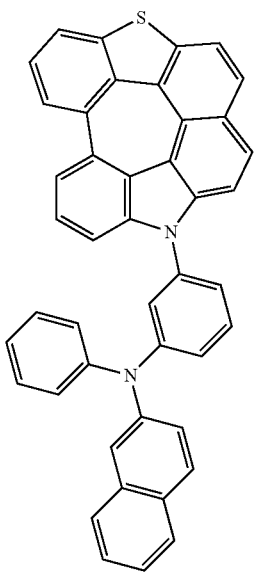
C1-11
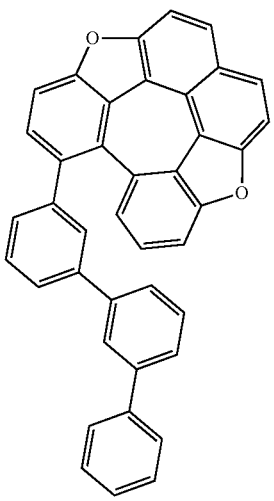
C1-12
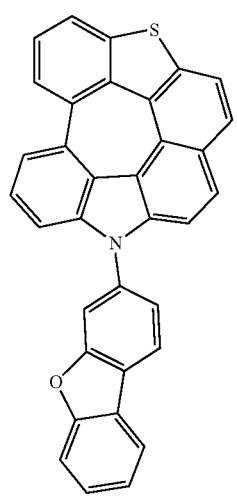
C1-13
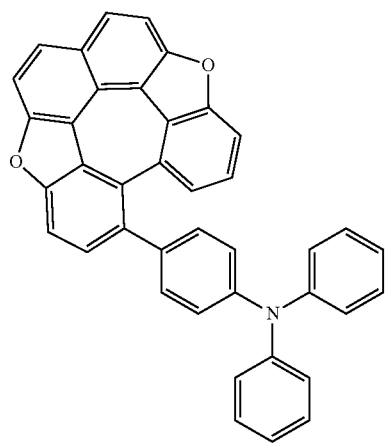
C1-14
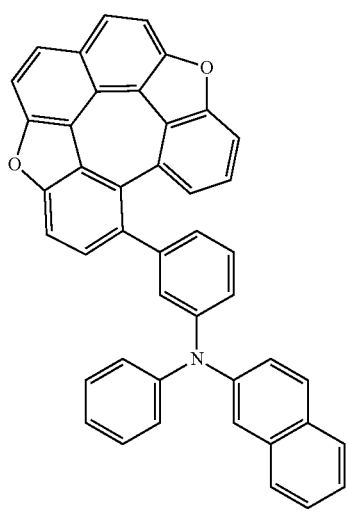
C1-15
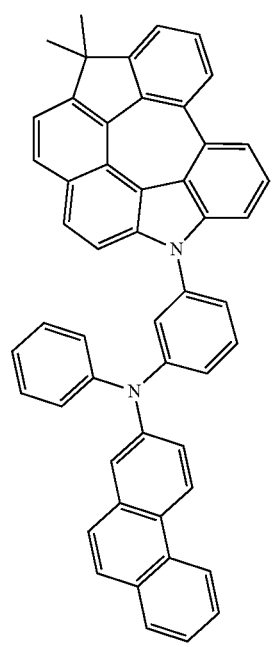

159
-continued
C1-16
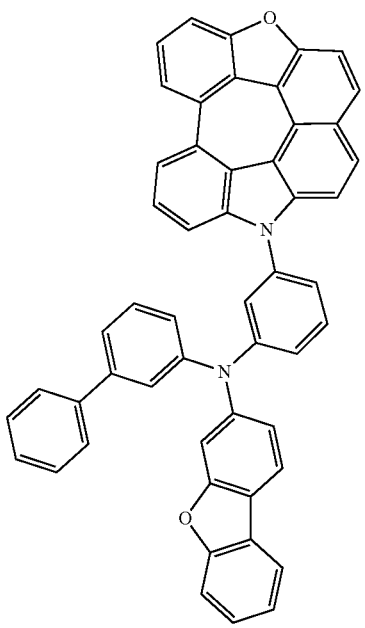
C1-17
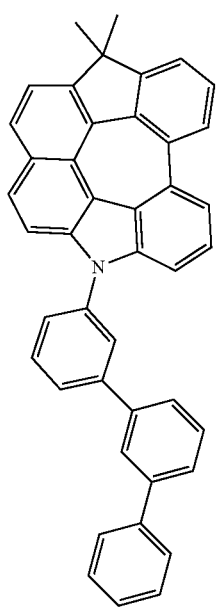
C1-18
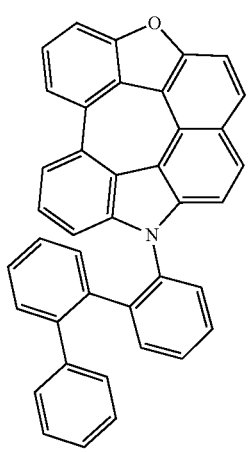
160
-continued
C1-19
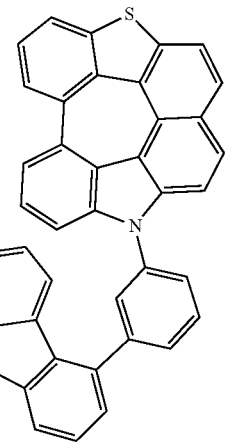
C1-20
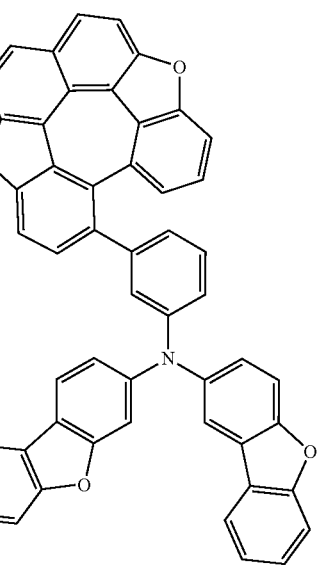
C1-21
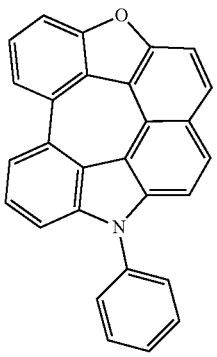

-continued
C1-22
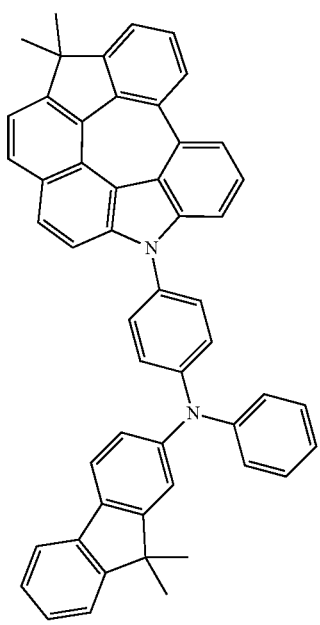
C1-23
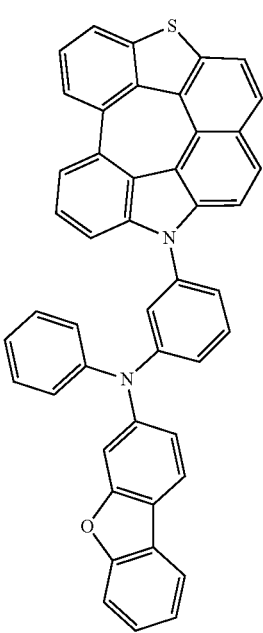
C1-24
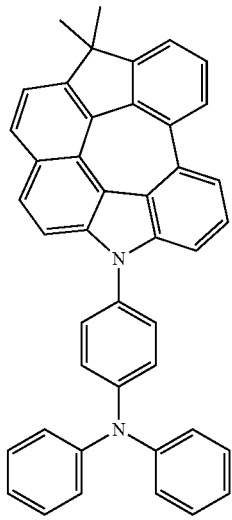
C1-25
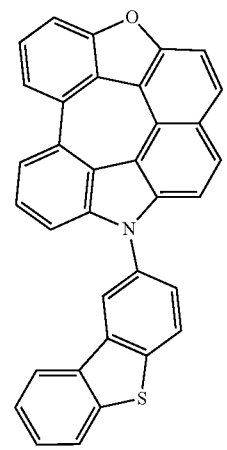
C1-26
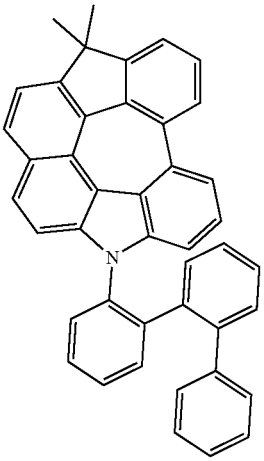

C1-27
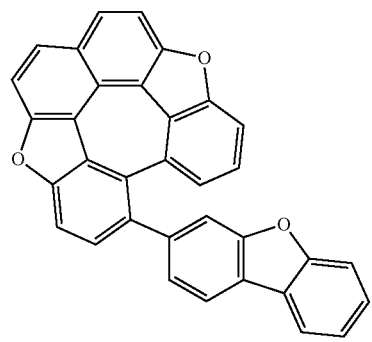
C1-28
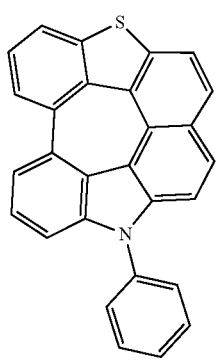
C1-29
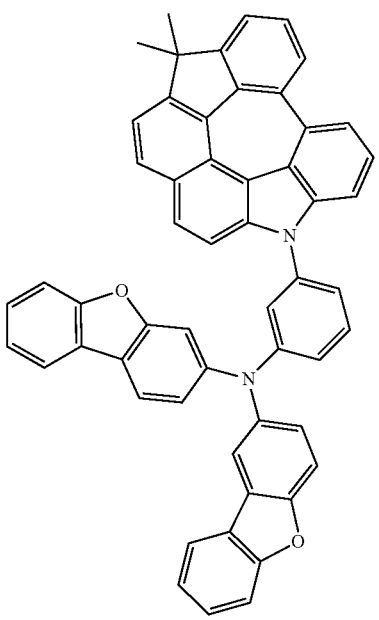
C1-30
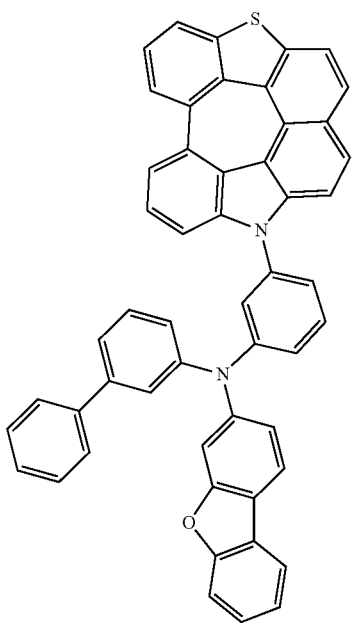
C1-31
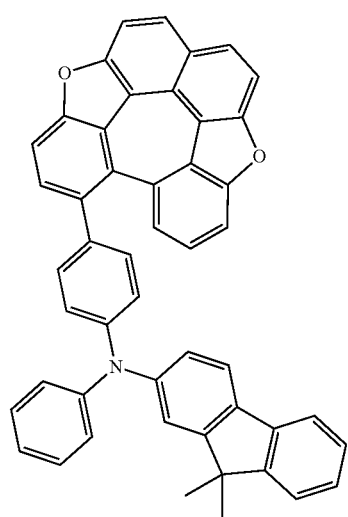
C1-32
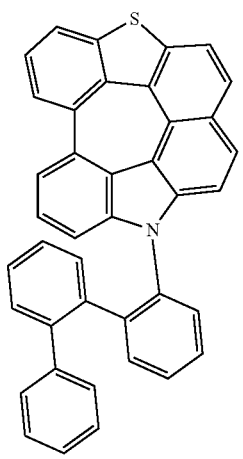

C1-33
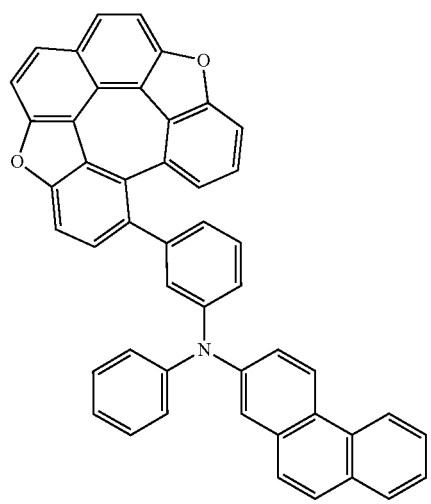
C1-34
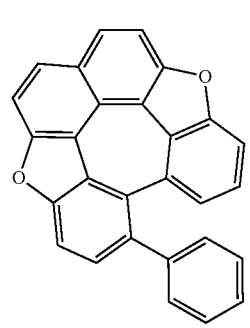
C1-35
C1-36
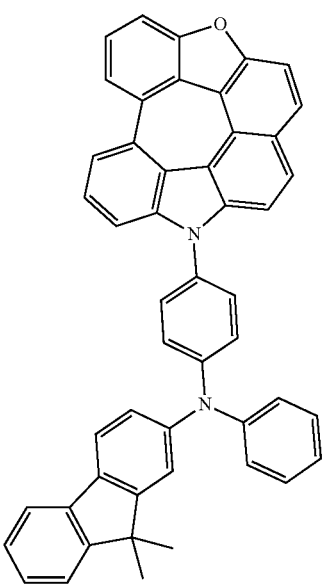
C1-37
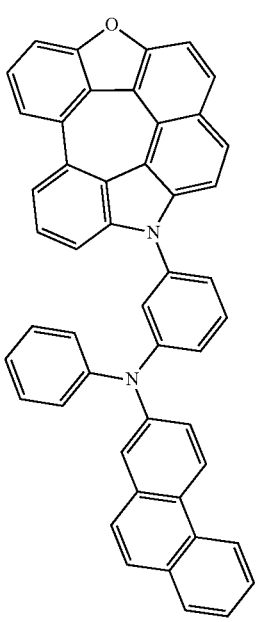

C1-38
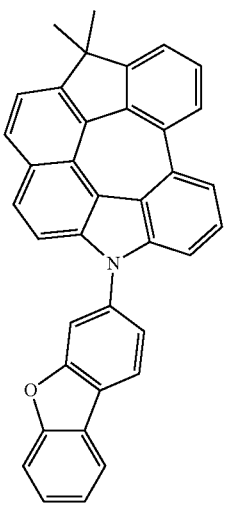
C1-39
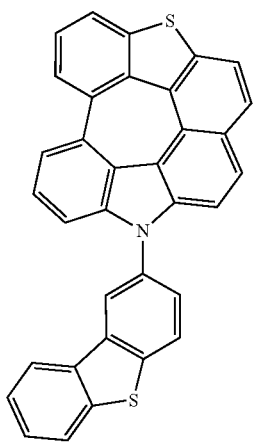
C1-40
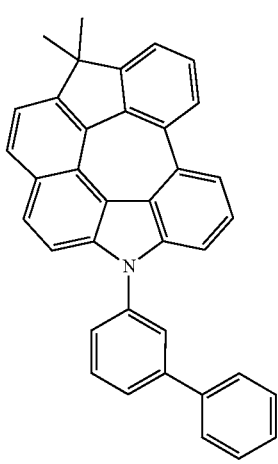
C1-41
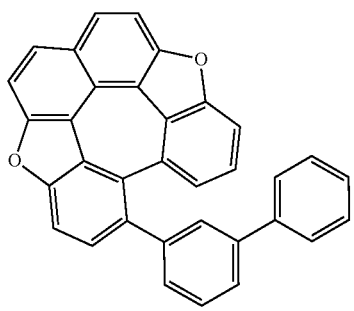
C1-42
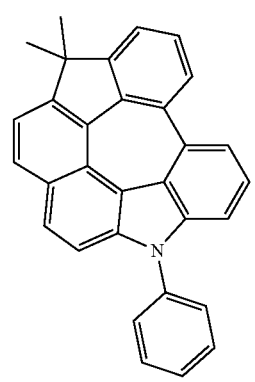
C1-43
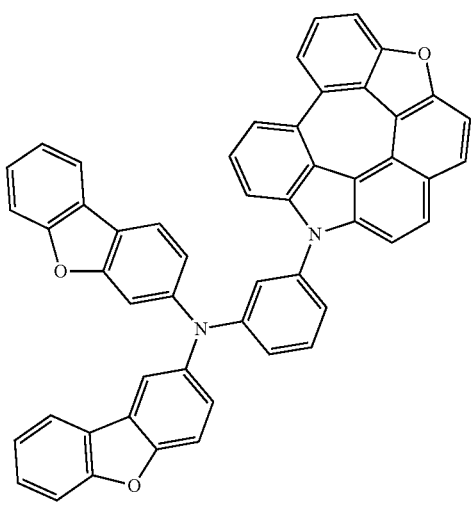

C1-44
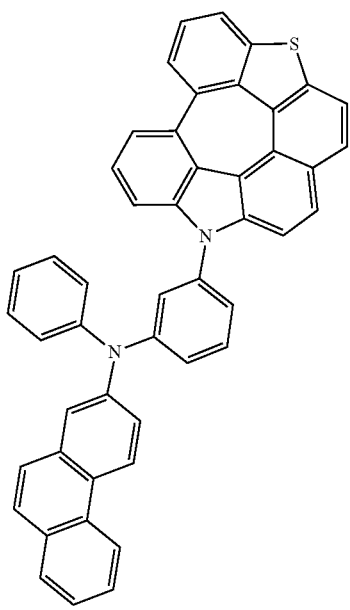
C1-47
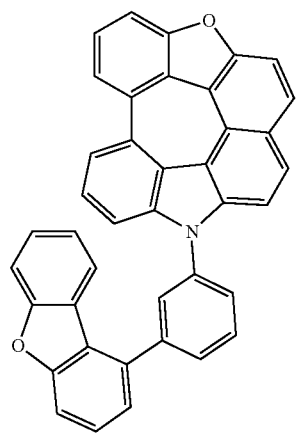
C1-45
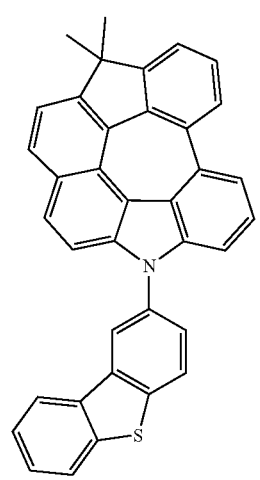
C1-48
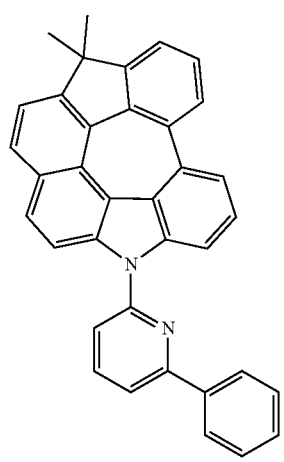
C1-46
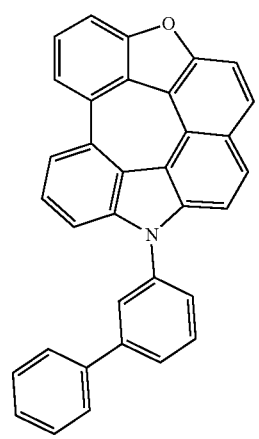
C1-49
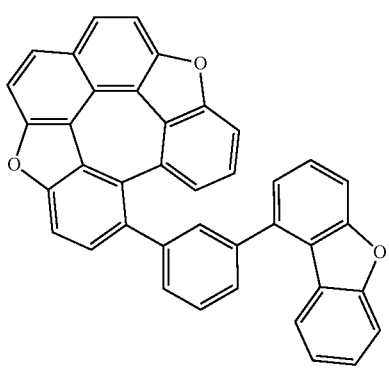

C1-50
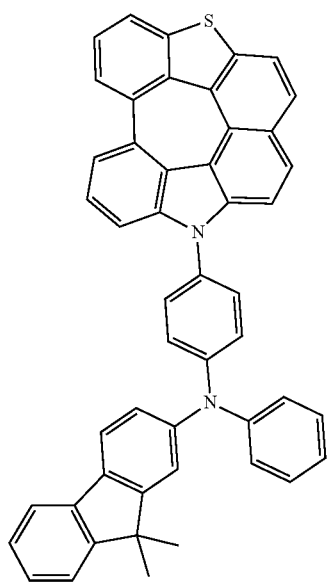
C1-51
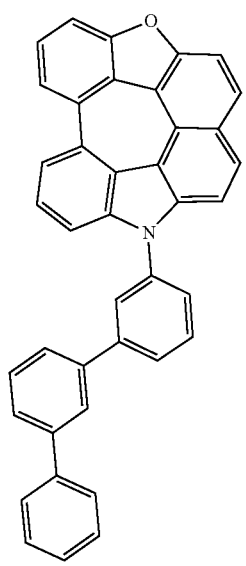
C1-52
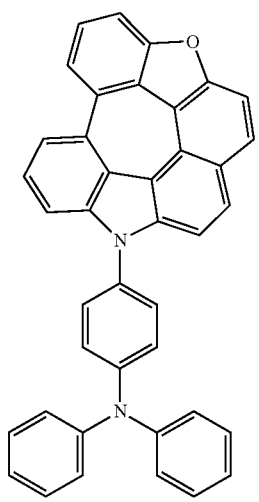
C1-53
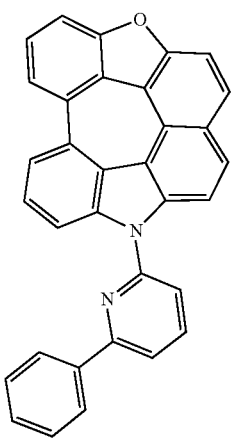
C1-54
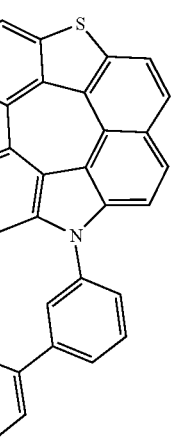
C1-55
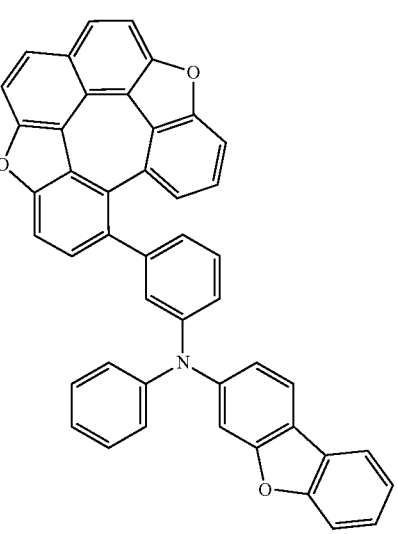

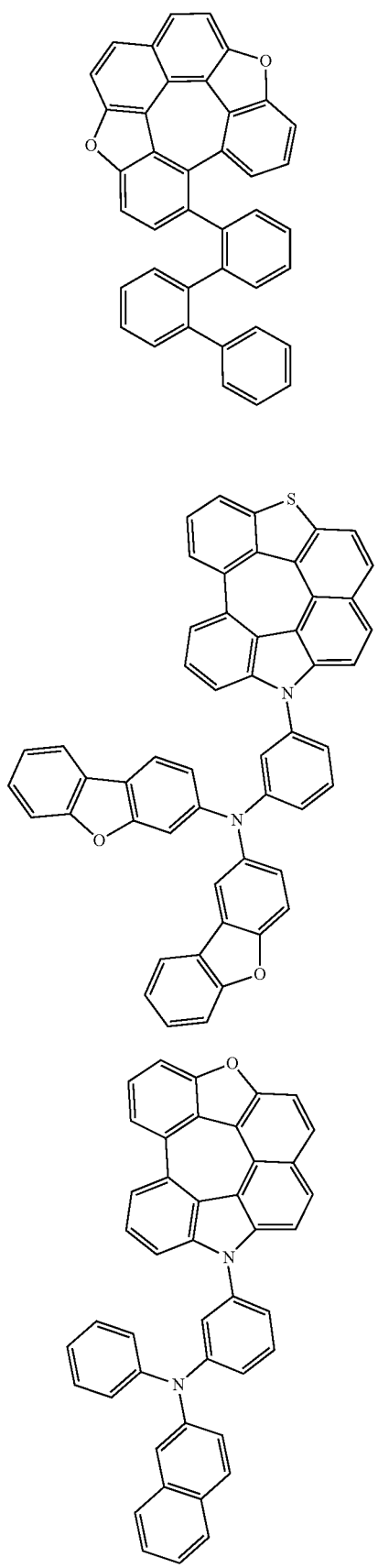
C1-56
C1-57
C1-58
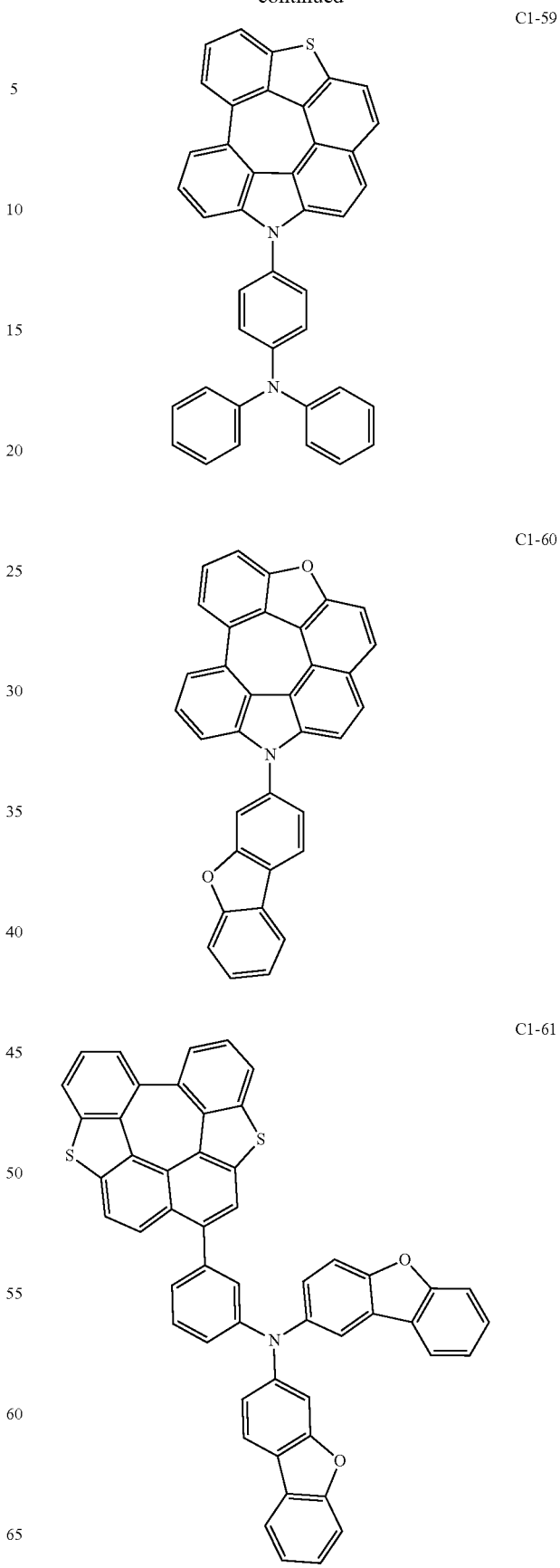
C1-59
C1-60
C1-61

C-62
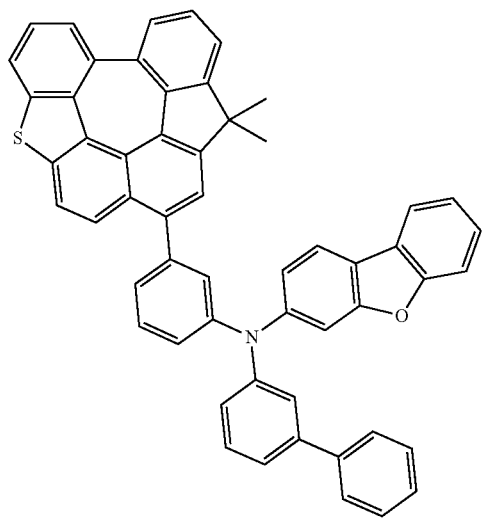
C1-63
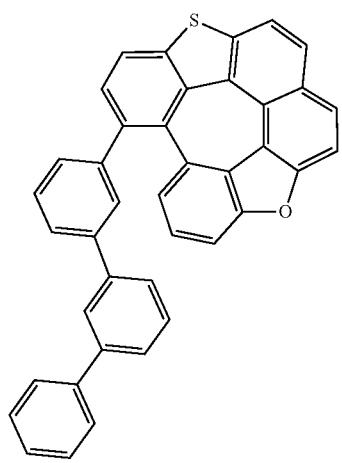
C1-64
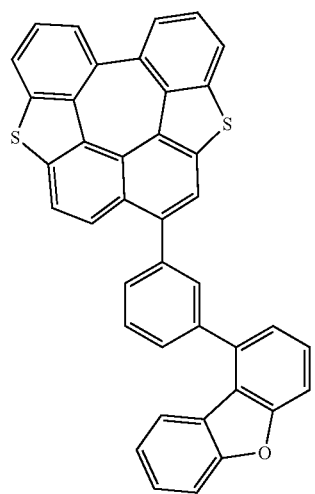
C1-65
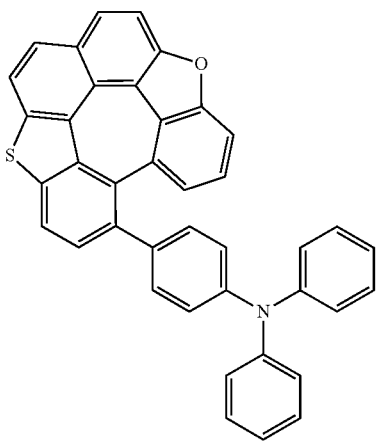
C1-66
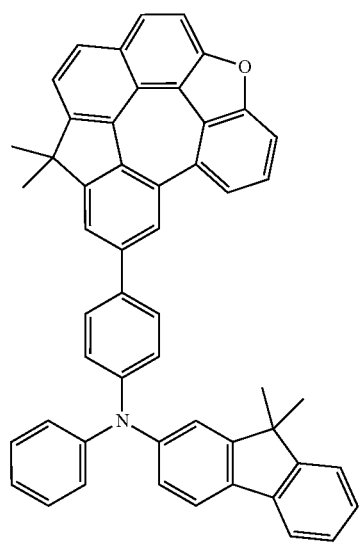
C1-67
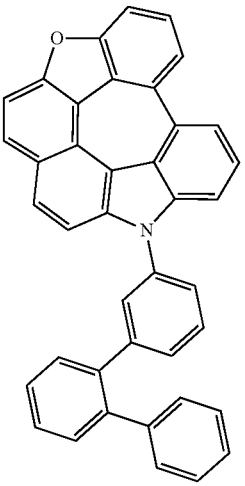

C1-68
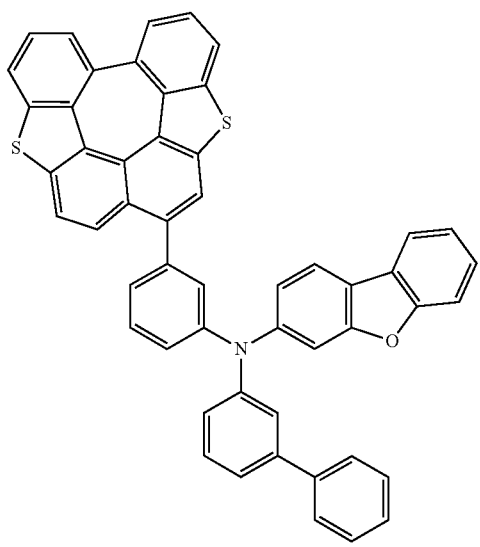
C1-69
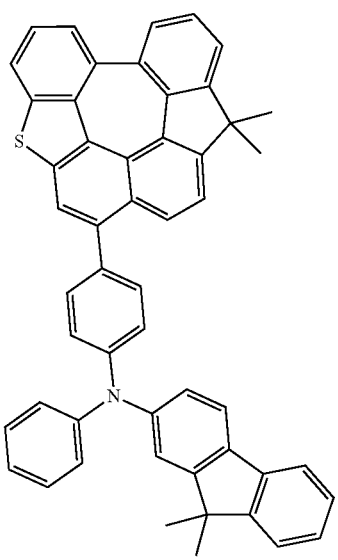
C1-70
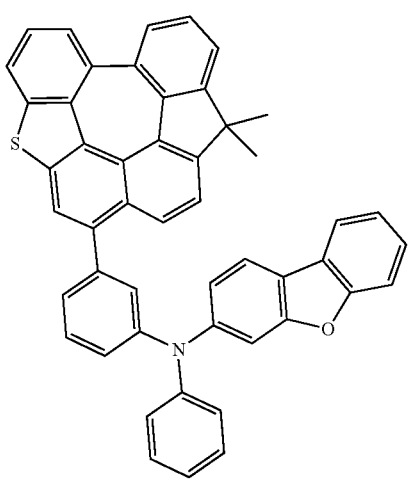
C1-71
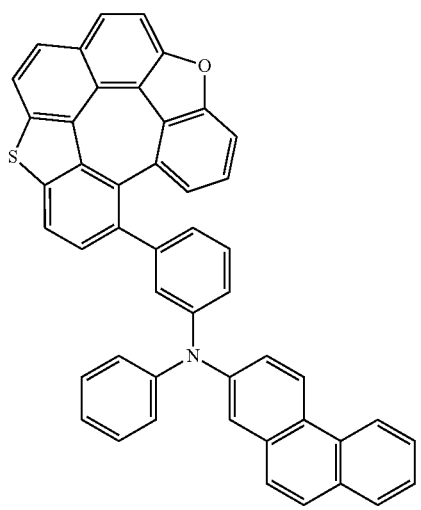
C1-72
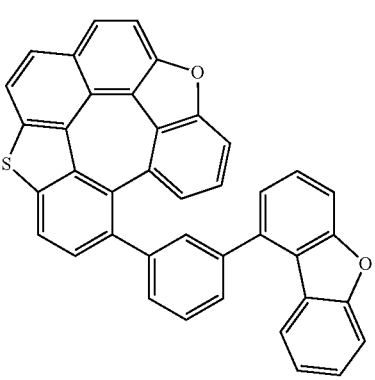
C1-73
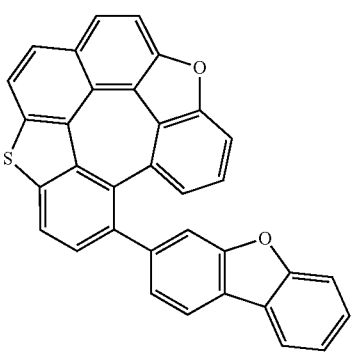

C1-74
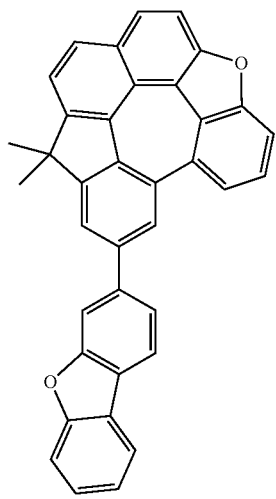
C1-75
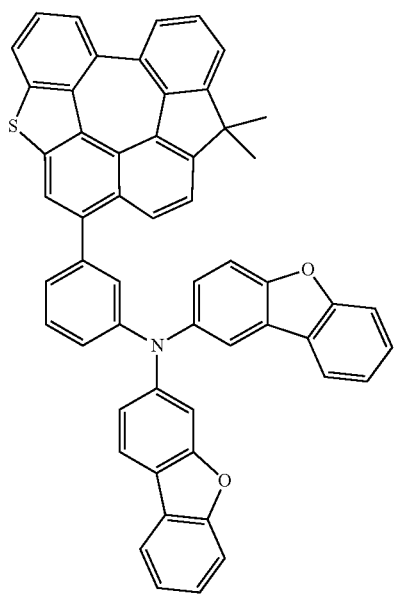
C1-76
C1-77
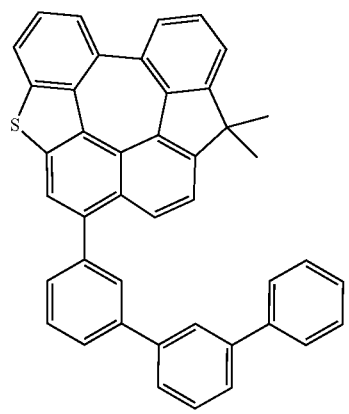
C1-78
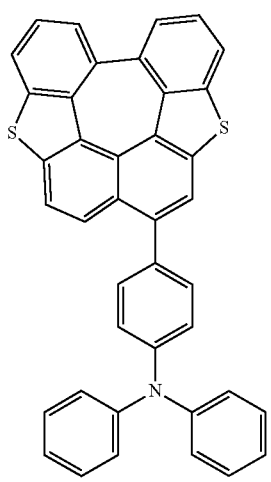
C1-79
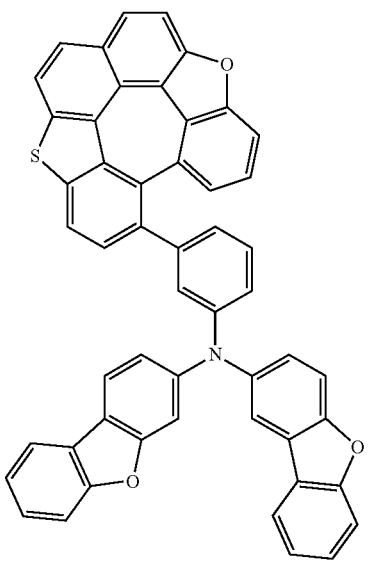

-continued
C1-80
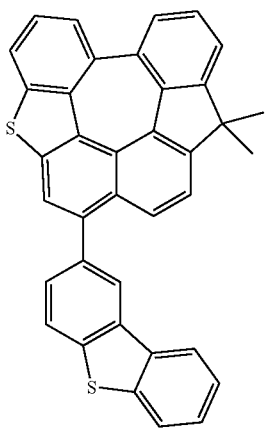
C1-81
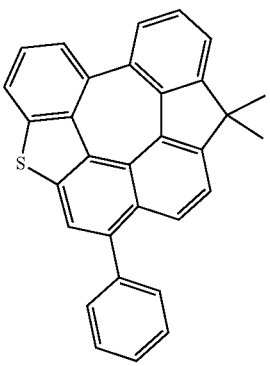
C1-82
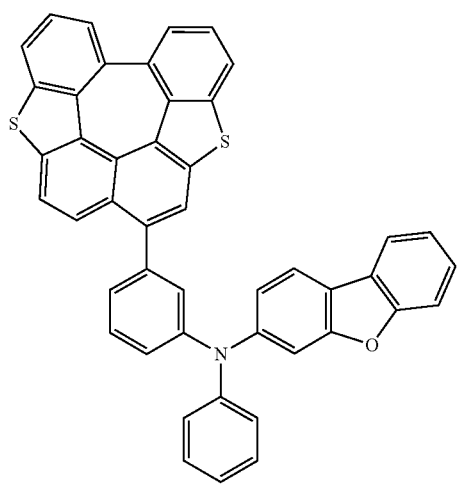
-continued
C1-83
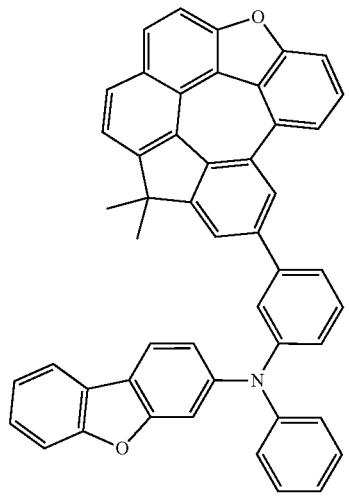
C1-84
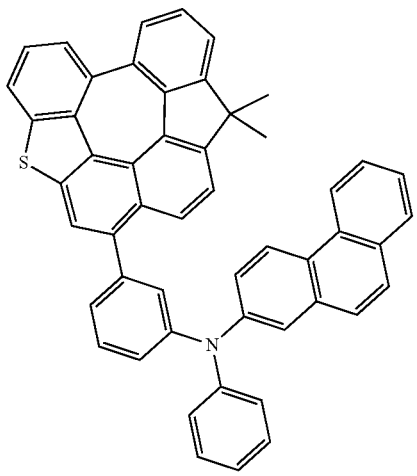
C1-85
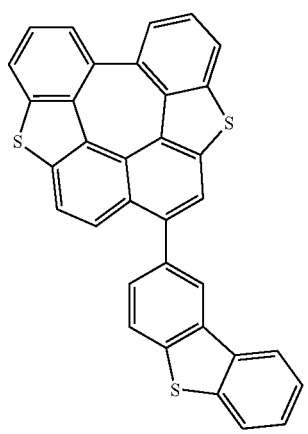

C1-86
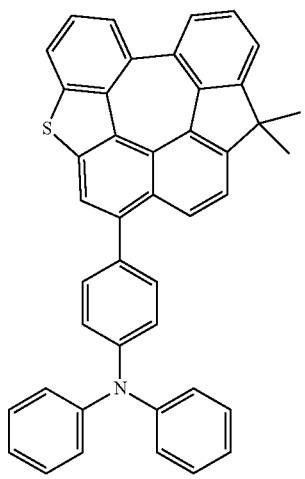
C1-87
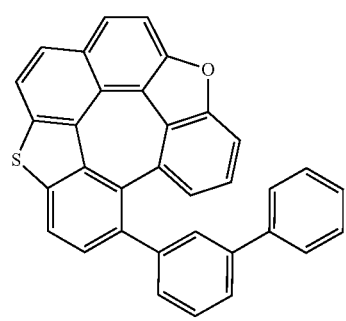
C1-88
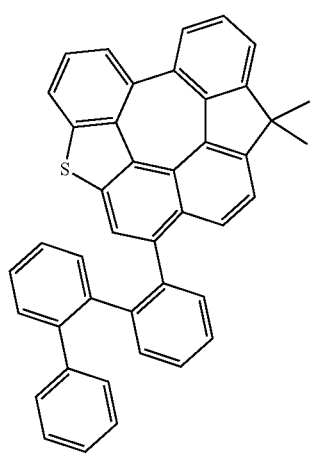
C1-89
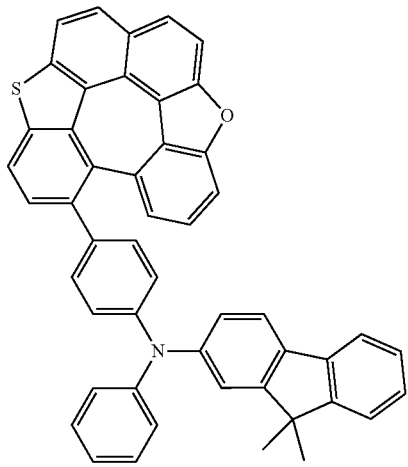
C1-90
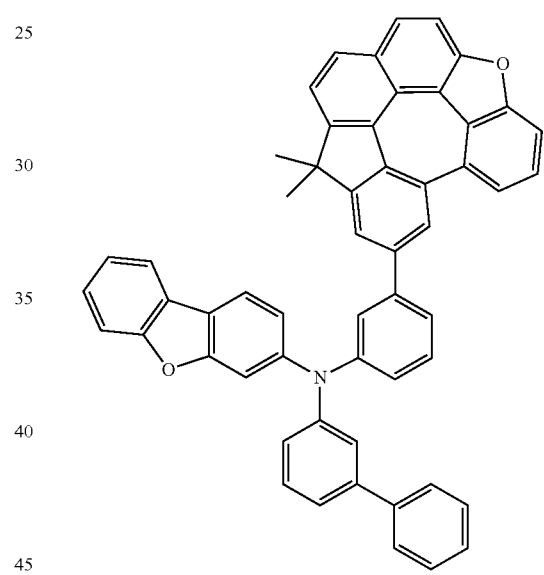
C1-91
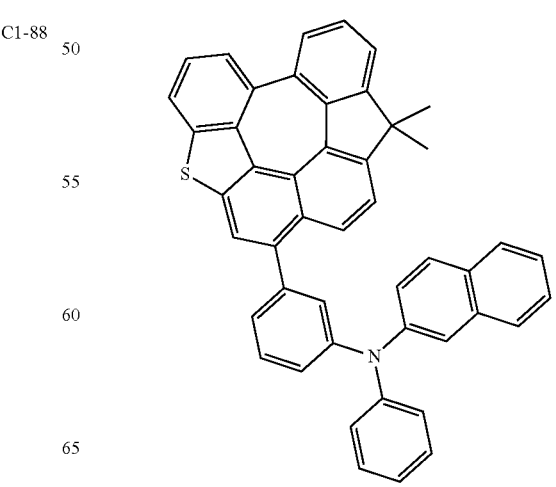

C1-92
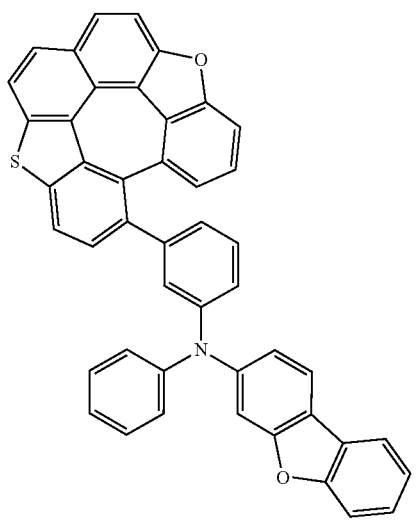
C1-93
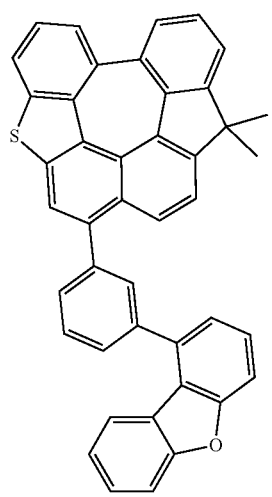
C1-94
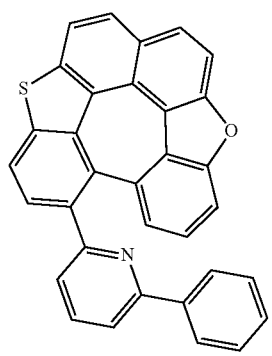
C1-95
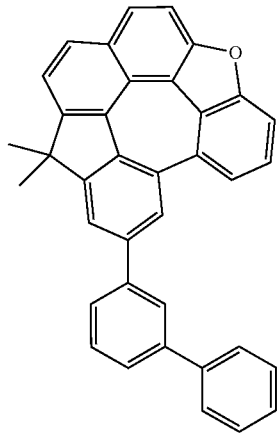
C1-96
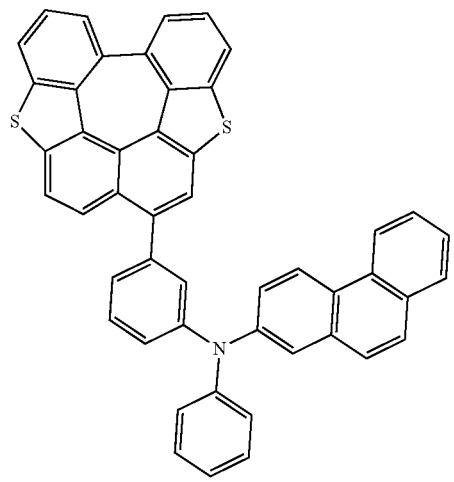
C1-97
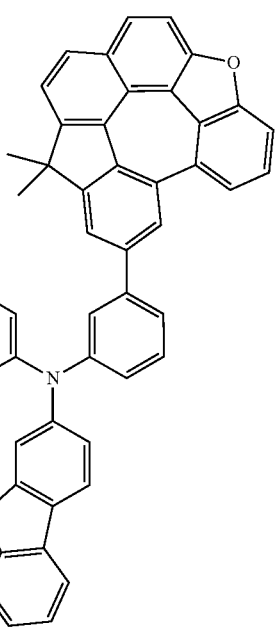

C1-98
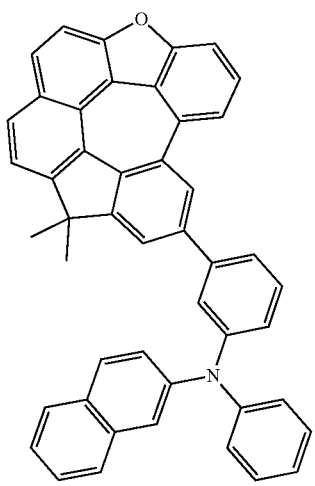
C1-99
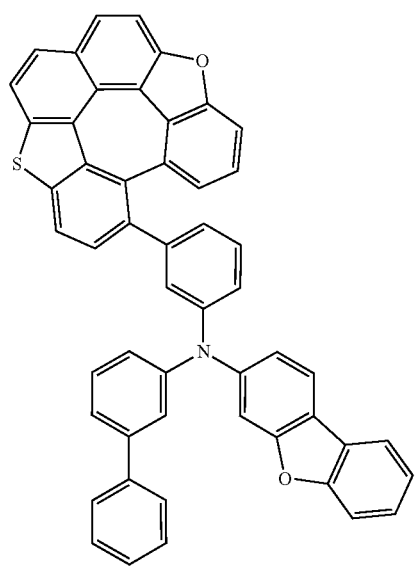
C1-100
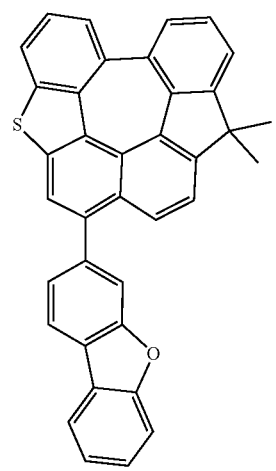
C1-101
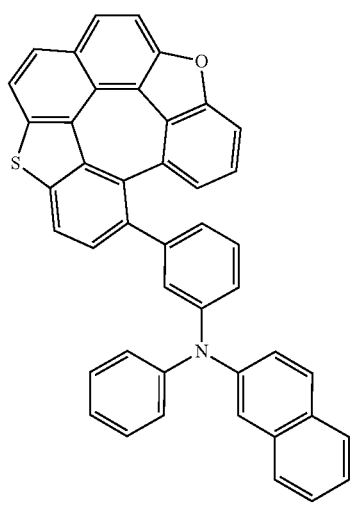
C1-102
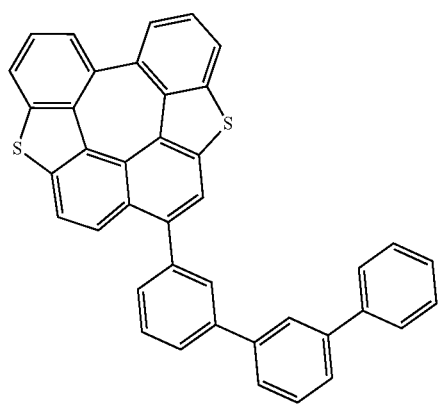
C1-103

-continued
C1-104
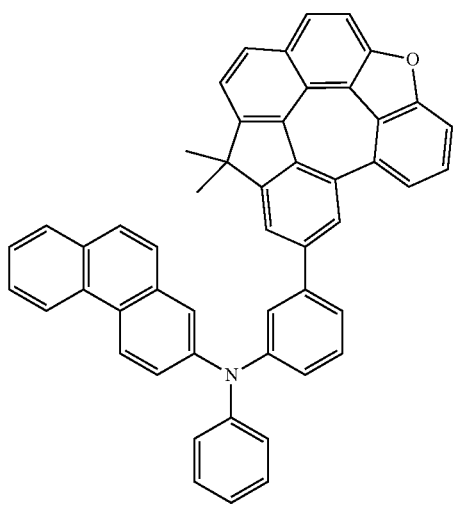
C1-105
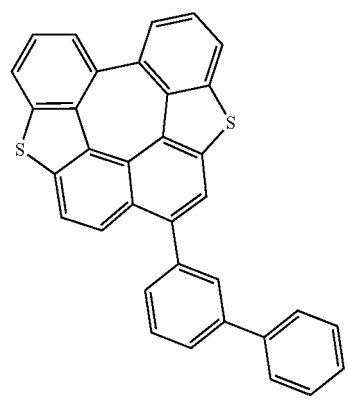
C1-106
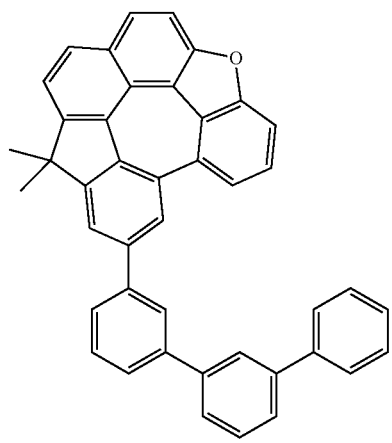
-continued
C1-107
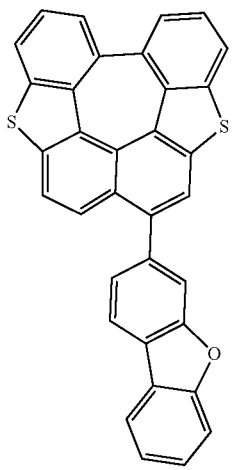
C1-108
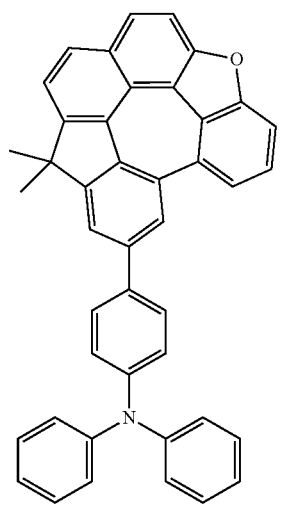
C1-109
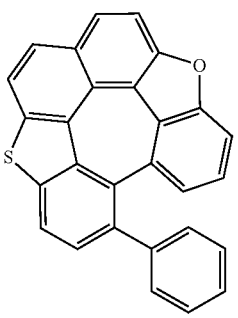

C1-110
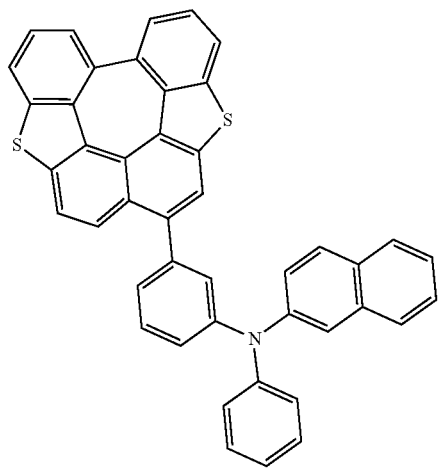
C1-111
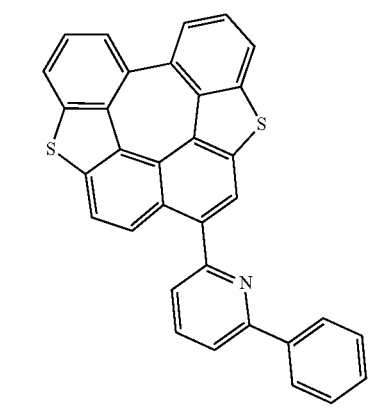
C1-112
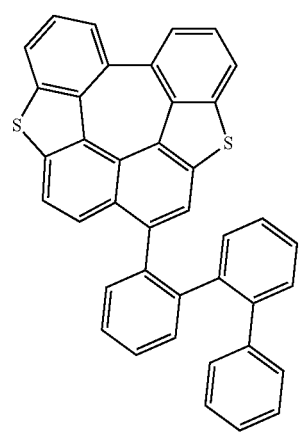
C1-113
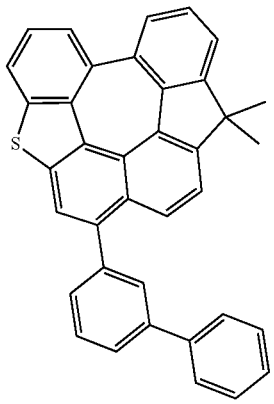
C1-114
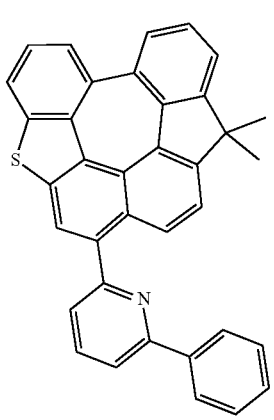
C1-115
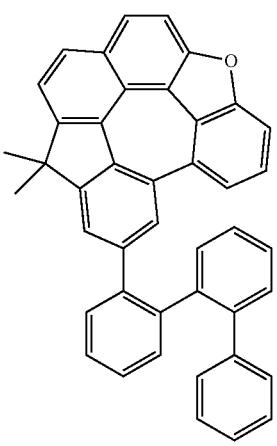

C1-116
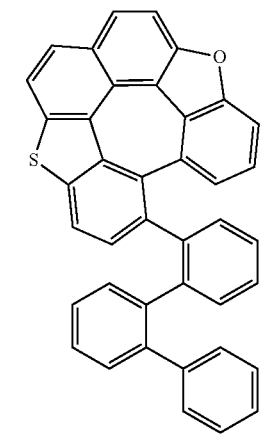
C1-117
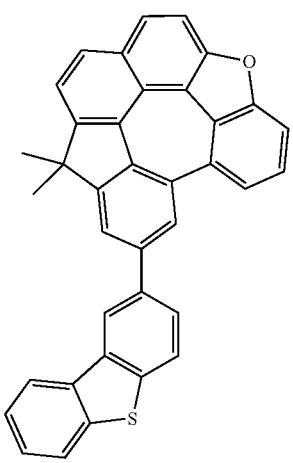
C1-118
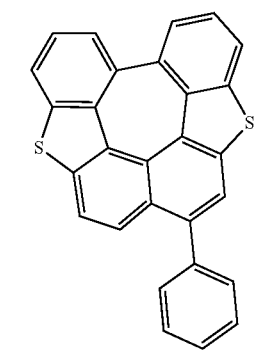
C1-119
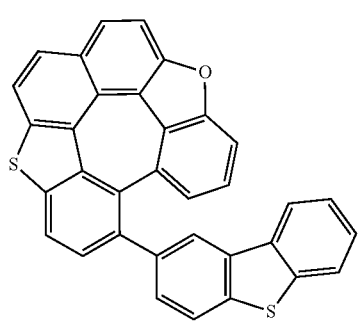
C1-120
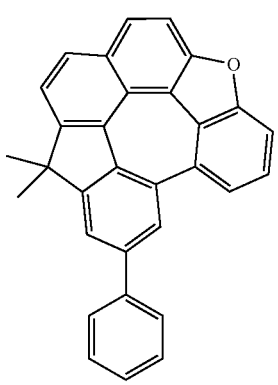
H-1
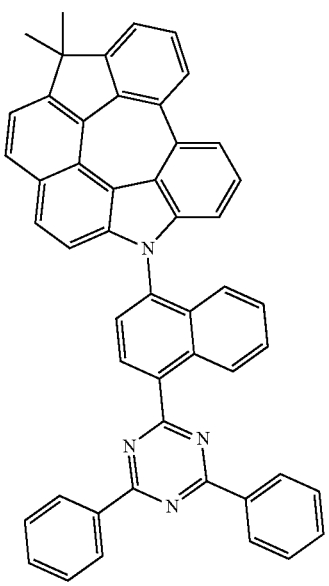
H-2
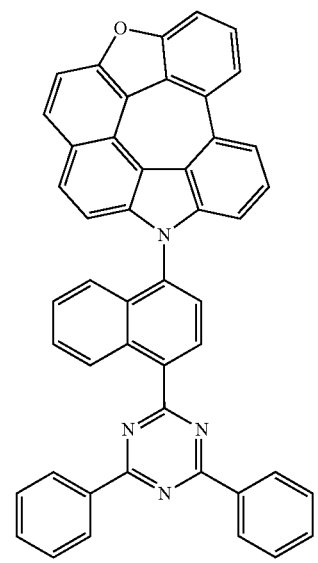

H-3
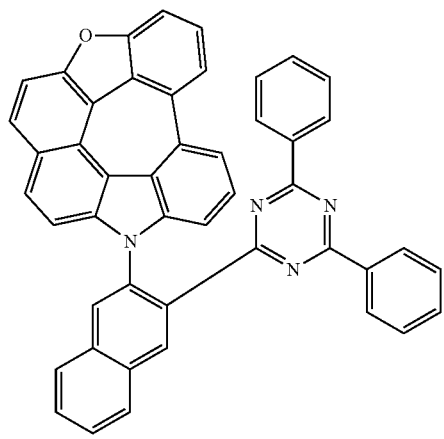
H-4
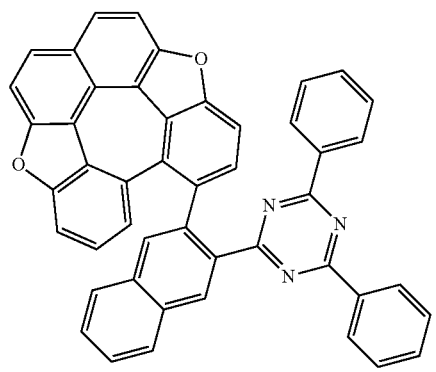
H-5
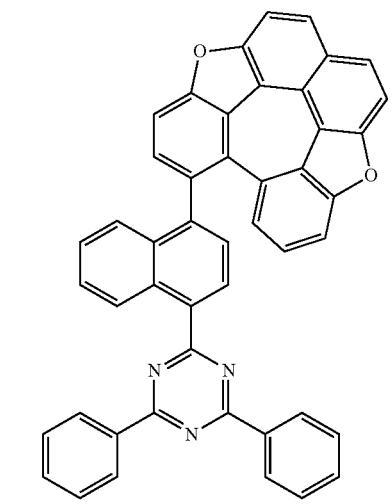
H-6
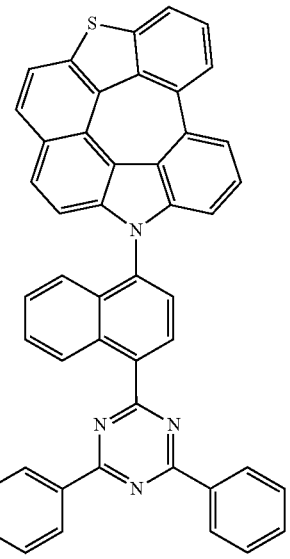
H-7
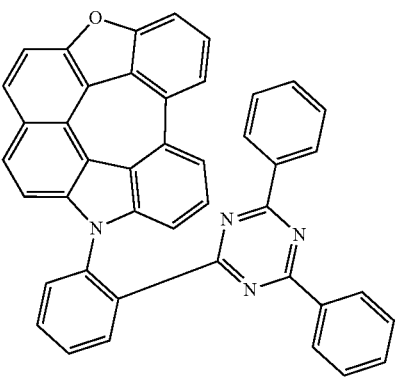
H-8
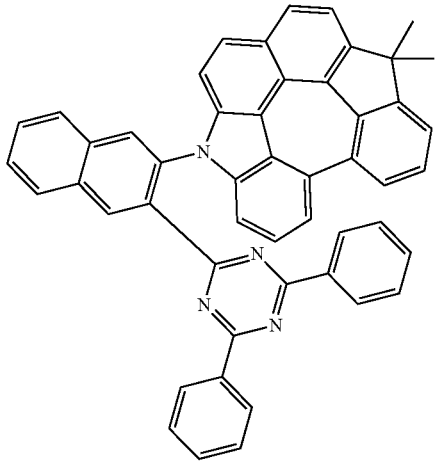

H-9
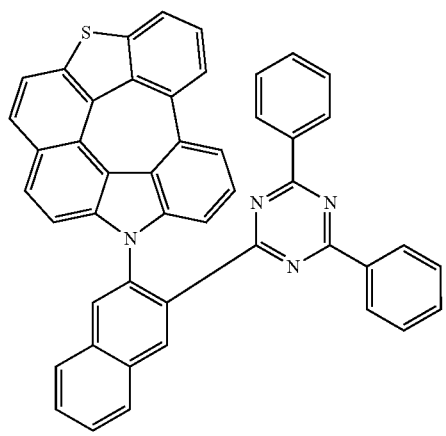
H-10
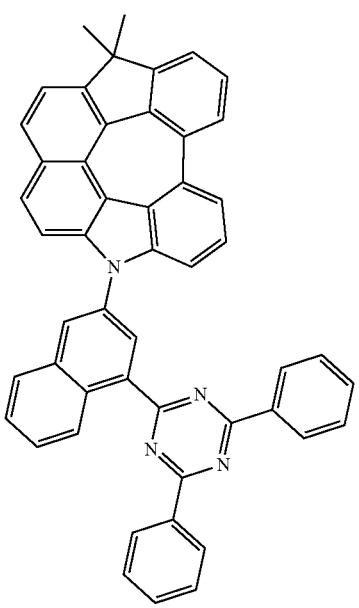
H-11
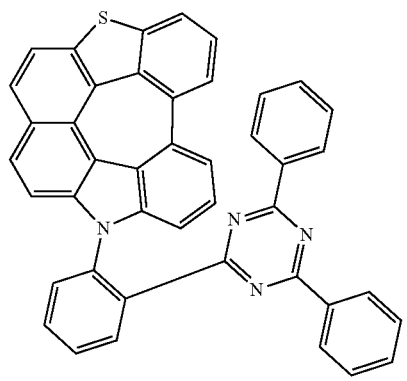
H-12
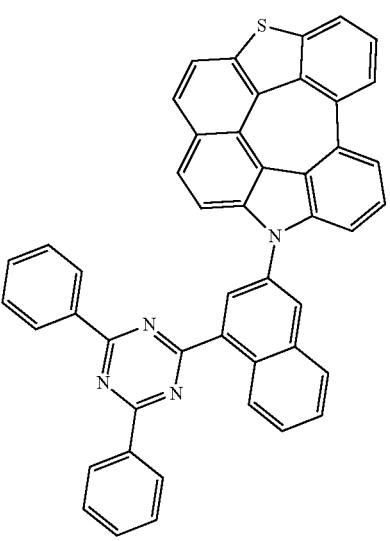
H-13
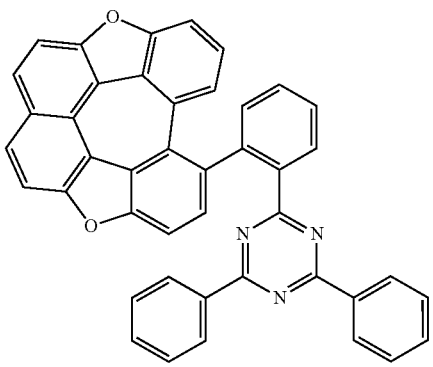
H-14
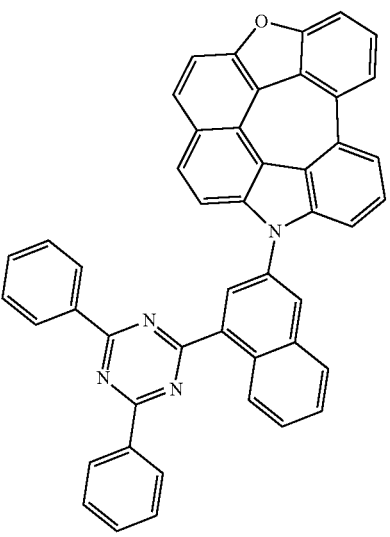

H-15
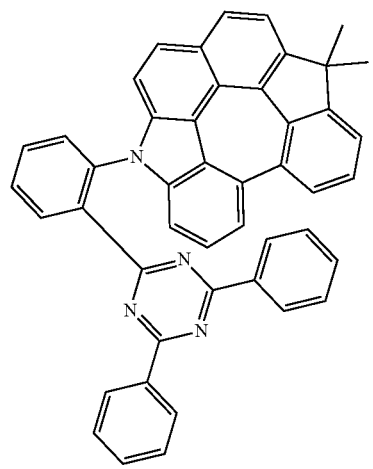
H-16
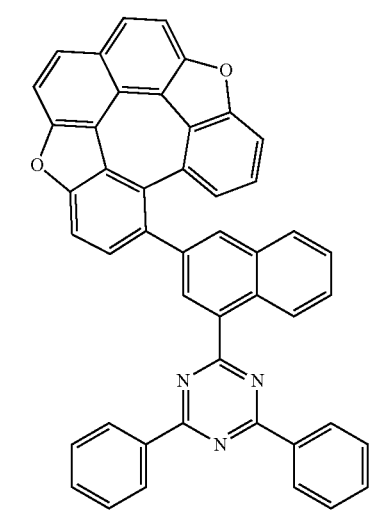
H-17
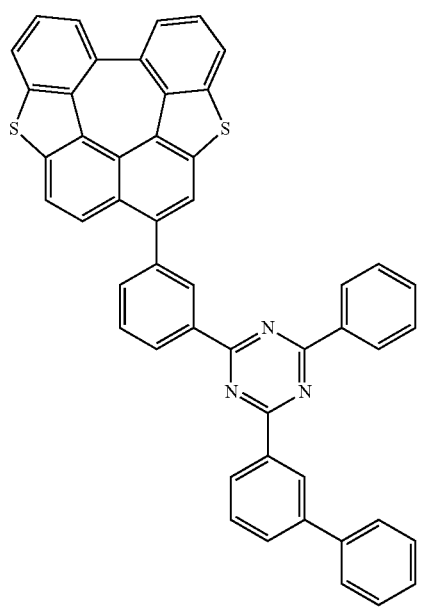
H-18
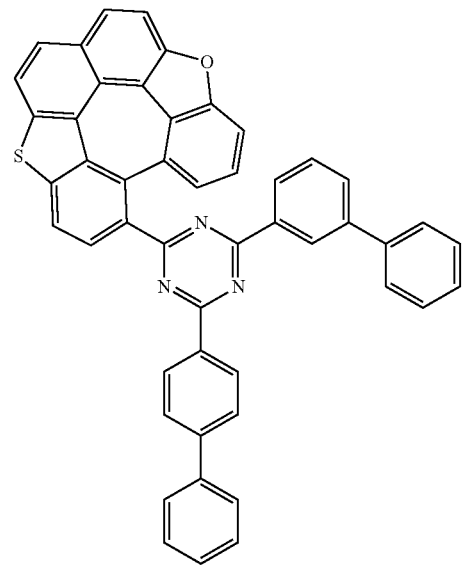
H-19
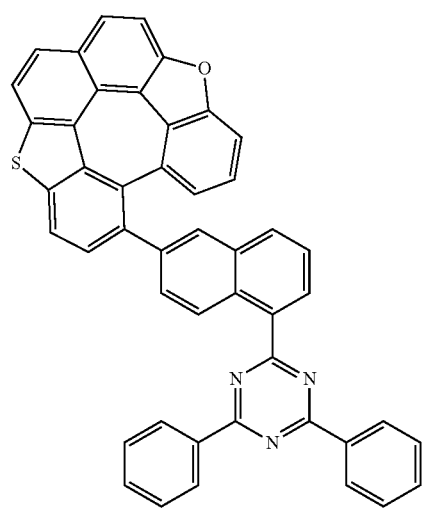
H-20
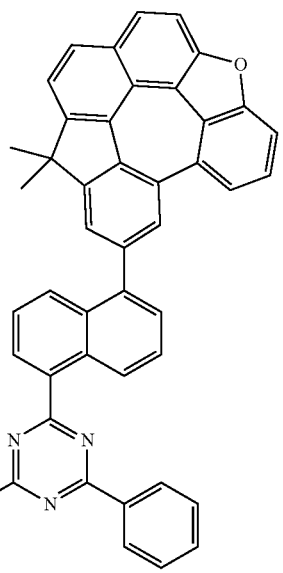

H-21
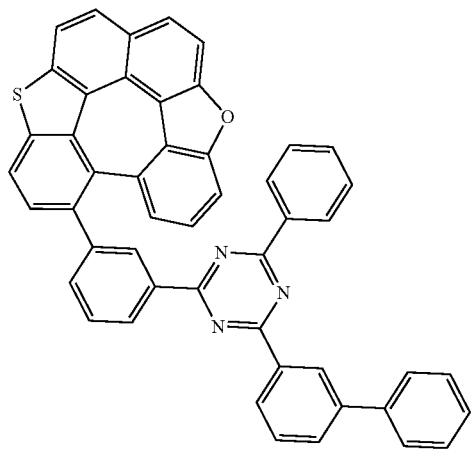
H-22
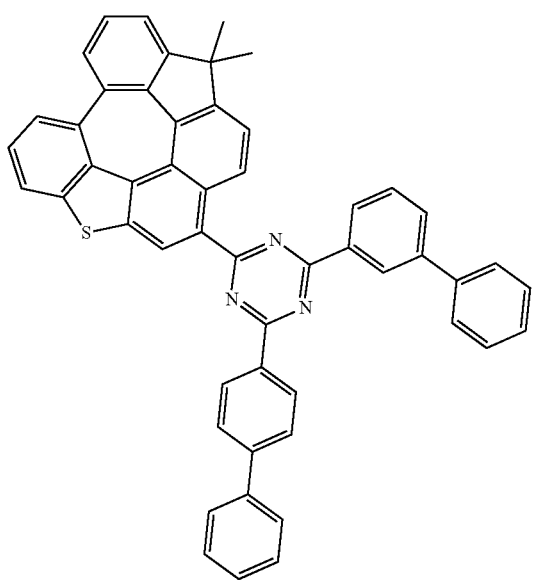
H-23
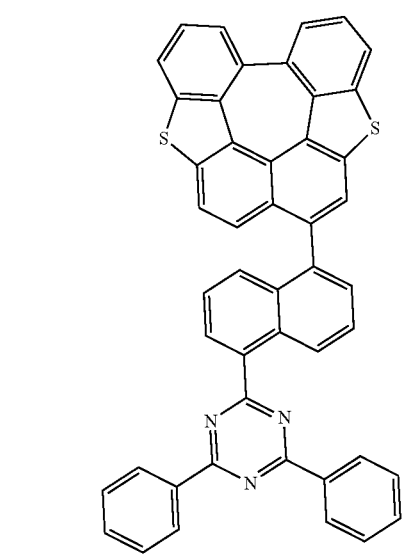
H-24
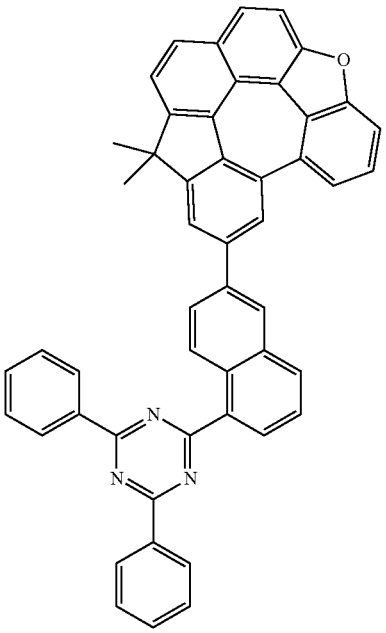
H-25
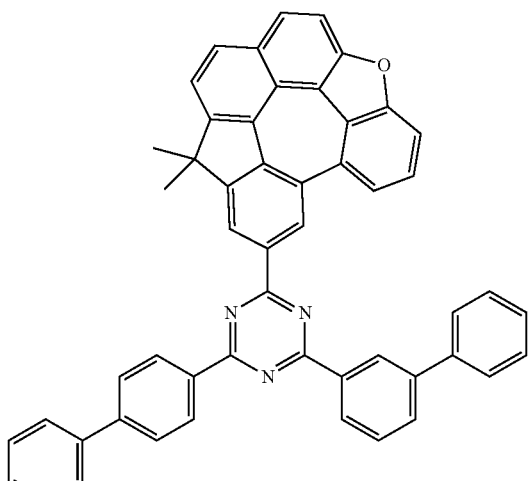
H-26
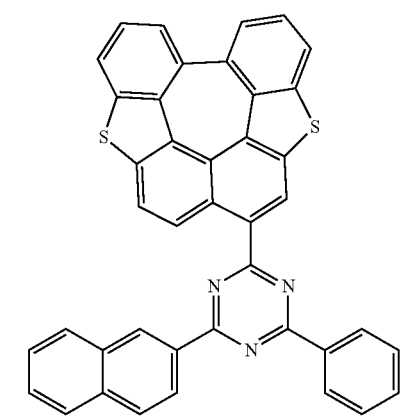

H-27
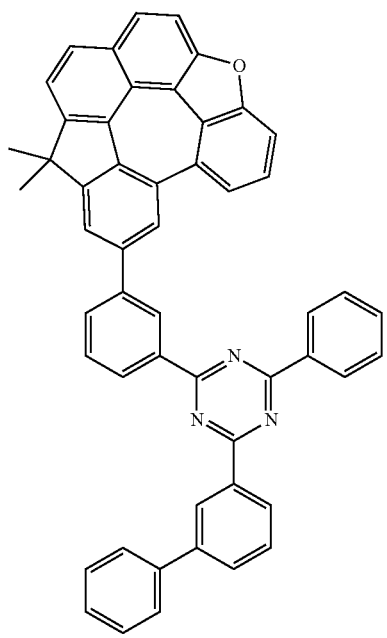
H-28
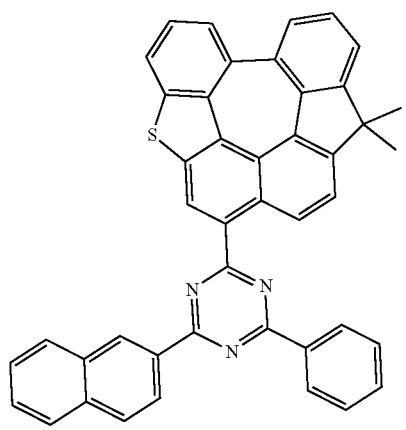
H-29
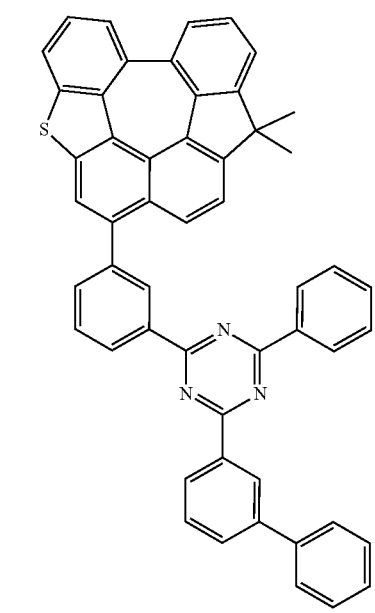
H-30
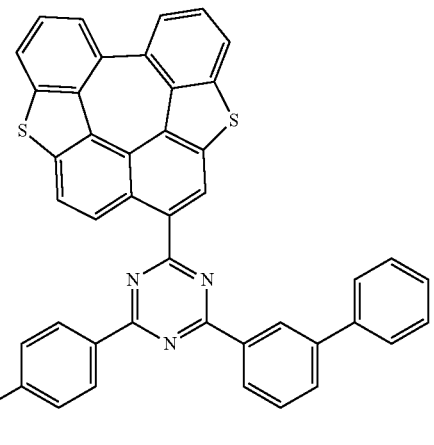
H-31
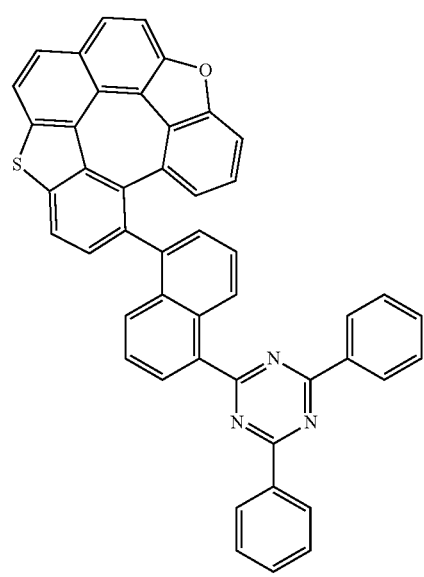
H-32
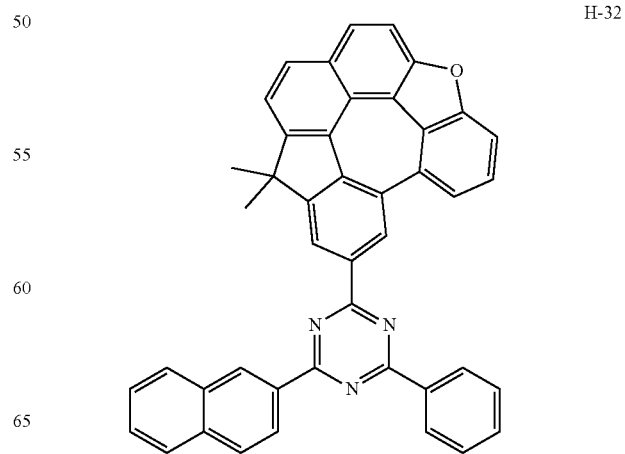

H-33

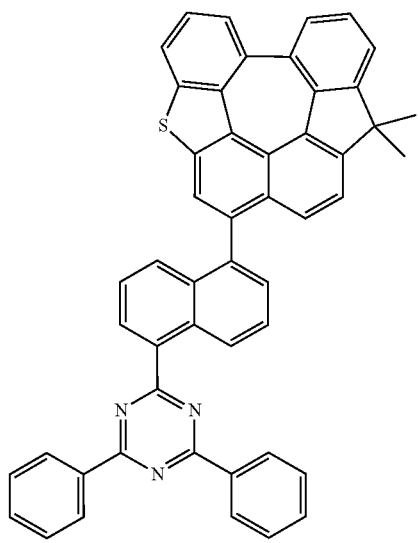

H-34

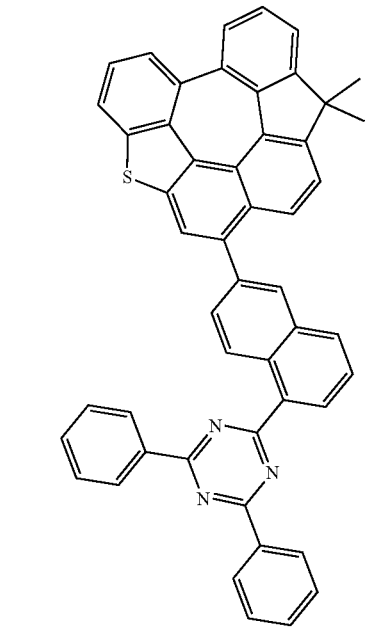

H-35

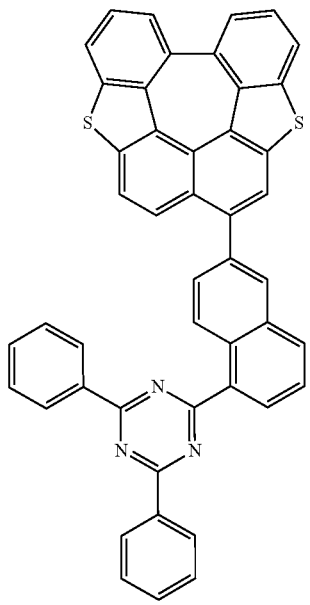

H-36

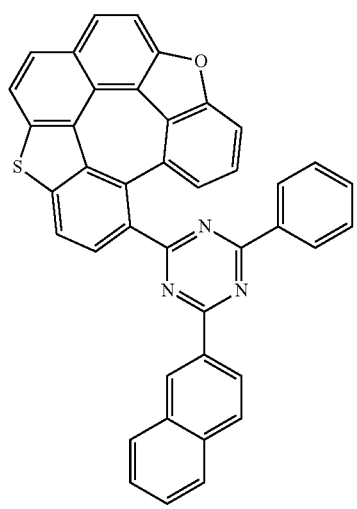

Hereinafter, an organic electroluminescent device to which the aforementioned plurality of host materials and/or the organic electroluminescent compound is(are) applied will be described.

The organic electroluminescent device according to one embodiment includes a first electrode; a second electrode; and at least one organic layer(s) interposed between the first electrode and the second electrode. The organic layer may include a light-emitting layer, and the light-emitting layer may comprise a plurality of host materials comprising a first host material comprising at least one compound represented by formula 1 above and a second host material comprising at least one compound represented by formula 2 above. According to another embodiment of the present disclosure, the organic electroluminescent device according to the present disclosure includes a first electrode; a second electrode; and at least one light-emitting layer(s) interposed between the first electrode and the second electrode and the at least one light-emitting layer(s) may include a compound represented by formula 1-1-1 above.

According to one embodiment, the organic electroluminescent material of the present disclosure includes at least one of compounds C1-1 to C1-120 as the first host material represented by formula 1 and at least one of compounds C2-1 to C2-275 as the second host material represented by formula 2. The plurality of host materials may be included in the same organic layer, e.g., a light-emitting layer, or may be included in different light-emitting layers, respectively. According to another embodiment, the organic electroluminescent material of the present disclosure includes at least one of compounds C1-1 to C1-120 and H-1 to H-36 represented by formula 1-1-1 alone or in combination of two or more, and the organic electroluminescent material may be included in an organic layer, e.g., a light-emitting layer, of an organic electroluminescent device.

The organic layer may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer, in addition to a light-emitting layer. The organic layer may further comprise an amine-based compound and/or an azine-based compound, in addition to the light-emitting material of the present disclosure. Specifically, the hole injection layer, the hole transport layer, the hole auxiliary layer, the light-emitting layer, the light-emitting auxiliary layer, or the electron blocking layer may comprise an amine-based compound, for example, arylamine-based compound, a styrylarylamine-based compound, etc., as a hole injection material, a hole transport material, a hole auxiliary material, a light-emitting material, a light-emitting auxiliary material, or an electron blocking material. In addition, the electron transport layer, the electron injection layer, the electron buffer layer, and the hole blocking layer may comprise an azine-based compound as an electron transport material, an electron injection material, an electron buffer material, and a hole blocking material. In addition, the organic layer further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising such a metal.

The plurality of host materials according to one embodiment may be used as light-emitting materials for a white organic light-emitting device. The white organic electroluminescent device has suggested various structures such as a parallel side-by-side arrangement method, a stacking arrangement method, or color conversion material (CCM) method, etc., according to the arrangement of R (Red), G (Green), YG (yellowish green), or B (Blue) light-emitting units. In addition, the organic electroluminescent material according to one embodiment may also be applied to the organic electroluminescent device comprising a QD (quantum dot).

One of the first electrode and the second electrode may be an anode and the other may be a cathode. Wherein, the first electrode and the second electrode may each be formed as a transmissive conductive material, a transflective conductive material, or a reflective conductive material. The organic electroluminescent device may be a top emission type, a bottom emission type, or a both-sides emission type according to the kinds of the material forming the first electrode and the second electrode.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. In addition, the hole injection layer may be doped as a p-dopant. Also, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, and wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer may be placed between the electron transport layer (or electron injection layer) and the light-emitting layer, and blocks the arrival of holes to the cathode, thereby improving the probability of recombination of electrons and holes in the light-emitting layer. The hole blocking layer or the electron transport layer may also be multi-layers, wherein each layer may use a plurality of compounds. Also, the electron injection layer may be doped as an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as the hole auxiliary layer or the electron blocking layer. The light-emitting auxiliary layer, the hole auxiliary layer, or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a halogenated metal layer, and a metal oxide layer may be placed on an inner surface(s) of one or both electrode(s). Specifically, a chalcogenide (including oxides) layer of silicon and aluminum is preferably placed on an anode surface of an electroluminescent medium layer, and a halogenated metal layer or a metal oxide layer is preferably placed on a cathode surface of an electroluminescent medium layer. The operation stability for the organic electroluminescent device may be obtained by the surface layer. Preferably, the chalcogenide includes $SiO_x(1 \leq X \leq 2)$, $AlO_x(1 \leq X \leq 1.5)$, SiON, SiAlON, etc.; the halogenated metal includes LiF, $MgF_2$, $CaF_2$, a rare earth metal fluoride, etc.; and the metal oxide includes $CS_2O$, $Li_2O$, MgO, SrO, BaO, CaO, etc.

Further, in the organic electroluminescent device of the present disclosure, preferably, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium, Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an organic electroluminescent device having two or more light-emitting layers and emitting white light.

The organic electroluminescent device according to one embodiment may further include at least one dopant in the light-emitting layer.

The dopant comprised in the organic electroluminescent device of the present disclosure may be at least one phosphorescent or fluorescent dopant, preferably a phosphorescent dopant. The phosphorescent dopant material applied to the organic electroluminescent device of the present disclosure is not particularly limited, but may be preferably a metallated complex compound(s) of a metal atom(s) selected from iridium (Ir), osmium (Os), copper (Cu), and platinum (Pt), as necessary; more preferably an ortho-metallated complex compound(s) of a metal atom(s) selected from iridium (Ir), osmium (Os), copper (Cu), and platinum (Pt), as necessary; and even more preferably an ortho-metallated iridium complex compound(s), as necessary.

The dopant comprised in the organic electroluminescent device of the present disclosure may use the compound represented by the following formula 101, but is not limited thereto.

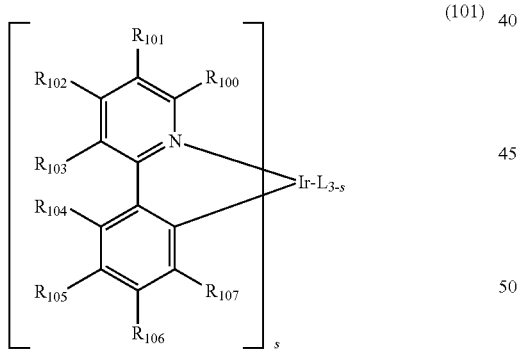

(101)

In formula 101,

L is selected from any one of the following structures 1 to 3:

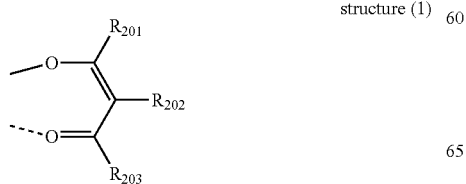

structure (1)

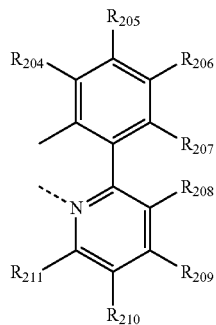

structure (2)

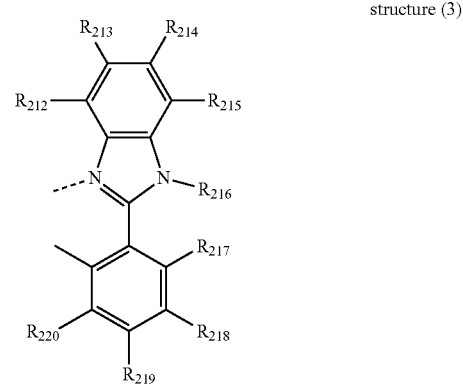

structure (3)

$R_{100}$ to $R_{103}$ each independently represent hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, cyano, a substituted or unsubstituted (3- to 30-membered)heteroaryl, or a substituted or unsubstituted (C1-C30)alkoxy; or may be linked to the adjacent substituents to form a ring(s), e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline, together with pyridine;

$R_{104}$ to $R_{107}$ each independently represent hydrogen, deuterium, halogen, (C1-C30)alkyl unsubstituted or substituted with deuterium and/or halogen, a substituted or unsubstituted (C3-C30)cycloalkyl, a substituted or unsubstituted (C6-C30)aryl, a substituted or unsubstituted (3- to 30-membered)heteroaryl, cyano, or a substituted or unsubstituted (C1-C30)alkoxy; or may be linked to the adjacent substituents to form a substituted or unsubstituted ring(s), e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted beznothienopyridine together with benzene;

$R_{201}$ to $R_{220}$ each independently represent hydrogen, deuterium, halogen, (C1-C30)alkyl unsubstituted or substituted with deuterium and/or halogen, a substituted or unsubstituted (C3-C30)cycloalkyl, or a substituted or unsubstituted (C6-C30)aryl; or may be linked to the adjacent substituents to form a substituted or unsubstituted ring(s); and s represents an integer of 1 to 3.

Specifically, the specific examples of the dopant compound include the following, but are not limited thereto.
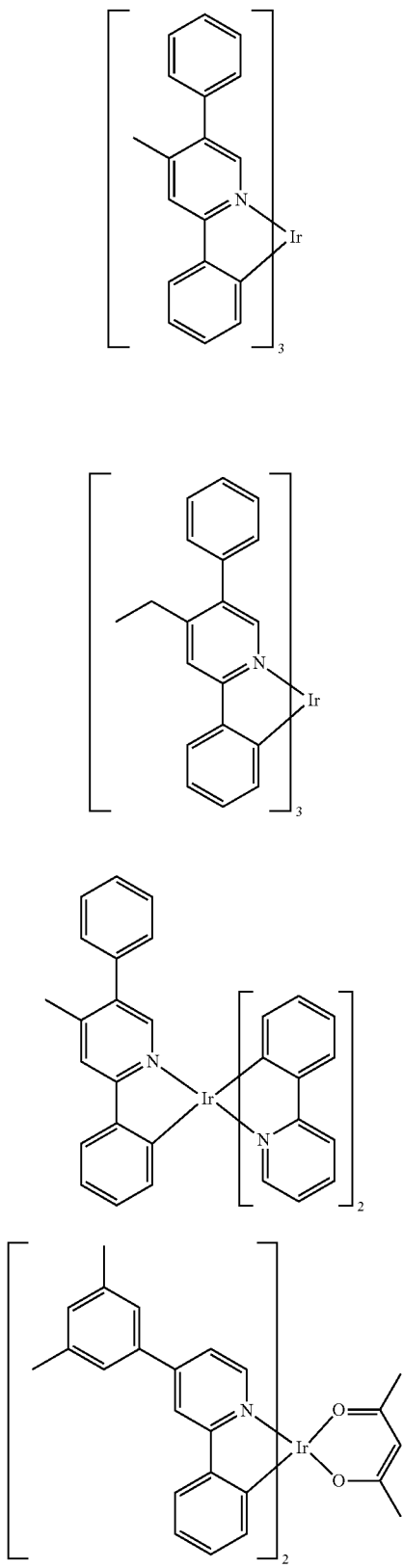
D-1
D-2
D-3
D-4
-continued
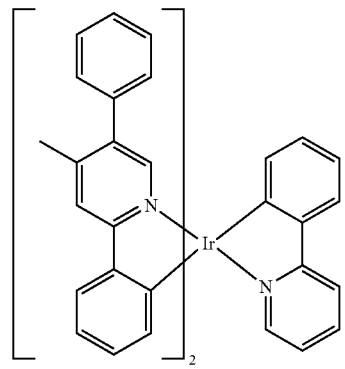
D-5
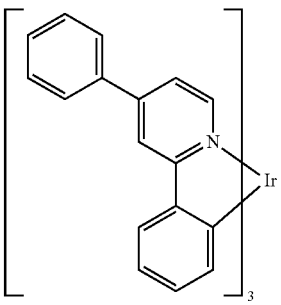
D-6
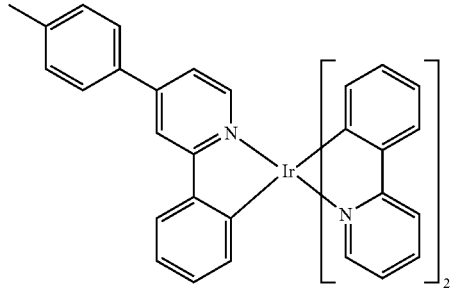
D-7
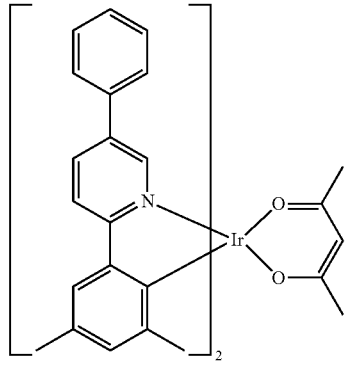
D-8

D-9
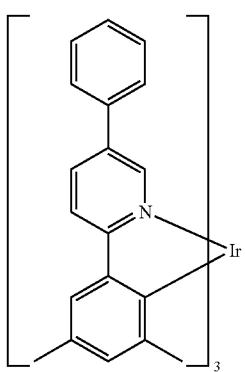
D-10
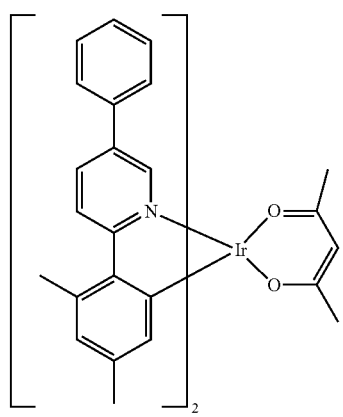
D-11
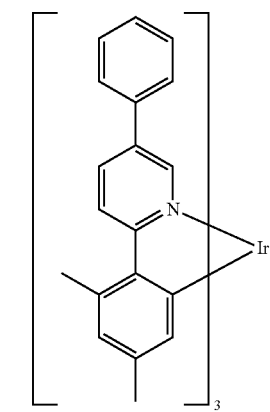
D-12
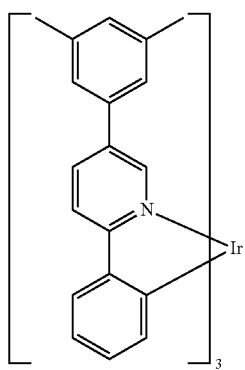
D-13
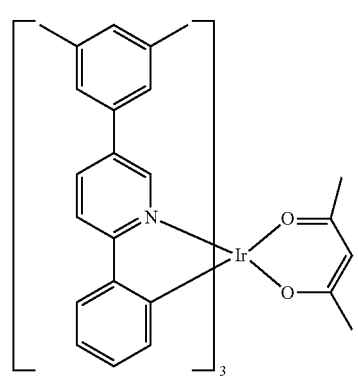
D-14
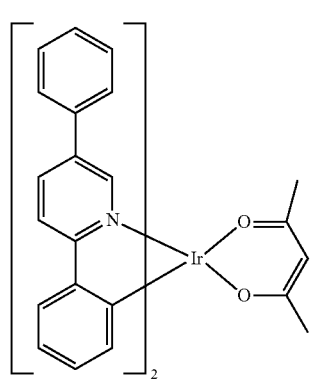
D-15
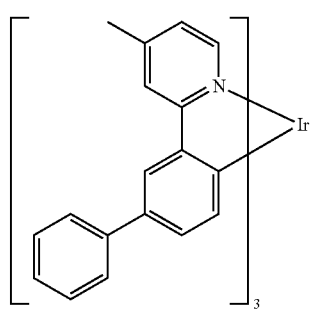
D-16

-continued
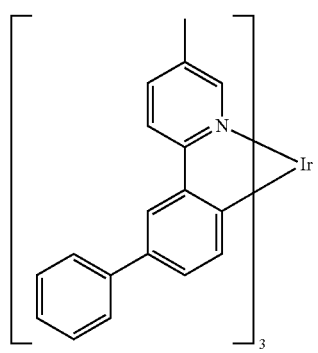
D-17
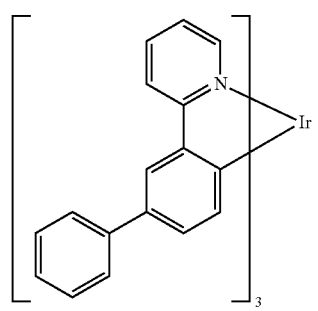
D-18
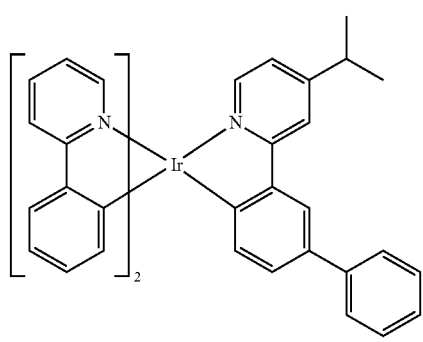
D-19
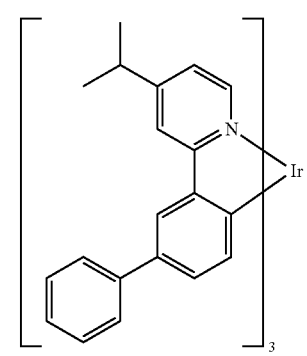
D-20
-continued
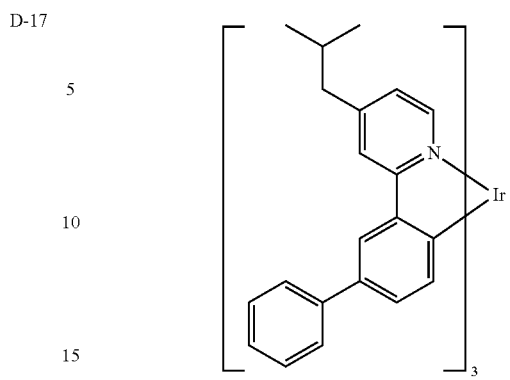
D-21
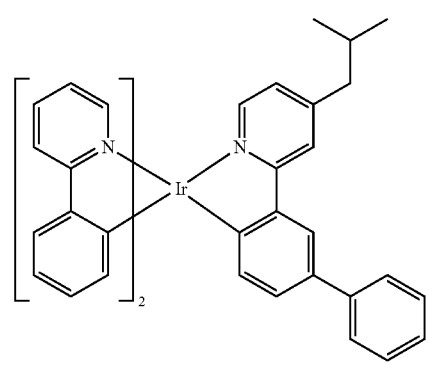
D-22
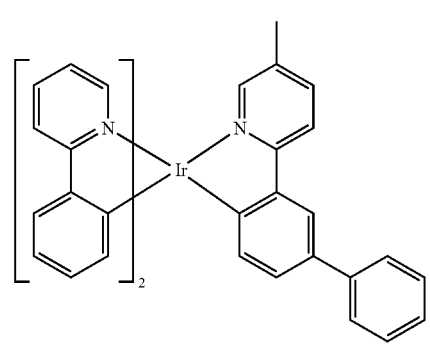
D-23
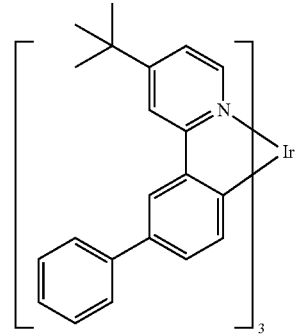
D-24

D-25
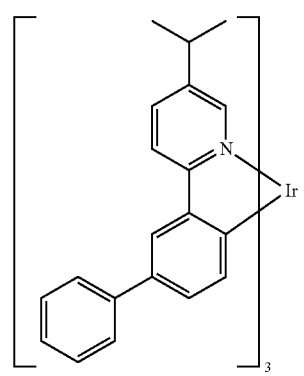
D-26
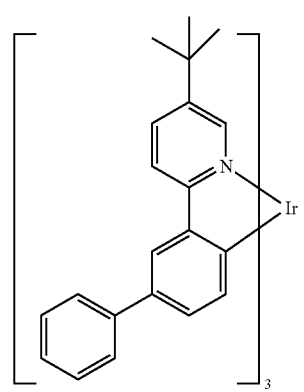
D-27
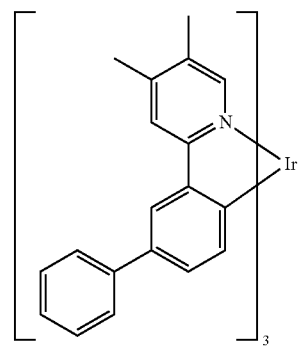
D-28
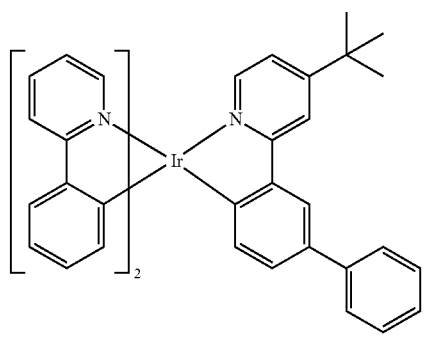
D-29
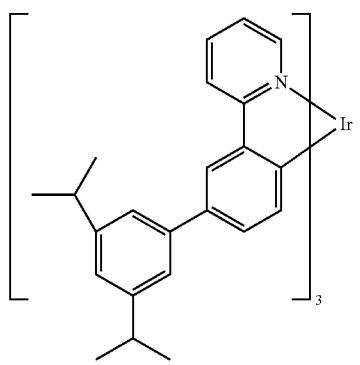
D-30
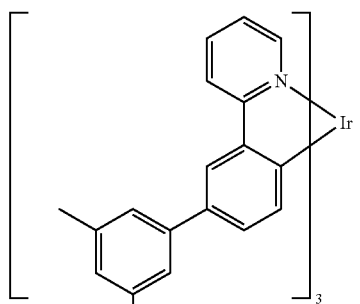
D-31
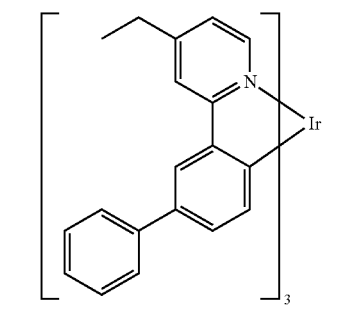
D-32
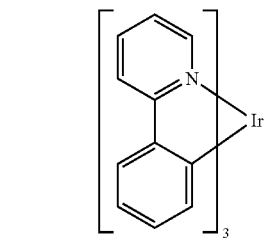
D-33
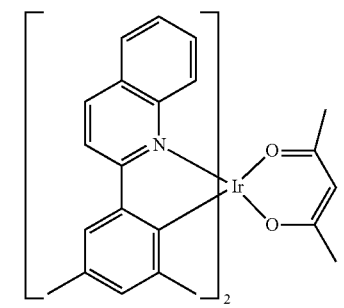

D-34
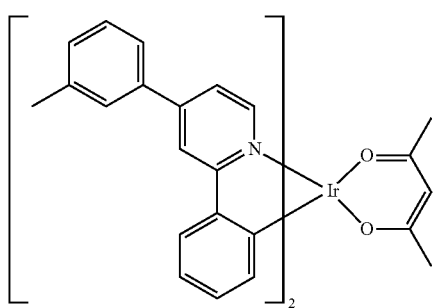
D-35
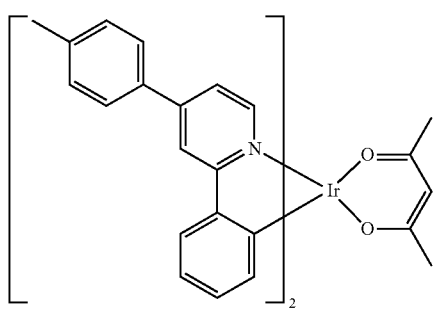
D-36
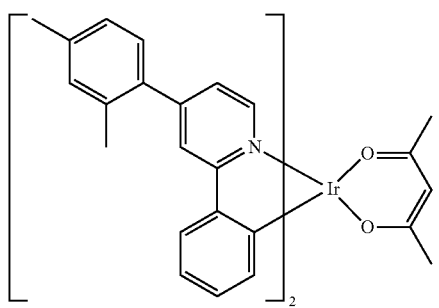
D-37
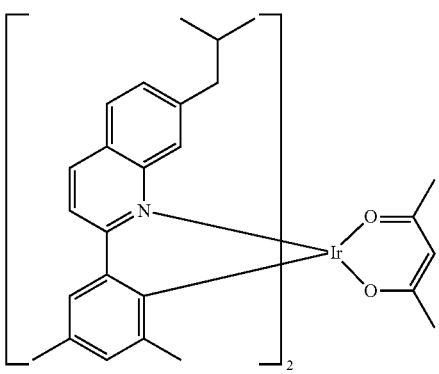
D-38
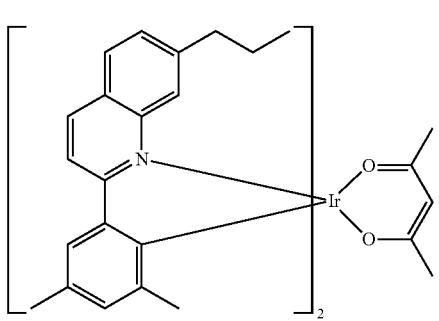
D-39
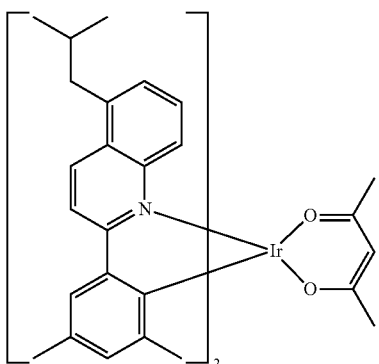
D-40
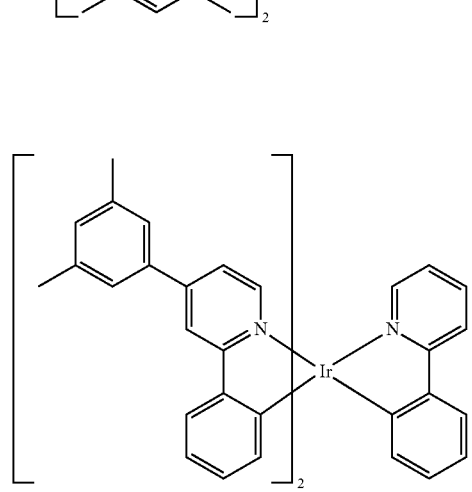
D-41
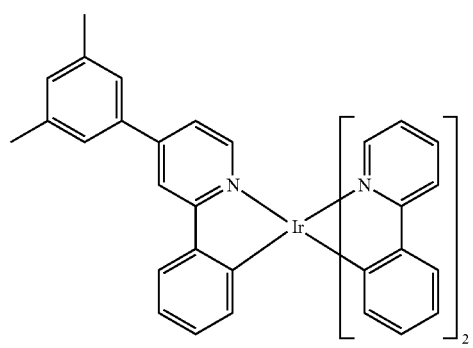
D-42
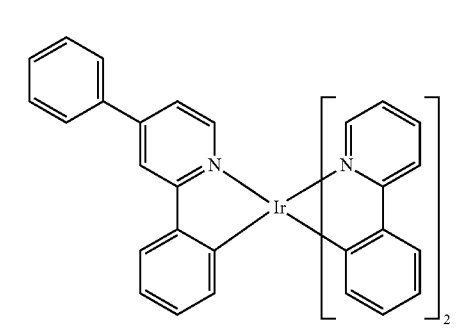

D-43
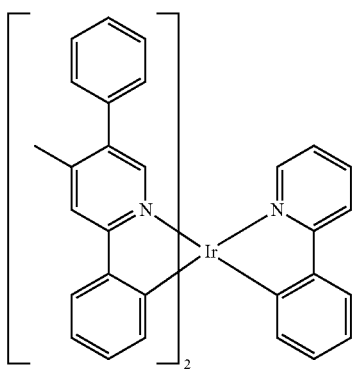
D-44
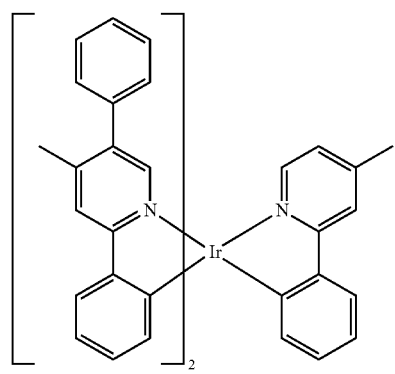
D-45
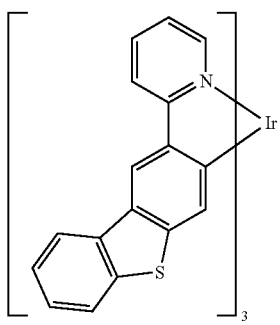
D-46
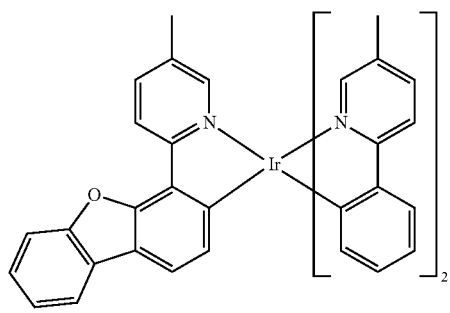
D-47
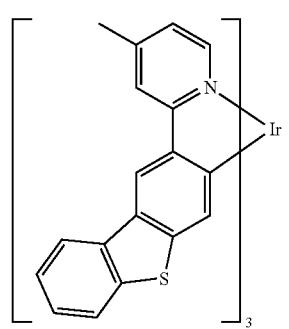
D-48
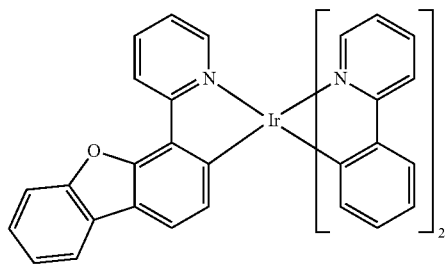
D-49
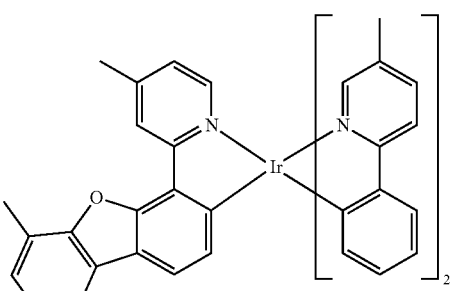
D-50
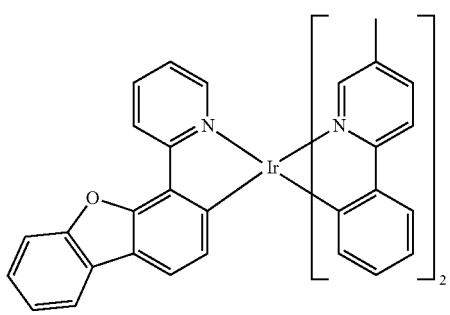
D-51
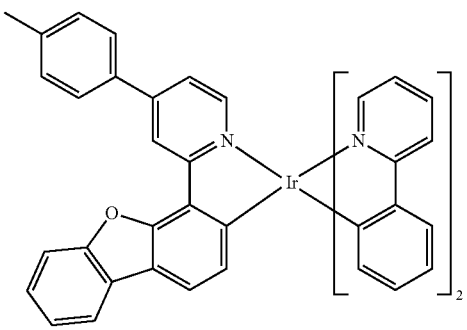

-continued
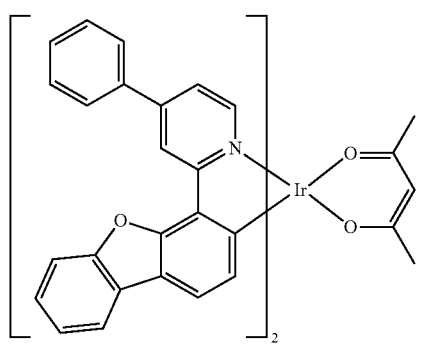
D-52
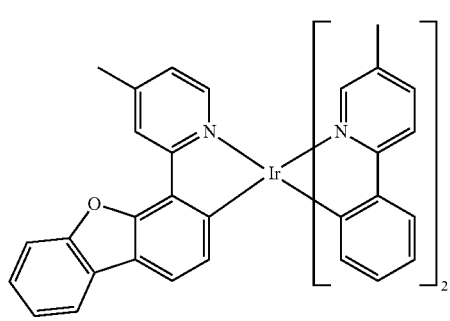
D-53
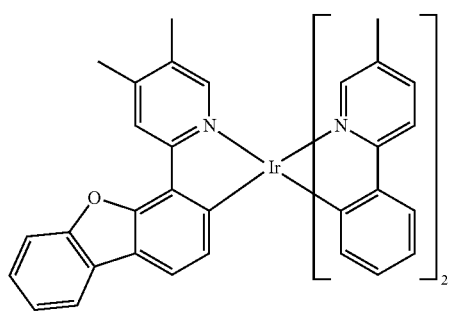
D-54
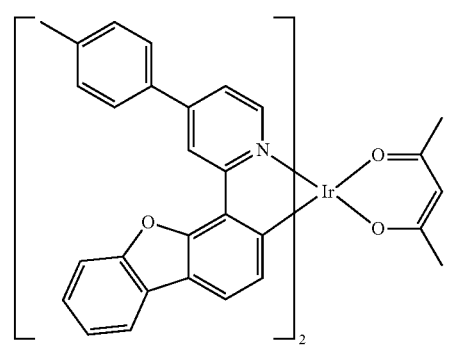
D-55
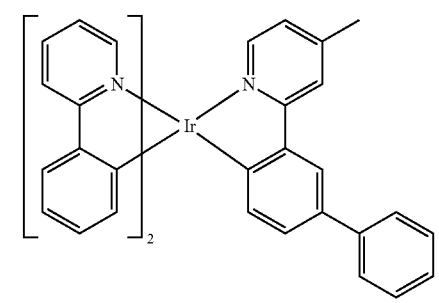
D-56
-continued
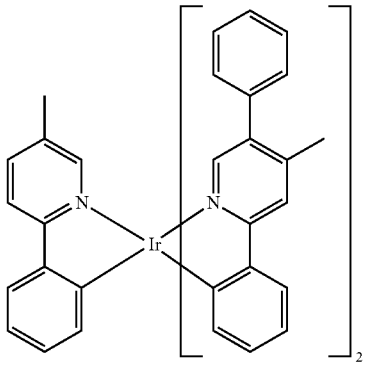
D-57
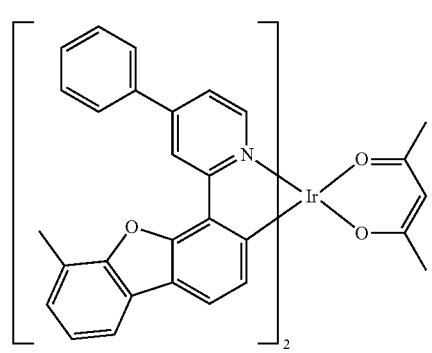
D-58
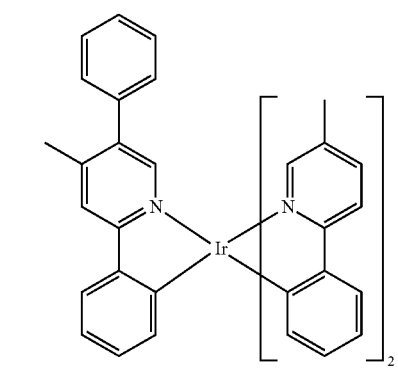
D-59
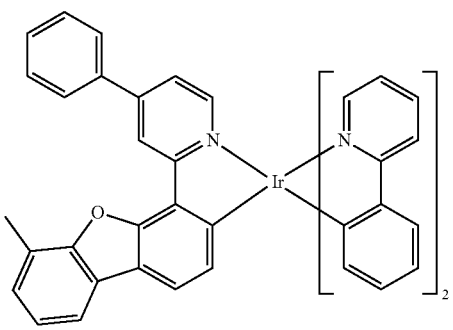
D-60

-continued
D-61
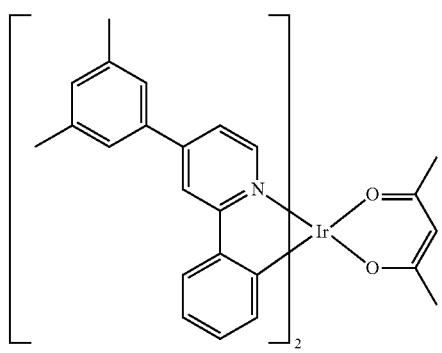
D-62
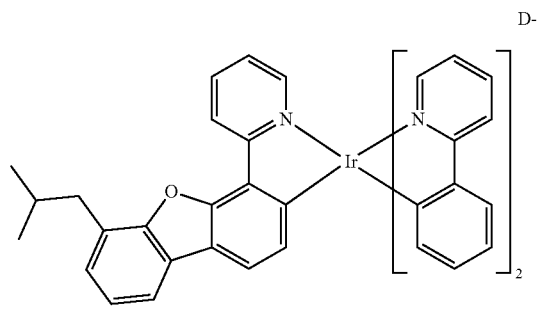
D-63
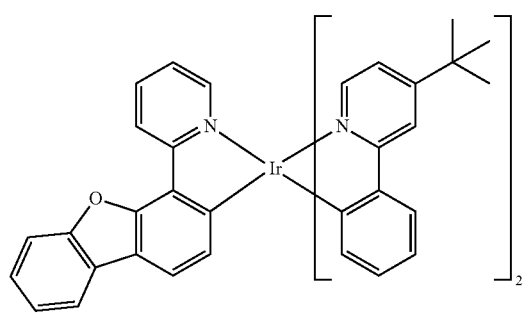
D-64
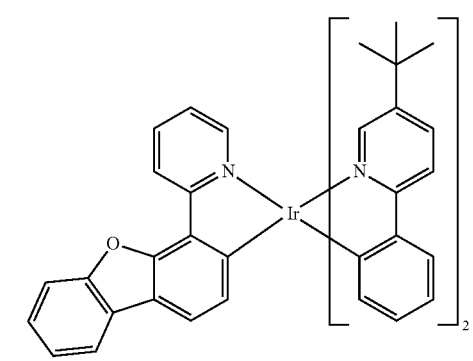
-continued
D-65
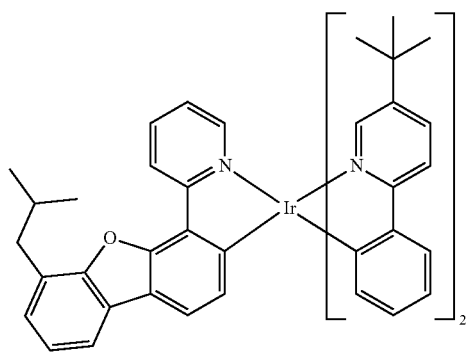
D-66
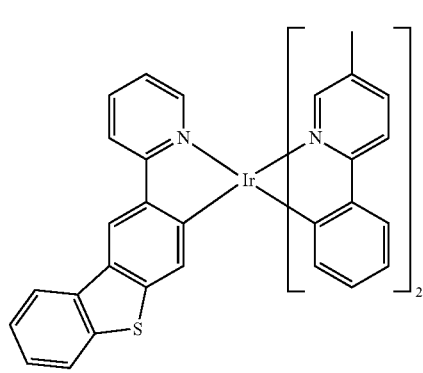
D-67
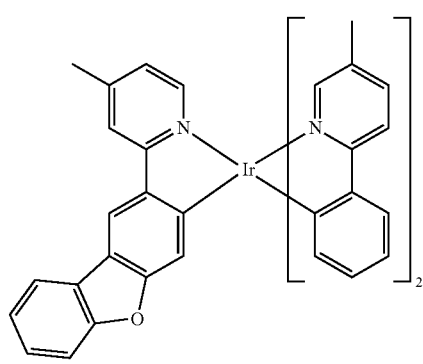
D-68
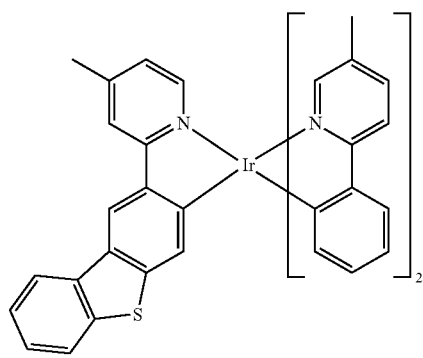

-continued
D-69
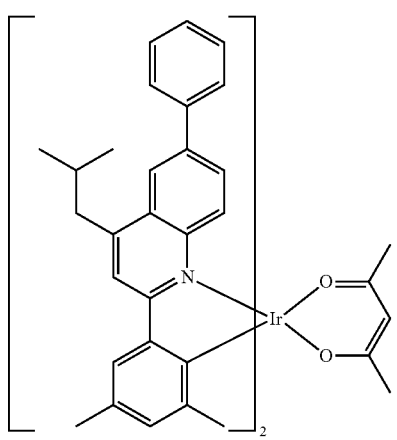
D-70
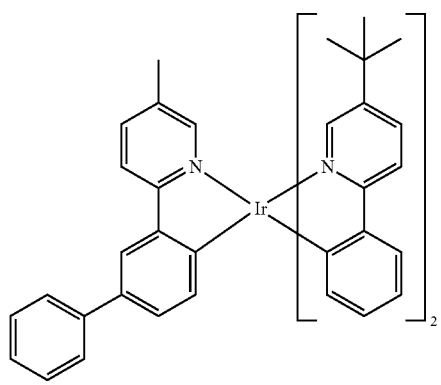
D-71
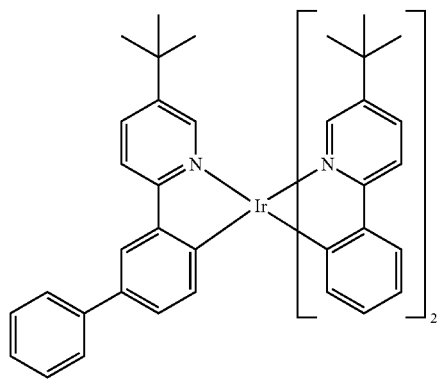
D-72
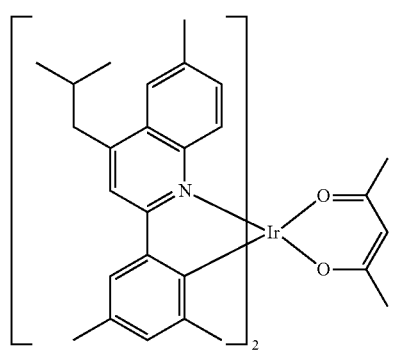
-continued
D-73
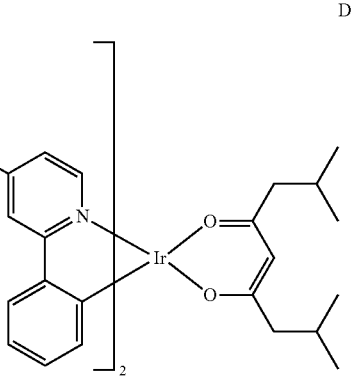
D-74
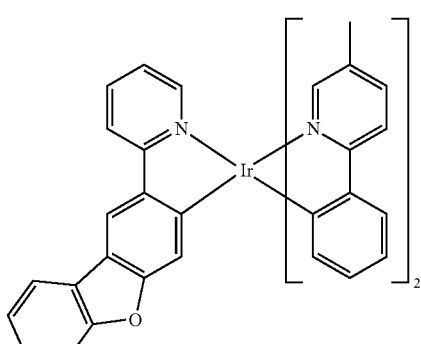
D-75
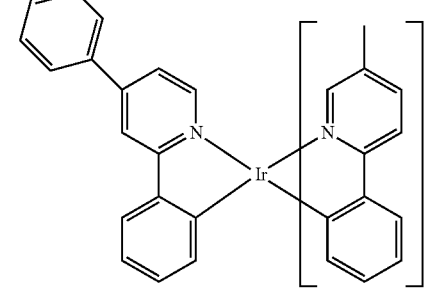
D-76
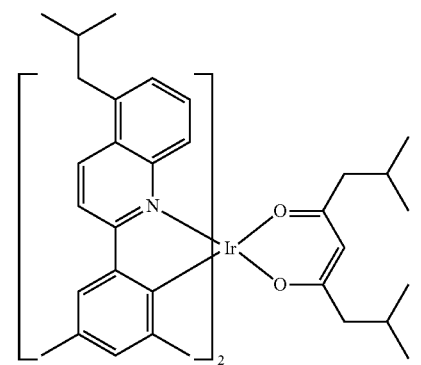

-continued
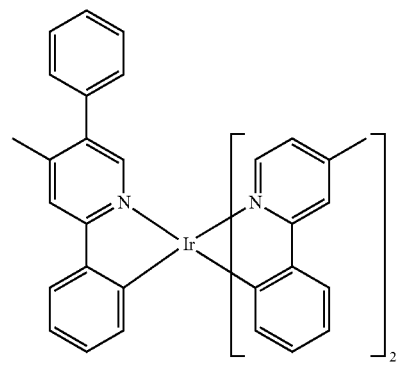
D-77
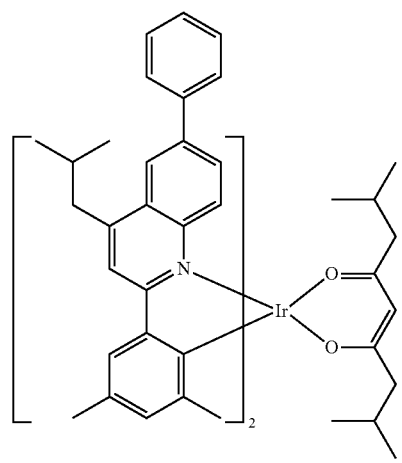
D-78
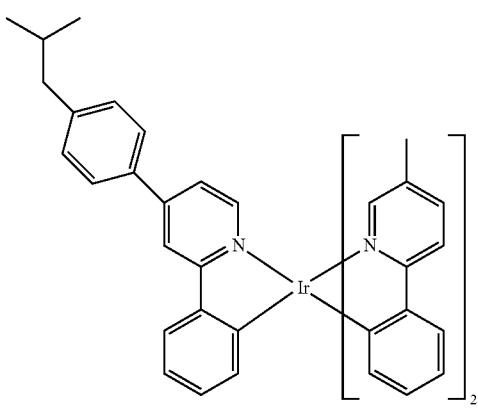
D-79
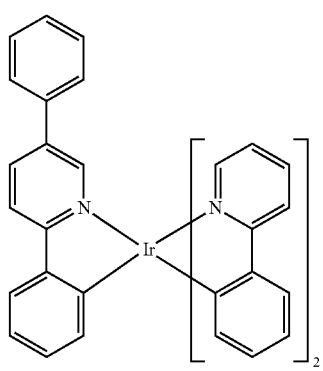
D-80
-continued
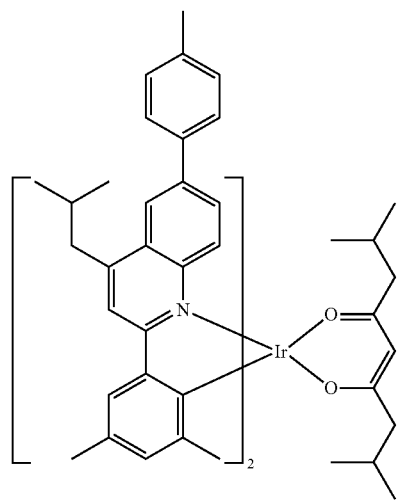
D-81
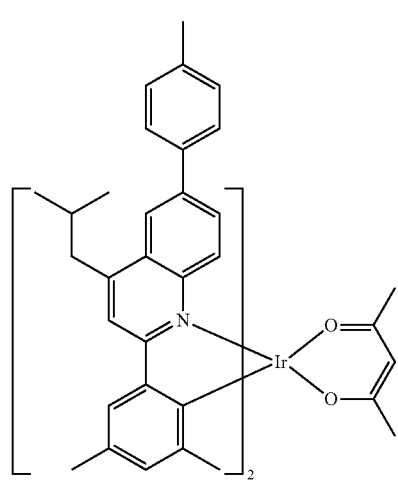
D-82
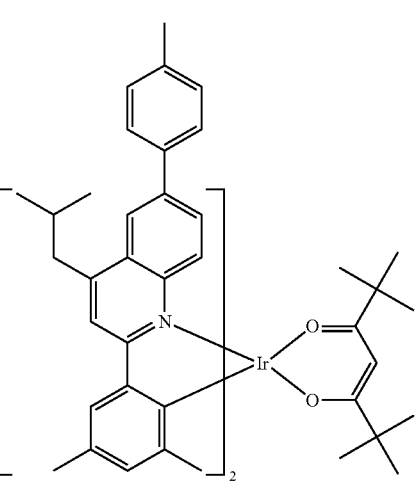
D-83

D-84
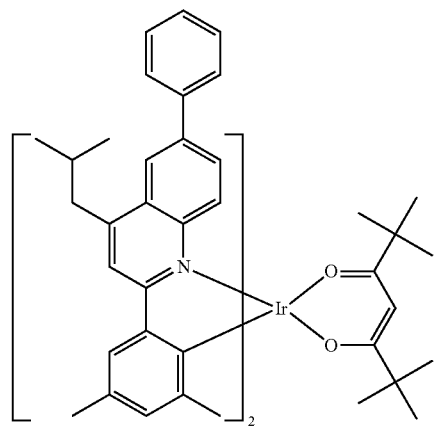
D-85
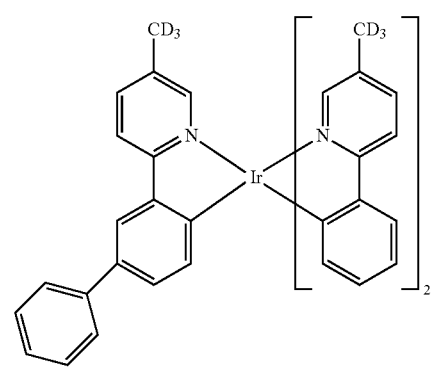
D-86
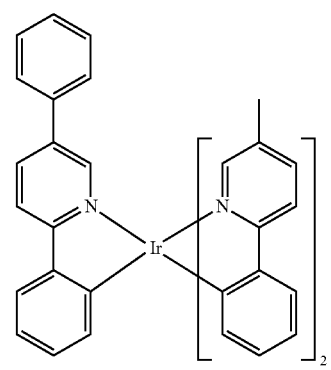
D-87
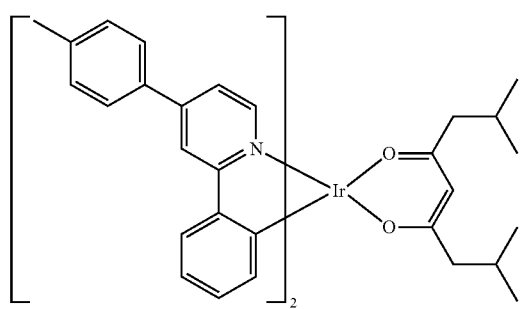
D-88
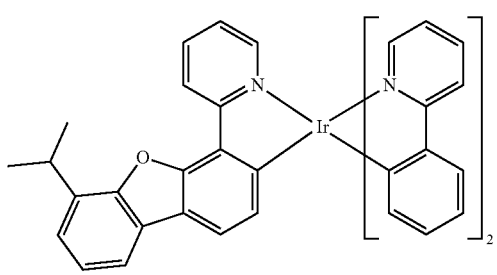
D-89
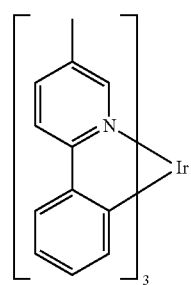
D-90
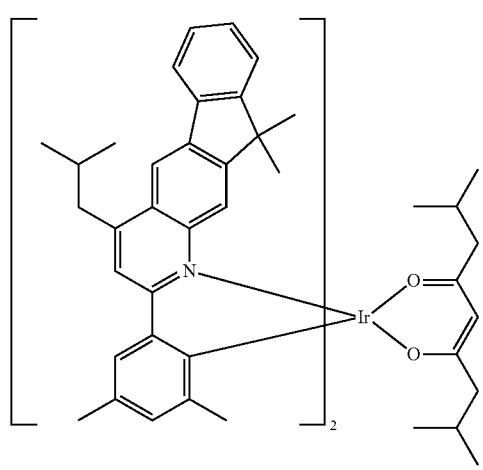
D-91
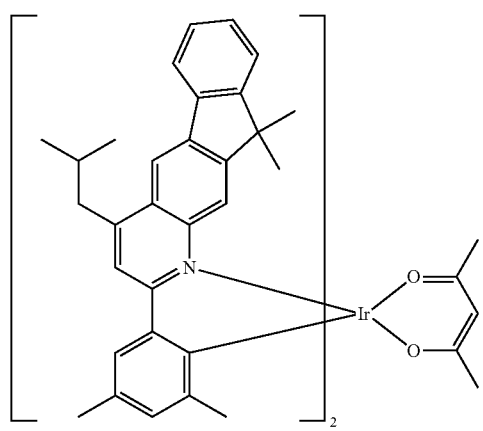

-continued
D-92
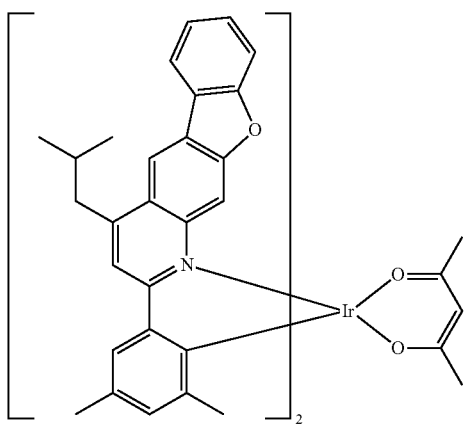
D-93
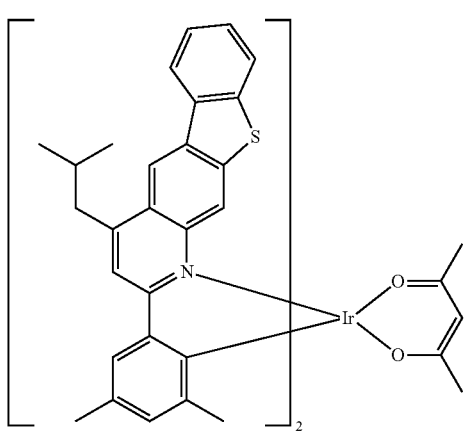
D-94
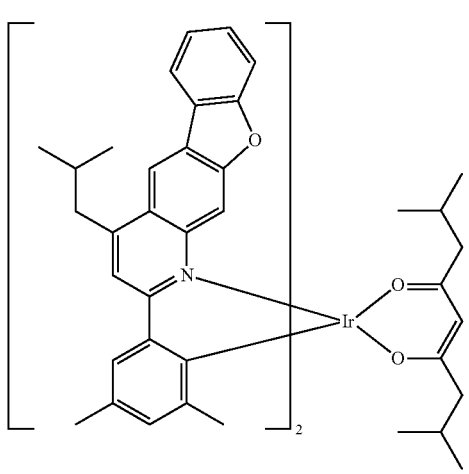
-continued
D-95
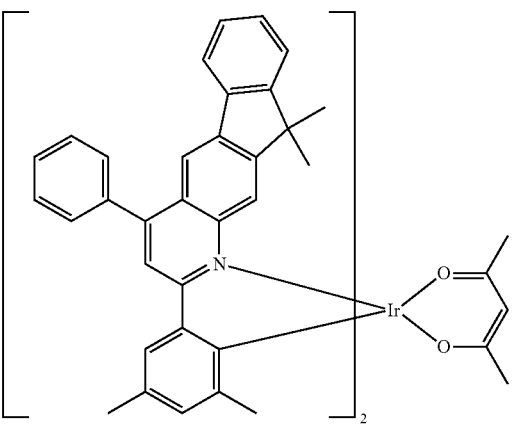
D-96
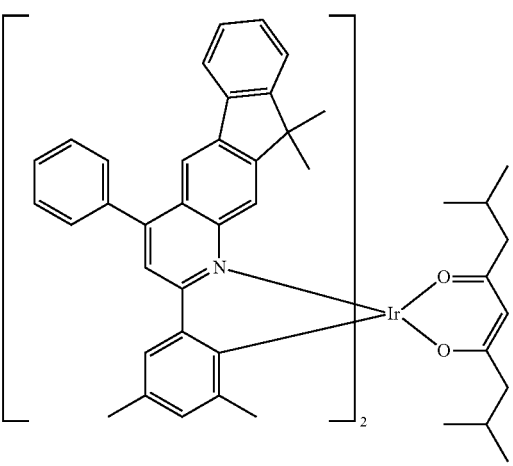
D-97
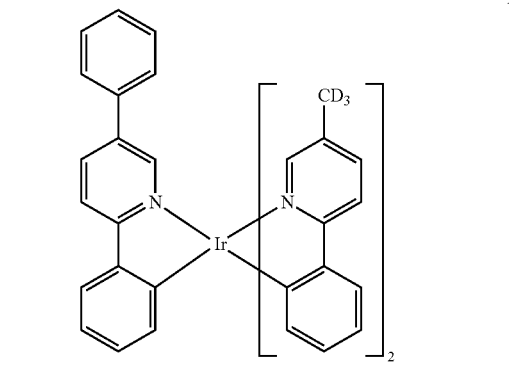
D-98
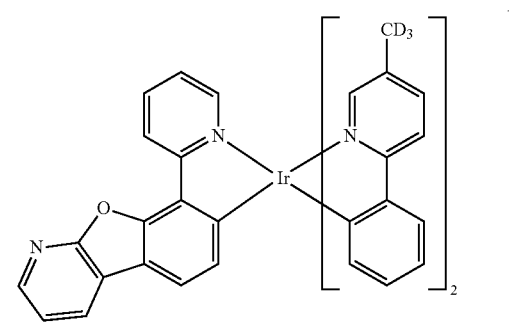

-continued
D-99
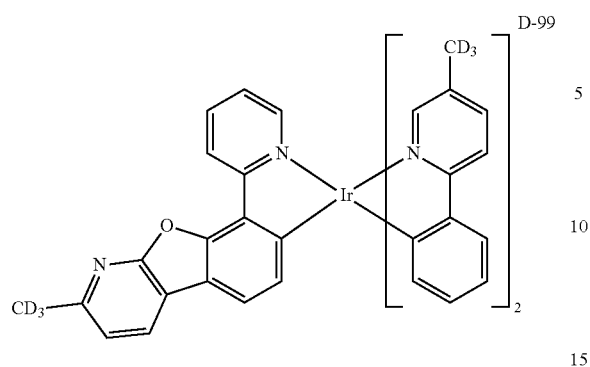
D-103
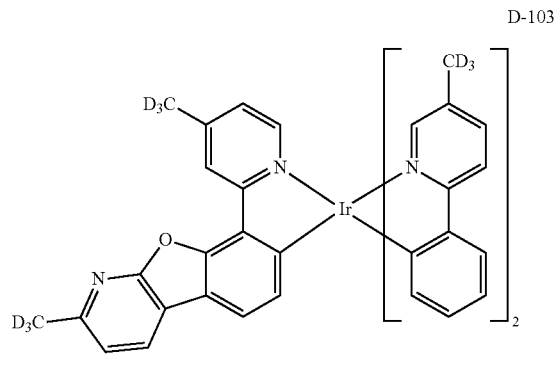
D-100
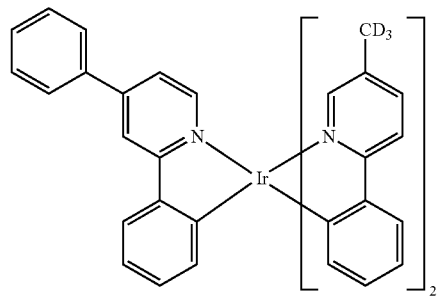
D-104
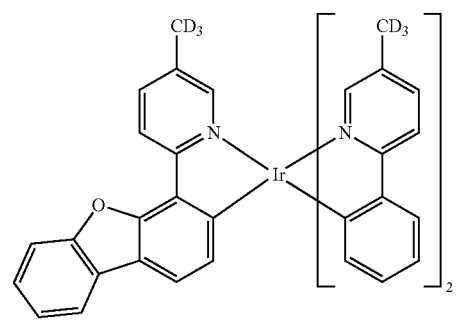
D-101
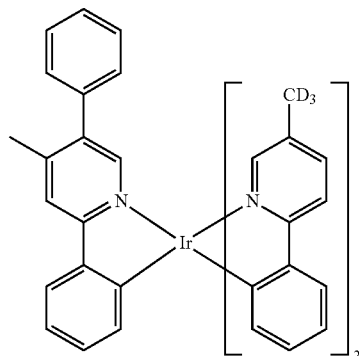
D-105
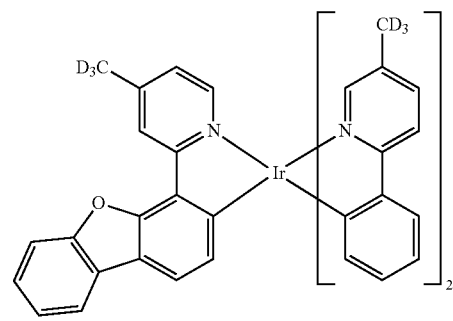
D-102
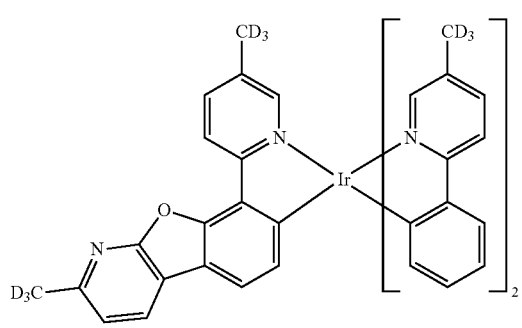
D-106
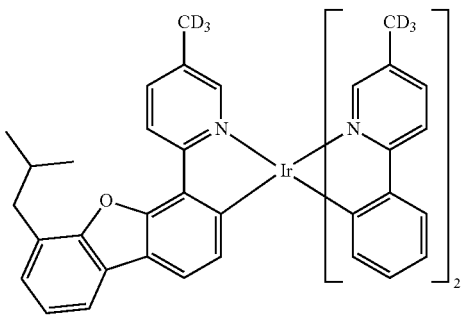

D-107
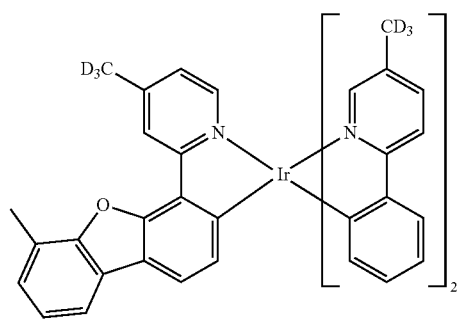
D-108
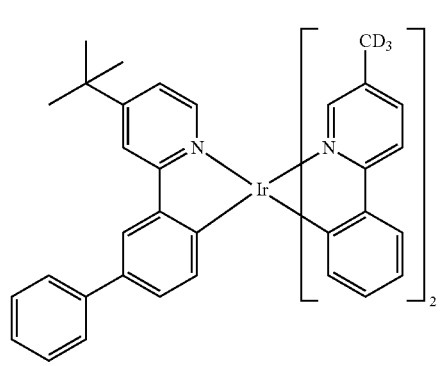
D-109
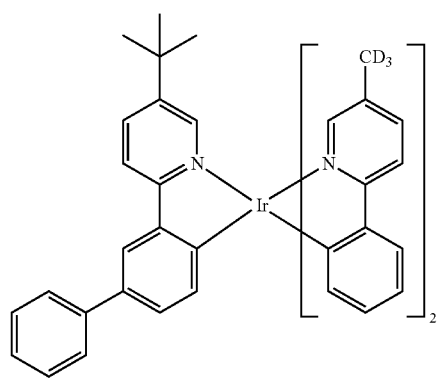
D-110
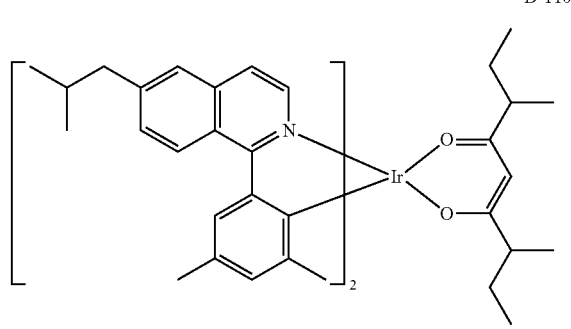
D-111
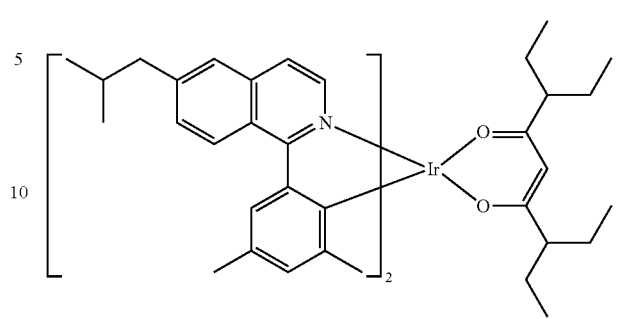
D-112
D-113
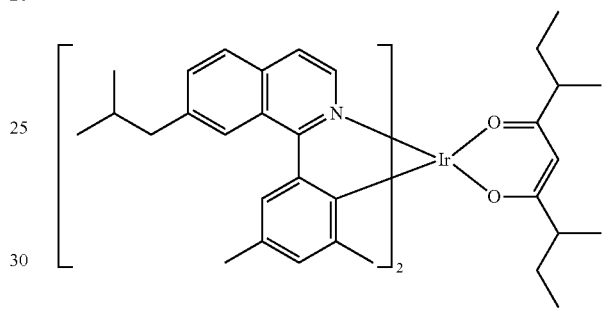
D-114
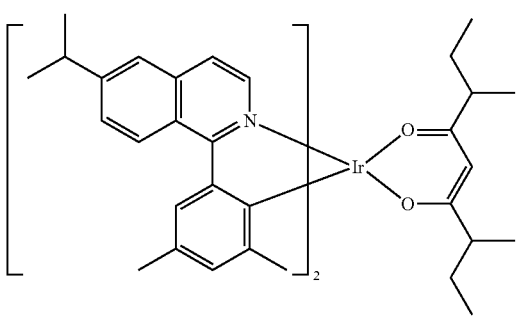

D-115
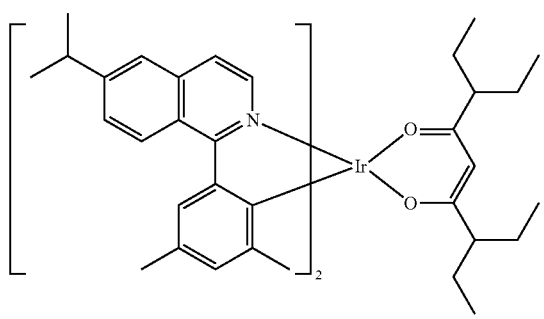
D-116
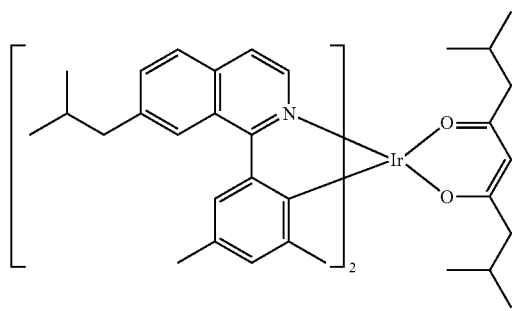
D-117
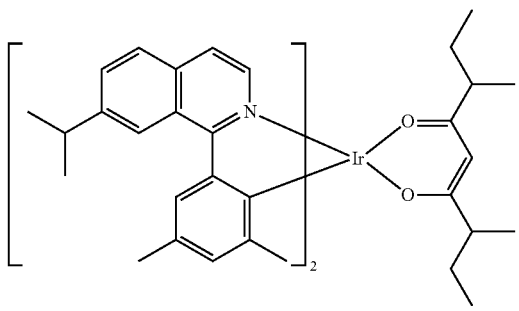
D-118
D-119
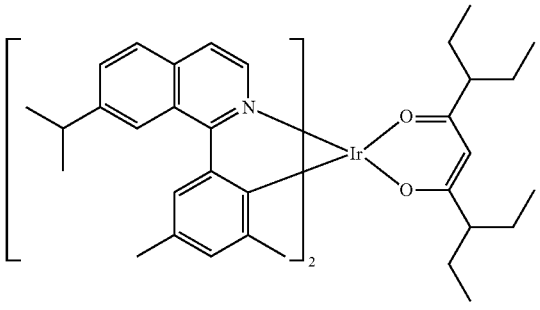
D-120
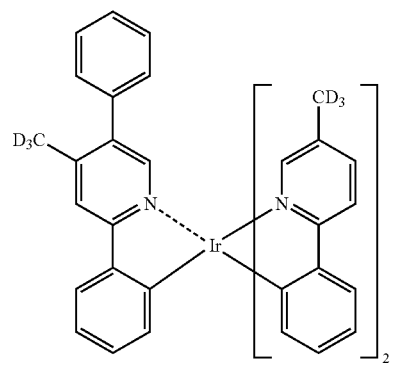
D-121
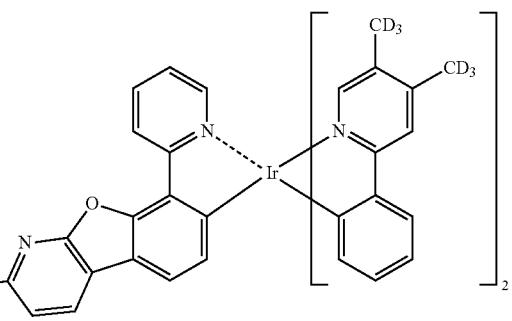
D-122
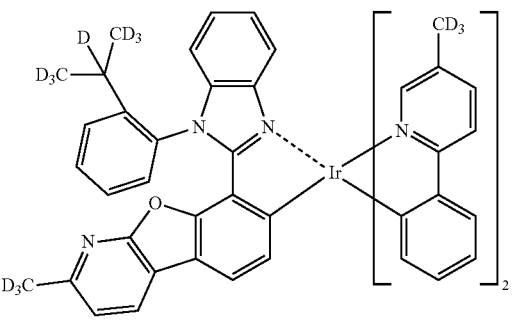

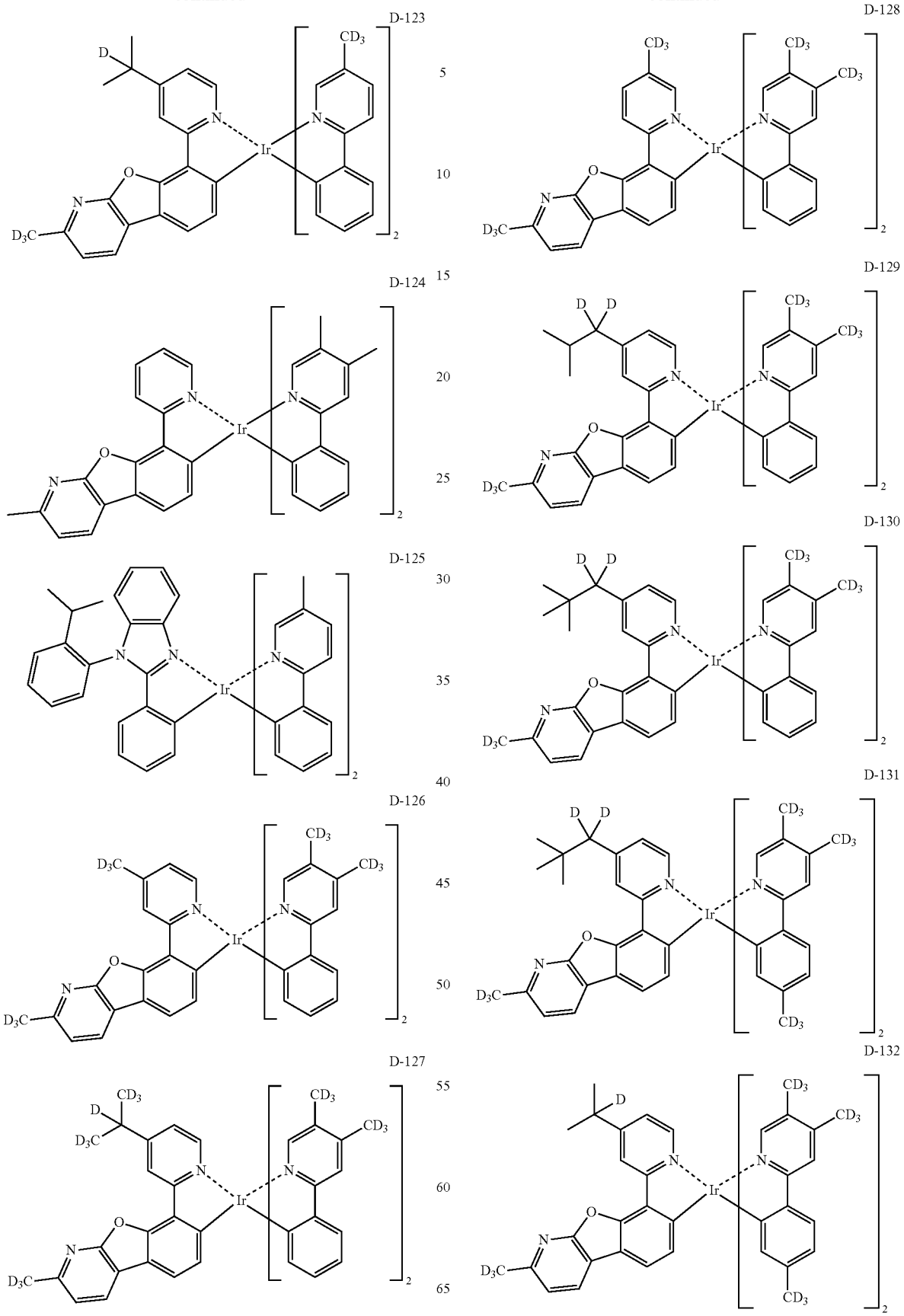

D-133 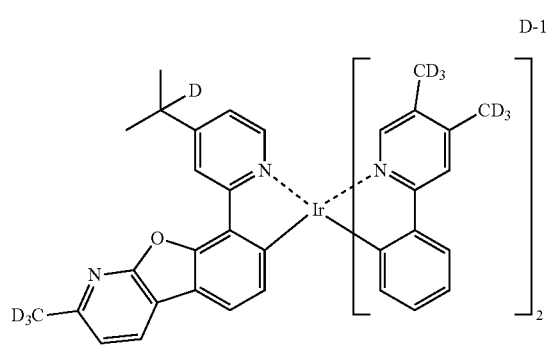
D-137 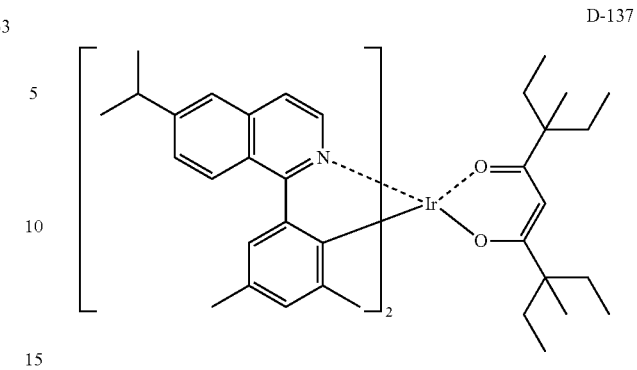
D-134 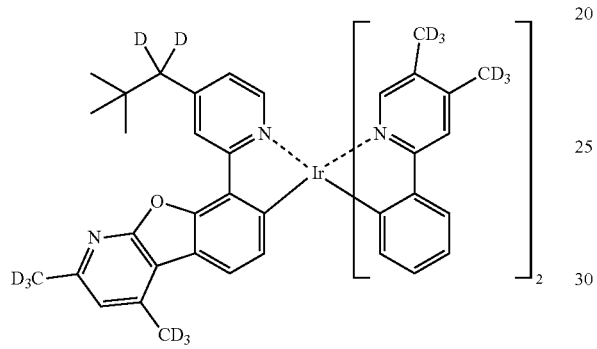
D-138 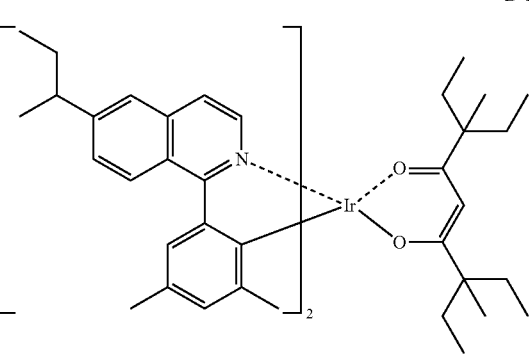
D-135 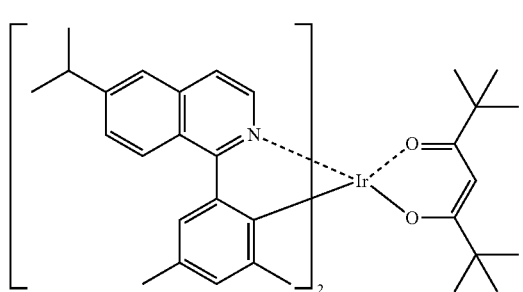
D-139 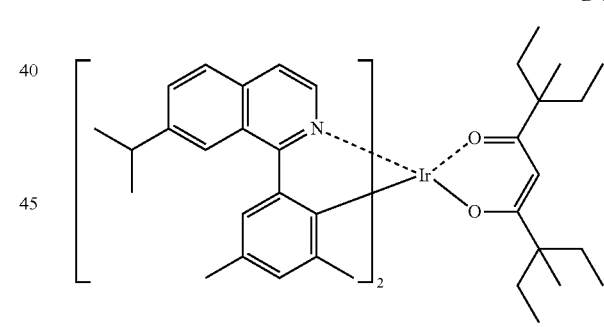
D-136 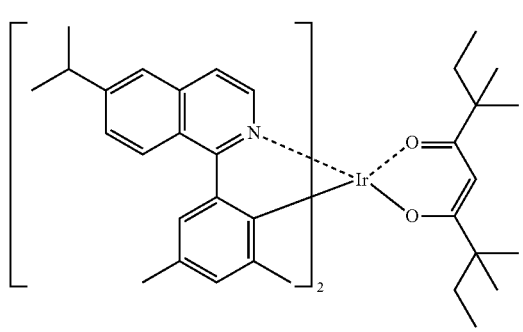
D-140 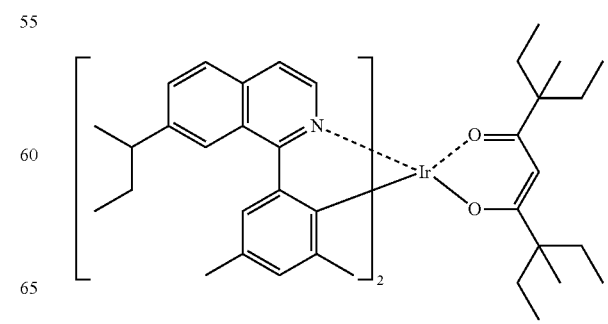

D-141
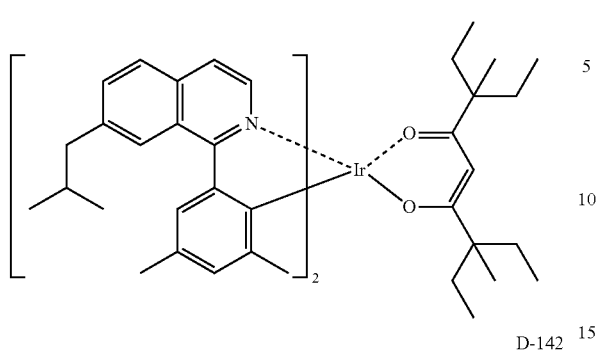
D-142
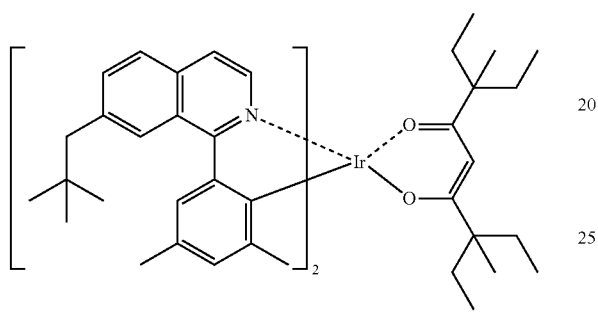
D-143
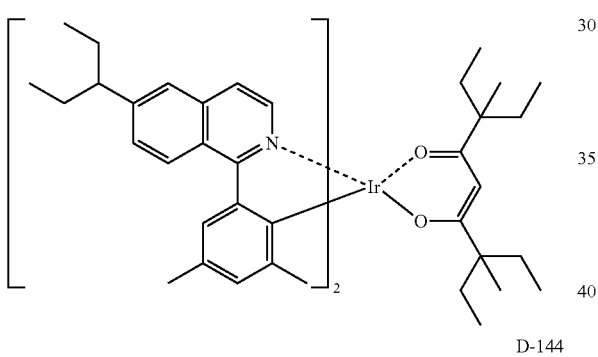
D-144
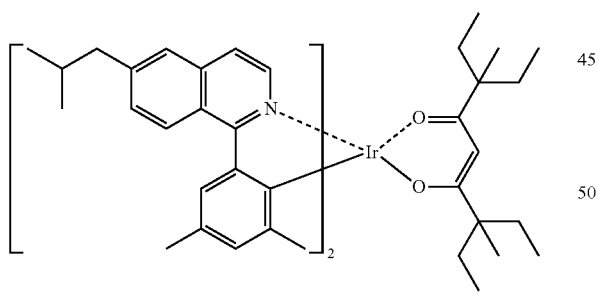
D-145
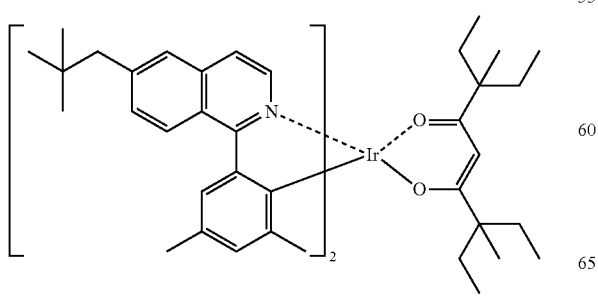
D-146
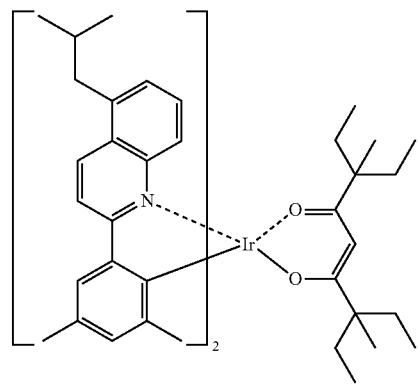
D-147
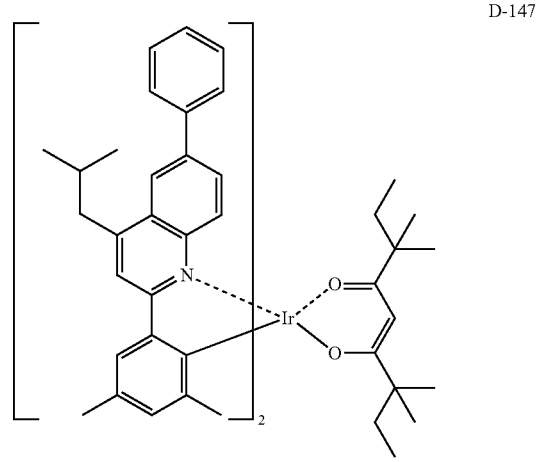
D-148
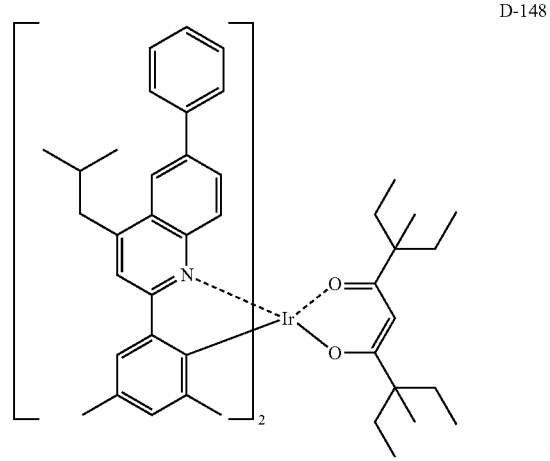

D-149

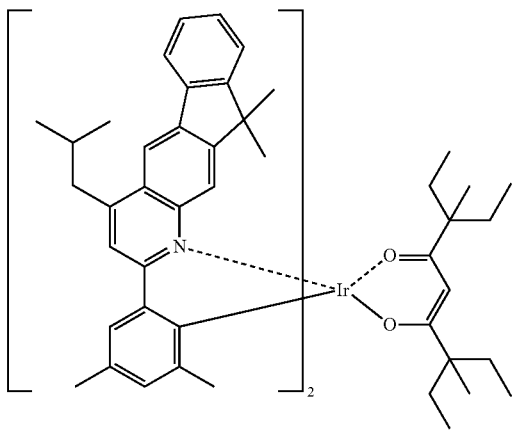

In order to form each layer of the organic electroluminescent device of the present disclosure, dry film-forming methods such as vacuum evaporation, sputtering, plasma, ion plating methods, etc., or wet film-forming methods such as spin coating, dip coating, flow coating methods, etc., can be used. When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

When forming a layer by the first host material and the second host material according to one embodiment, the layer can be formed by the above-listed methods, and can often be formed by co-deposition or mixture-deposition. The co-deposition is a mixed deposition method in which two or more materials are put into respective individual crucible sources and a current is applied to both cells simultaneously to evaporate the materials and to perform mixed deposition; and the mixed deposition is a mixed deposition method in which two or more materials are mixed in one crucible source before deposition, and then a current is applied to one cell to evaporate the materials.

According to one embodiment, when the first host material and the second host material exist in the same layer or different layers in the organic electroluminescent device, the layers by the two host compounds may be separately formed. For example, after depositing the first host material, a second host material may be deposited.

According to one embodiment, the present disclosure can provide display devices comprising a plurality of host materials including a first host material comprising the compound represented by formula 1 and a second host material comprising the compound represented by formula 2. In addition, by using the organic electroluminescent device of the present disclosure, display devices such as smartphones, tablets, notebooks, PCs, TVs, or display devices for vehicles, or lighting devices such as outdoor or indoor lighting can be prepared.

Hereinafter, the preparation method of compounds according to the present disclosure will be explained with reference to the synthesis method of a representative compound or intermediate compound in order to understand the present disclosure in detail.

[Example 1] Preparation of Compound C1-47

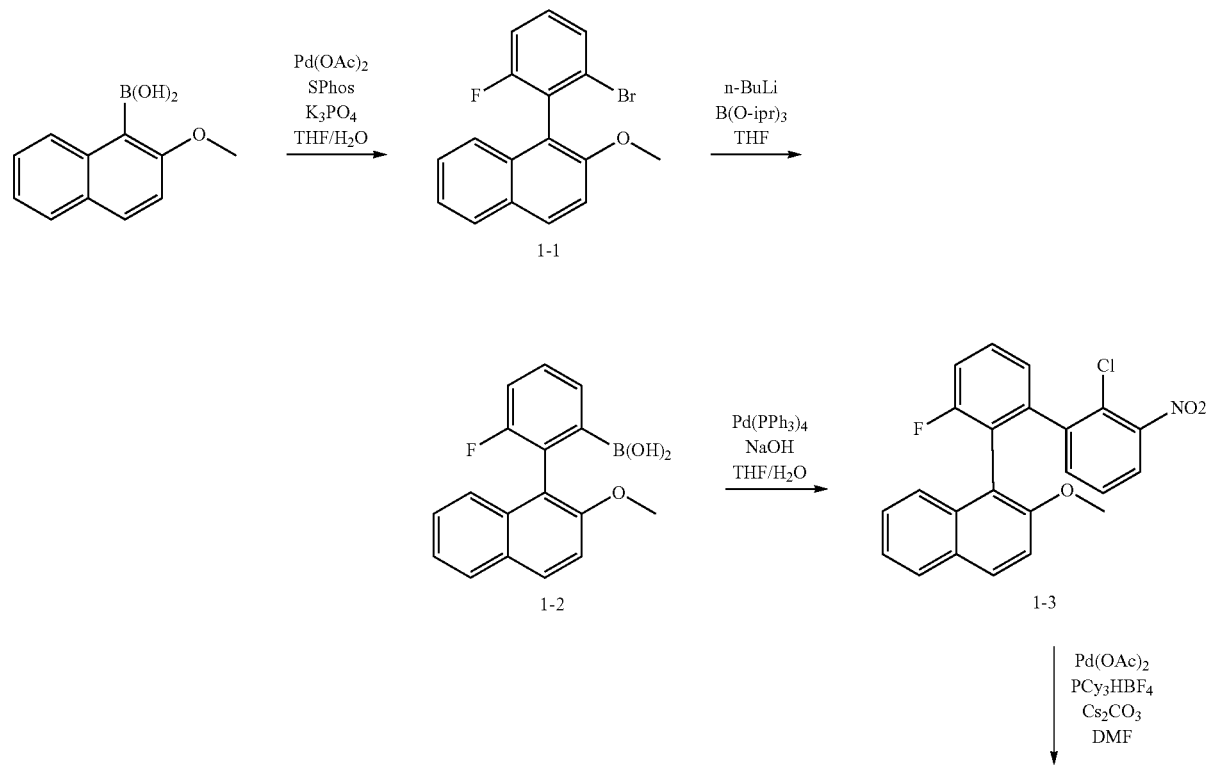

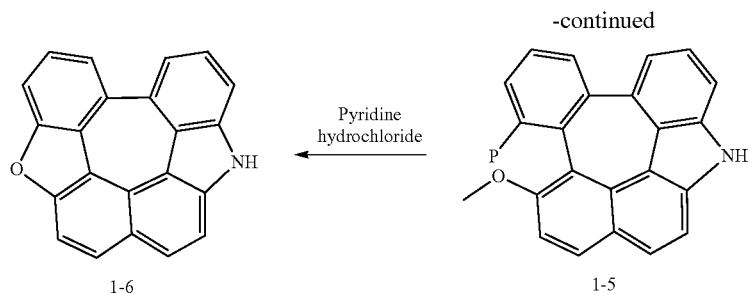
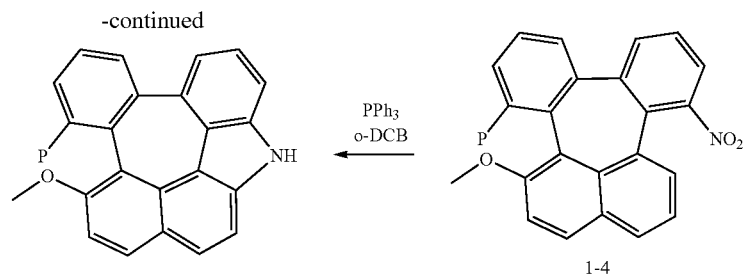

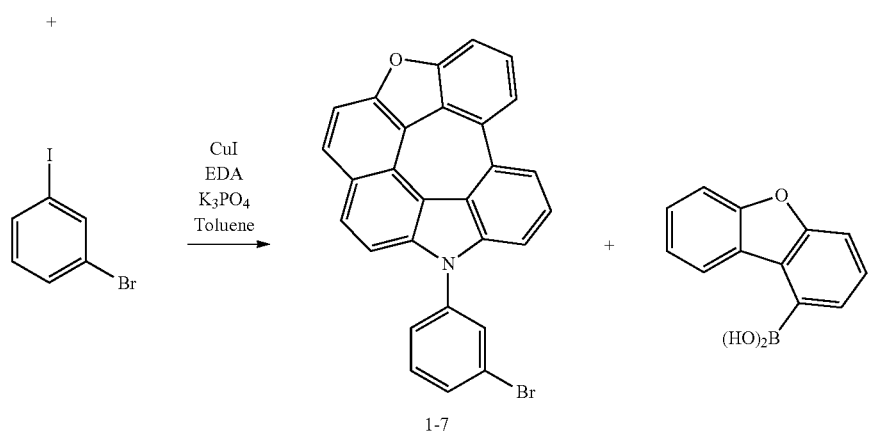

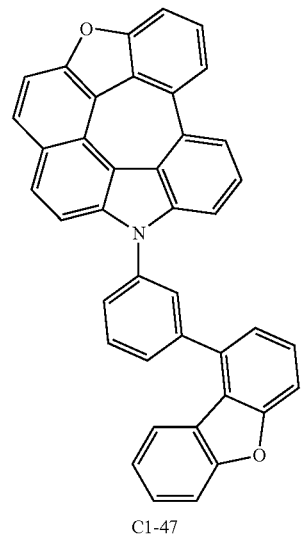

1) Synthesis of Compound 1-1

2-methoxynaphthalen-1-yl-1-boronic acid (30 g, 149 mmol), 1-bromo-2-iodo-3-fluorobenzene (49.2 g, 163 mmol), K₃PO₄ (94.5 g, 446 mmol), Pd(OAc)₂ (1.67 g, 7.43 mmol), and SPhos (6.1 g, 14.8 mmol) were added to a flask and dissolved in 667 mL of THF and 222 mL of distilled water followed by refluxing for 24 hours. After completion of the reaction, the organic layer was extracted with ethyl acetate followed by drying with magnesium sulfate. Next, it was separated by column chromatography to obtain compound 1-1 (38.5 g, yield: 78.3%).

2) Synthesis of Compound 1-2

Compound 1-1 (81.6 g, 246 mmol) was added to a flask and dissolved in 1.6 L of THF. After cooling to −78° C., 108 mL of n-BuLi was added thereto and stirred for 1 hour. Next, B(O-ipr)₃ (60 mL, 492 mmol) was added thereto and stirred for 24 hours at room temperature. After completion of the reaction, the reaction was stopped with 1M HCl, and the organic layer was extracted with ethyl acetate followed by drying with magnesium sulfate. Next, it was recrystallized with hexane to obtain compound 1-2 (46.5 g, yield: 63.7%).

3) Synthesis of Compound 1-3

Compound 1-2 (46.5 g, 157 mmol), 1-bromo-2-chloro-3-nitrobenzene (48.3 g, 204 mmol), Pd(PPh₃)₄ (10.9 g, 9.42 mmol), NaOH (18.8 g, 471 mmol), 706 mL of THF, and 200 mL of distilled water were added to a flask and refluxed at 120° C. for 24 hours. After completion of the reaction, the organic layer was extracted with ethyl acetate and the residual water was removed with magnesium sulfate followed by drying. Next, it was separated by column chromatography to obtain compound 1-3 (52.6 g, yield: 82.1%).

4) Synthesis of Compound 1-4

Compound 1-3 (52.6 g 129 mmol), Pd(OAc)₂ (5.79 g, 25.8 mmol), Pcy₃HBF₄ (14.2 g, 38.7 mmol), Cs₂CO₃ (126 g, 387 mmol), and 861 mL of DMF were added to a flask and stirred under reflux for 1 hour. After completion of the reaction, the organic layer was extracted with ethyl acetate and the residual water was removed with magnesium sulfate followed by drying. Next, it was separated by column chromatography to obtain compound 1-4 (23.2 g, yield: 48.4%).

5) Synthesis of Compound 1-5

Compound 1-4 (23.2 g, 62.5 mmol), triphenylphosphine (49.2 g, 187 mmol), and 416 mL of o-DCB 416 mL were added to a flask and dissolved, and then refluxed at 200° C. After completion of the reaction, the solvent was removal by distillation under reduced pressure. Next, it was separated by column chromatography to obtain compound 1-5 (21.2 g, yield: 89.6%).

6) Synthesis of Compound 1-6

Compound 1-5 (19 g, 56 mmol) and pyridinum hydrochloride (97 g, 840 mmol) were added to a flask and refluxed at 200° C. for 2 hours. After completion of the reaction, the mixture was dissolved by adding ethyl acetate thereto, and neutralized with an aqueous calcium carbonate solution. Thereafter, the organic layer was extracted followed by drying with magnesium sulfate. Next, it was separated by column chromatography to obtain compound 1-6 (14.8 g, yield: 86.6%).

7) Synthesis of Compound 1-7

Compound 1-6 (4 g, 12.5 mmol), 1-iodo-3-bromobenzene (2.4 mL, 18.75 mmol), CuI (1.2 g, 6.25 mmol), EDA (0.85 mL, 12.5 mmol), K₃PO₄ (8 g, 37.5 mmol), and 63 mL of toluene were added to a flask and refluxed at 120° C. for 3 hours. After completion of the reaction, the organic layer was extracted with ethyl acetate, followed by drying with magnesium sulfate. Next, it was separated by column chromatography to obtain compound 1-7 (5.3 g, yield: 92.9%).

8) Synthesis of Compound C1-47

Compound 1-7 (5.3 g, 11.5 mmol), dibenzo[b,d]furan-1-boronic acid (3.13 g, 13.7 mmol), Pd(PPh₃)₄ (665 mg, 0.575 mmol), potassium carbonate (4.78 g, 34.5 mmol), 52 mL of toluene, 17.2 mL of ethanol, and 17.2 mL of distilled water were added to a flask, and dissolved, and then refluxed at 120° C. for 3 hours. After completion of the reaction, the organic layer was extracted with ethyl acetate, followed by drying with magnesium sulfate. Next, it was separated by column chromatography to obtain compound C1-47 (1.4 g, yield: 22%).

[Example 2] Preparation of Compound C1-67

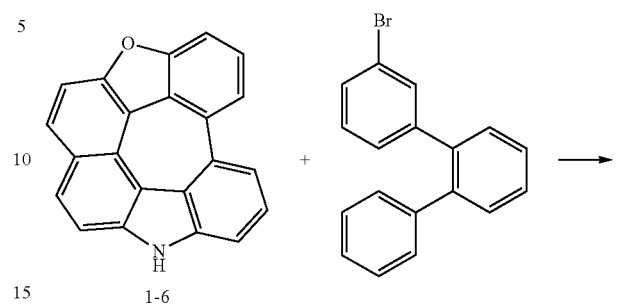

1-6

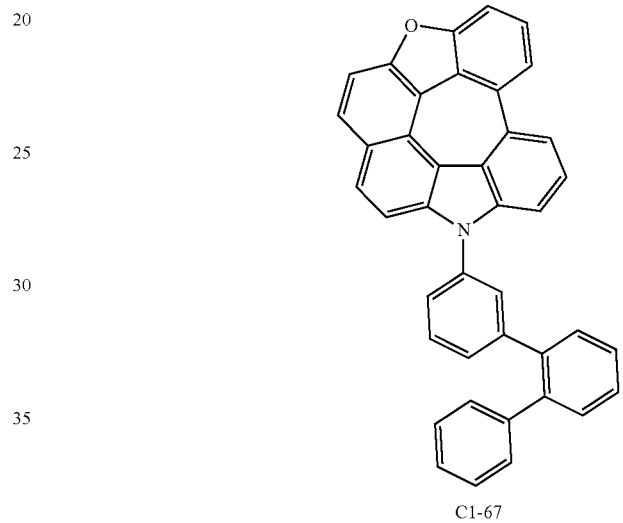

C1-67

Compound 1-6 (3 g, 9.4 mmol), 3-bromo-1,1':2',1"-terphenyl (4.3 g, 14.1 mmol), tris(dibenzylideneacetone)dipalladium (0) (427 g, 047 mmol), SPhos (385 mg, 0.94 mmol), Sodium-tert-butoxide (2.7 g, 28.2 mmol), and 63 mL of o-xylene were added to a flask and refluxed at 200° C. for 24 hours. After completion of the reaction, the organic layer was extracted with ethyl acetate followed by drying with magnesium sulfate. Next, it was separated by column chromatography to obtain compound C1-67 (1.2 g, yield: 24%).

[Example 3] Preparation of Compound H-3

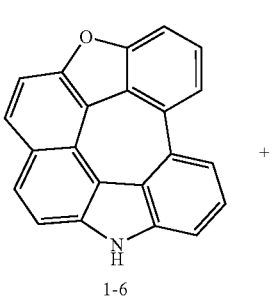

1-6

+

-continued

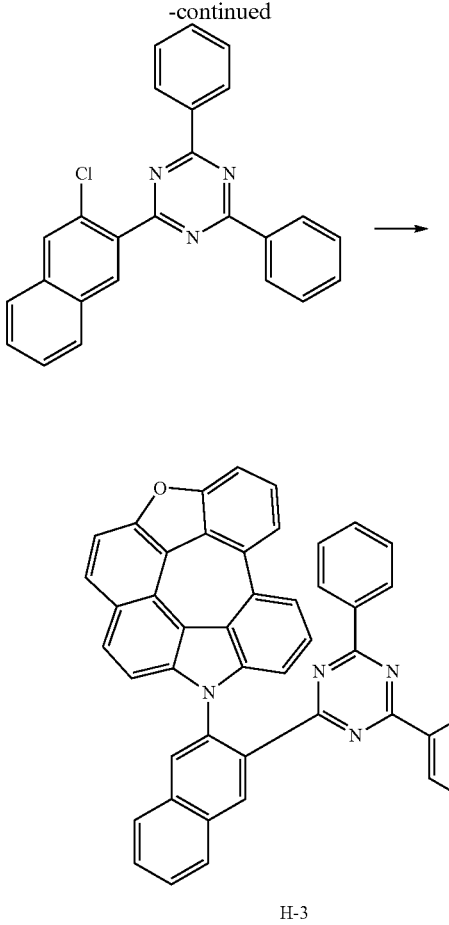

H-3

Compound 1-6 (2.8 g, 8.75 mmol), 2-(3-chloronaphthalen-2-yl)-4,6-diphenyl-1,3,5-triazine (3.45 g, 8.75 mmol), copper sulfate (0.7 g, 4.37 mmol), calcium carbonate (2.42 g, 17.4 mmol), and 60 mL of o-DCB were added to a flask, and then refluxed at 220° C. for 6 hours. After completion of the reaction, the solvent was removed by distillation under reduced pressure, and the organic layer was extracted with ethyl acetate followed by drying with magnesium sulfate. Next, it was separated by column chromatography to obtain compound H-3 (3.0 g, yield: 50%).

Hereinafter, the preparation method of an organic electroluminescent device comprising the plurality of host materials according to the present disclosure, and the property thereof will be explained in order to understand the present disclosure in detail.

[Device Example 1 and 2] Preparation of OLEDs Comprising the Compounds According to the Present Disclosure as Hosts OLEDs according to the present disclosure were produced. First, a transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and thereafter was stored in isopropanol and then used. Thereafter, the ITO substrate was mounted on a substrate holder of a vacuum vapor deposition apparatus. Then, compound HI-1 as a first hole injection compound was introduced into a cell of the vacuum vapor deposition apparatus, and compound HT-1 as a first hole transport compound was introduced into another cell of the vacuum vapor deposition apparatus. Compound HI-1 was deposited in a doping amount of 3 wt % based on the total amount of compound HI-1 and compound HT-1 to form a first hole injection layer having a thickness of 10 nm. Next, compound HT-1 was introduced into a cell of the vacuum vapor deposition apparatus and was evaporated by applying an electric current to the cell, thereby forming a first hole transport layer having a thickness of 80 nm on the first hole injection layer. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: the first host compound and the second host compound described in the following Table 1 were introduced into two cells of the vacuum vapor deposition apparatus as hosts of the light-emitting layer, respectively, and compound D-39 was introduced into another cell as a dopant. The two host materials were evaporated at a rate of 1:1 and the dopant material was evaporated at a different rate, simultaneously, and was deposited in a doping amount of 3 wt % based on the total amount of the hosts and dopant to form a light-emitting layer having a thickness of 40 nm on the second hole transport layer. Next, compounds ETL-1 and EIL-1 in another two cells of the vacuum vapor deposition apparatus were evaporated at a rate of 1:1 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, OLEDs were produced.

[Device Example 3] Preparation of an OLED Comprising the Compound According to the Present Disclosure as a Host An OLED was produced in the same manner as in Device Example 1, except that the compound shown in the following Table 1 alone was used as the host of the light-emitting layer.

[Comparative Examples 1 and 2] Preparation of OLEDs Comprising a Conventional Compound as a Host OLEDs were produced in the same manner as in Device Example 1, except that the compound shown in the following Table 1 alone was used as the host of the light-emitting layer.

The driving voltage, the luminous efficiency, and the light-emitting color at a luminance of 1,000 nits, and the time taken for luminance to decrease from 100% to 95% at a luminance of 5,000 nits (lifespan; T95) of the organic electroluminescent devices according to Device Examples 1 to 3 and Comparative Examples 1 and 2 produced as described above, are measured, and the results thereof are shown in Table 1 below:

TABLE 1

| | First Host Compound | Second Host Compound | Driving Voltage (V) | Luminous Efficiency (cd/A) | Light-Emitting Color | Lifespan (T95, hr) |
|---|---|---|---|---|---|---|
| Device Example 1 | C1-47 | C2-114 | 3.1 | 31.4 | Red | 408 |
| Device Example 2 | C1-67 | C2-114 | 2.9 | 26.3 | Red | 426 |
| Device Example 3 | H-3 | — | 2.9 | 24.4 | Red | 124 |
| Comparative Example 1 | T-1 | — | 3.1 | 19.5 | Red | 120 |
| Comparative Example 2 | T-2 | — | 3.6 | 17.8 | Red | 7.8 |

Referring to Table 1 above, by comprising a specific combination of compounds according to the present disclosure as host materials, an organic electroluminescent device having low driving voltage, high efficiency luminous characteristics, and significantly improved lifespan characteristics can be provided, compared to an organic electroluminescent device including a single host material. In addition, it can be seen that an organic electroluminescent device comprising the organic electroluminescent compounds according to the present disclosure as a host material exhibits high efficiency luminescence characteristics, compared to the organic electroluminescent device comprising a conventional single host material.

The compounds used in Device Examples 1 to 3 and Comparative Examples 1 and 2 above are shown in the following Table 2.

TABLE 2

Hole Injection Layer/ Hole Transport Layer

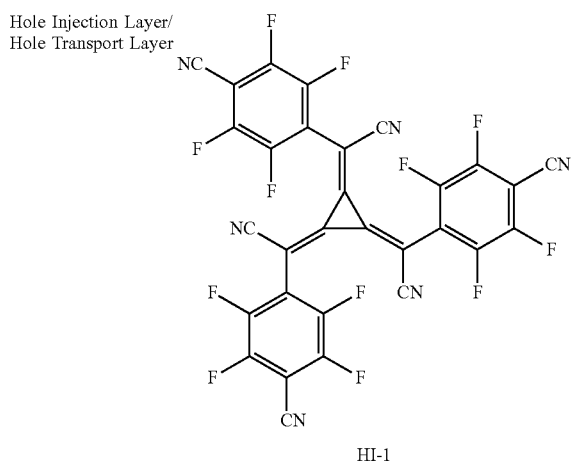

HI-1

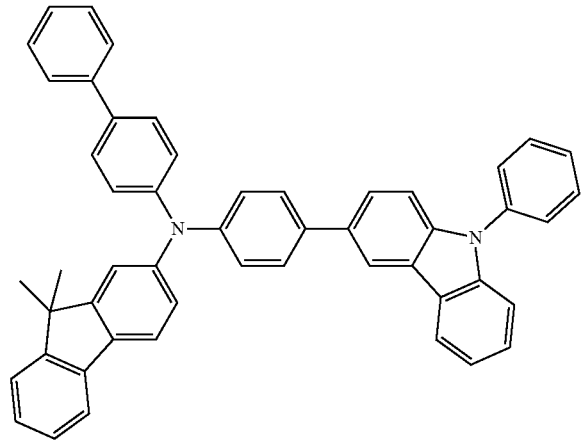

HT-1

TABLE 2-continued
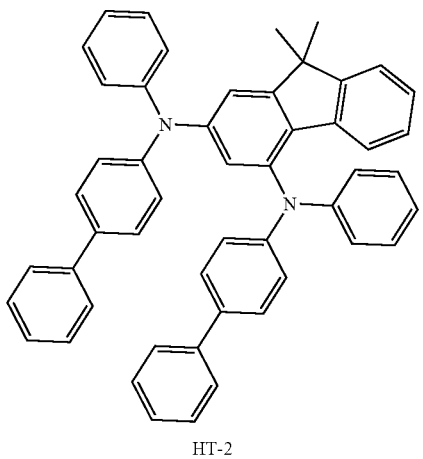
HT-2
Light-Emitting Layer
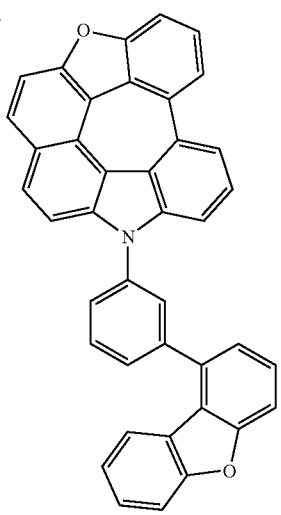
C1-47
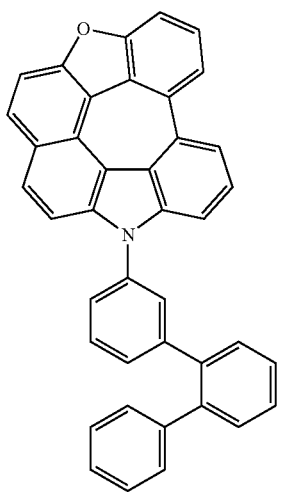
C1-67

TABLE 2-continued
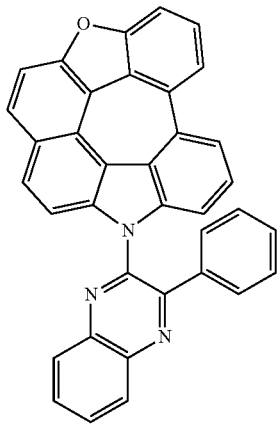
T-1
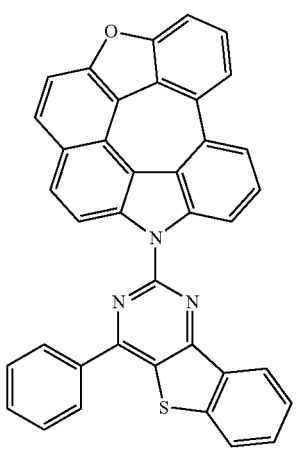
T-2
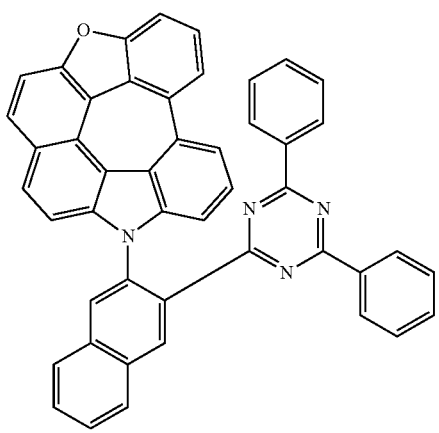
H-3

TABLE 2-continued
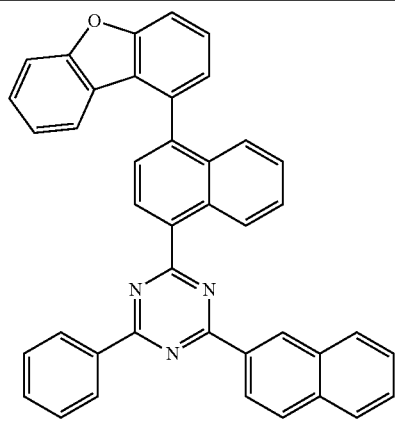
C2-114
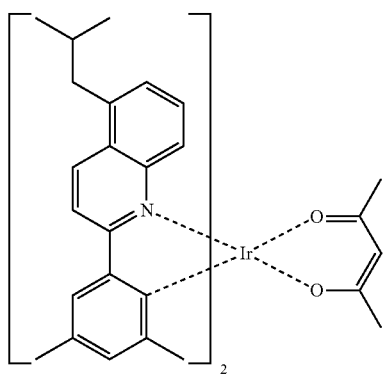
D-39
Electron Transport Layer/Electron Injection Layer
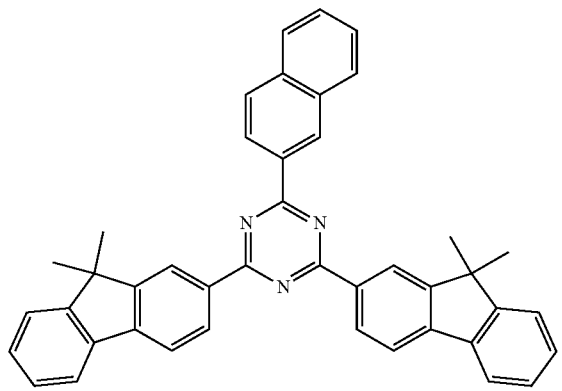
ETL-1
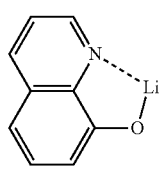
EIL-1

The invention claimed is:
1. A plurality of host materials comprising a first host material and a second host material, wherein the first host material comprises a compound represented by the following formula 1 and the second host material comprises a compound represented by the following formula 2:

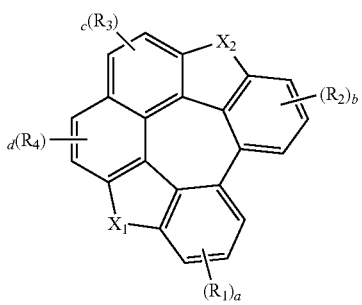
(1)

wherein
$X_1$ and $X_2$ each independently represent $NR_5$, $CR_6R_7$, O, or S;
$R_1$ to $R_4$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30) alkenylamino, a substituted or unsubstituted mono- or di- (C6-C30)arylamino, a substituted or unsubstituted (C1-C30)alkyl(C6-C30)arylamino, a substituted or unsubstituted mono- or di- (3- to 30-membered)heteroarylamino, a substituted or unsubstituted (C1-C30) alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, or a substituted or unsubstituted (C6-C30)aryl(3- to 30-membered)heteroarylamino;
$R_5$ to $R_7$ each independently represent a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30)alkenylamino, a substituted or unsubstituted mono- or di- (C6-C30) arylamino, a substituted or unsubstituted (C1-C30) alkyl(C6-C30)arylamino, a substituted or unsubstituted mono- or di- (3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;
a and b each independently represent an integer of 1 to 3, and c and d each independently represent an integer of 1 or 2; and
when a to d each independently are an integer of 2 or more, each of $R_1$, each of $R_2$, each of $R_3$, and each of $R_4$ may be the same or different;

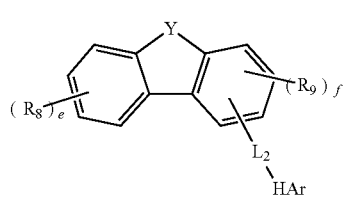
(2)

wherein
Y represents —O— or —S—;
HAr represents a substituted or unsubstituted (3- to 30-membered)heteroaryl containing one or more nitrogen atoms;
$L_2$ represents a single bond, a substituted or unsubstituted (C6-C30)arylene, or a substituted or unsubstituted (3- to 30-membered)heteroarylene;
$R_8$ and $R_9$ each independently represent hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di- (C2-C30)alkenylamino, a substituted or unsubstituted (C1-C30) alkyl(C2-C30)alkenylamino, a substituted or unsubstituted mono- or di- (C6-C30)arylamino, a substituted or unsubstituted (C1-C30)alkyl(C6-C30)arylamino, a substituted or unsubstituted mono- or di- (3- to 30-membered)heteroarylamino, a substituted or unsubstituted (C1-C30)alkyl(3- to 30-membered)heteroarylamino, a substituted or unsubstituted (C2-C30) alkenyl(C6-C30)arylamino, a substituted or unsubstituted (C2-C30)alkenyl(3- to 30-membered) heteroarylamino, or a substituted or unsubstituted (C6-C30)aryl(3- to 30-membered)heteroarylamino; or may be linked to the adjacent substituents to form a ring(s);
e represents an integer of 1 to 4, and f represents an integer of 1 to 3; and
when e and f each independently are an integer of 2 or more, each of $R_8$ and each of $R_9$ may be the same or different.
2. The plurality of host materials according to claim 1, wherein the substituent of the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted fused ring of aliphatic ring and aromatic ring, the substituted mono- or di- alkylamino, the substituted mono- or di- alkenylamino, the substituted alkylalkenylamino, the substituted mono- or di- arylamino, the substituted alkylarylamino, the substituted mono- or di- heteroarylamino, the substituted alkylheteroarylamino, the substituted alkenylarylamino, the substituted alkenylheteroarylamino, and the substituted arylheteroarylamino each independently represents at least one selected from the group consisting of deuterium, halogen, cyano, carboxyl, nitro, hydroxy, (C1-C30)alkyl, halo(C1-C30)alkyl, (C2-C30)alkenyl, (C2-C30)alkynyl, (C1-C30)alkoxy, (C1-C30)alkylthio, (C3-C30)cycloalkyl, (C3-C30)cycloalkenyl, (3- to 7-membered)heterocycloalkyl, (C6-C30)aryloxy, (C6-C30)arylthio, (5- to 30-membered)heteroaryl unsubstituted or substituted with (C6-C30)aryl, (C6-C30)aryl unsubstituted or substituted with (5- to 30-membered)heteroaryl, tri(C1-C30)alkylsilyl, tri(C6-C30)arylsilyl, di(C1-C30)alkyl(C6-C30)arylsilyl, (C1-C30)alkyldi(C6-C30)arylsilyl, a fused ring of (C3-C30) aliphatic ring and (C6-C30) aromatic ring, amino, mono- or di- (C1-C30)alkylamino, mono- or di- (C2-C30)alkenylamino, (C1-C30)alkyl(C2-C30)alkenylamino, a substituted or unsubstituted mono- or di- (C6-C30)arylamino, (C1-C30)alkyl(C6-C30)arylamino, mono- or di- (3- to 30-membered)heteroarylamino, (C1-C30)alkyl(3- to 30-membered)heteroarylamino, (C2-C30)alkenyl(C6-C30)arylamino, (C2-C30)alkenyl(3-to 30-membered)heteroarylamino, (C6-C30)aryl(3- to 30-membered)heteroarylamino, (C1-C30)alkylcarbonyl, (C1-C30)alkoxycarbonyl, (C6-C30)arylcarbonyl, (C6-C30)arylphosphinyl, di(C6-C30)arylboronyl, di(C1-C30)alkylboronyl, (C1-C30)alkyl(C6-C30)arylboronyl, (C6-C30)ar(C1-C30)alkyl, and (C1-C30)alkyl(C6-C30)aryl.

3. The plurality of host materials according to claim 1, wherein the formula 1 is represented by any one of the following formulas 1-1 to 1-6:

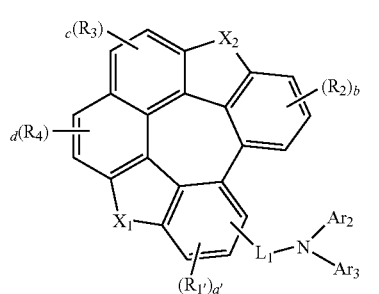

(1-1)

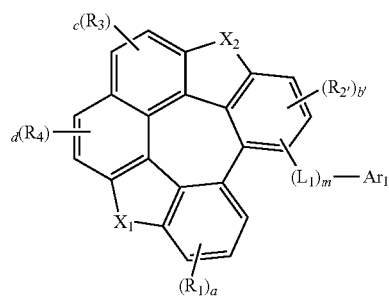

(1-2)

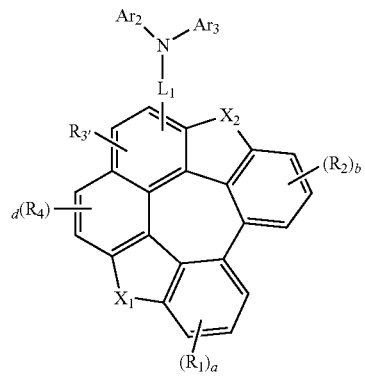

(1-3)

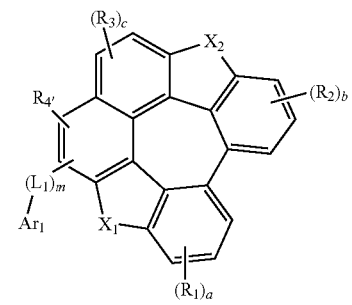

(1-4)

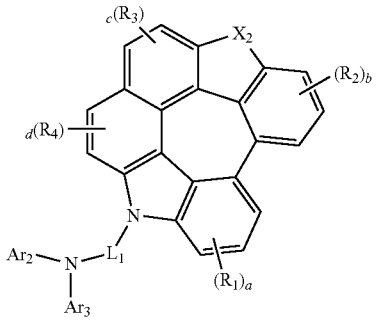

(1-5)

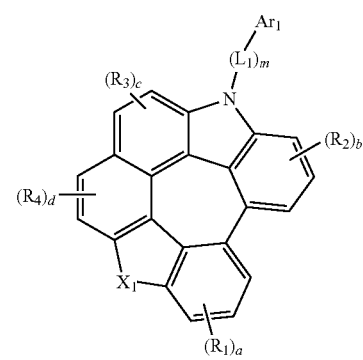

(1-6)

wherein $X_1$, $X_2$, $R_1$ to $R_4$, and a to d are as defined in claim 1;

$R_{1'}$ to $R_{4'}$ are as defined as $R_1$ to $R_4$ in claim 1;

$L_1$ represents a single bond, a substituted or unsubstituted (C6-C30)arylene, a substituted or unsubstituted fused ring of (C3-C30) aliphatic ring and (C6-C30) aromatic ring, or a substituted or unsubstituted (3- to 30-membered)heteroarylene;

$Ar_1$ represents a substituted or unsubstituted (C6-C30) aryl, a substituted or unsubstituted fused ring of (C3-

C30) aliphatic ring and (C6-C30) aromatic ring, or a substituted or unsubstituted (3- to 30-membered)heteroaryl;

Ar₂ and Ar₃ each independently represent a substituted or unsubstituted (C1-C30)alkyl, a substituted or unsubstituted (C2-C30)alkenyl, a substituted or unsubstituted fused ring of (C3-C30) aliphatic ring and (C6-C30) aromatic ring, a substituted or unsubstituted (C6-C30) aryl, or a substituted or unsubstituted (3- to 30-membered)heteroaryl;

a', b', and m each independently represent an integer of 1 or 2; and when a', b', and m are an integer of 2, each of $R_{1'}$, each of $R_{2'}$, and each of $L_1$ may be the same or different.

4. The plurality of host materials according to claim 1, wherein the formula 2 is represented by the following formula 2-1 or 2-2:

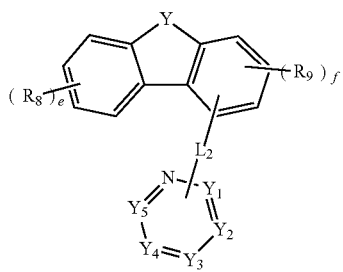

(2-1)

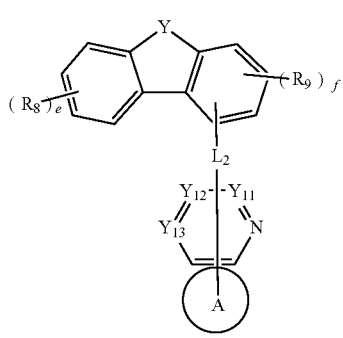

(2-2)

wherein

Y, $R_8$, $R_9$, $L_2$, e, and f are as defined in claim 1;

A represents a substituted or unsubstituted (C6-C10) aromatic ring where the carbon atom of the aromatic ring may be replaced with one or more heteroatoms selected from N, O, and S;

$Y_1$ to $Y_5$ and $Y_{11}$ to $Y_{13}$ each independently represent N or $CR_a$;

$R_a$ represents hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30)alkenylamino, a substituted or unsubstituted mono- or di- (C6-C30)arylamino, a substituted or unsubstituted (C1-C30)alkyl(C6-C30)arylamino, a substituted or unsubstituted mono- or di- (3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or the adjacent $R_a$'s may be linked to each other to form a ring(s).

5. The plurality of host materials according to claim 1, wherein HAr represents a substituted or unsubstituted pyridyl, a substituted or unsubstituted pyrimidinyl, a substituted or unsubstituted triazinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, a substituted or unsubstituted benzofuropyrimidinyl, a substituted or unsubstituted benzothienopyrimidinyl, a substituted or unsubstituted carbazolyl, or a substituted or unsubstituted pyridopyrazinyl.

6. The plurality of host materials according to claim 1, wherein the compound represented by the formula 1 is selected from the following compounds:

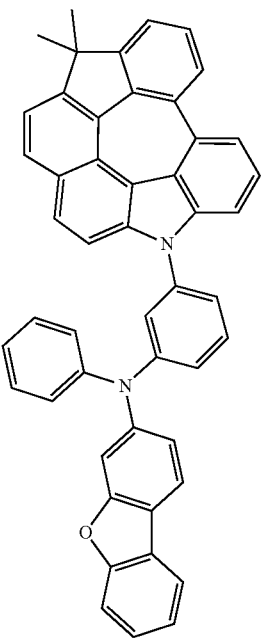

C1-1

C1-2
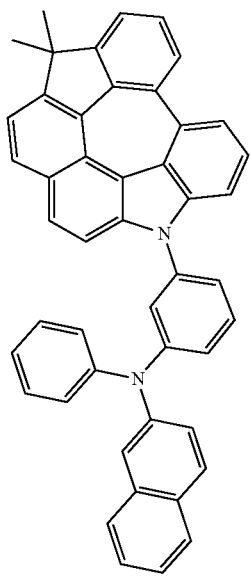
C1-3
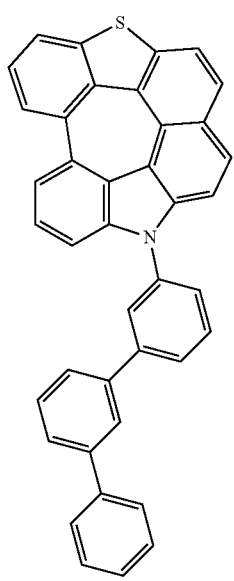
C1-4
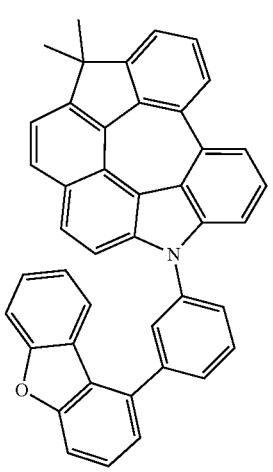
C1-5
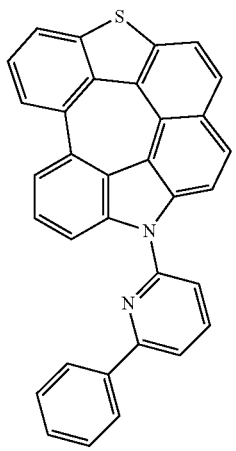
C1-6
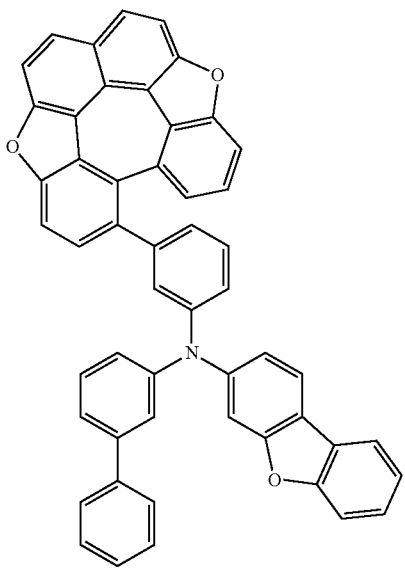
C1-7
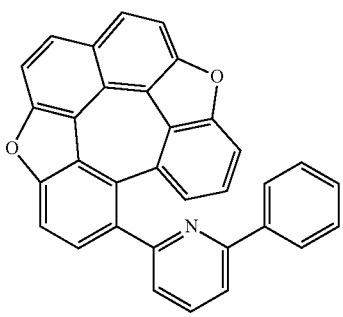

271
-continued
C1-8
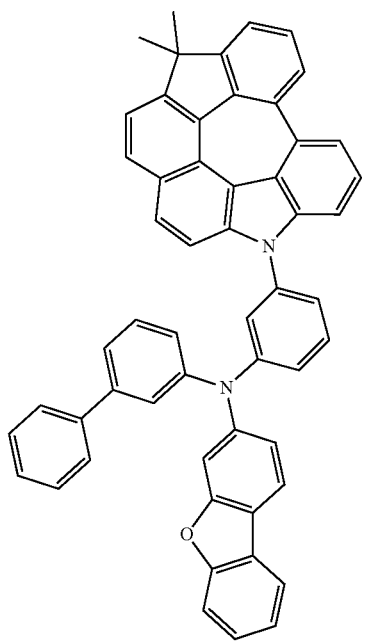
C1-9
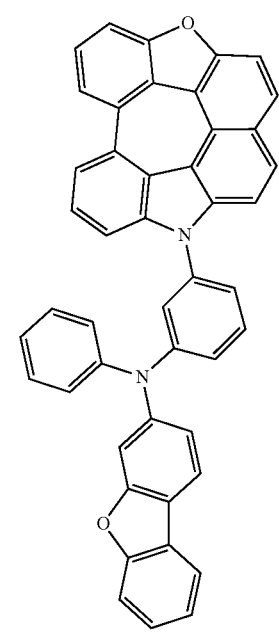
272
-continued
C1-10
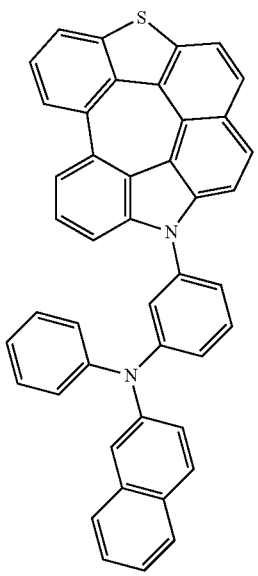
C1-11
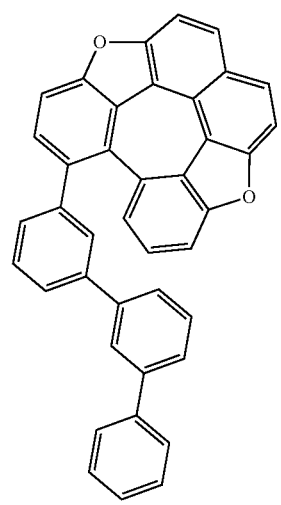
C1-12
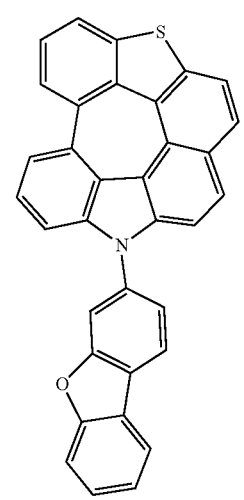

C1-13
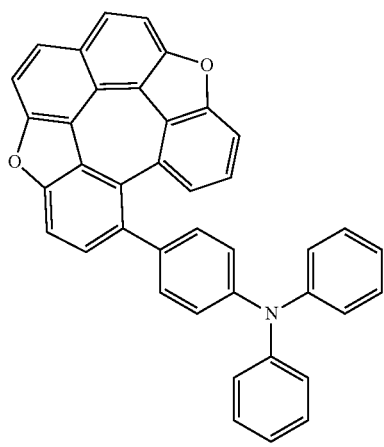
C1-14
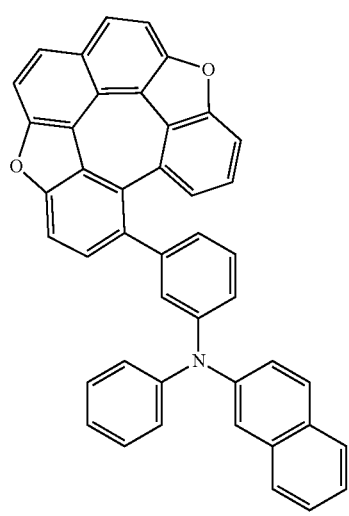
C1-15
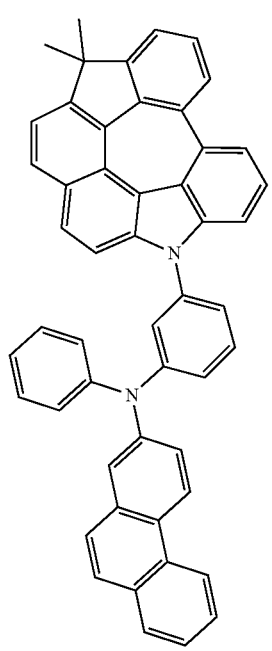
C1-16
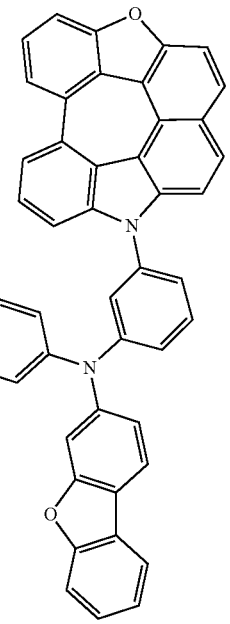
C1-17
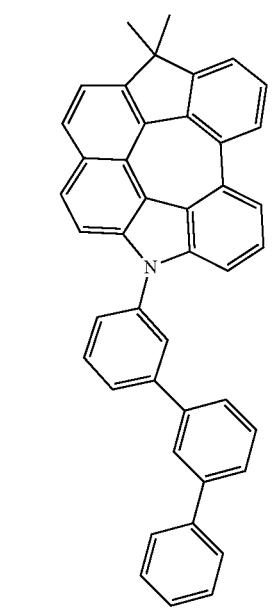
C1-18
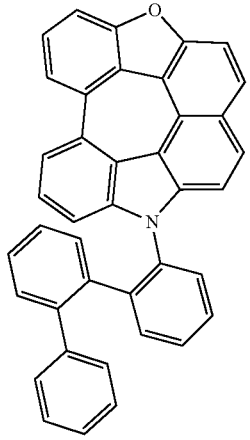

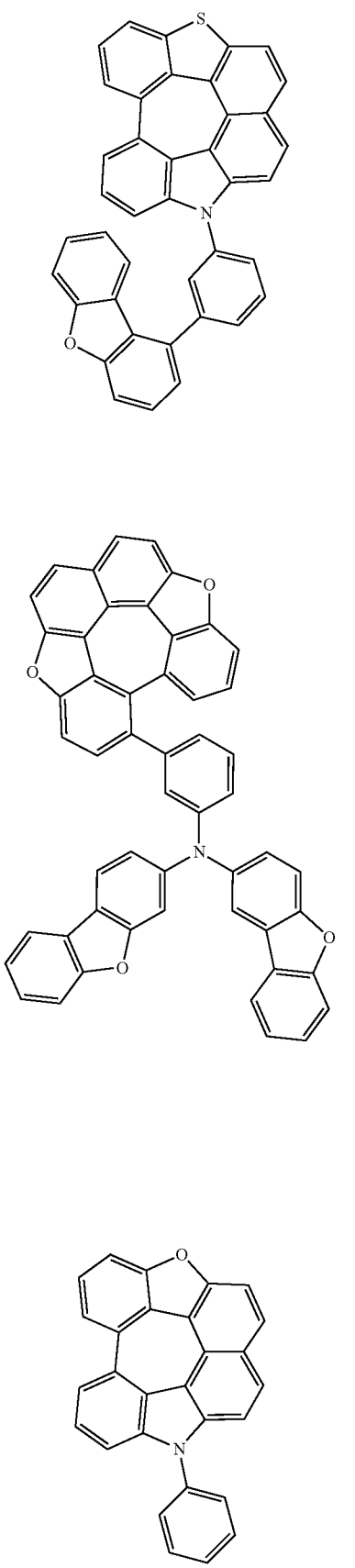
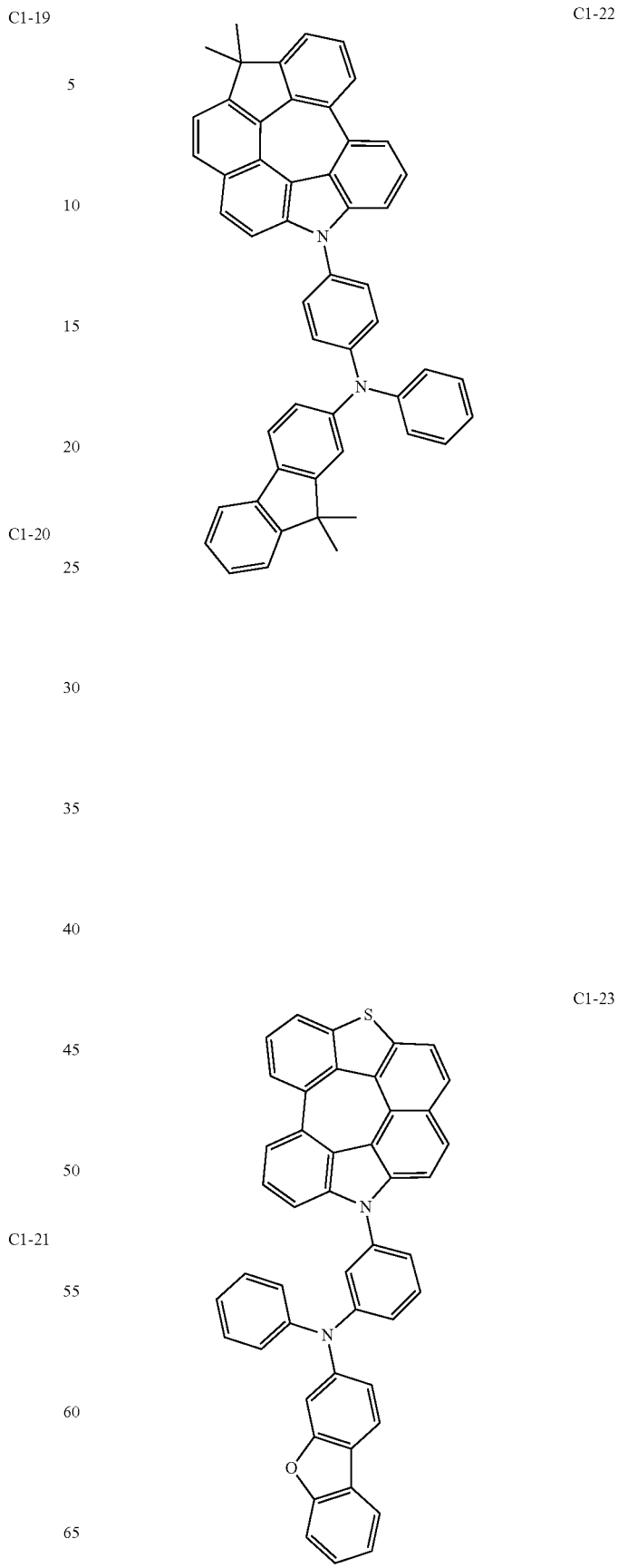

C1-24
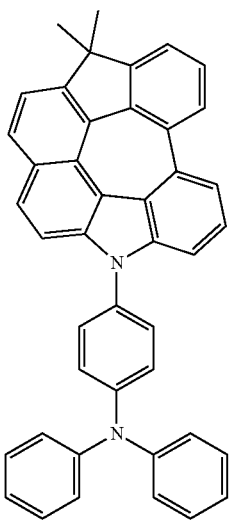
C1-25
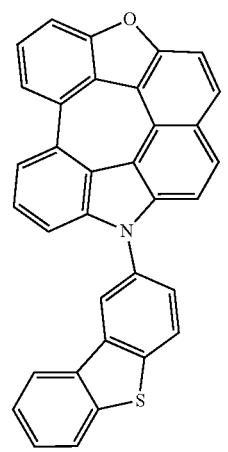
C1-26
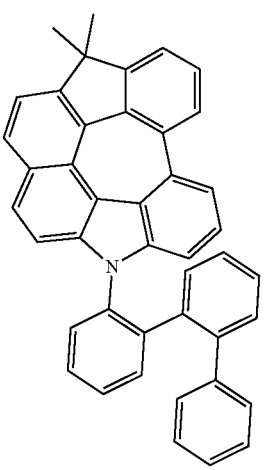
C1-27
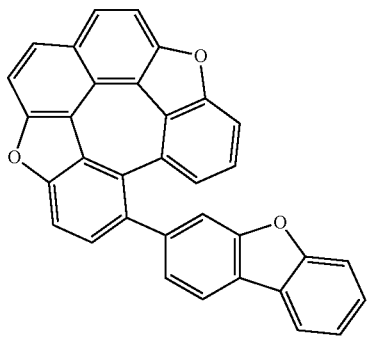
C1-28
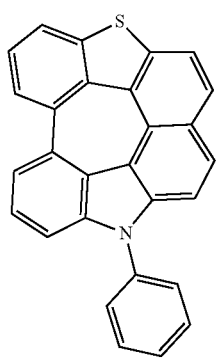
C1-29
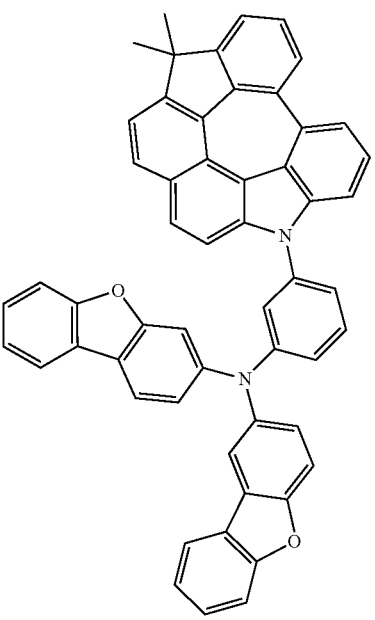

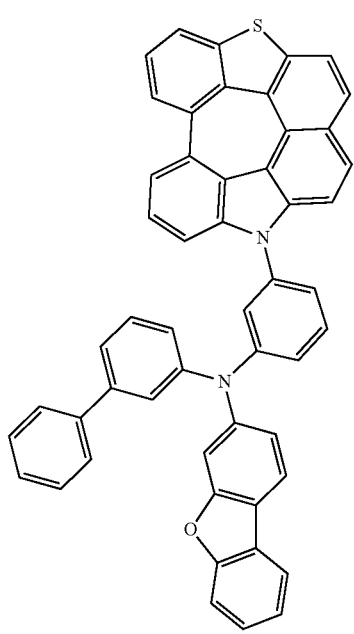
C1-30
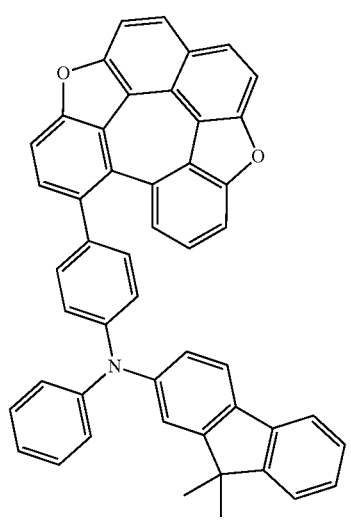
C1-31
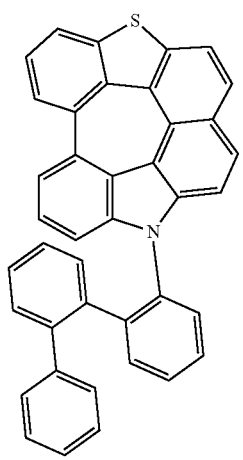
C1-32
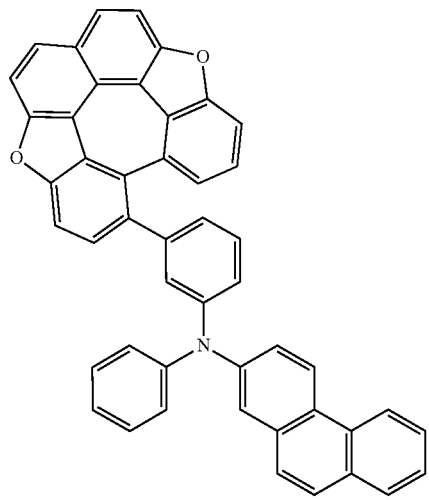
C1-33
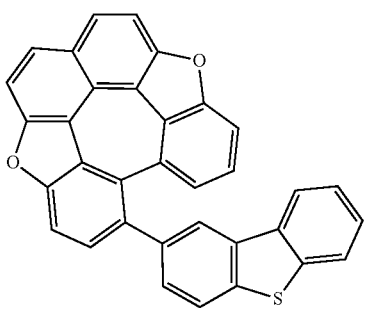
C1-34
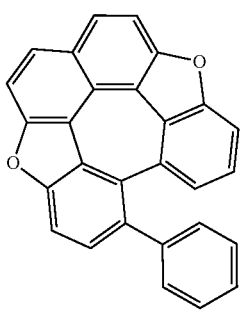
C1-35

C1-36
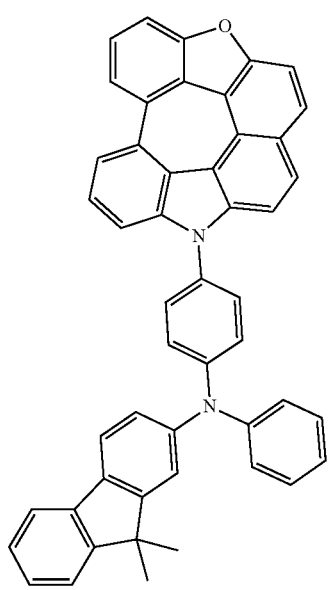
C1-38
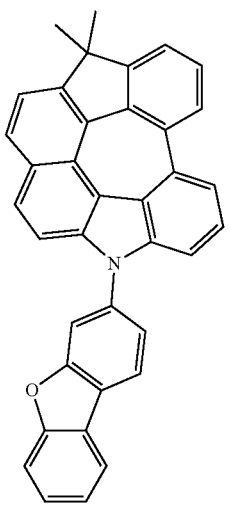
C1-39
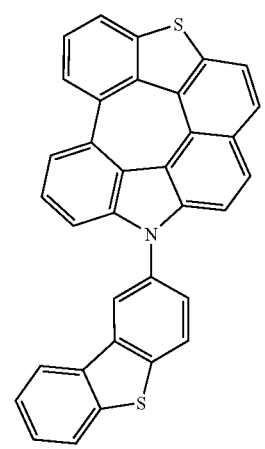
C1-37
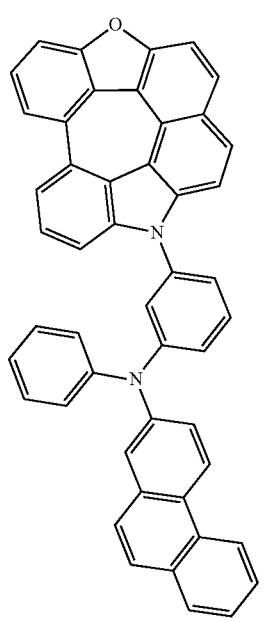
C1-40
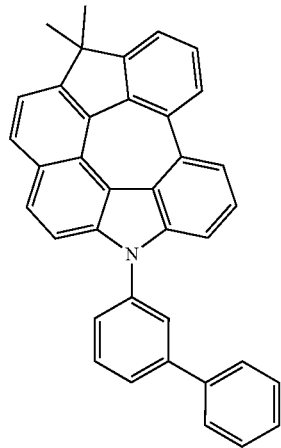

C1-41
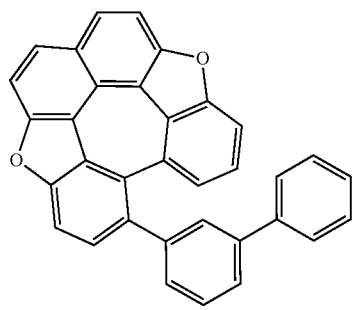
C1-42
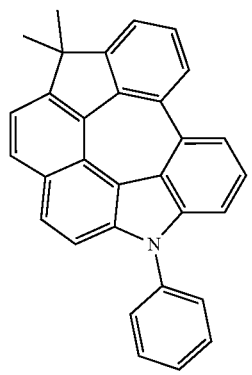
C1-43
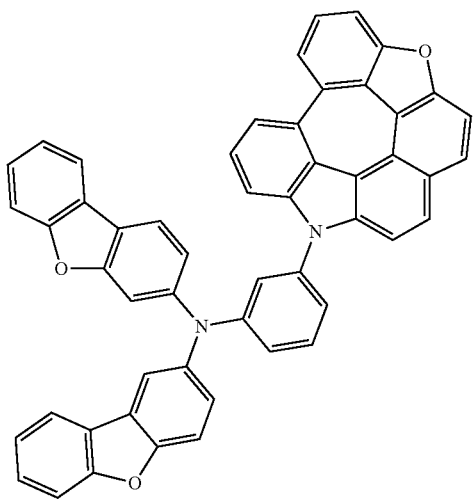
C1-44
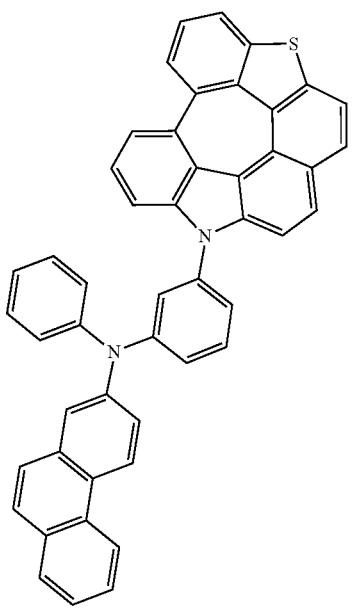
C1-45
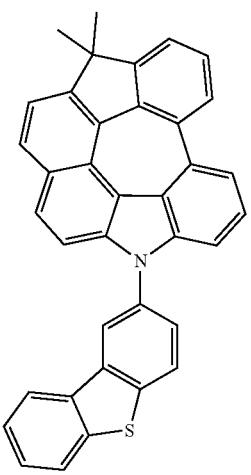
C1-46
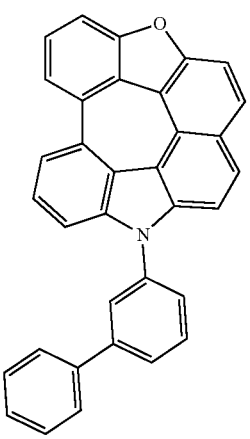

C1-47
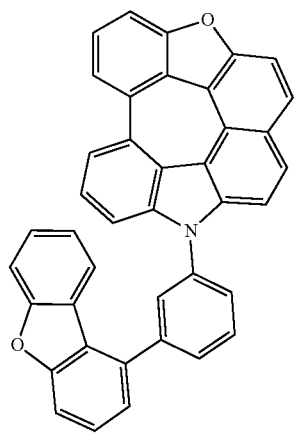
C1-48
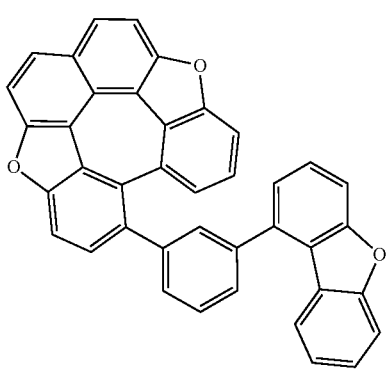
C1-49
C1-50
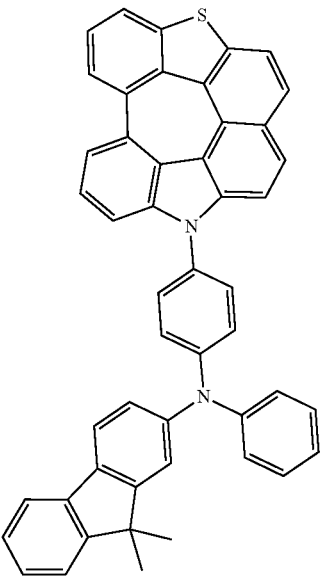
C1-51
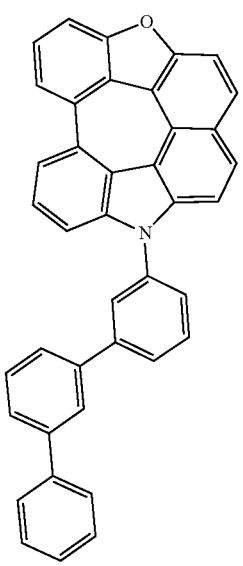
C1-52
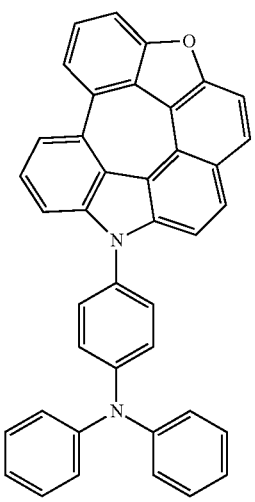

287
-continued
C1-53
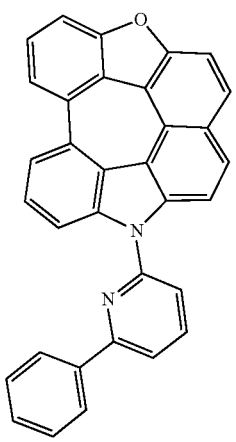
C1-54
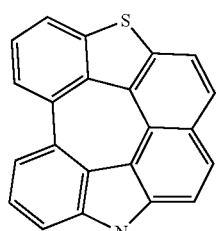
C1-55
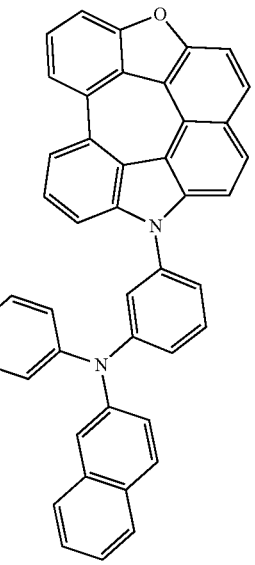
288
-continued
C1-56
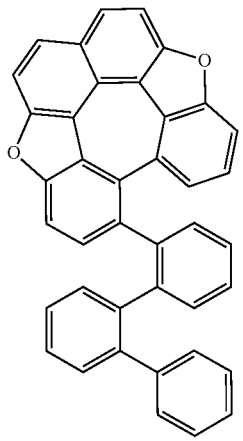
C1-57
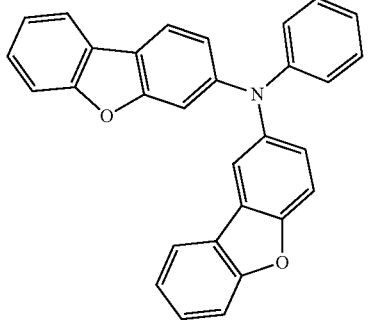
C1-58

-continued
C1-59
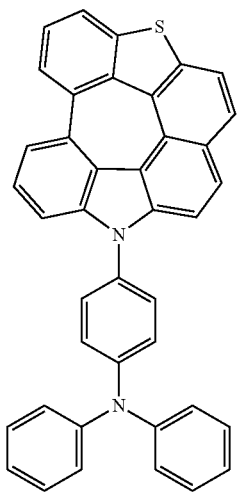
C1-60
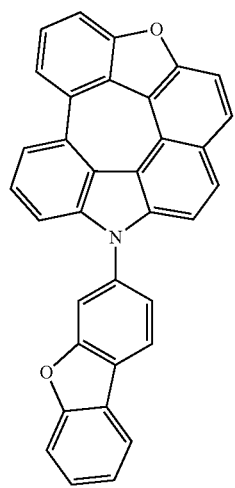
C1-61
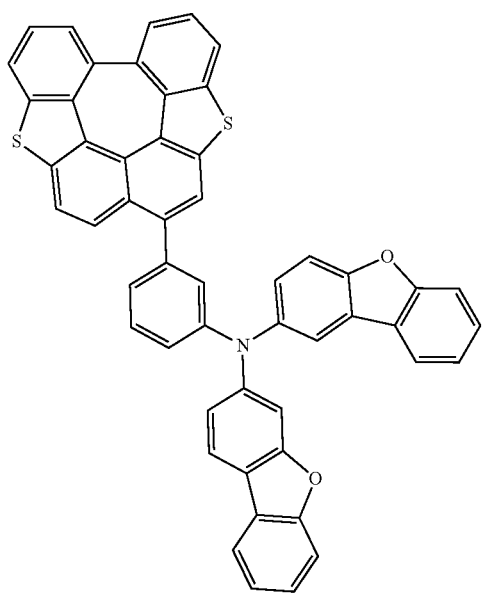
-continued
C-62
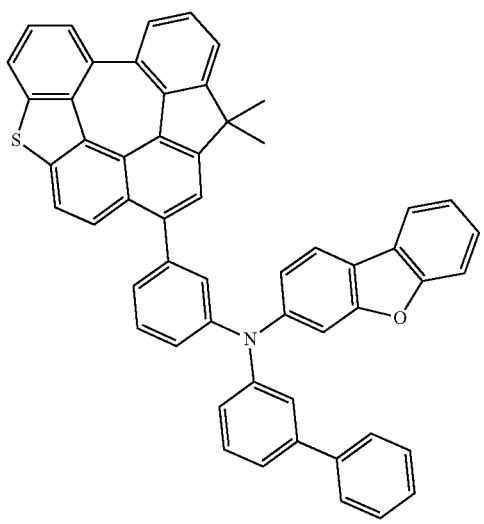
C1-63
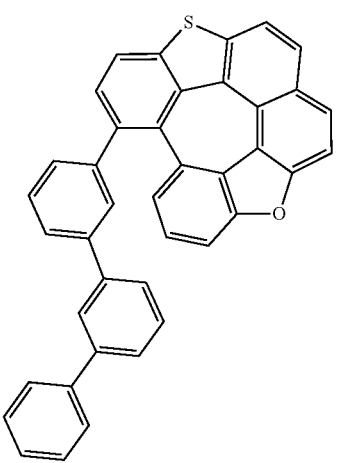
C1-64
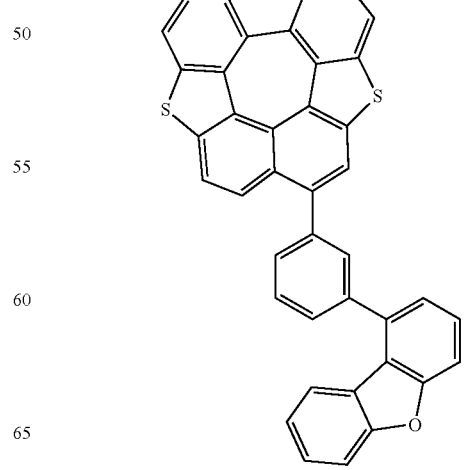

C1-65
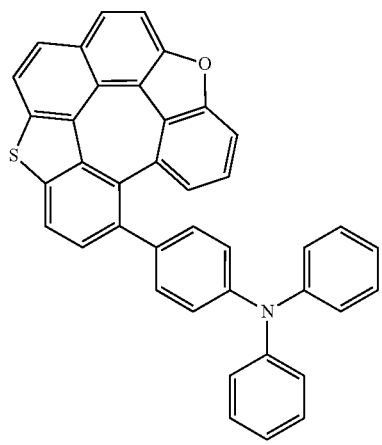
C1-66
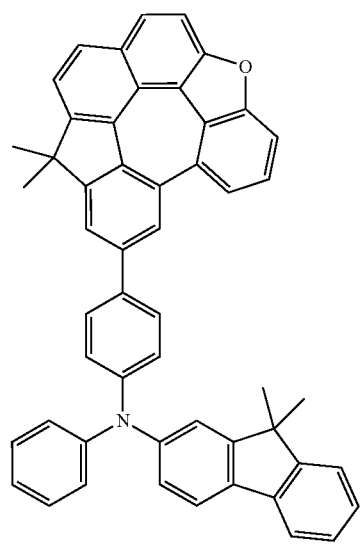
C1-67
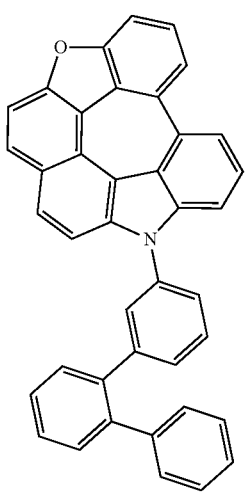
C1-68
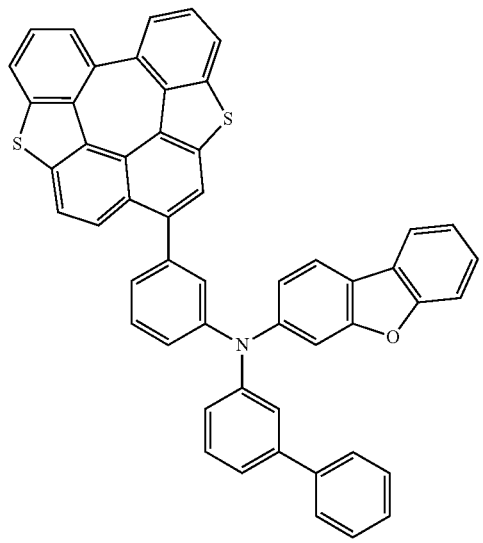
C1-69
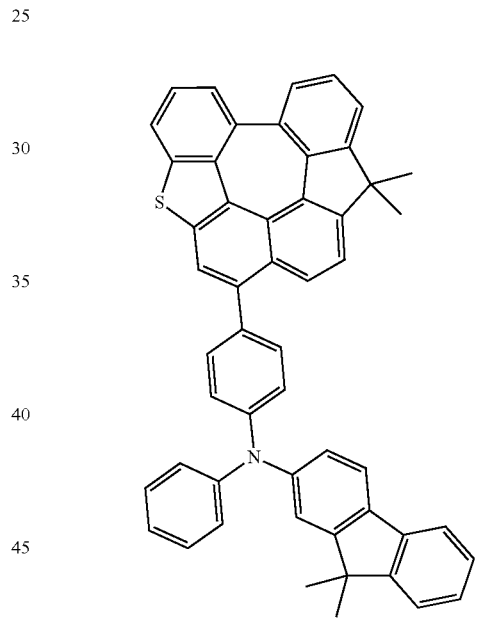
C1-70
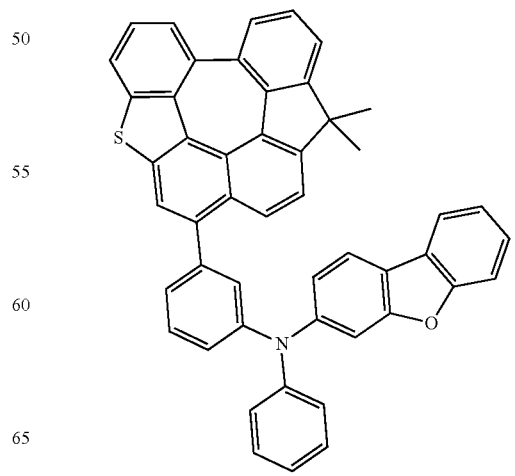

C1-71
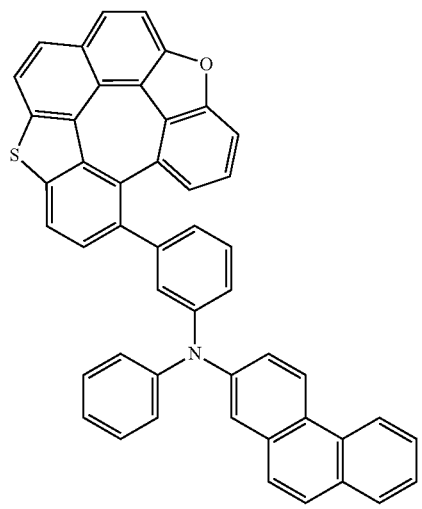
C1-72
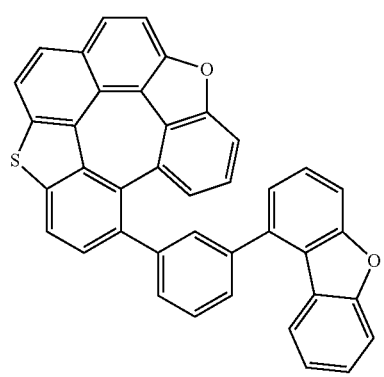
C1-73
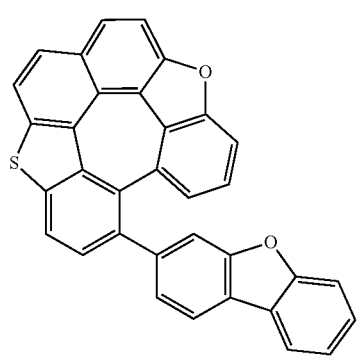
C1-74
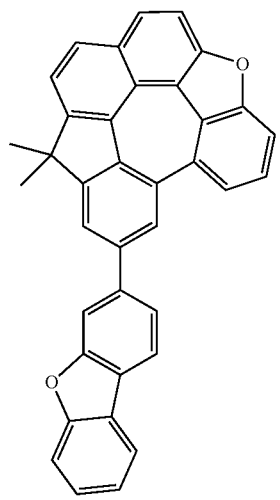
C1-75
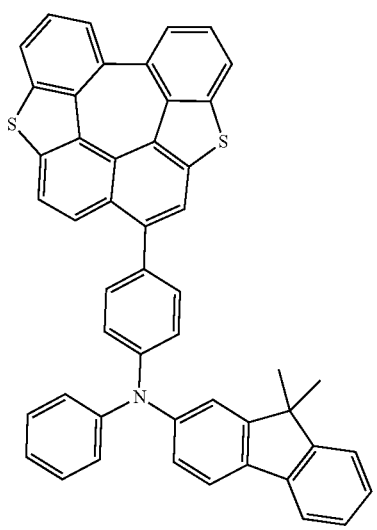
C1-76
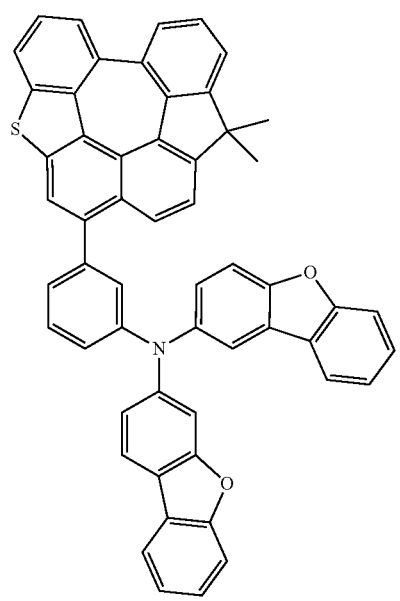

C1-77
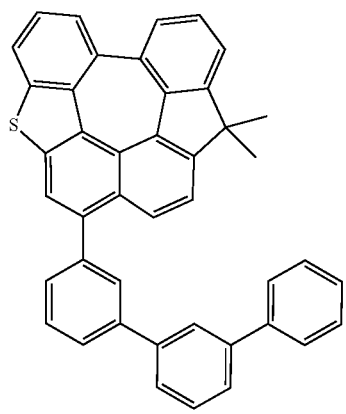
C1-78
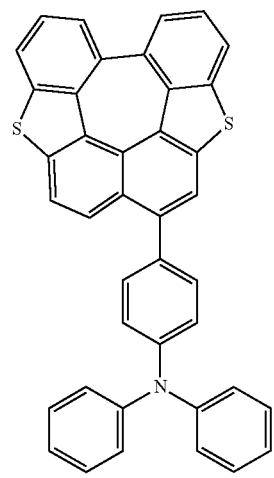
C1-79
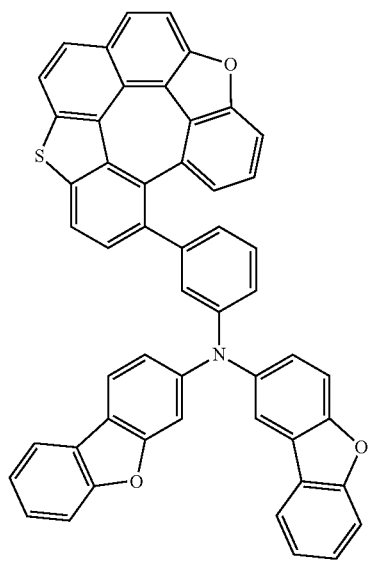
C1-80
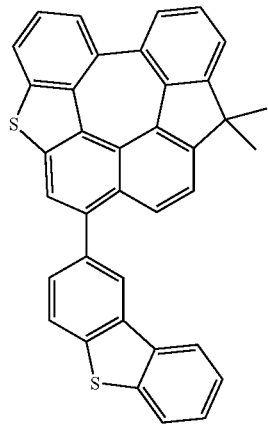
C1-81
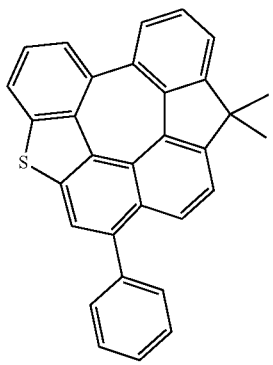
C1-82
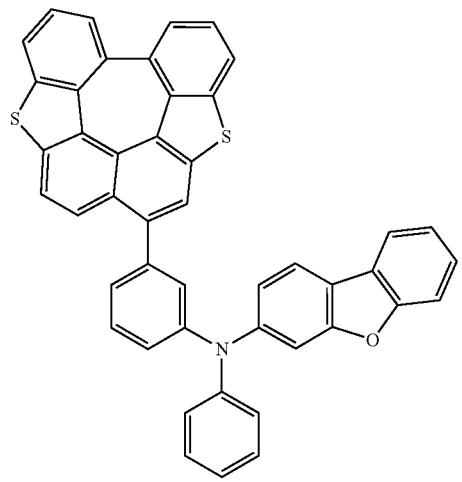

C1-83
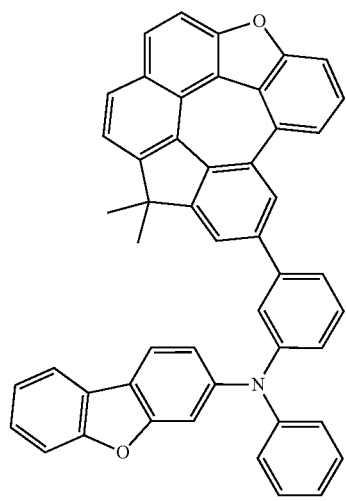
C1-84
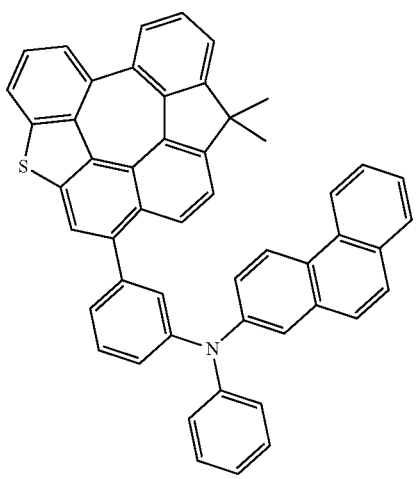
C1-85
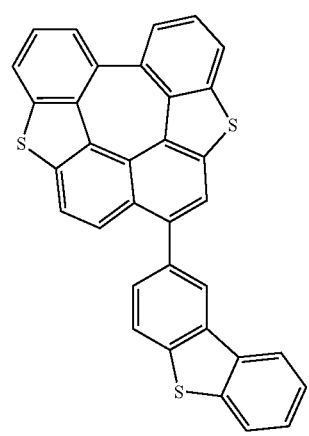
C1-86
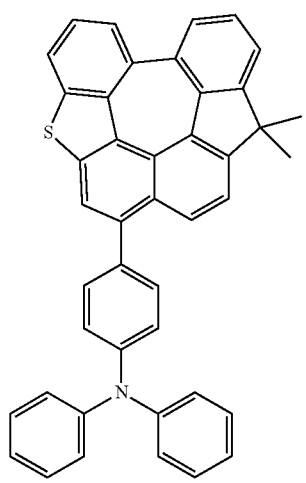
C1-87
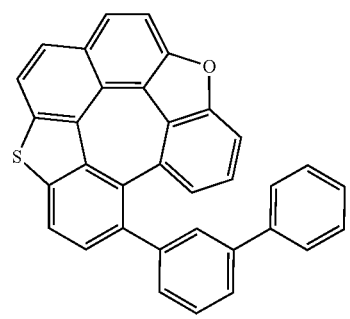
C1-88
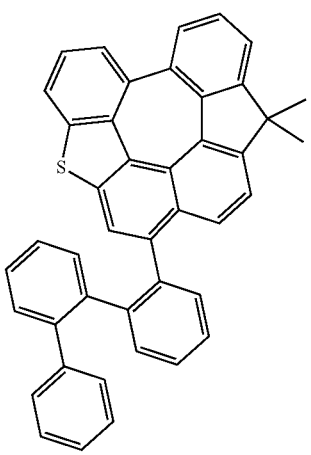

C1-89
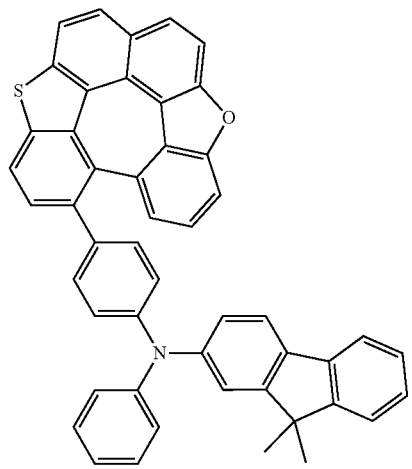
C1-90
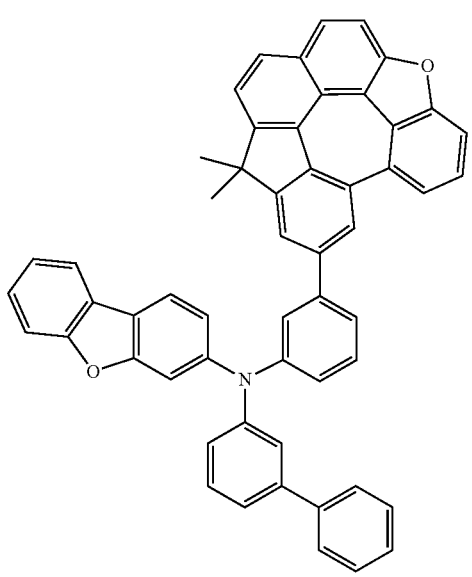
C1-91
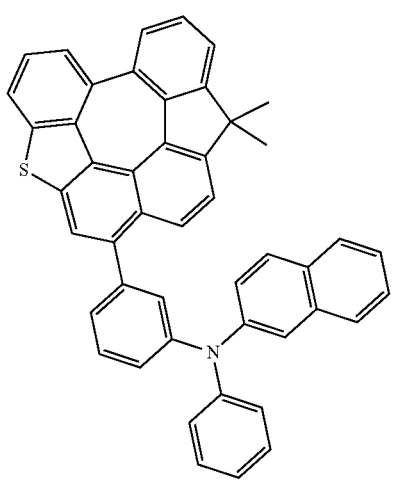
C1-92
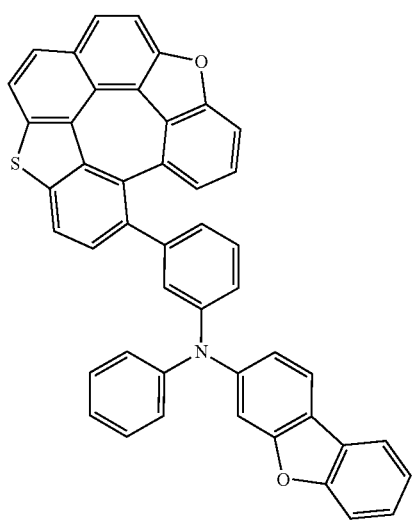
C1-93
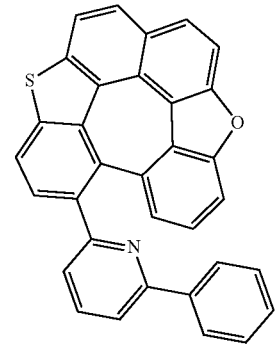
C1-94

C1-95
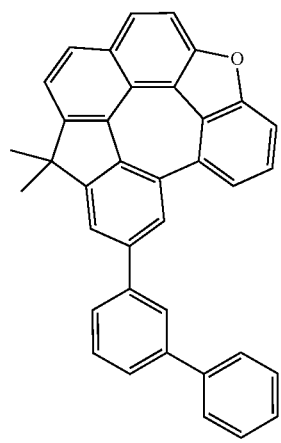
C1-96
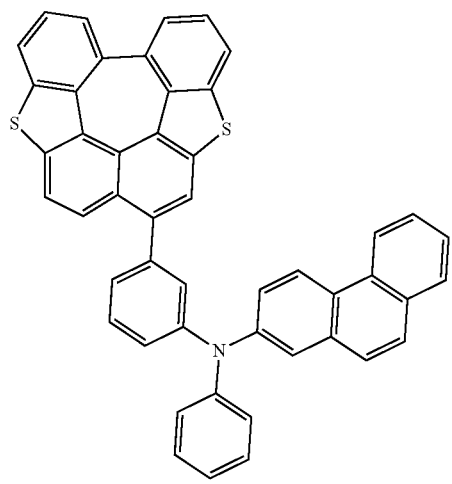
C1-97
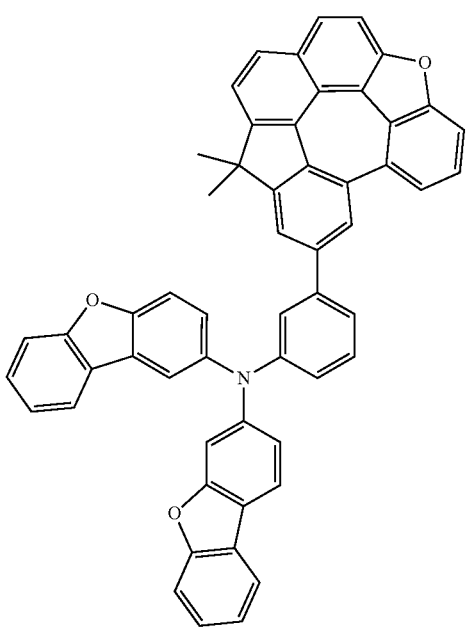
C1-98
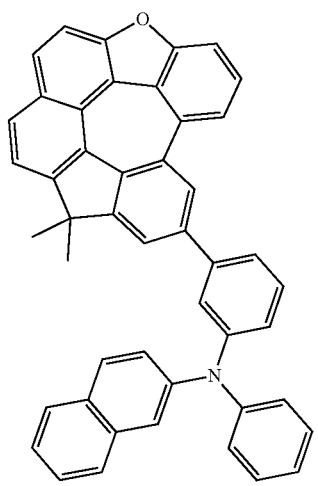
C1-99
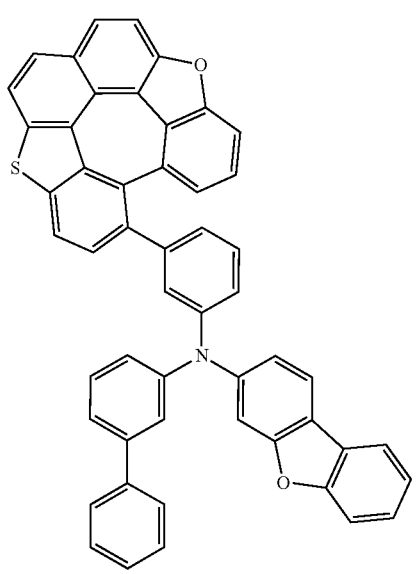
C1-100
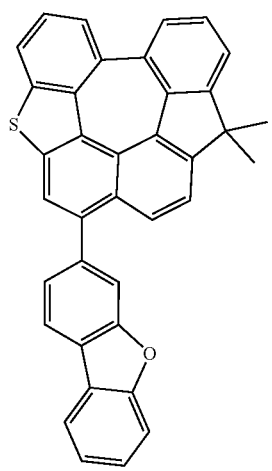

C1-101
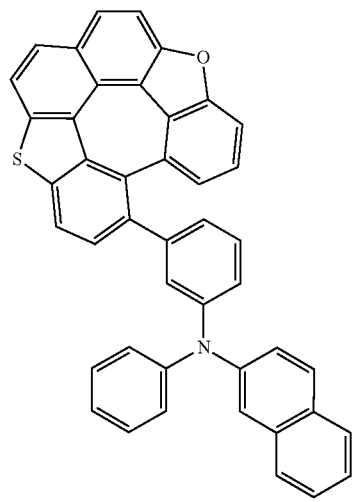
C1-102
C1-103
C1-104
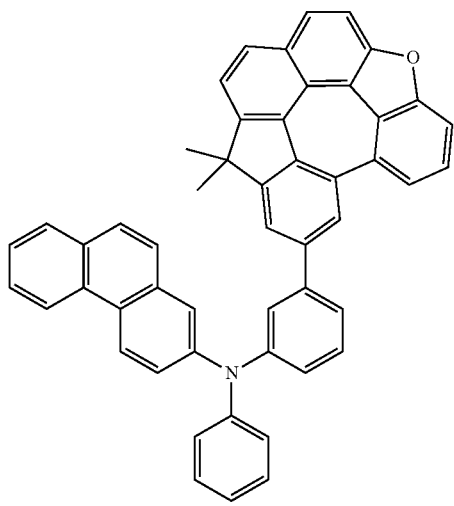
C1-105
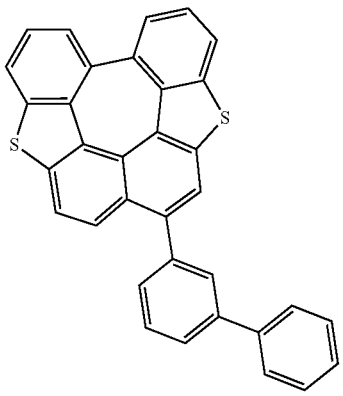
C1-106
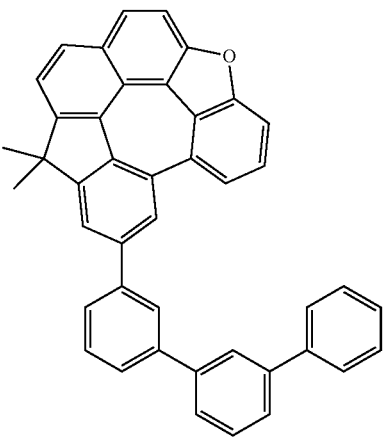

C1-107
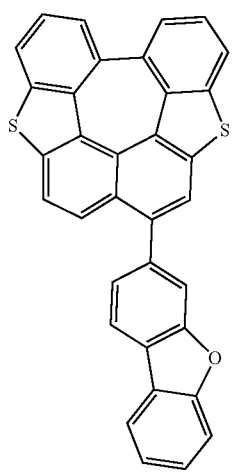
C1-110
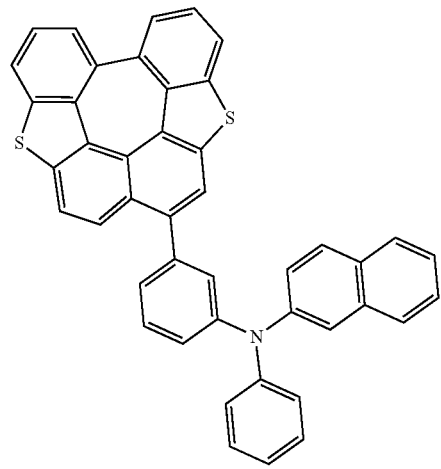
C1-108
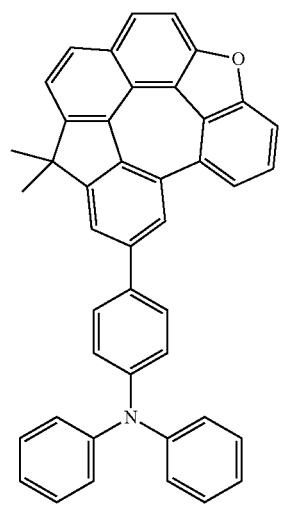
C1-111
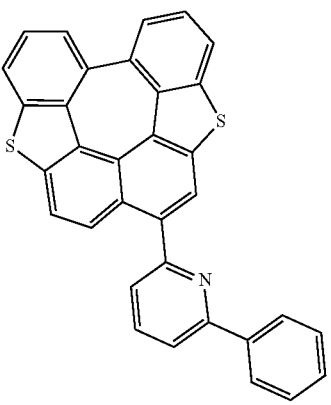
C1-109
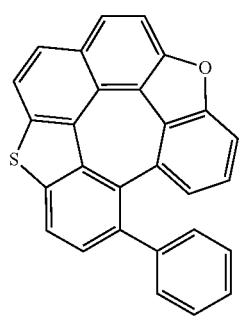
C1-112

C1-113
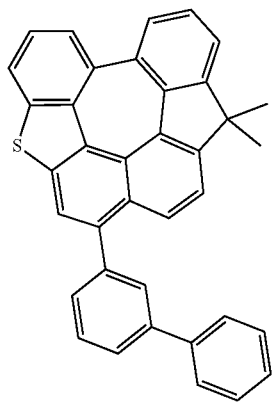
C1-114
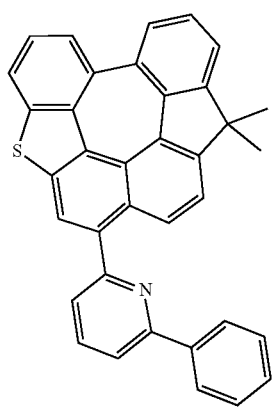
C1-115
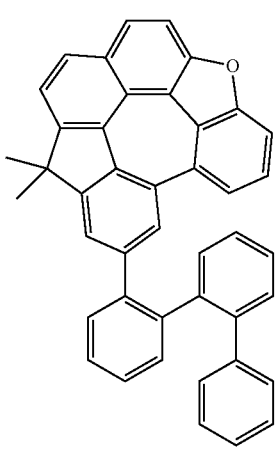
C1-116
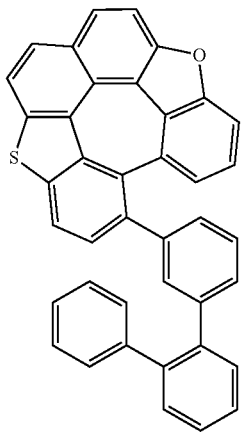
C1-117
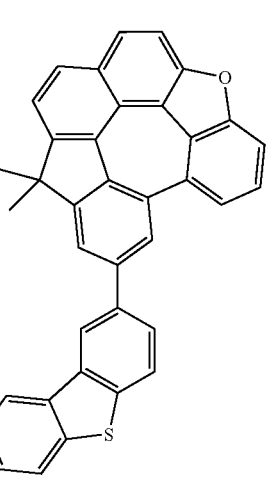
C1-118
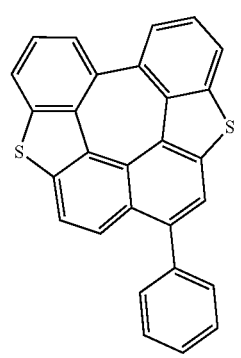
C1-119
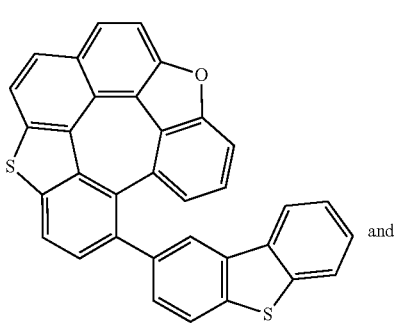
and C1-120
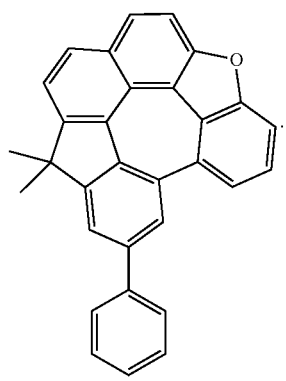
7. The plurality of host materials according to claim 1, wherein the compound represented by formula 2 is selected from the following compounds:
C2-1
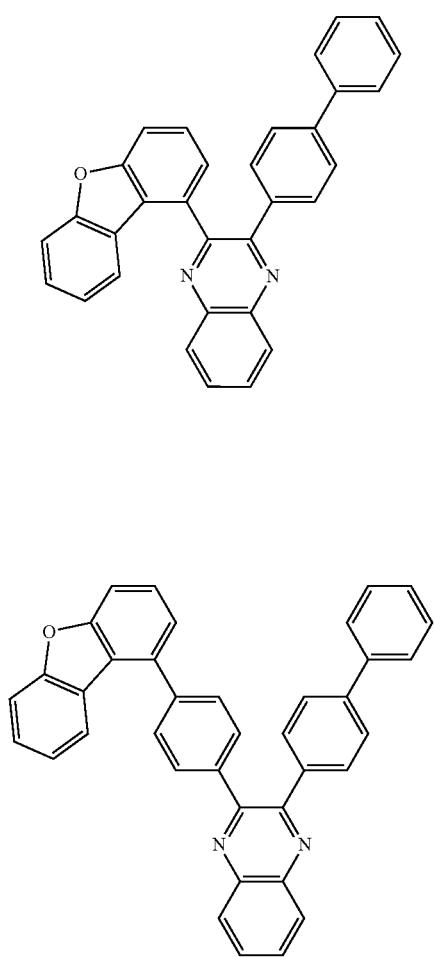
C2-3
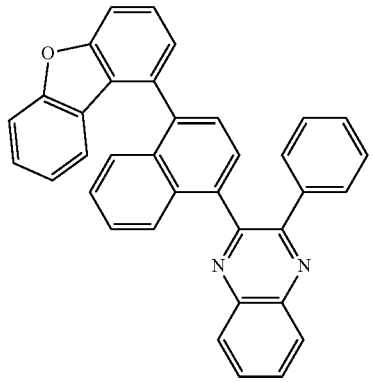
C2-4
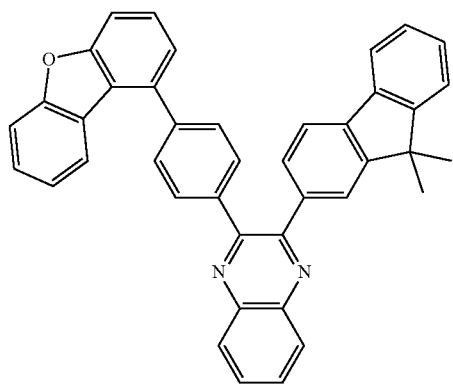
C2-5
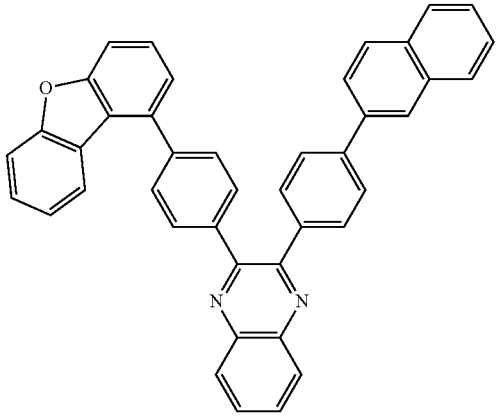
C2-2
C2-6
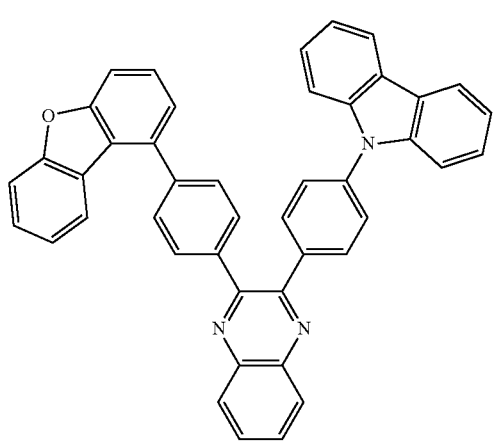

C2-7
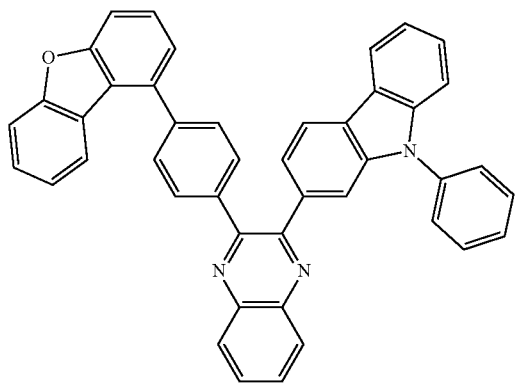
C2-8
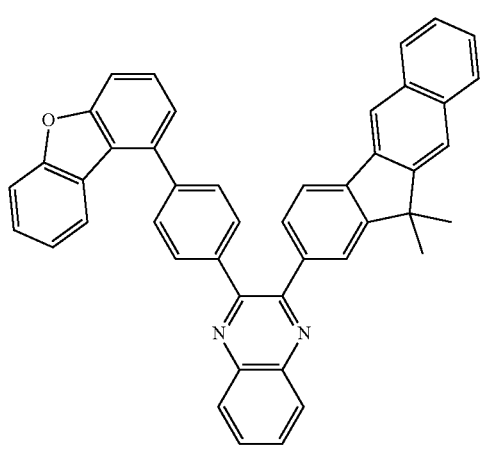
C2-9
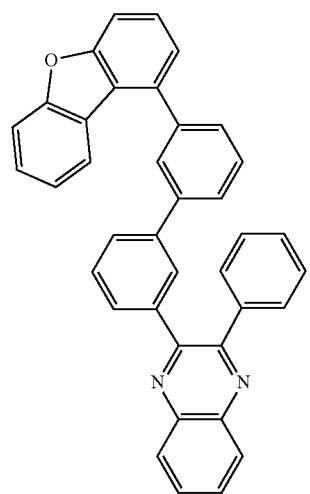
C2-10
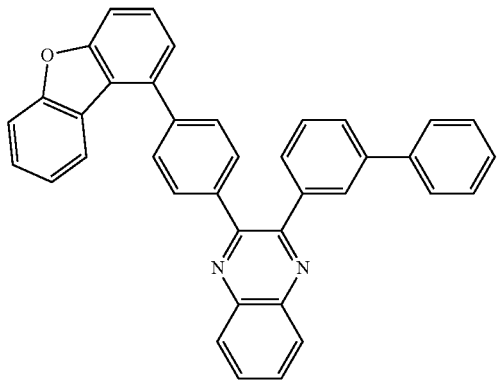
C2-11
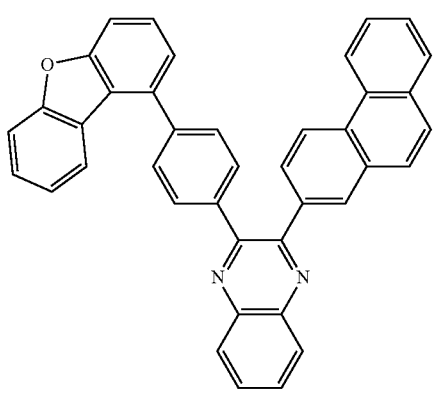
C2-12
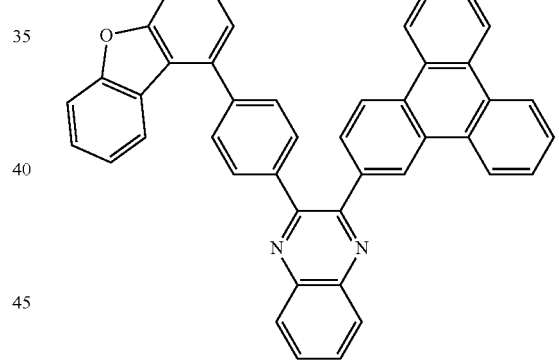
C2-13
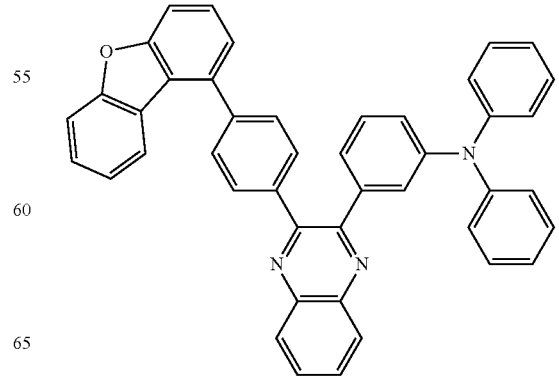

C2-14
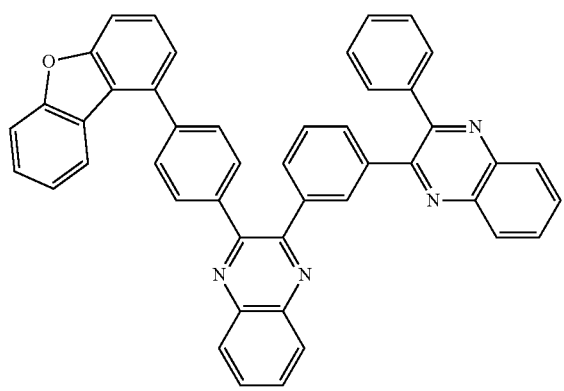
C2-15
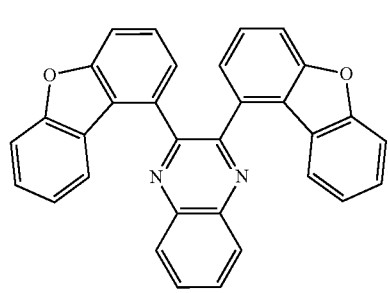
C2-16
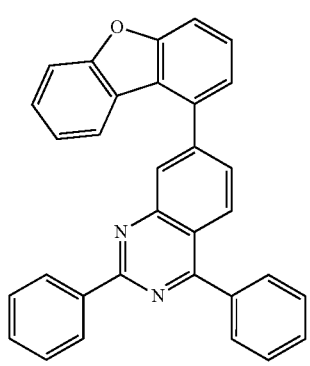
C2-17
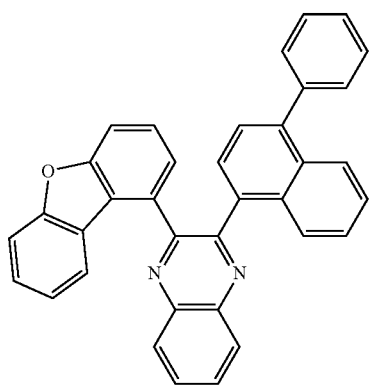
C2-18
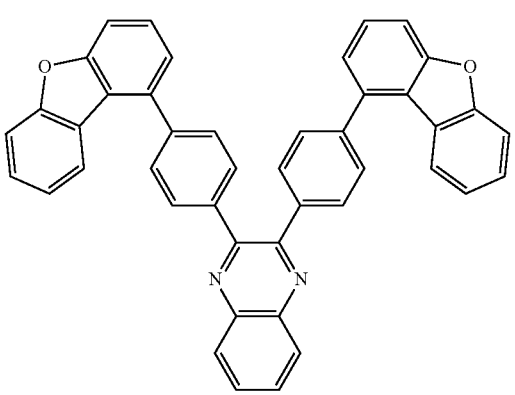
C2-19
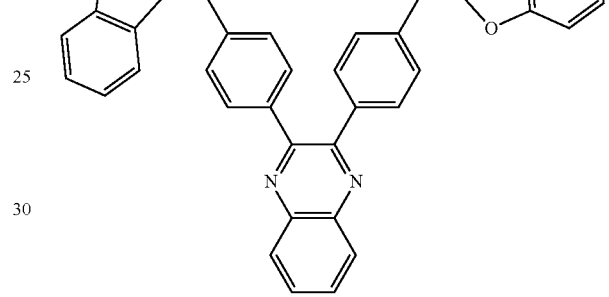
C2-20
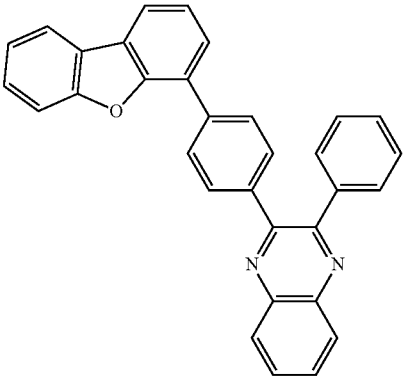
C2-21
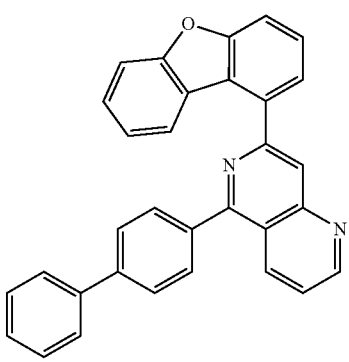

C2-22
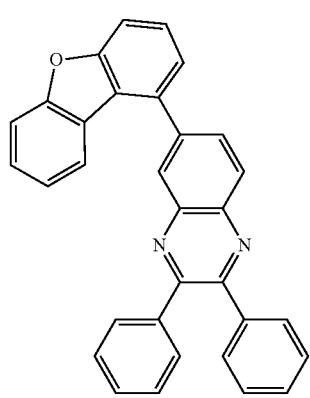
C2-23
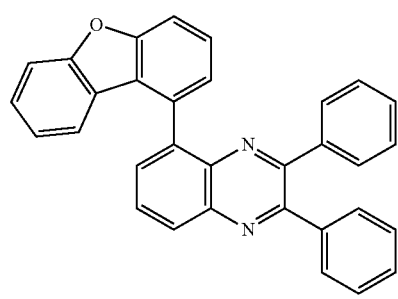
C2-24
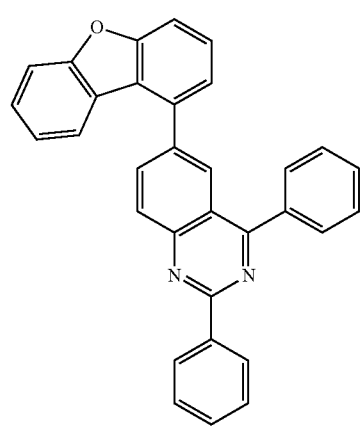
C2-25
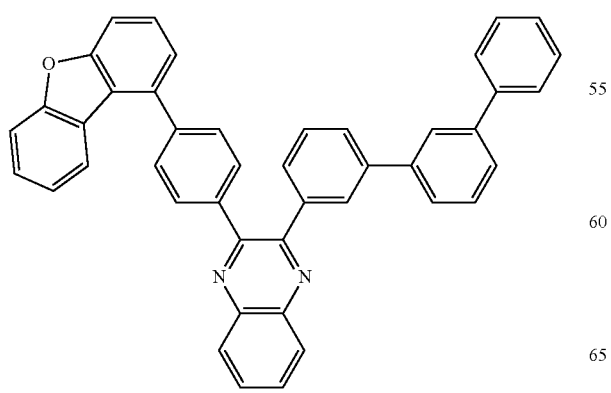
C2-26
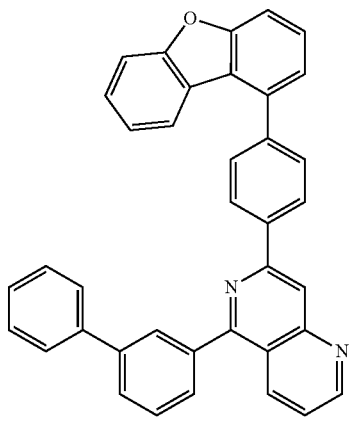
C2-27
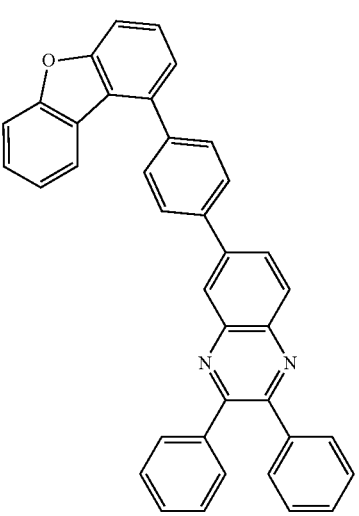
C2-28
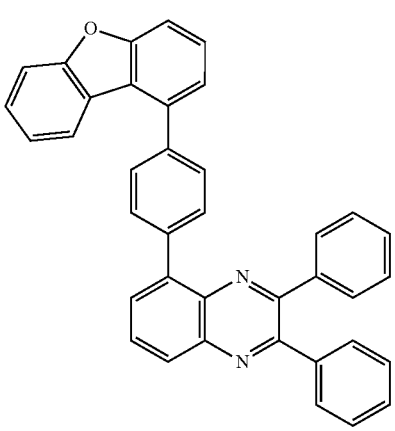

-continued
C2-29
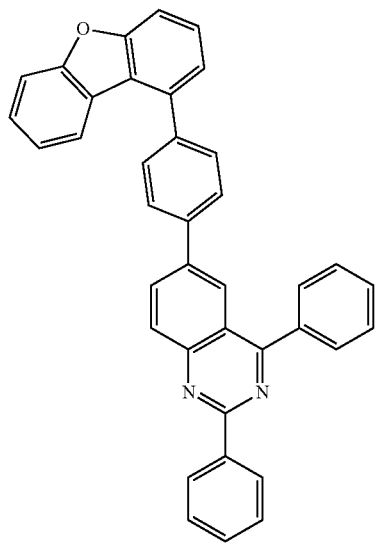
C2-30
C2-31
-continued
C2-32
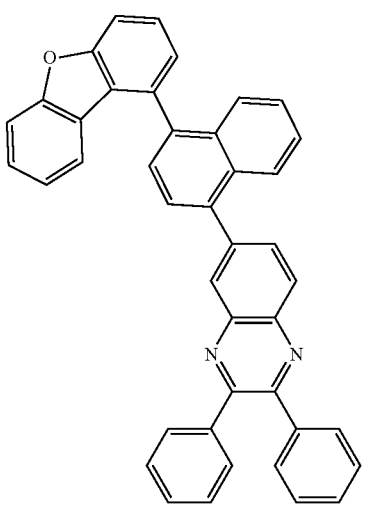
C2-33
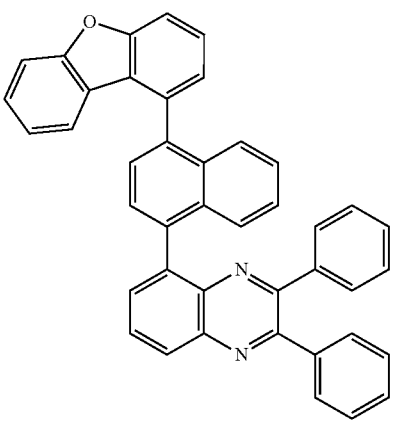
C2-34
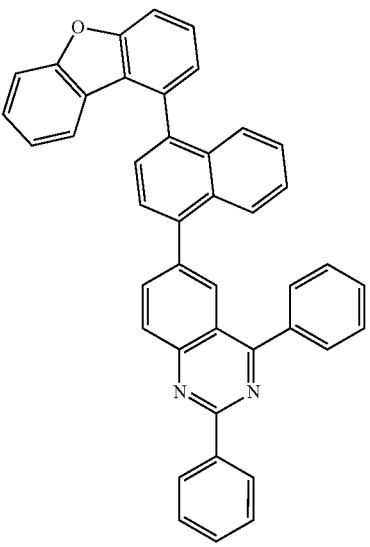

-continued
C2-35
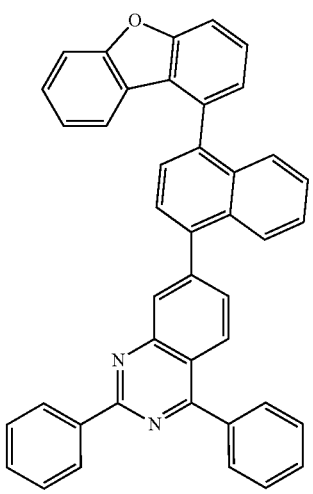
C2-36
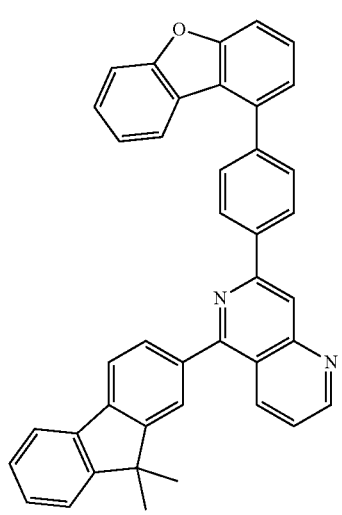
C2-37
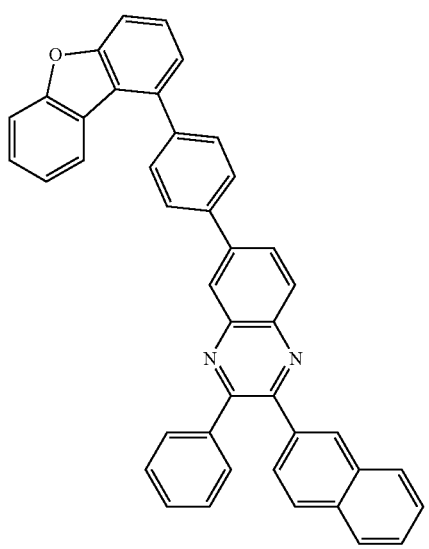
-continued
C2-38
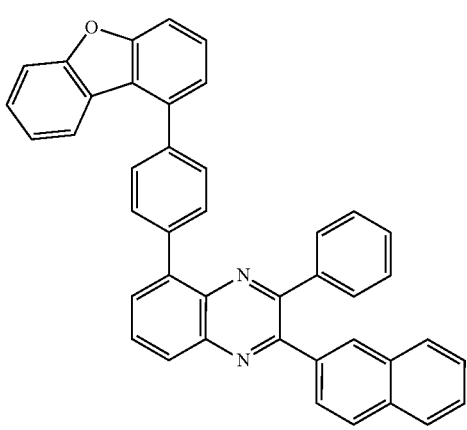
C2-39
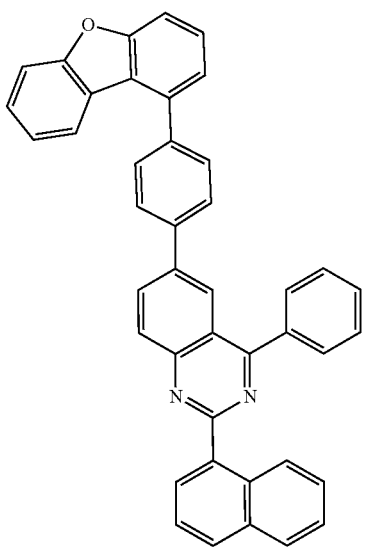
C2-40
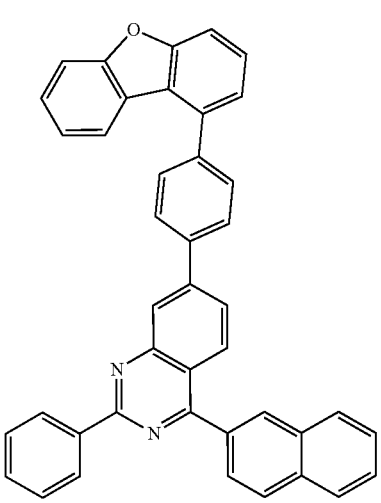

C2-41
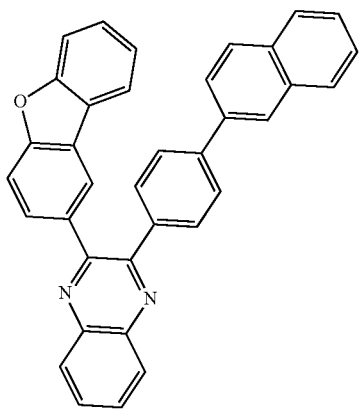
C2-42
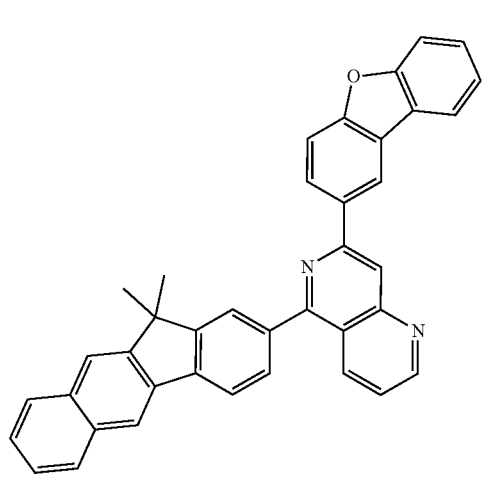
C2-43
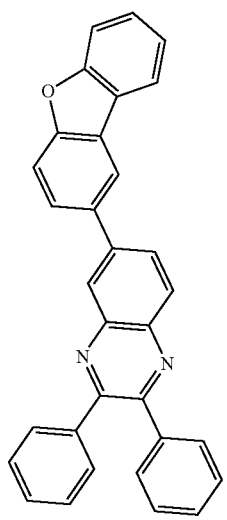
C2-44
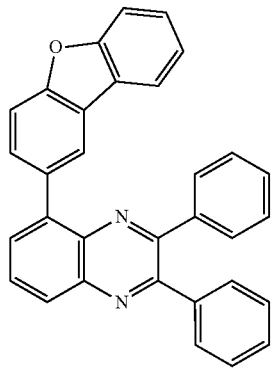
C2-45
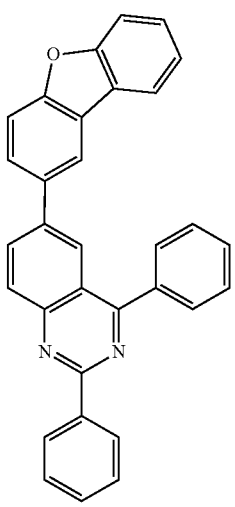
C2-46
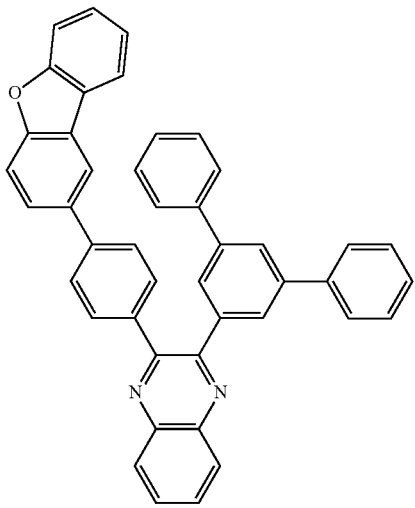

C2-47
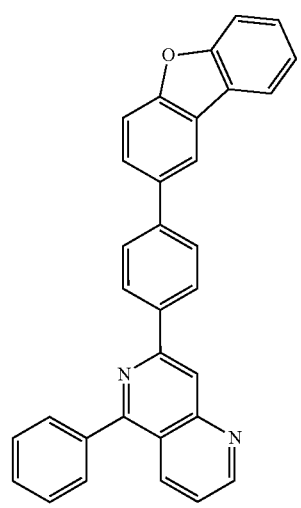
C2-48
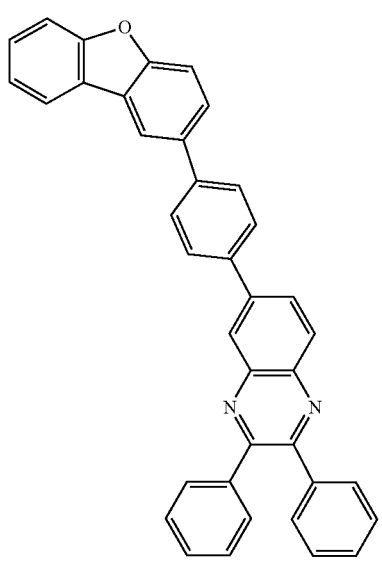
C2-49
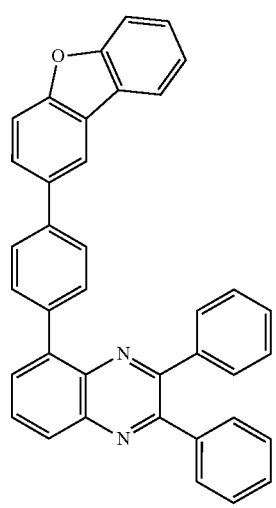
C2-50
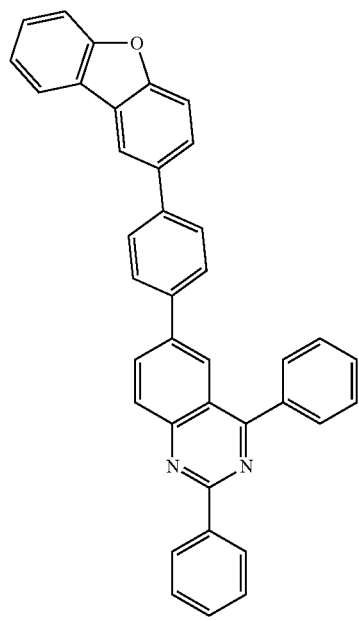
C2-51
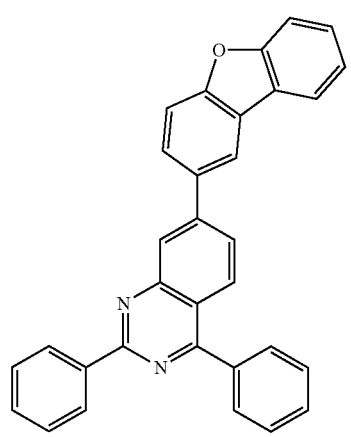
C2-52
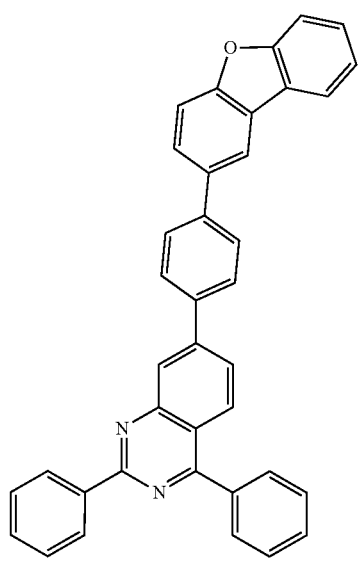

C2-53
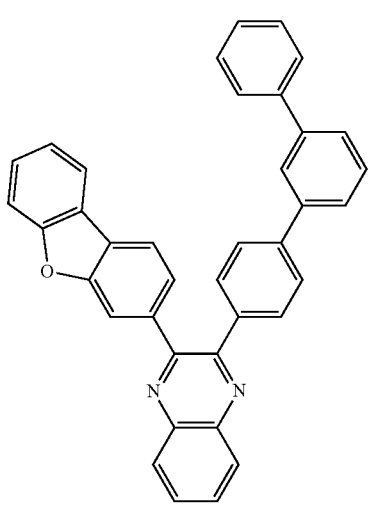
C2-54
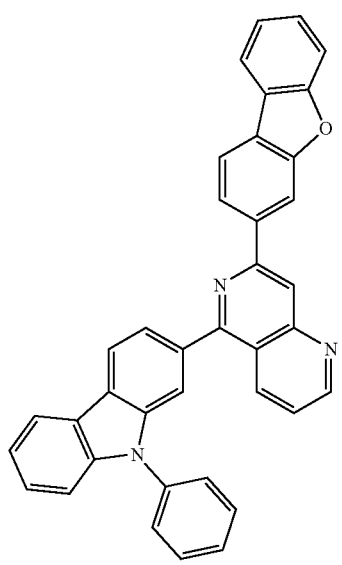
C2-55
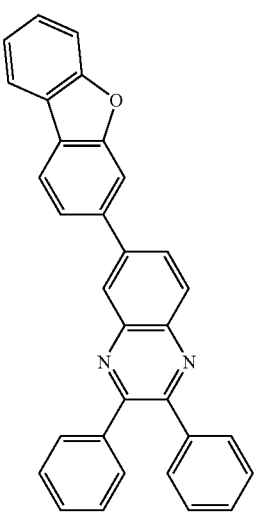
C2-56
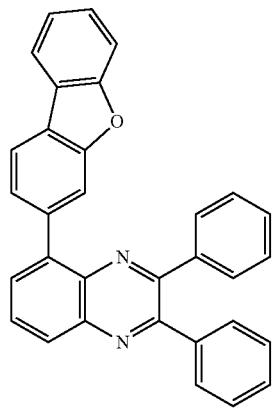
C2-57
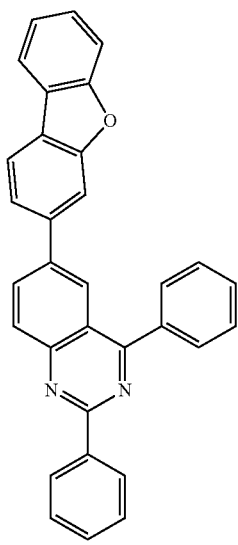
C2-58
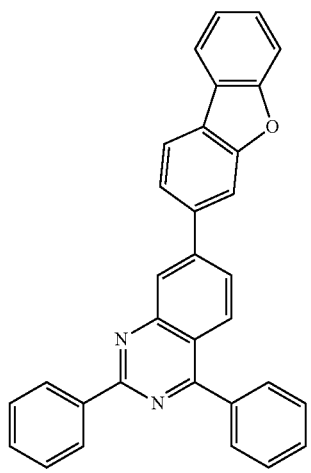

-continued
C2-59
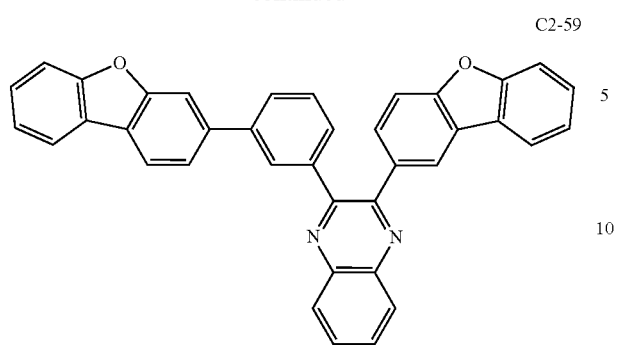
C2-60
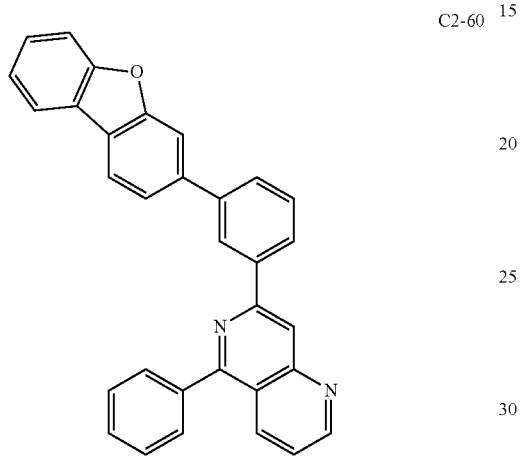
C2-61
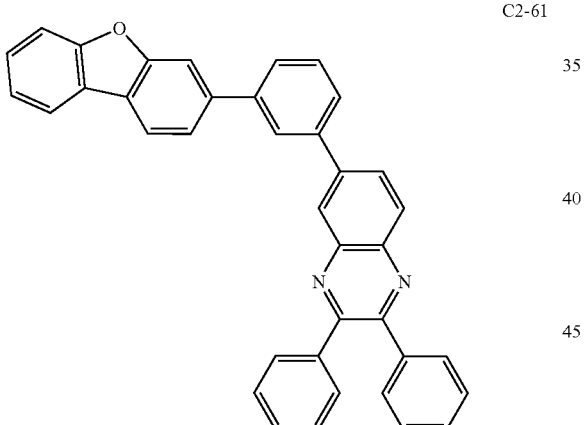
C2-62
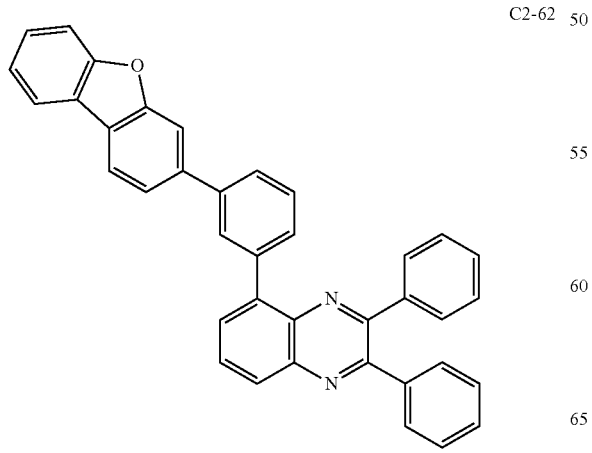
-continued
C2-63
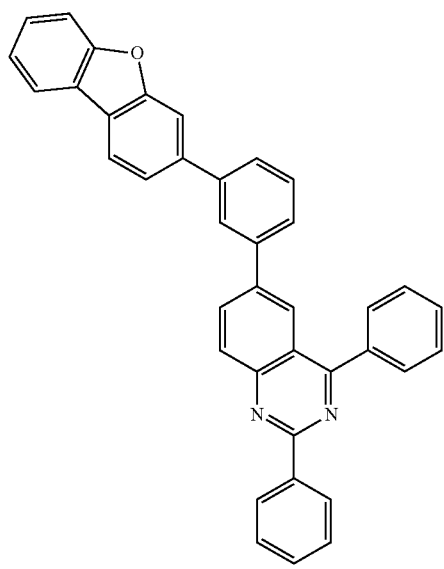
C2-64
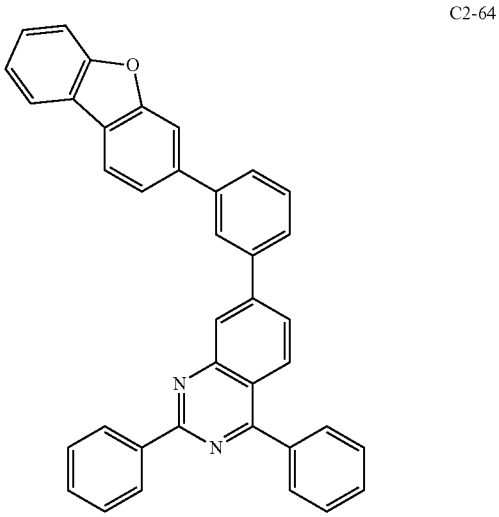
C2-65
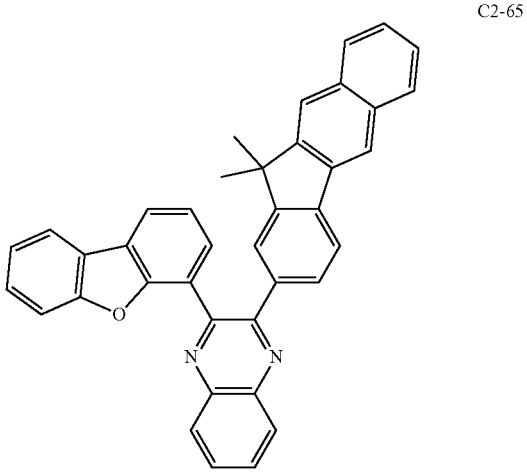

C2-66
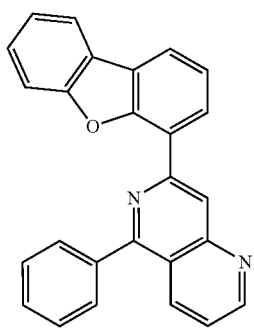
C2-67
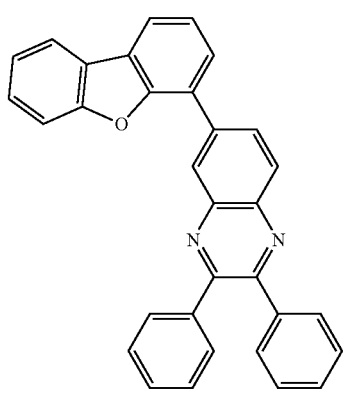
C2-68
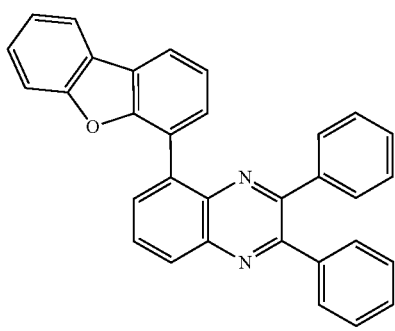
C2-69
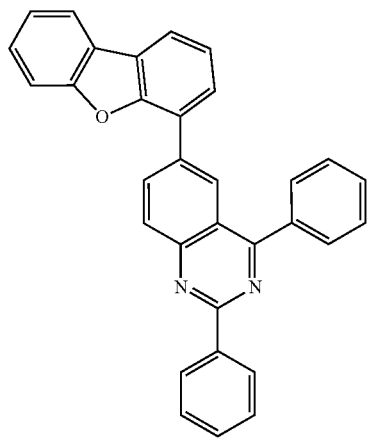
C2-70
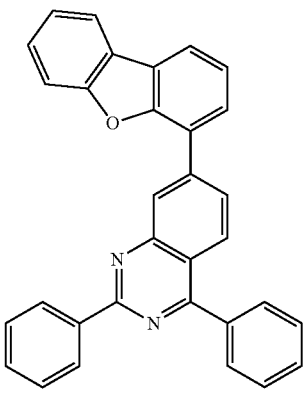
C2-71
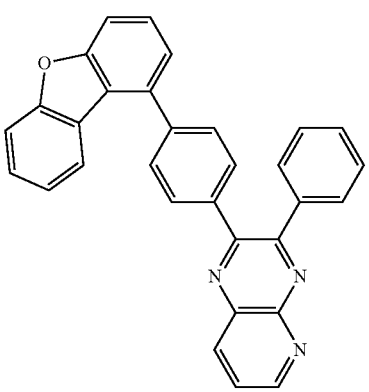
C2-72
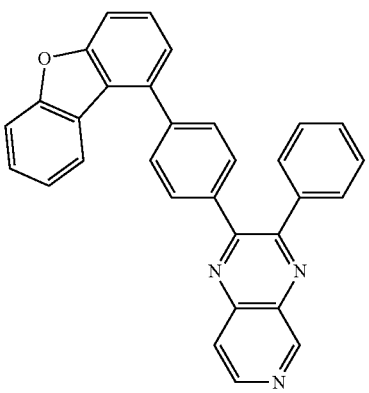
C2-73

C2-74
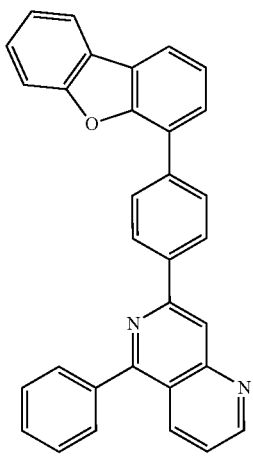
C2-75
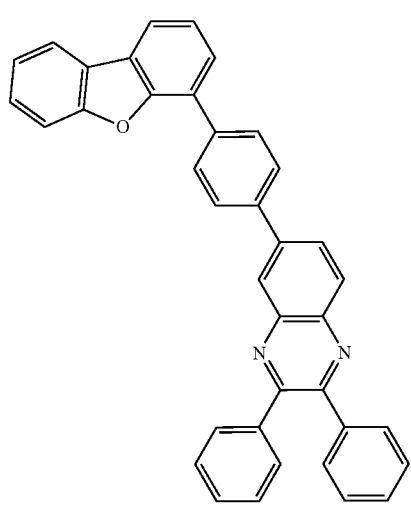
C2-76
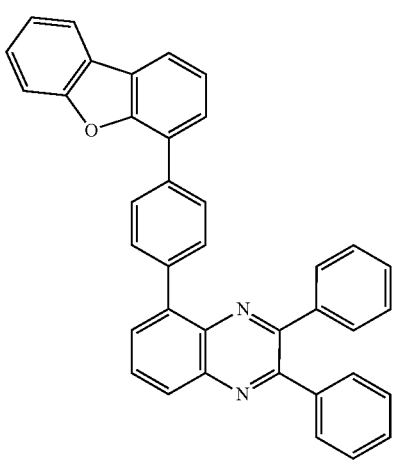
C2-77
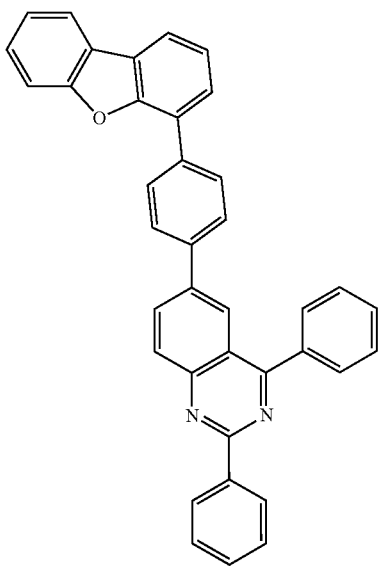
C2-78
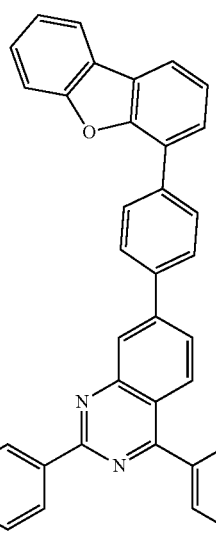
C2-79
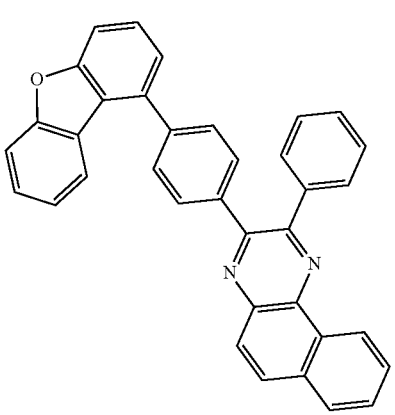

C2-80
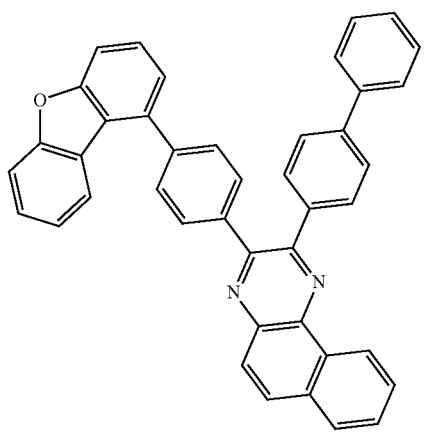
C2-81
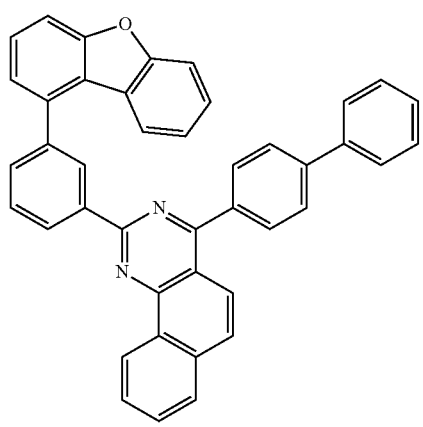
C2-82
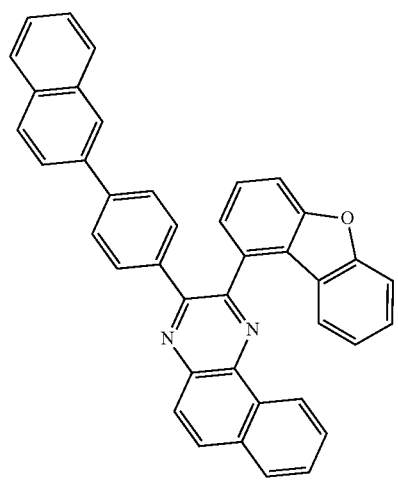
C2-83
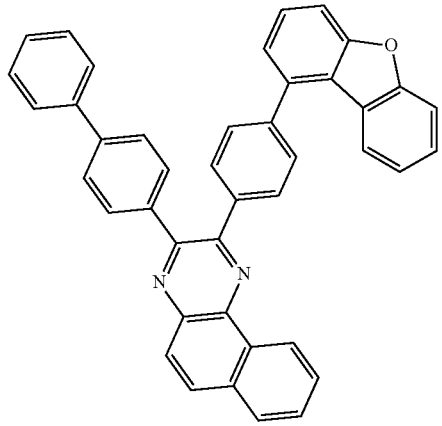
C2-84
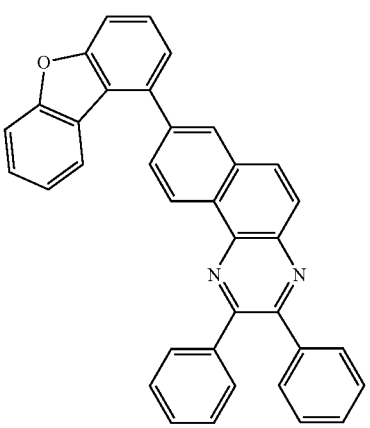
C2-85

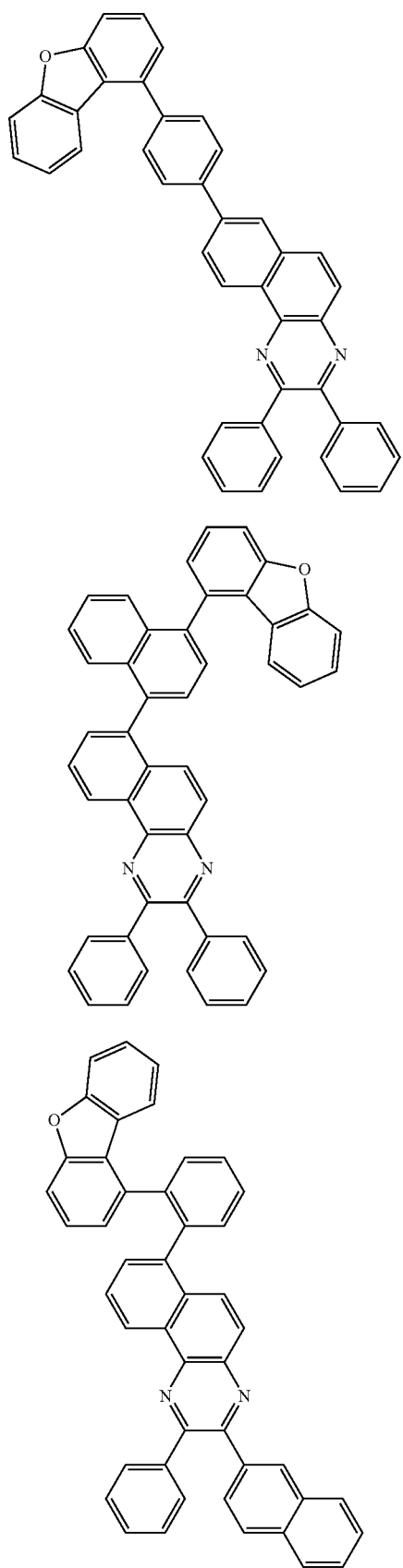
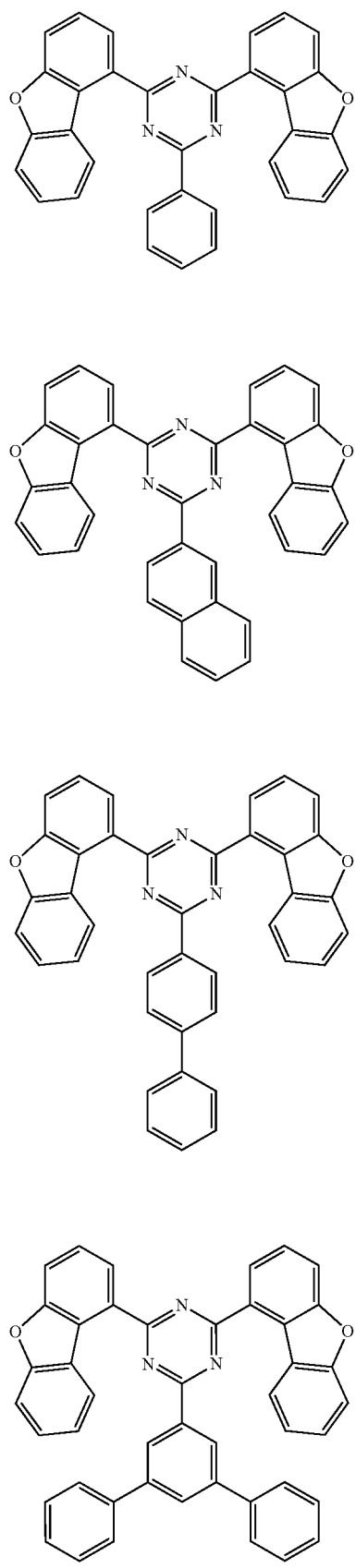

C2-93
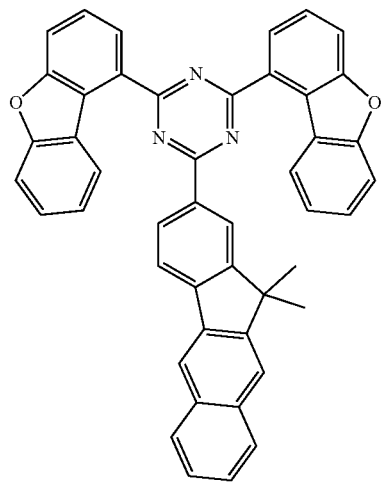
C2-96
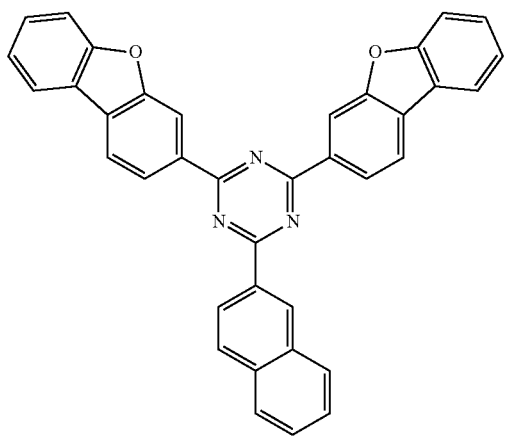
C2-94
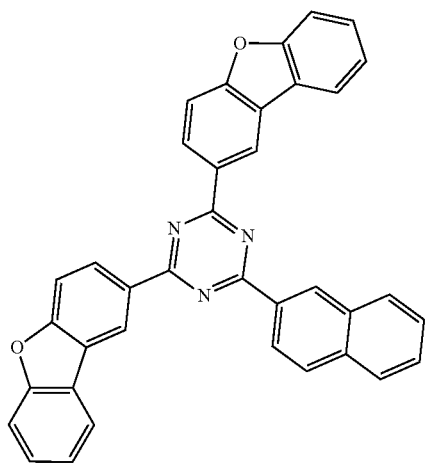
C2-97
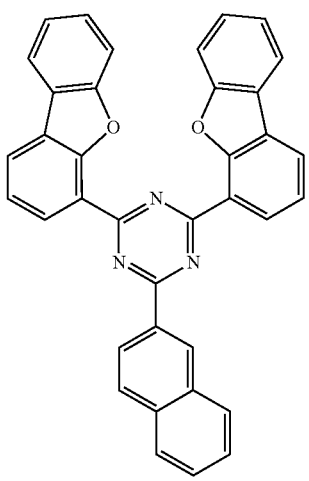
C2-95
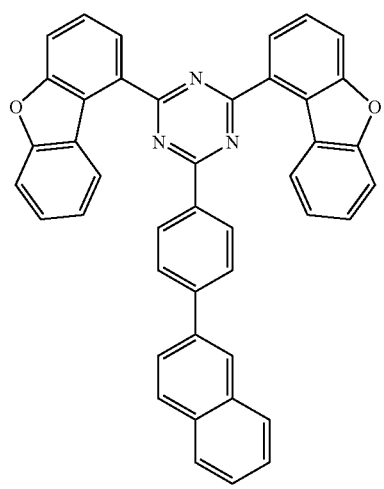
C2-98
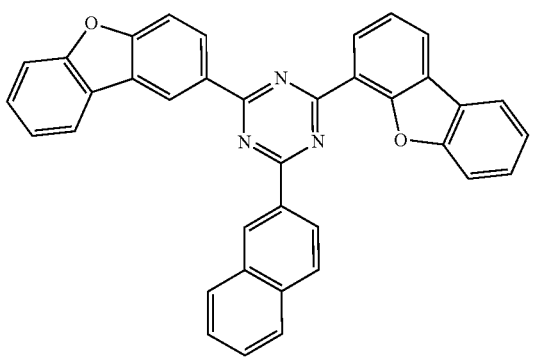

C2-99
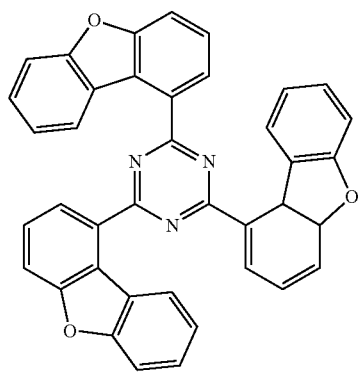
C2-102
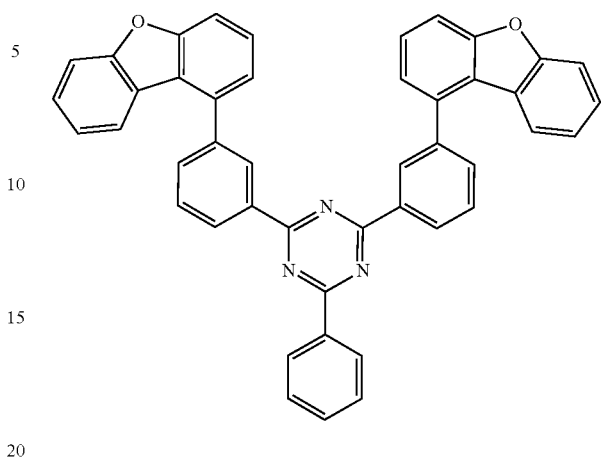
C2-100
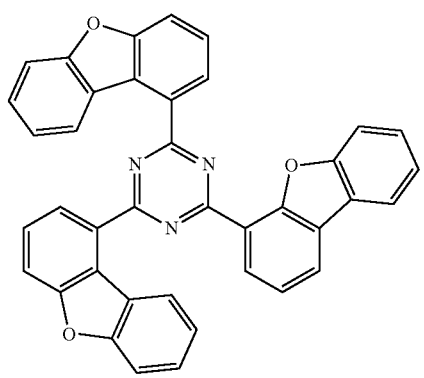
C2-103
C2-101
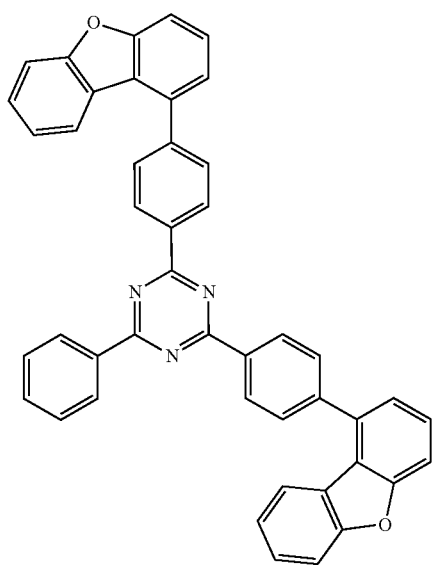
C2-104
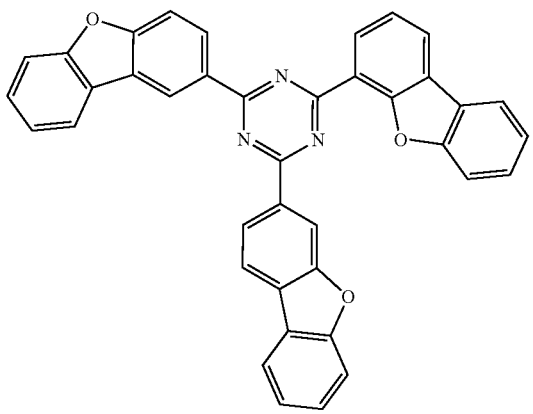

C2-105
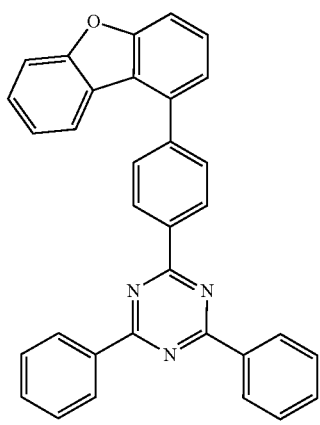
C2-106
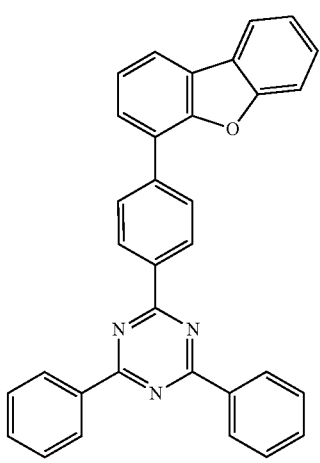
C2-107
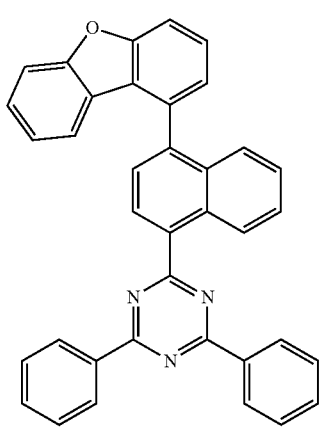
C2-108
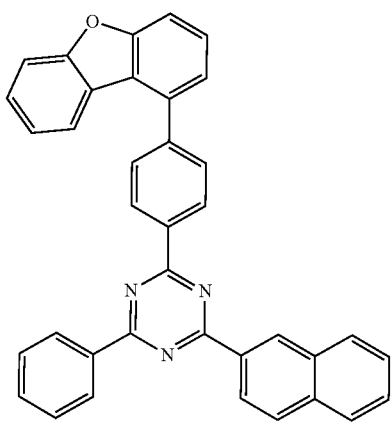
C2-109
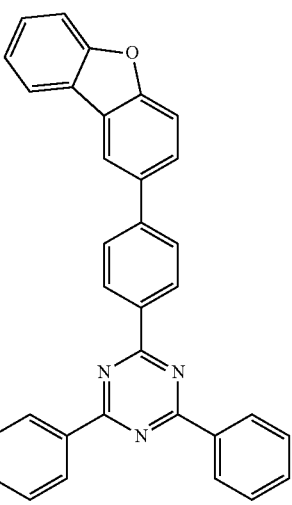
C2-110
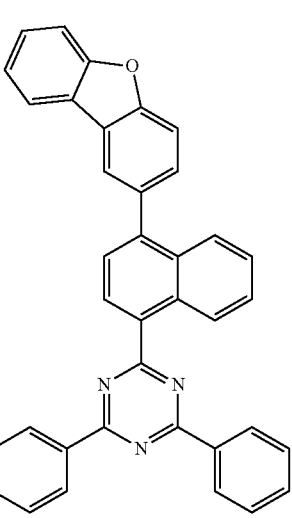

C2-111
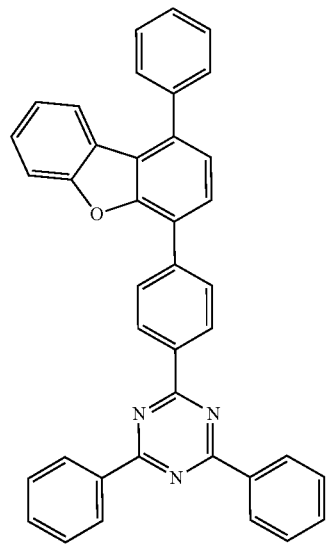
C2-112
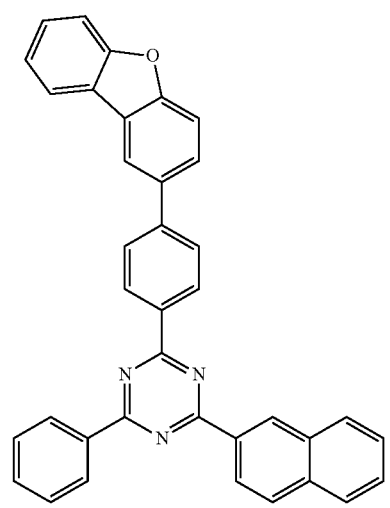
C2-113
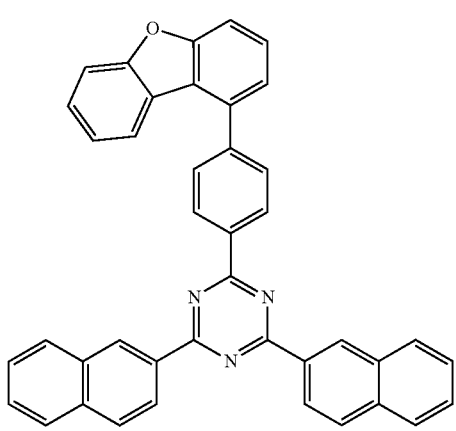
C2-114
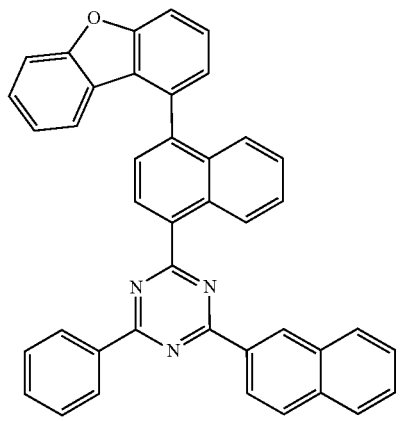
C2-115
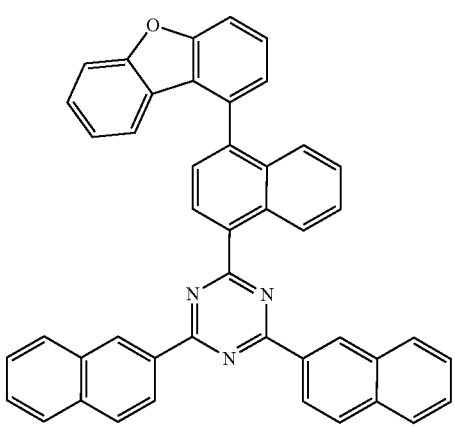
C2-116
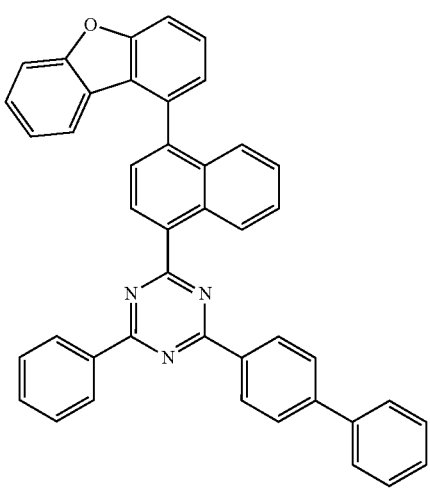

C2-117
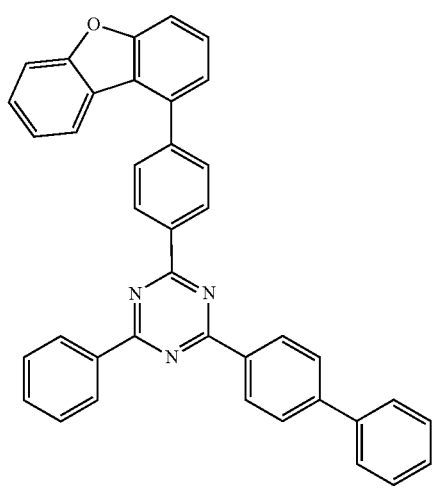
C2-118
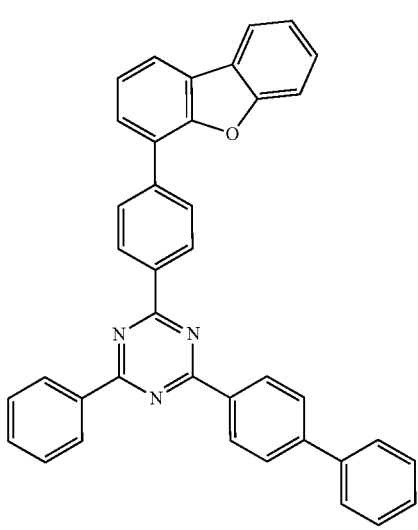
C2-119
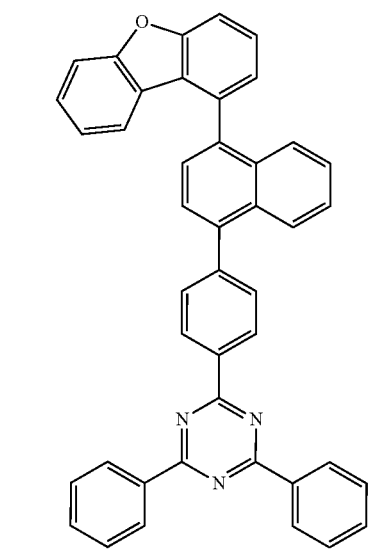
C2-120
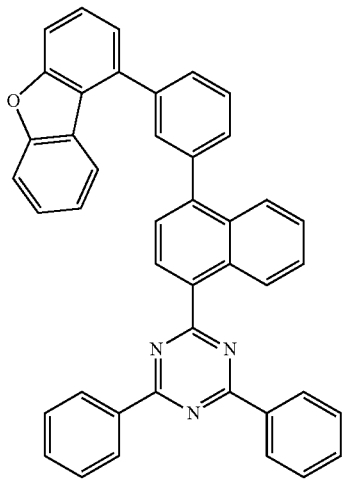
C2-121
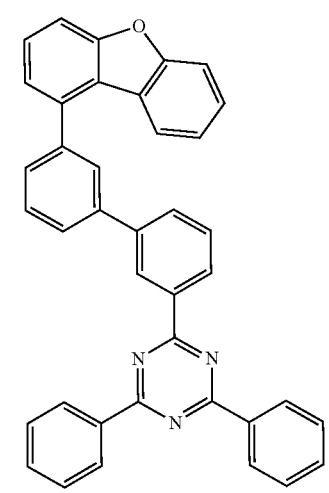
C2-122
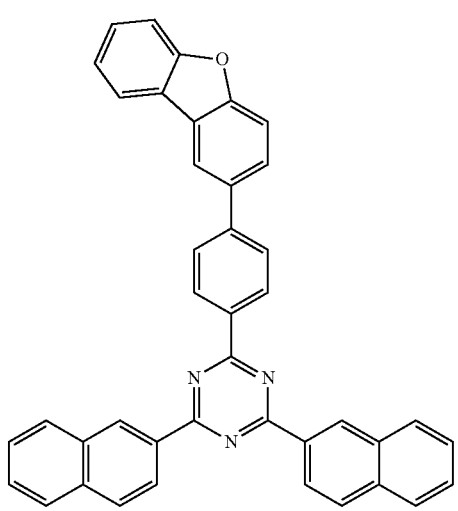

C2-123
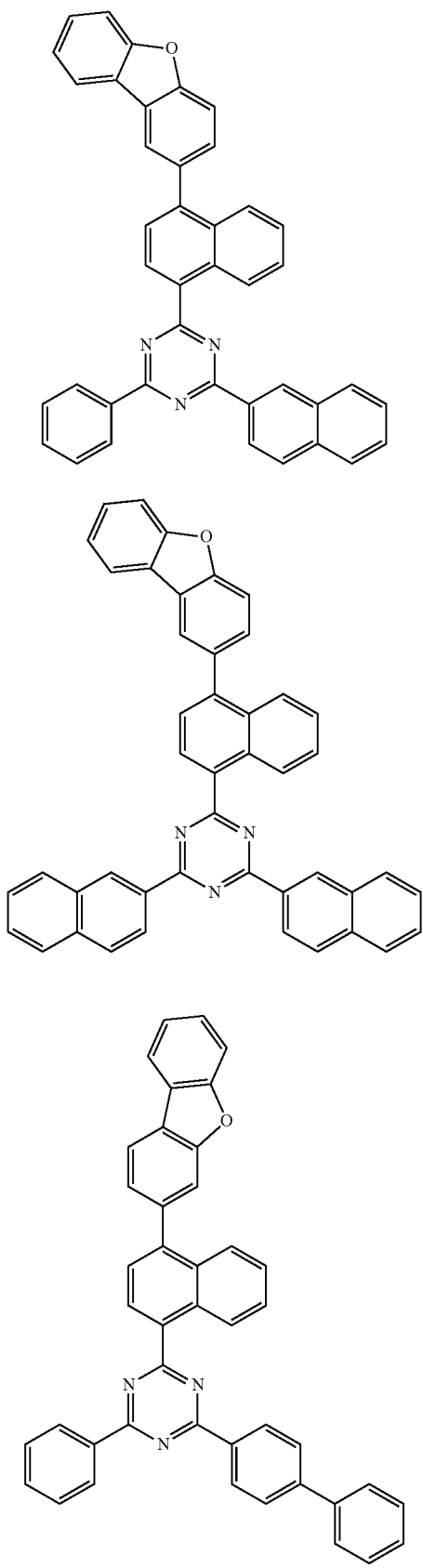
C2-124
C2-125
CS-126
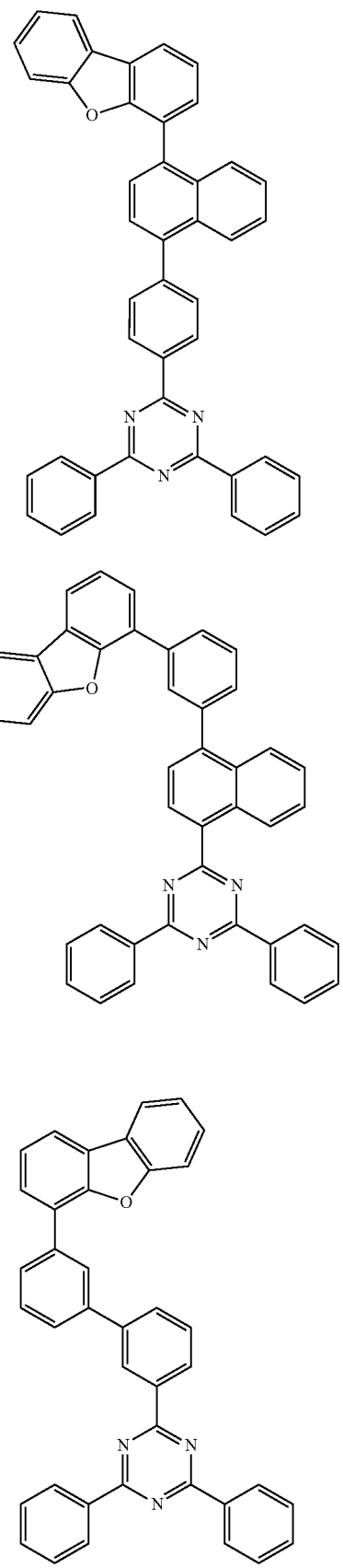
CS-127
CS-128

CS-129
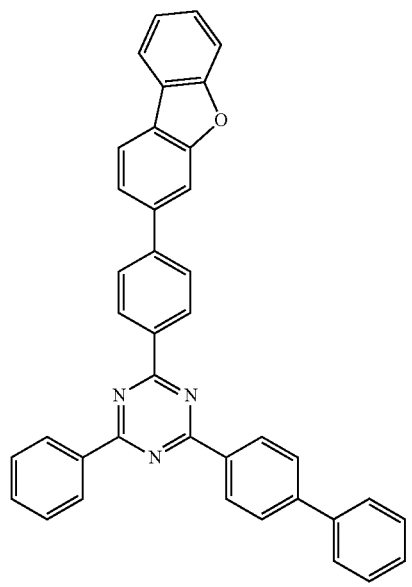
CS-130
CS-131
CS-132
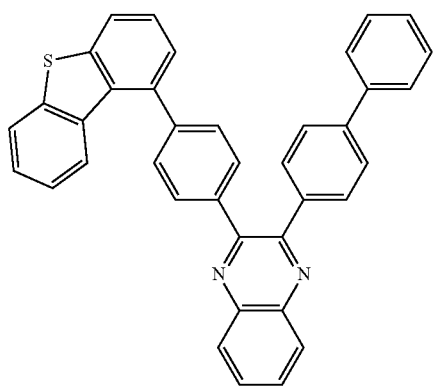
CS-133
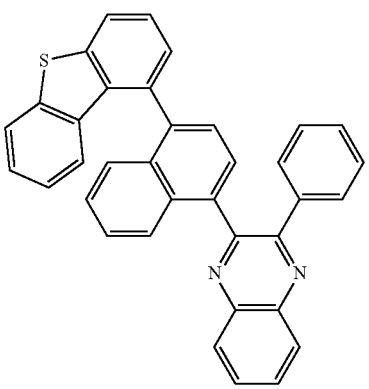
CS-134
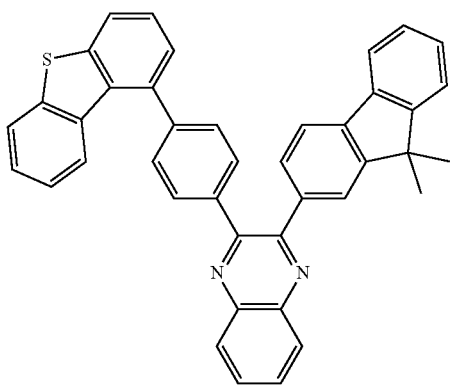
CS-135
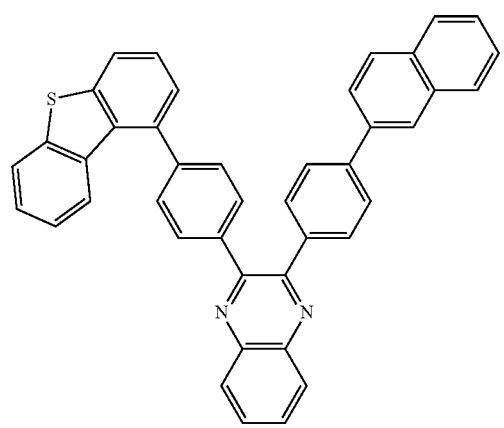

-continued
C2-136
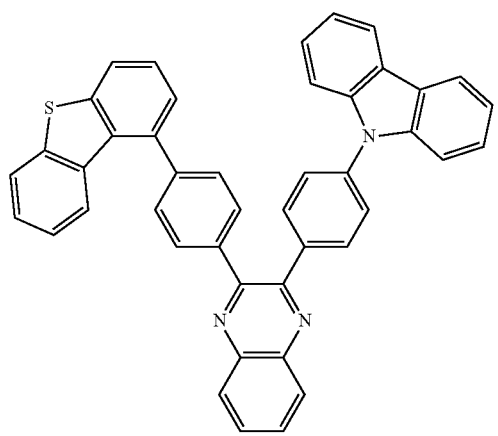
C2-137
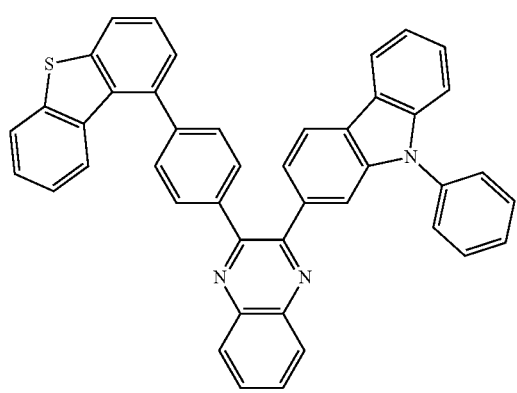
C2-138
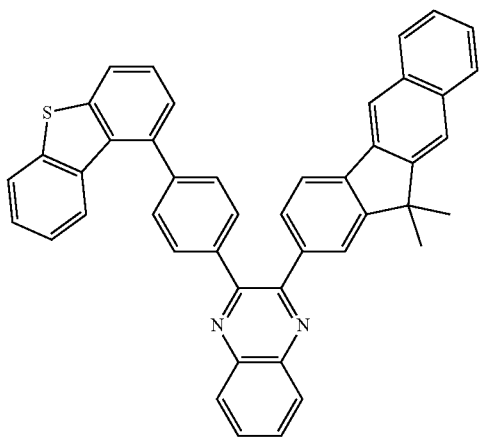
C2-139
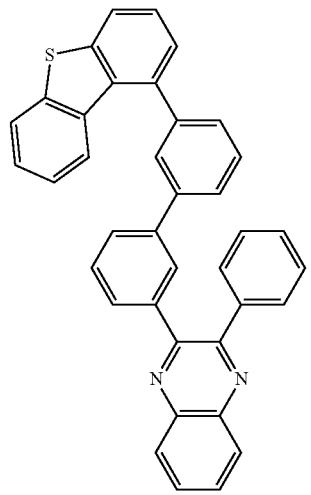
C2-140
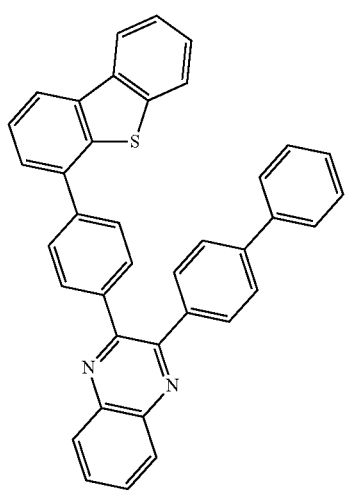
C2-141
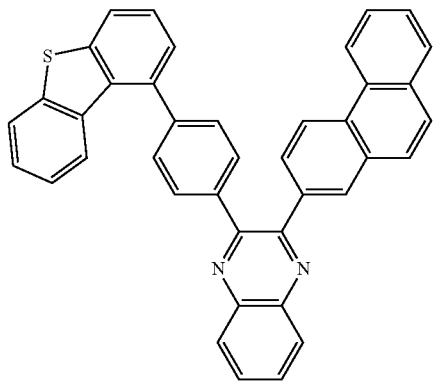

C2-142
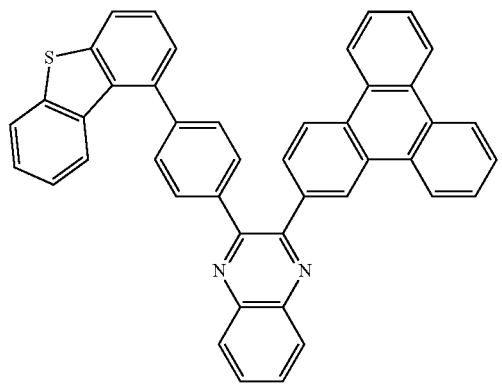
C2-143
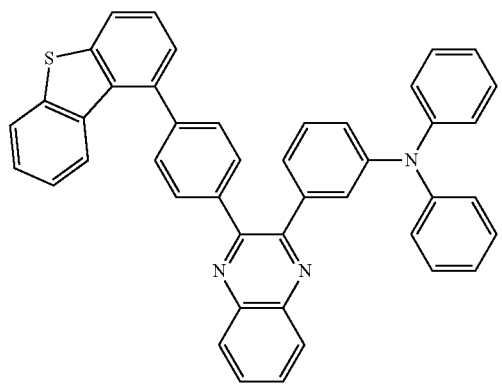
C2-144
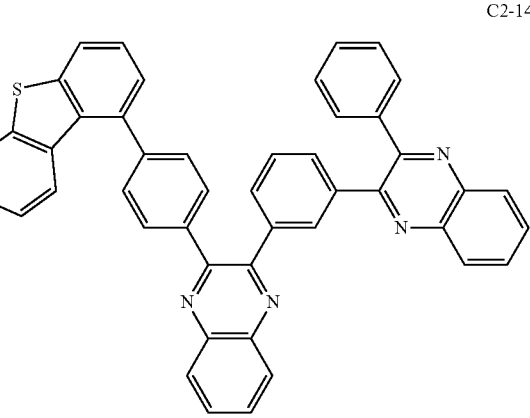
C2-145
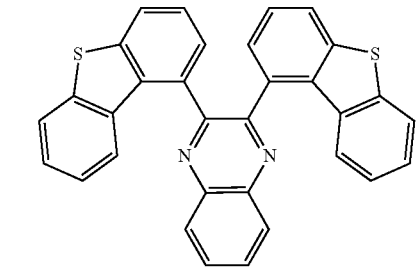
C2-146
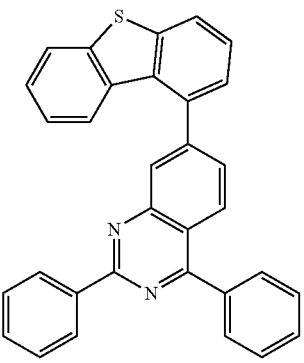
C2-147
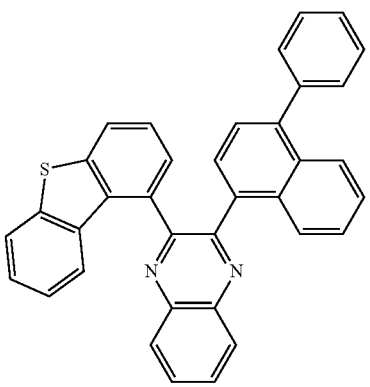
C2-148
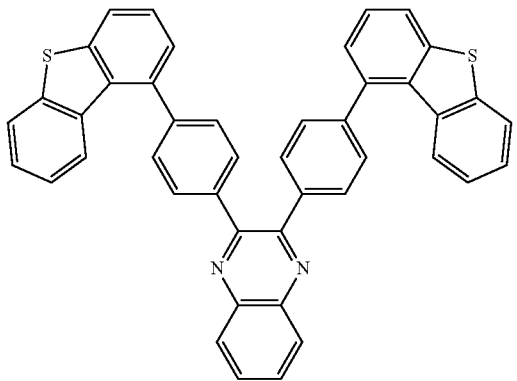
C2-149
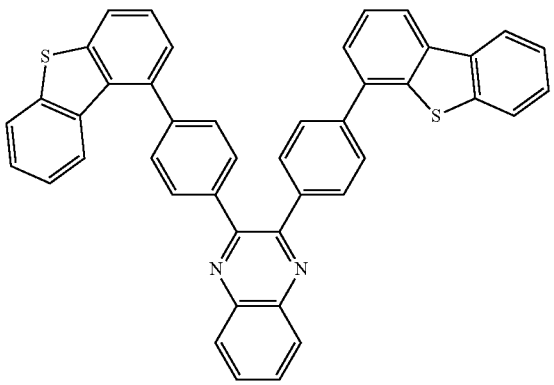

C2-150
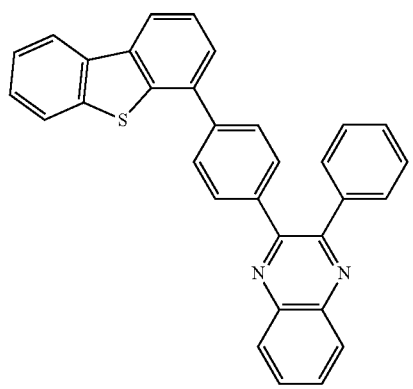
C2-151
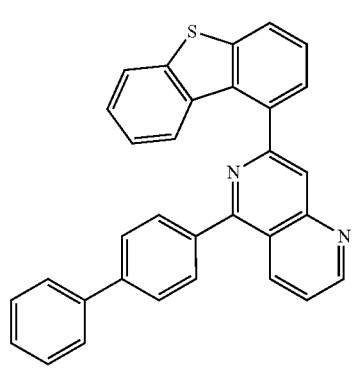
C2-152
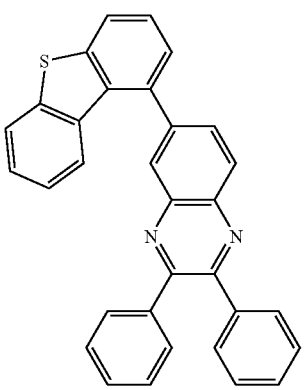
C2-153
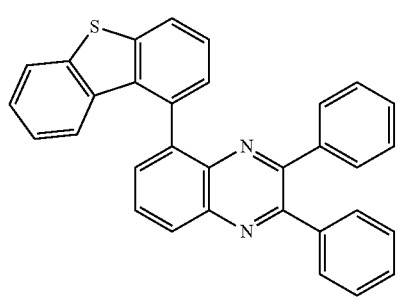
C2-154
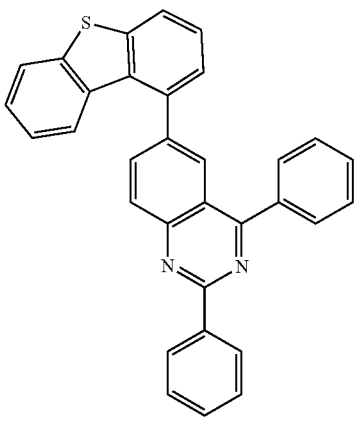
C2-155
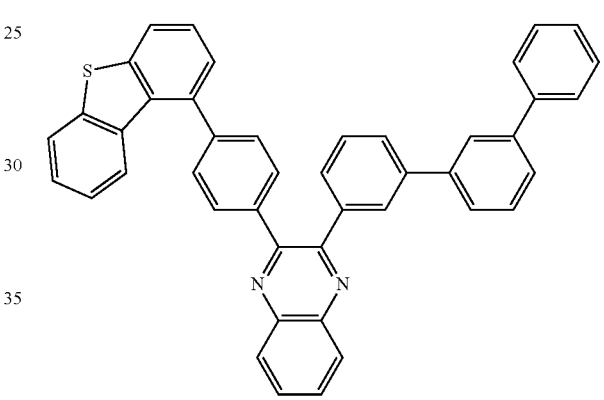
C2-156
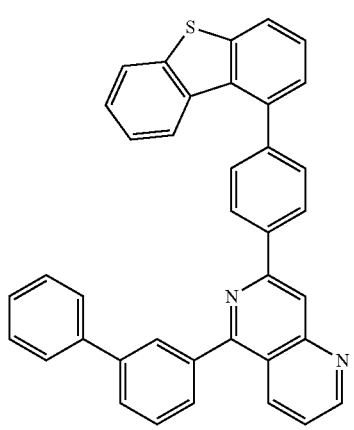

C2-157
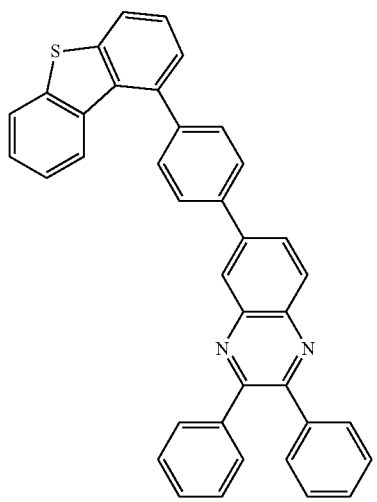
C2-160
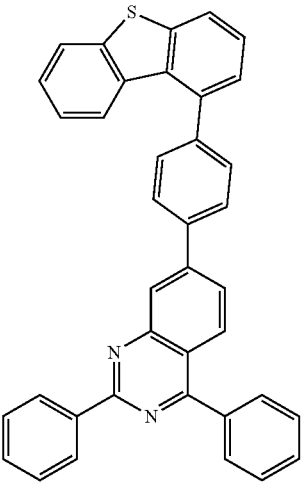
C2-158
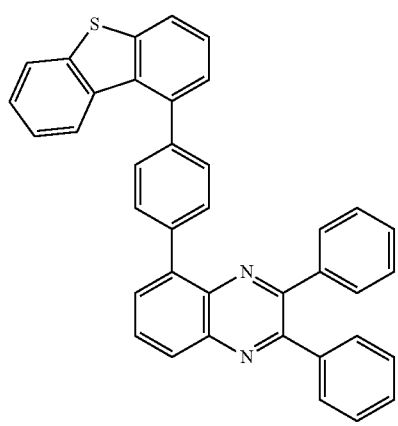
C2-161
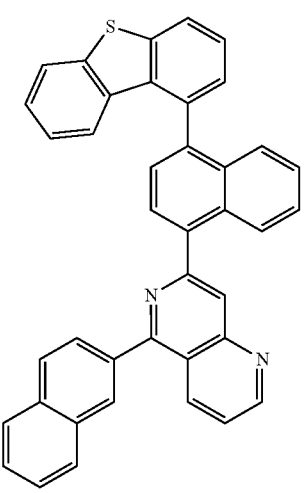
C2-159
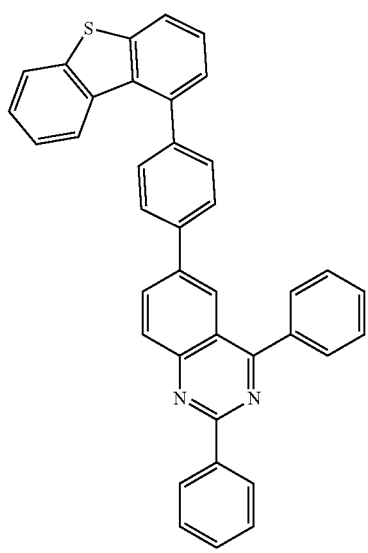
C2-162
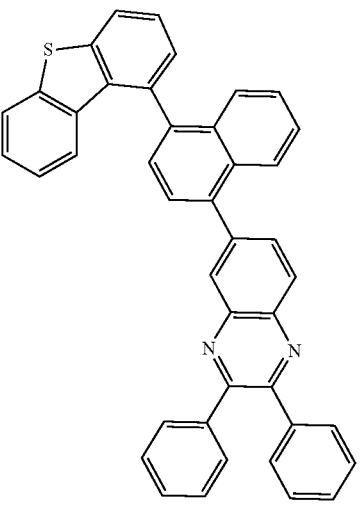

C2-163
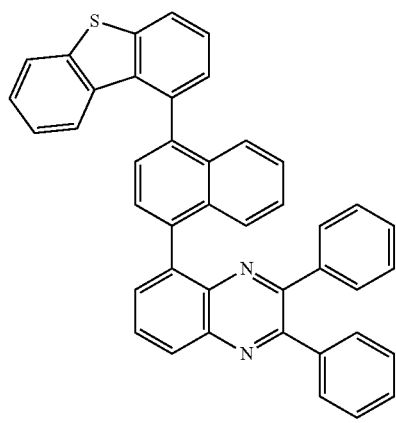
C2-164
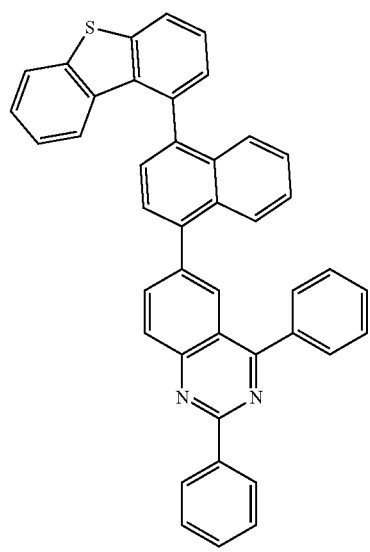
C2-165
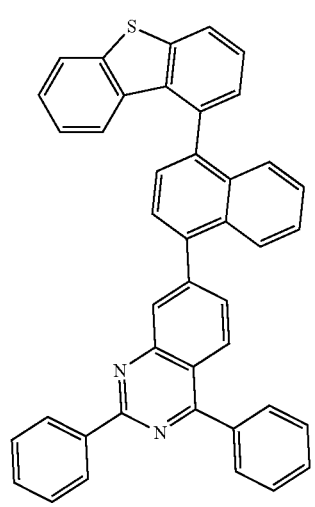
C2-166
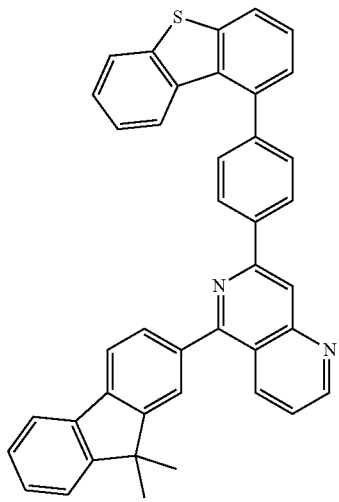
C2-167
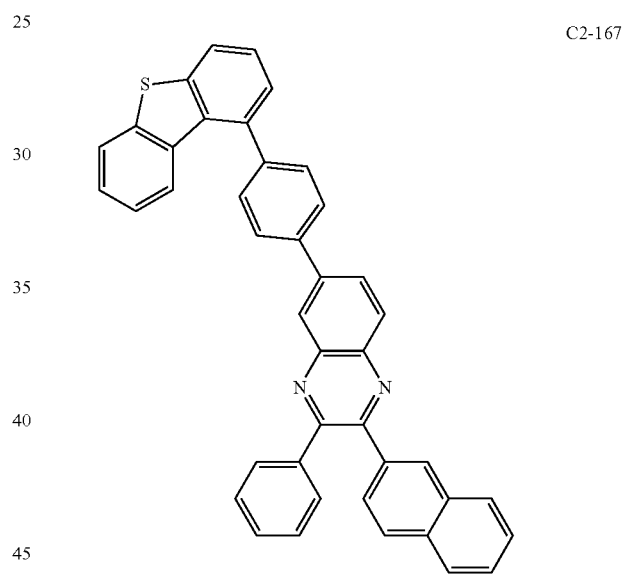
C2-168
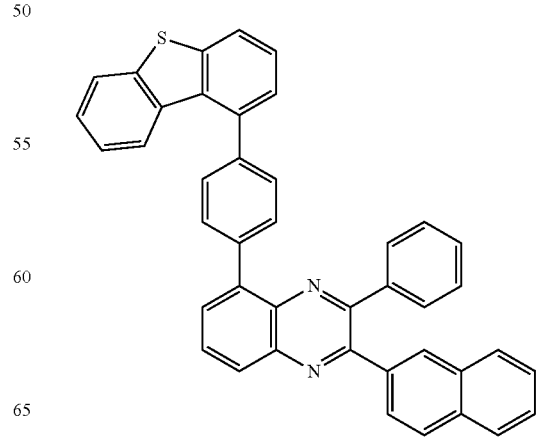

C2-169
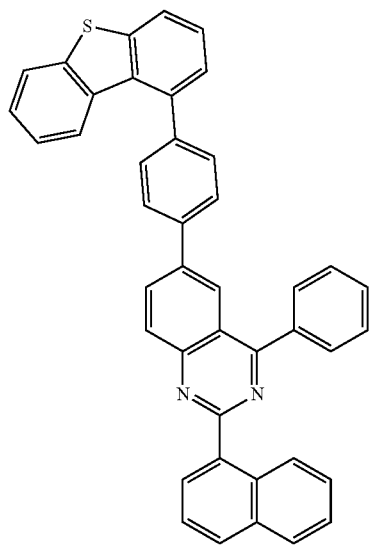
C2-170
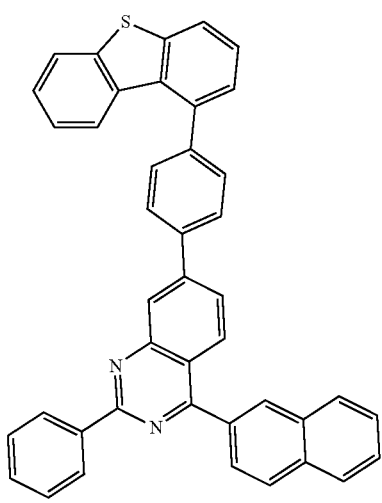
C2-171
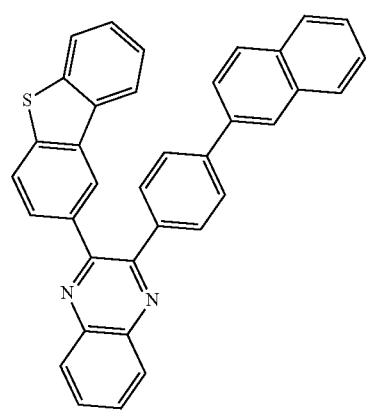
C2-172
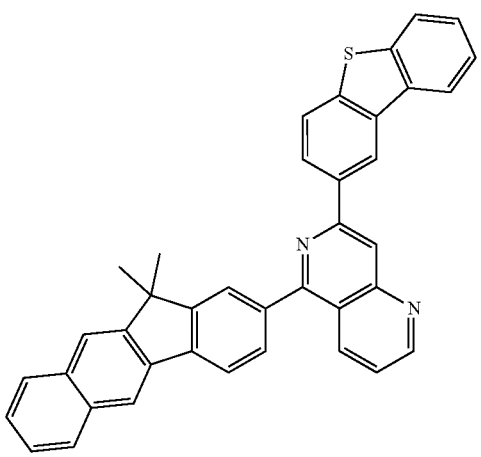
C2-173
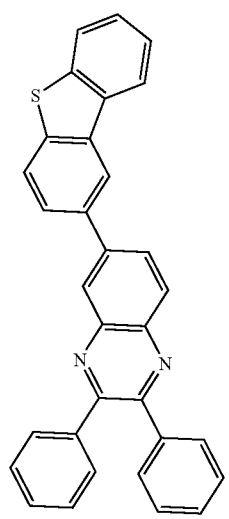
C2-174
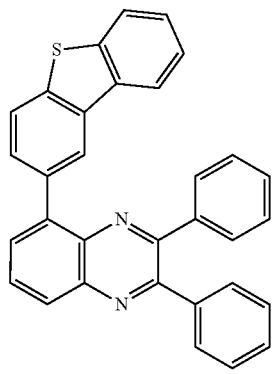

C2-175
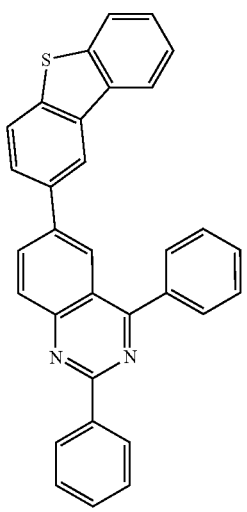
C2-176
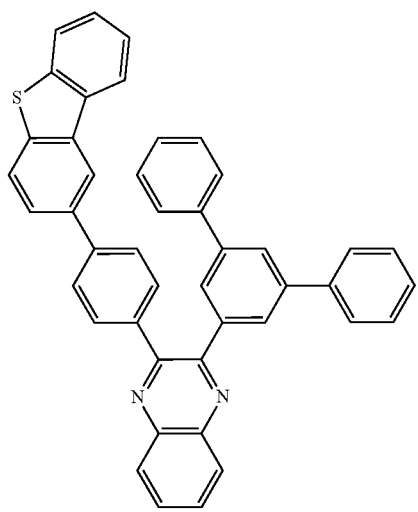
C2-177
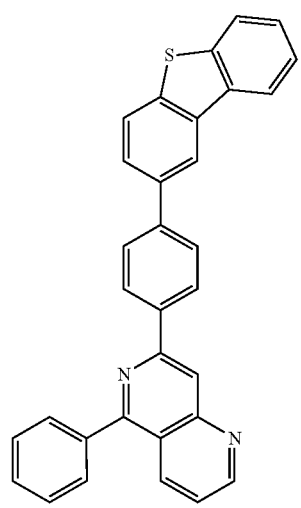
C2-178
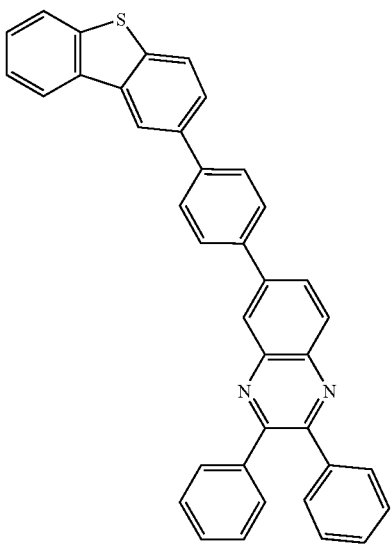
C2-179
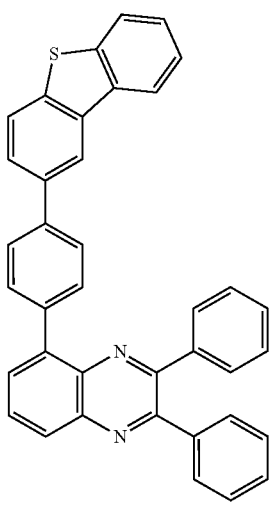
C2-180
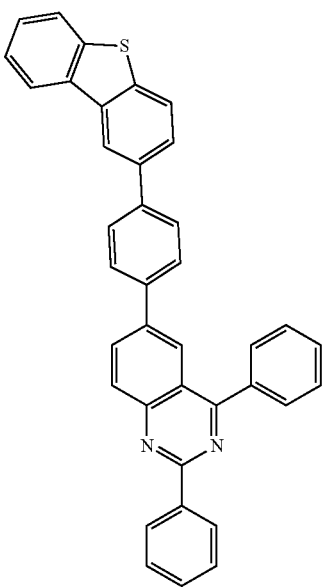

C2-181
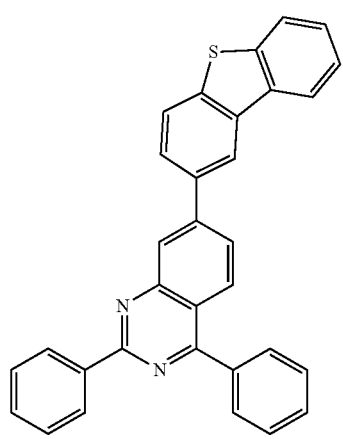
C2-182
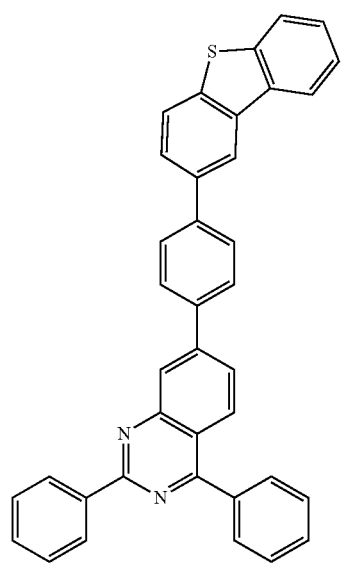
C2-183
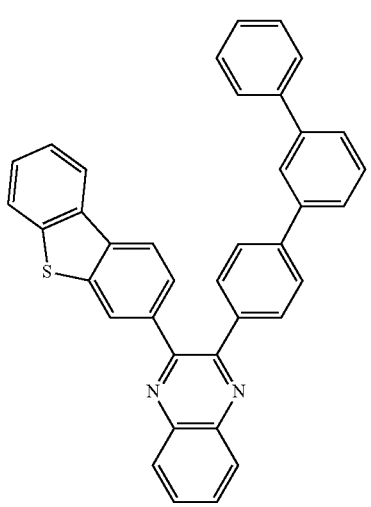
C2-184
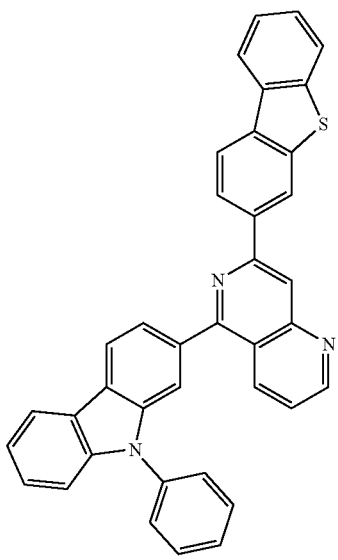
C2-185
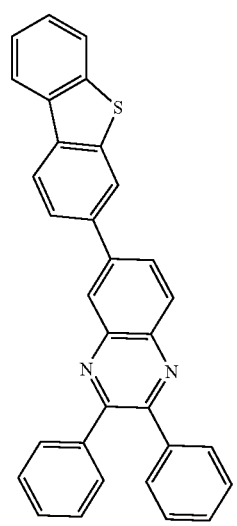
C2-186
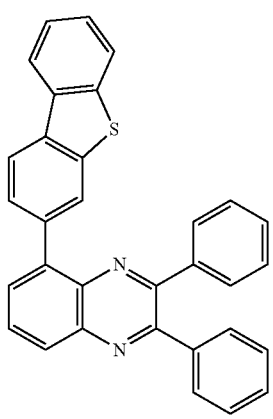

C2-187
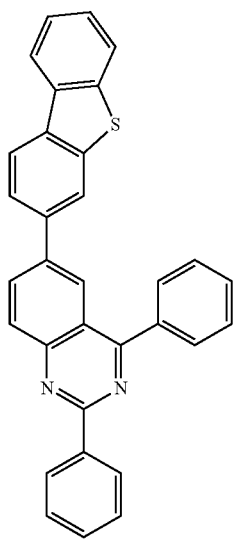
C2-188
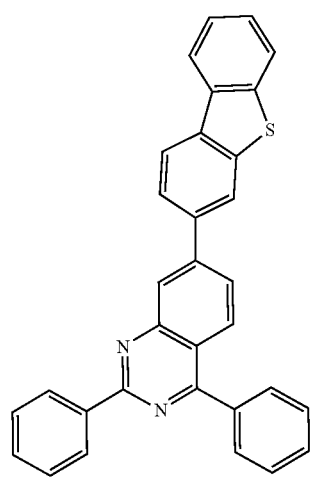
C2-189
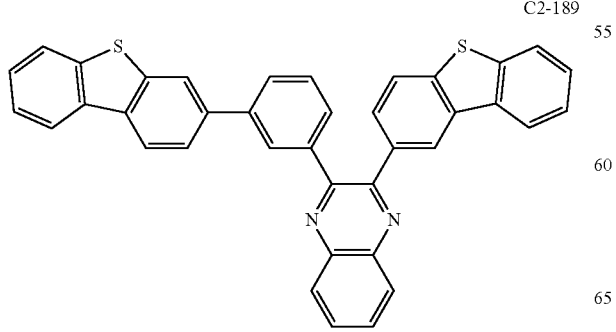
C2-190
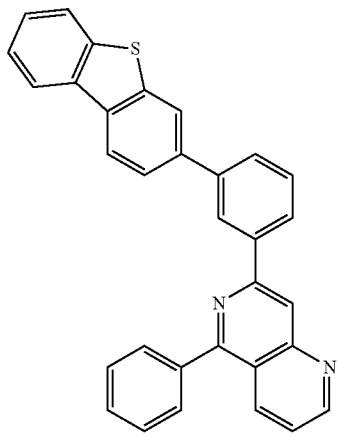
C2-191
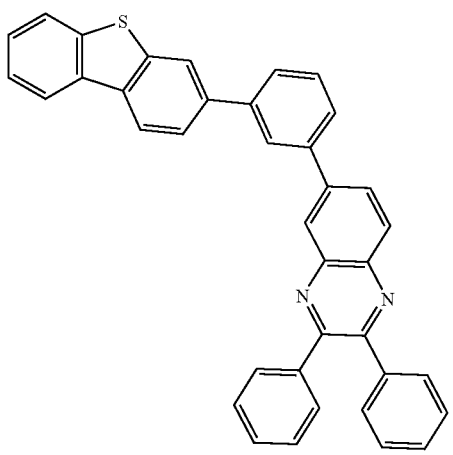
C2-192
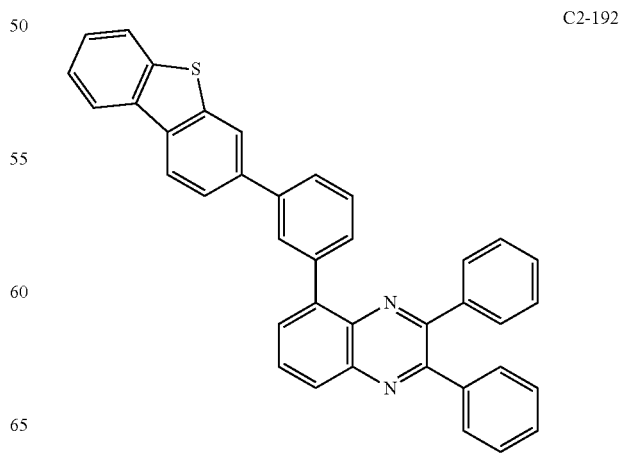

-continued
C2-193
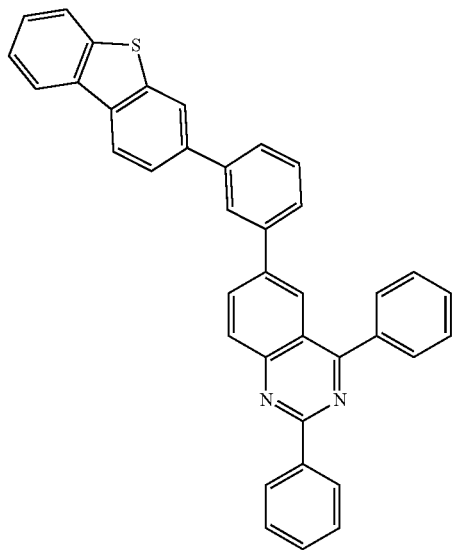
C2-194
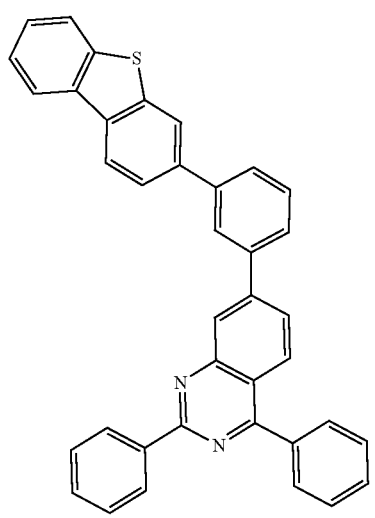
C2-195
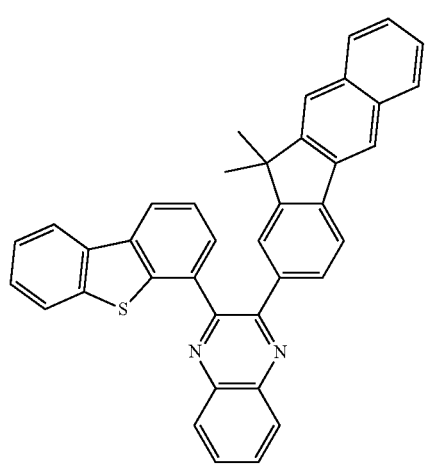
-continued
C2-196
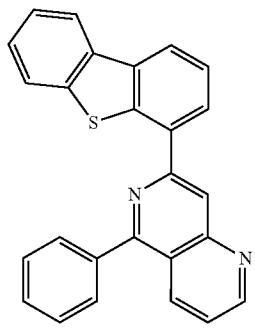
C2-197
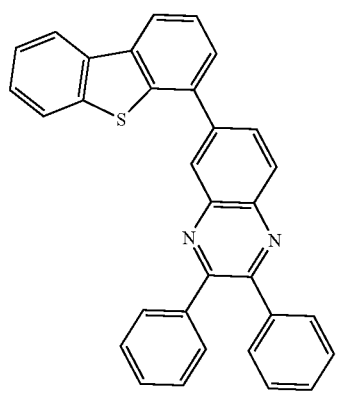
C2-198
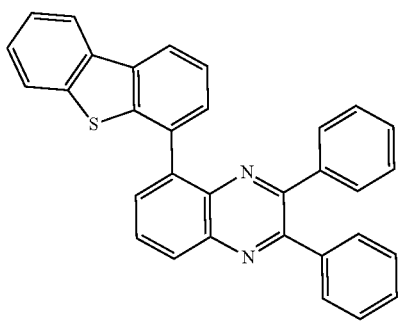
C2-199
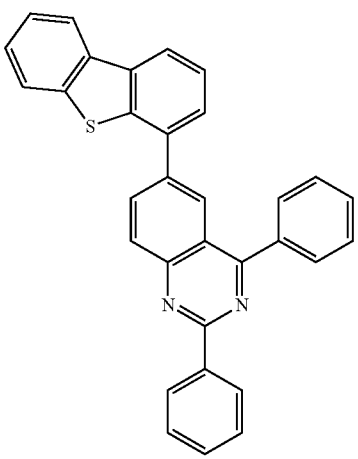

-continued
C2-200
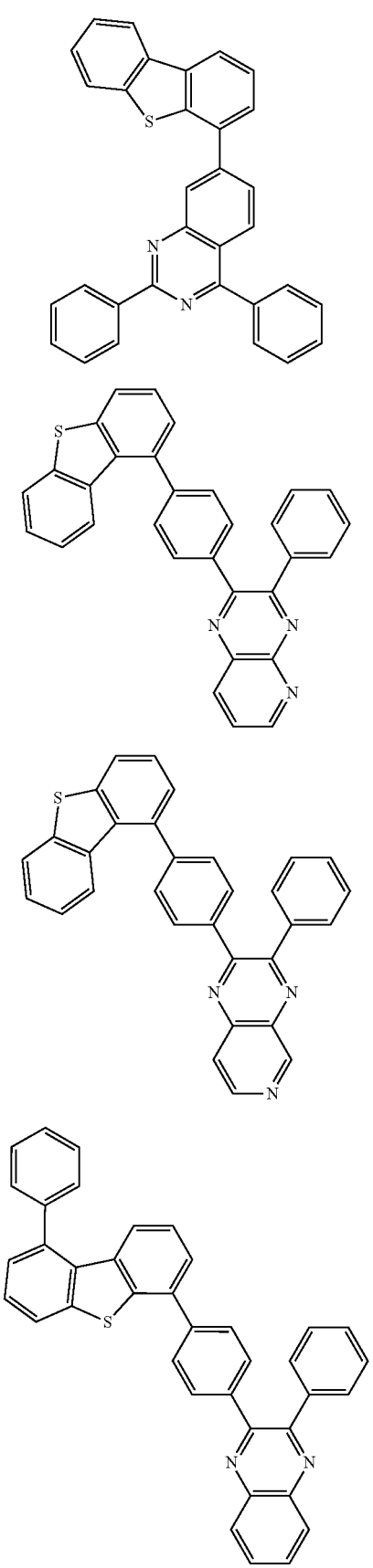
C2-201
C2-202
C2-203
C2-204
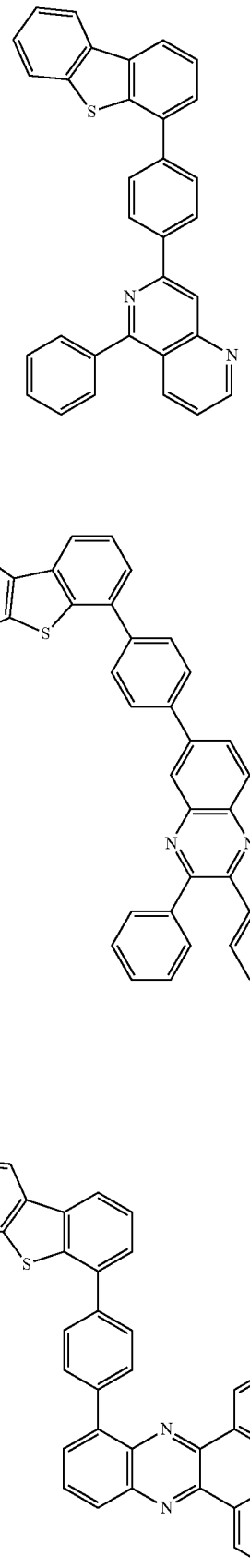
C2-205
C2-206

-continued
C2-207
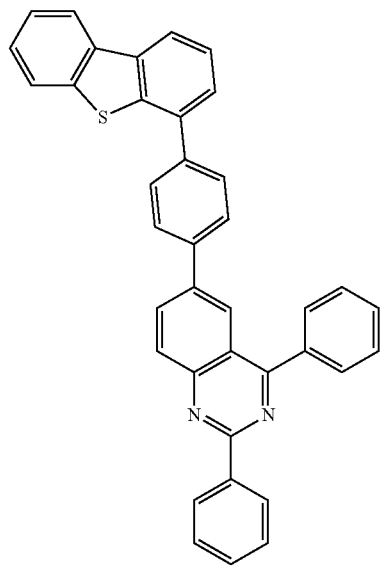
C2-208
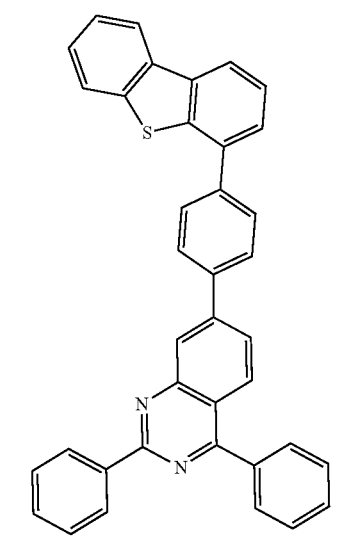
C2-209
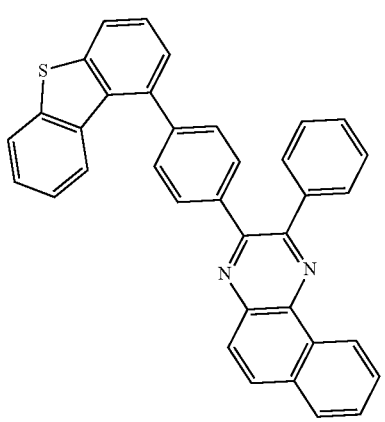
-continued
C2-210
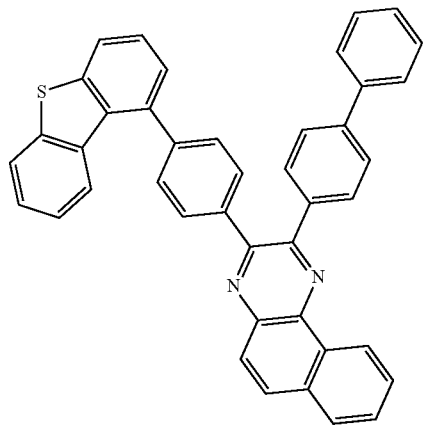
C2-211
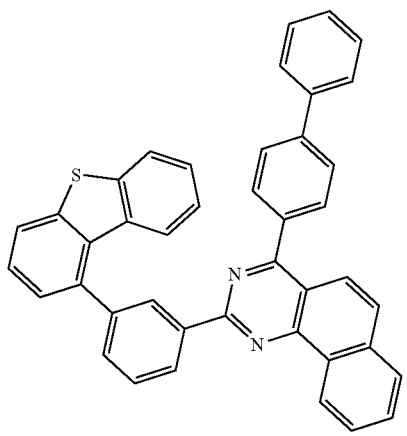
C2-212
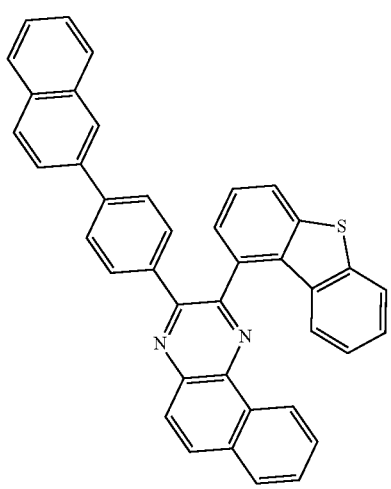

-continued
C2-213
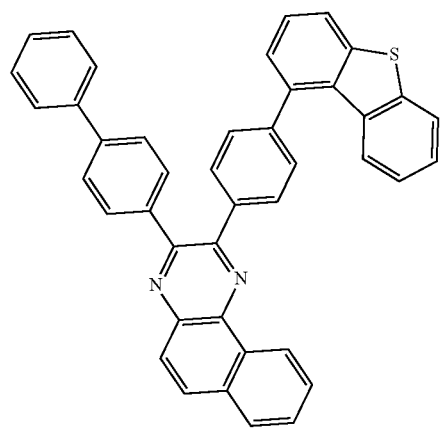
C2-214
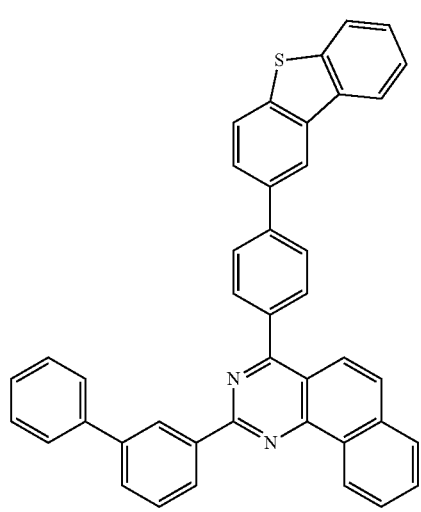
C2-215
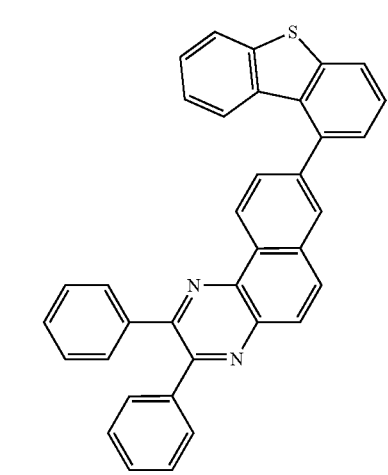
-continued
C2-216
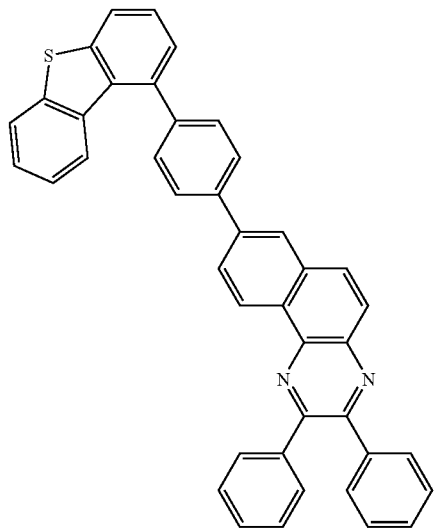
C2-217
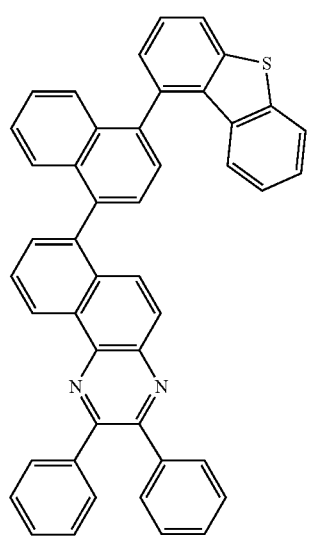
C2-218
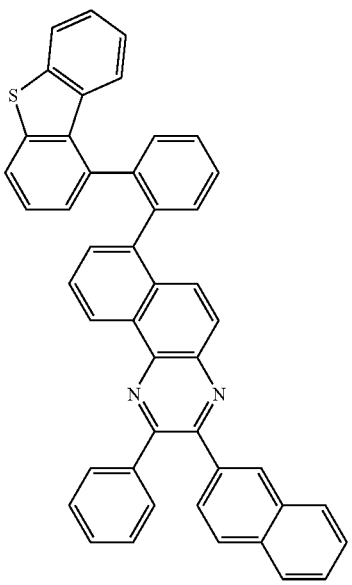

-continued
C2-219
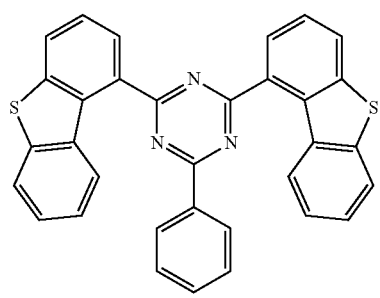
C2-220
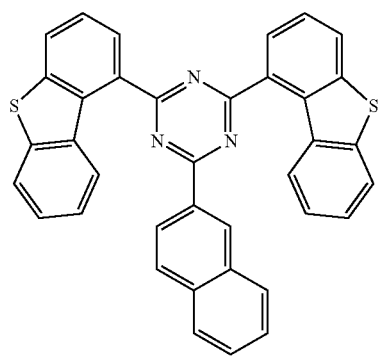
C2-221
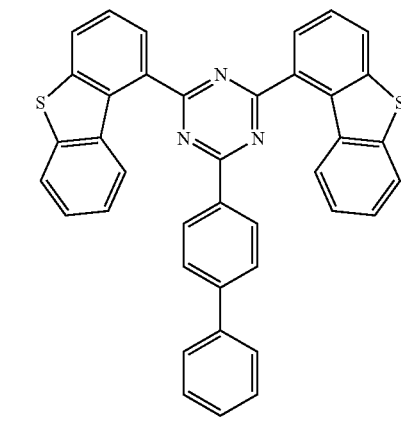
C2-222
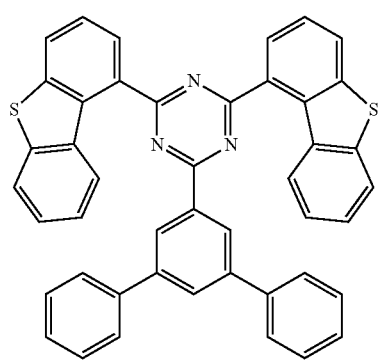
-continued
C2-223
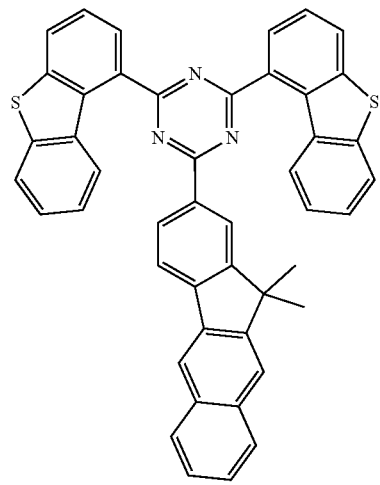
C2-224
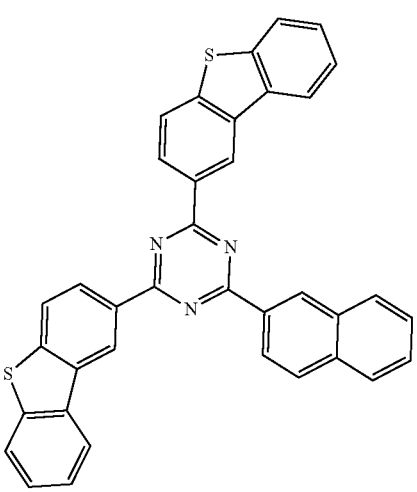
C2-225
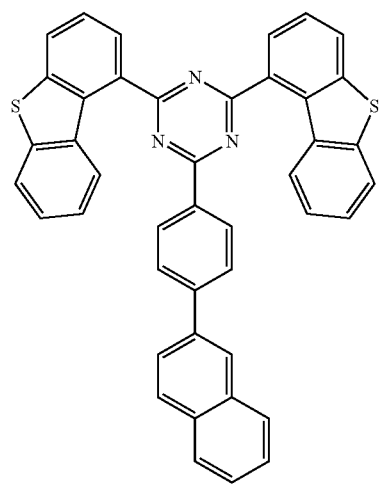

C2-226
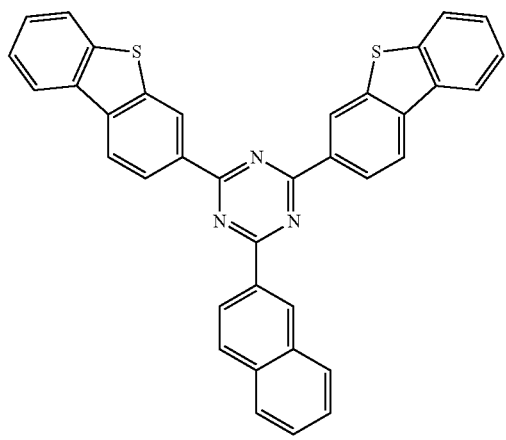
C2-227
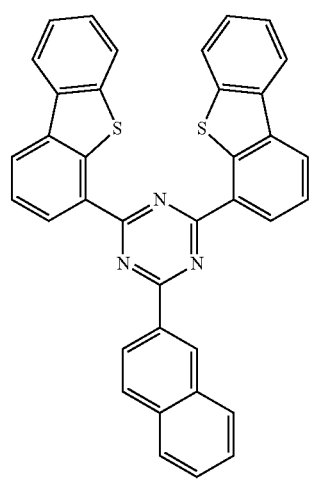
C2-228
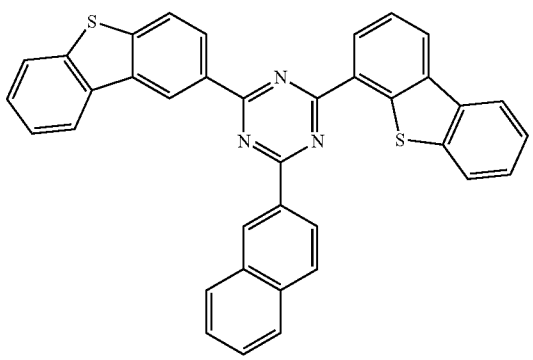
C2-229
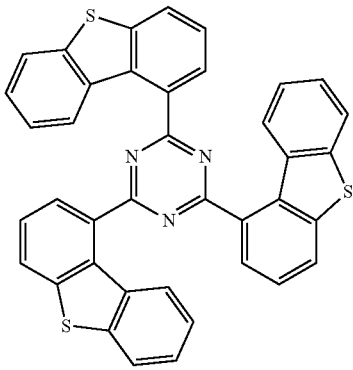
C2-230
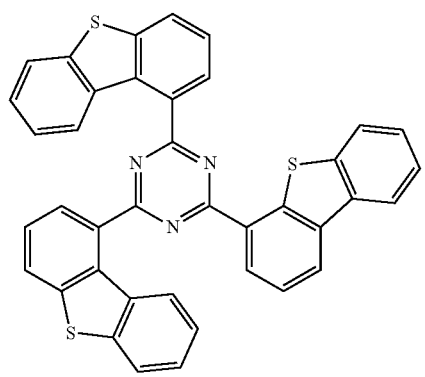
C2-231
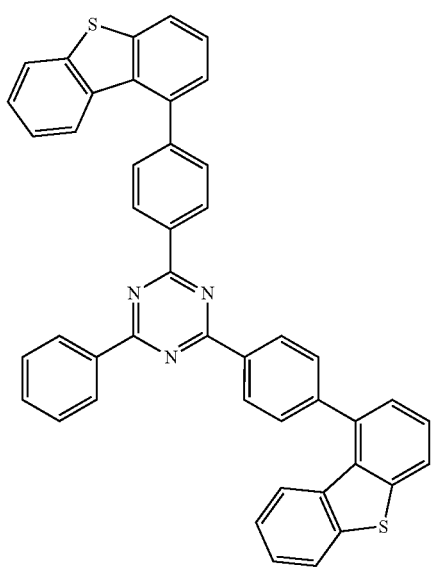

C2-232
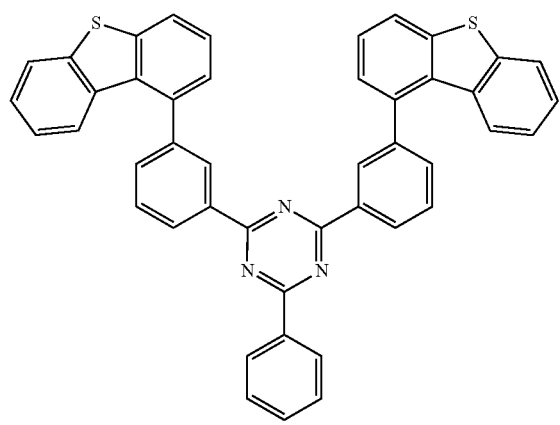
C2-233
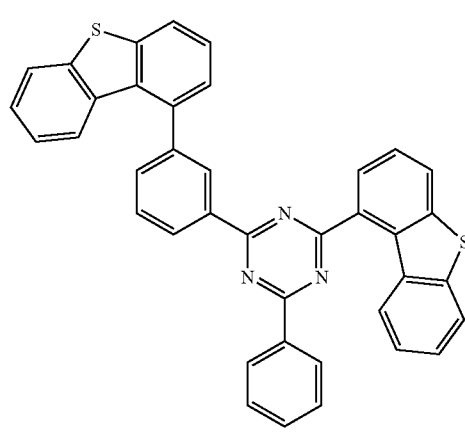
C2-234
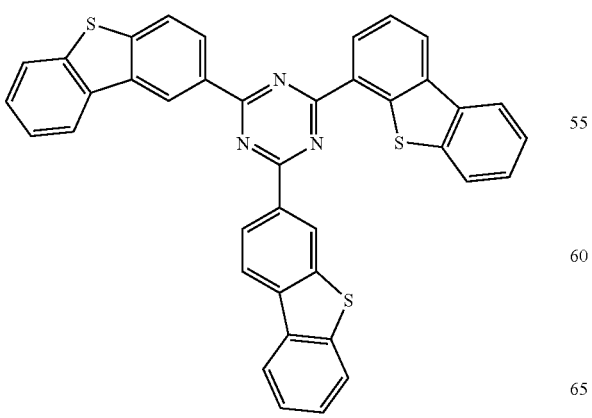
C2-235
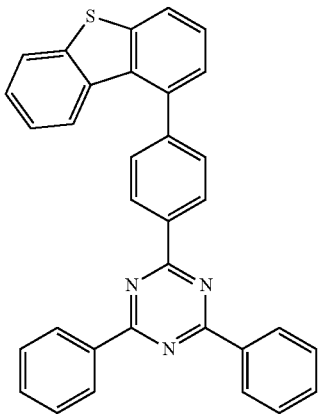
C2-236
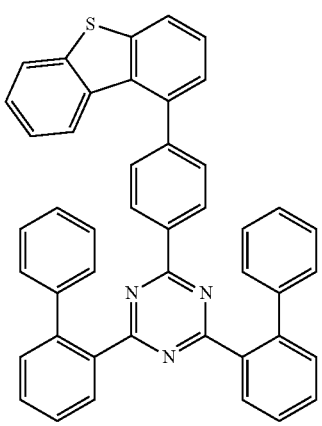
C2-237
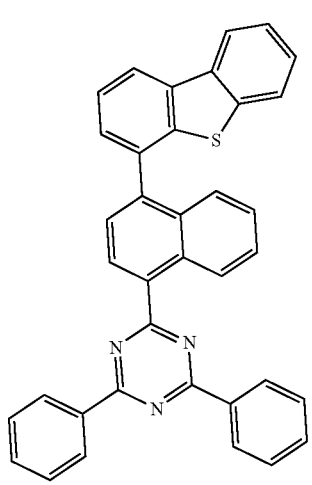

C2-238
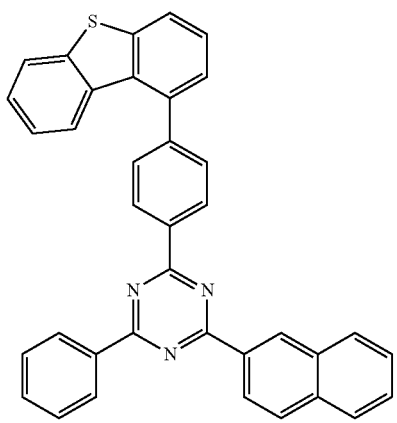
C2-239
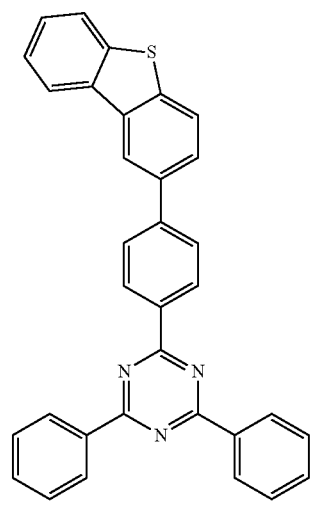
C2-240
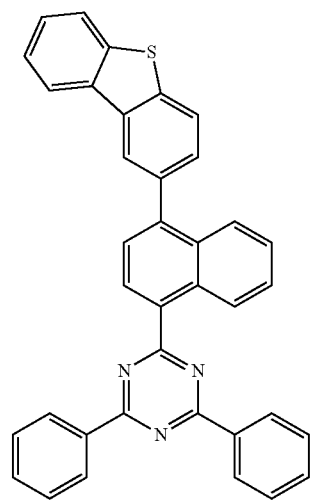
C2-241
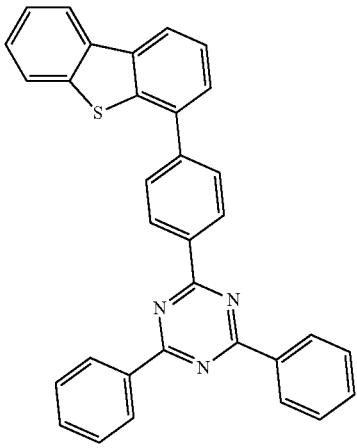
C2-242
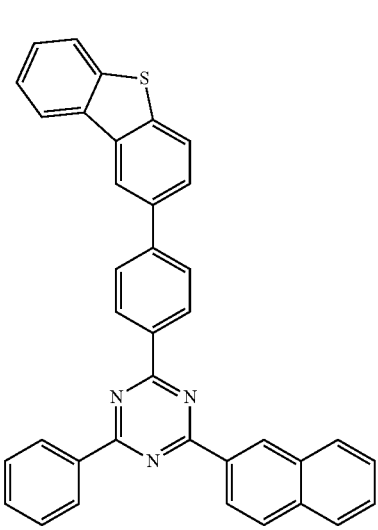
C2-243
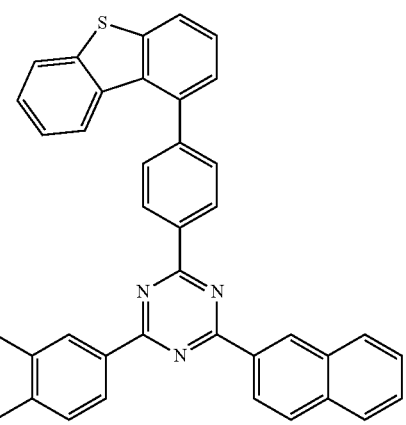

C2-244
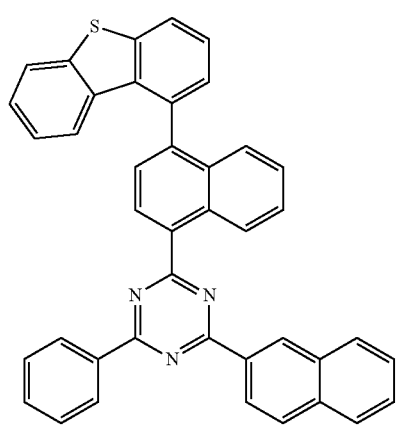
C2-245
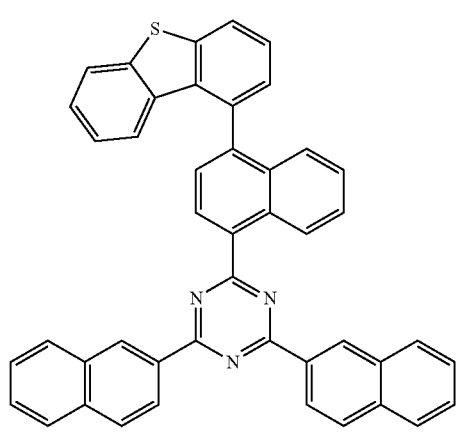
C2-246
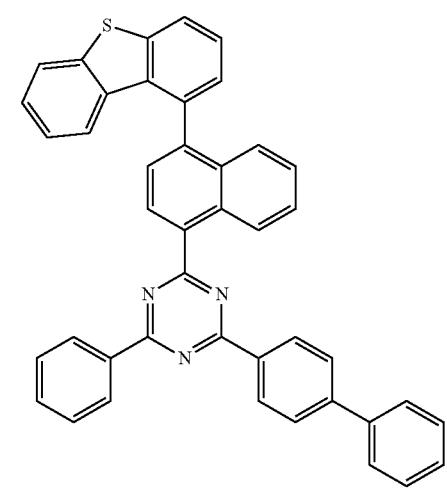
C2-247
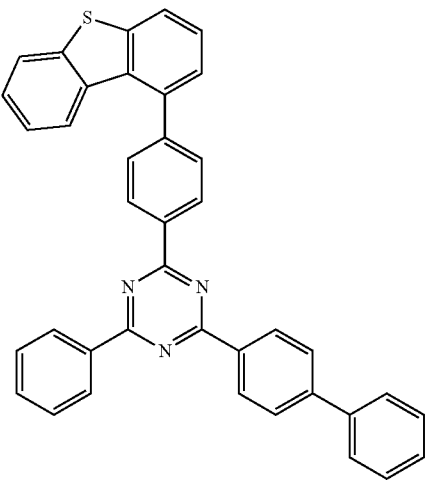
C2-248
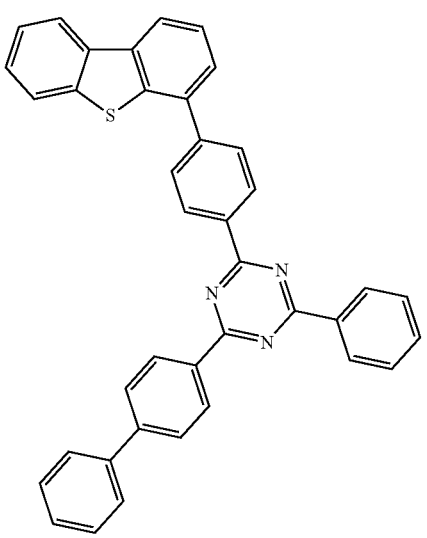
C2-249
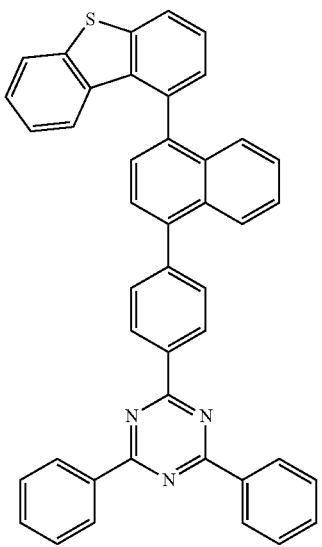

C2-250
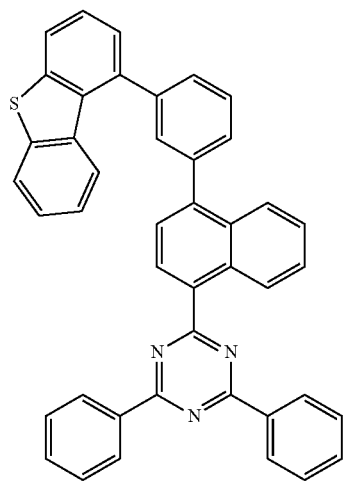
C2-253
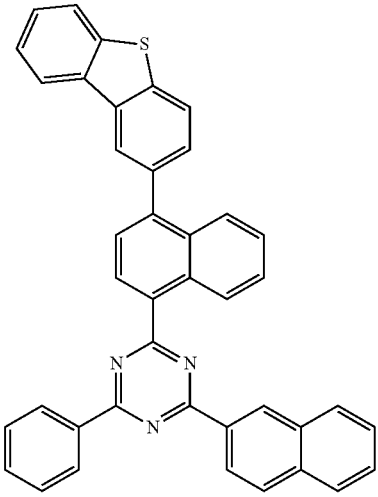
C2-251
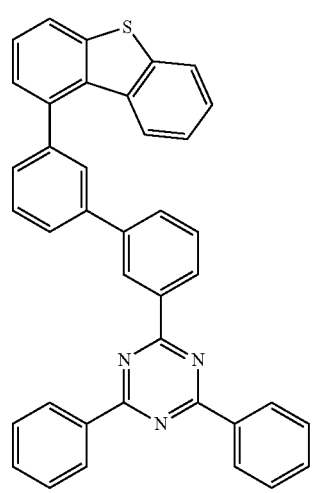
C2-254
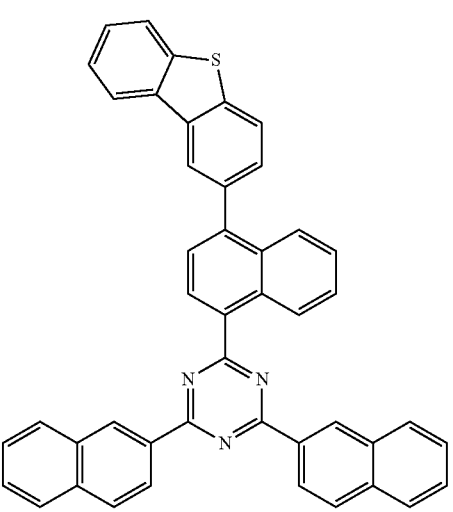
C2-252
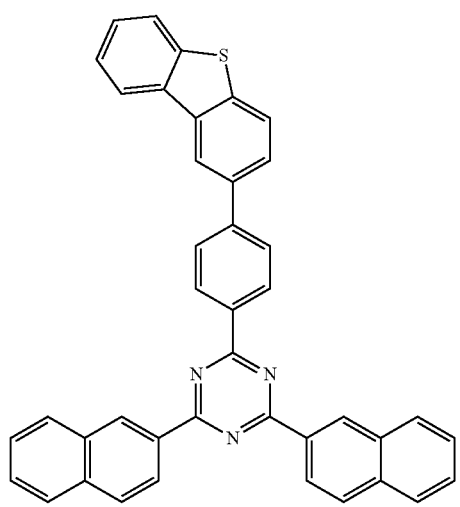
C2-255
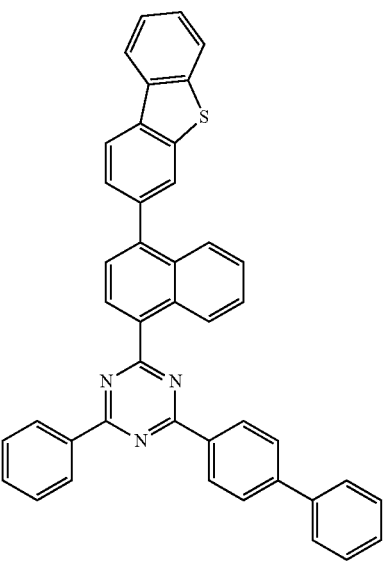

C2-256
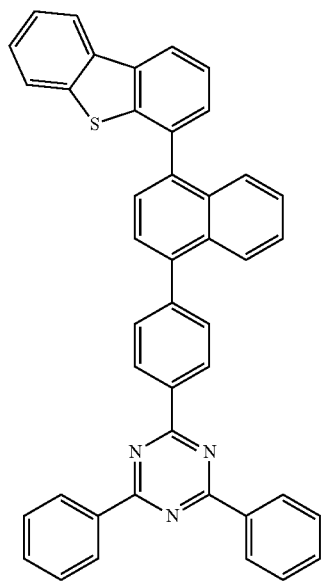
C2-257
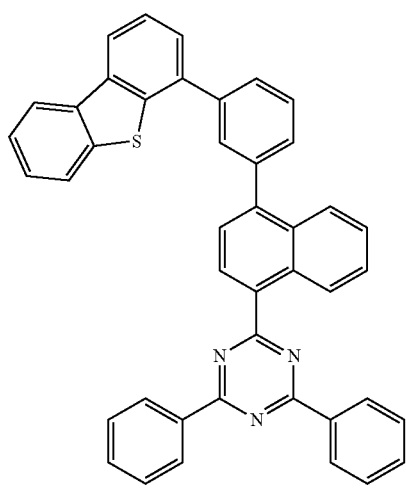
C2-258
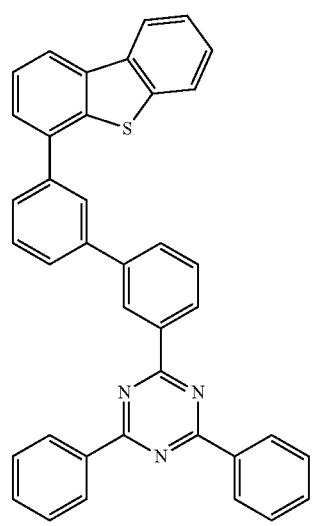
C2-259
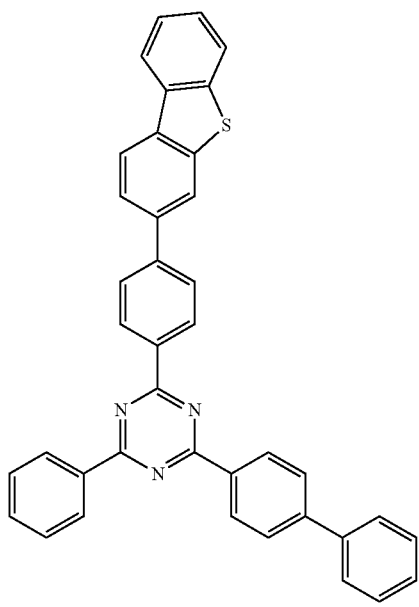
C2-260
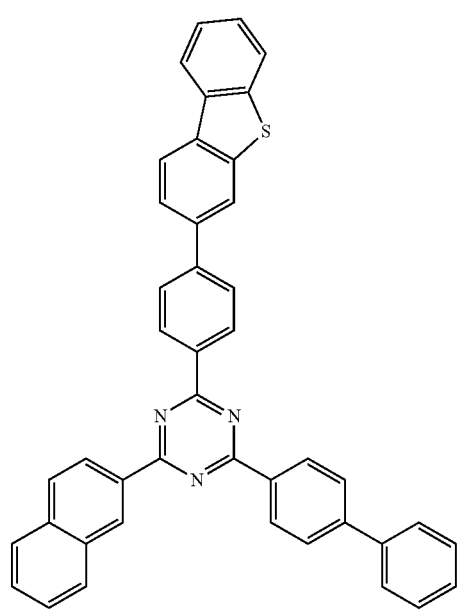
C2-261
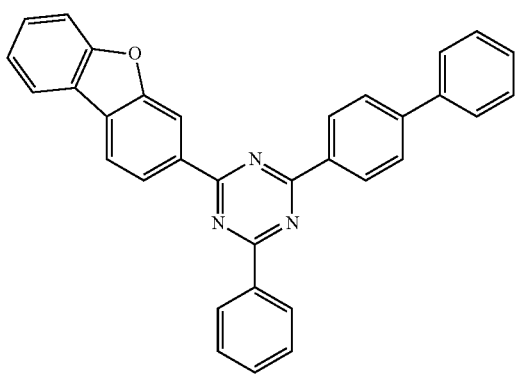

C2-262
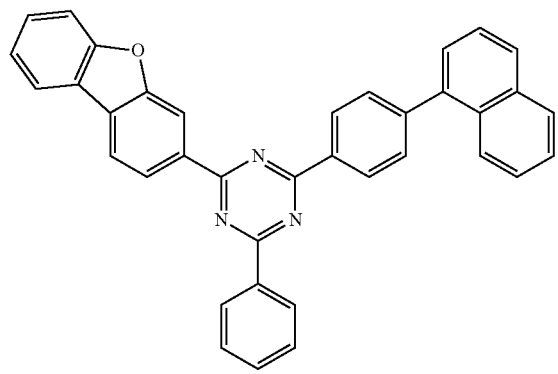
C2-263
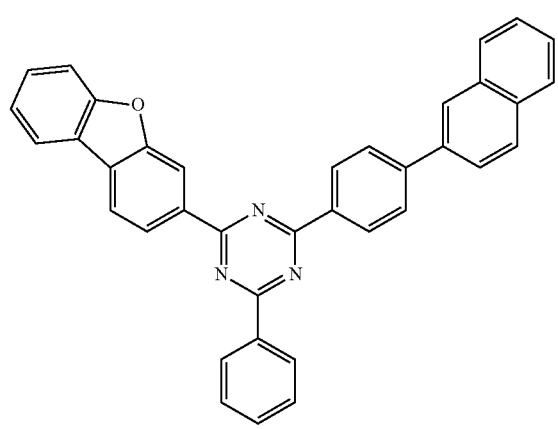
C2-264
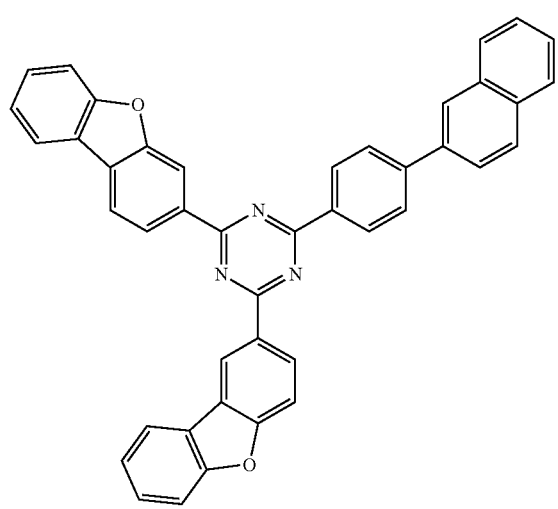
C2-265
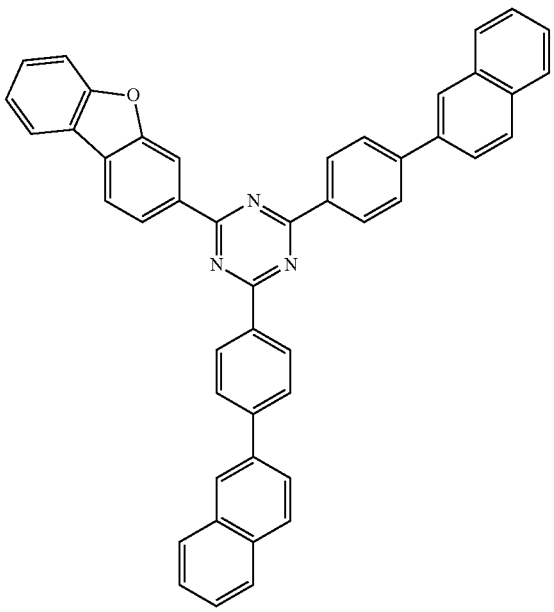
C2-266
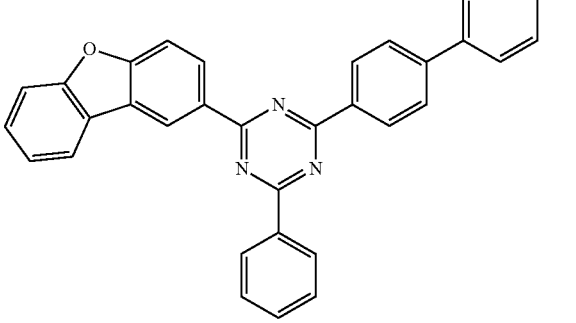
C2-267
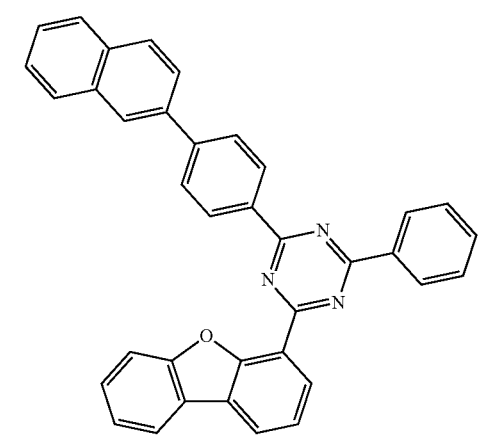

C2-268
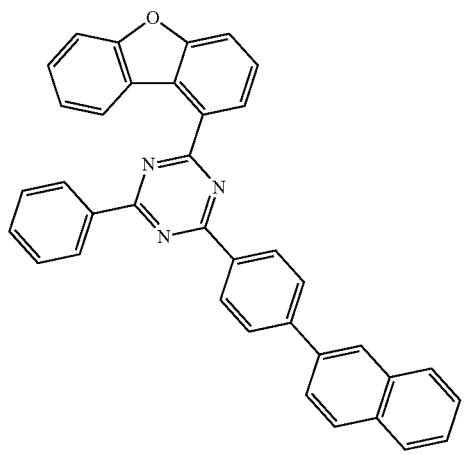
C2-269
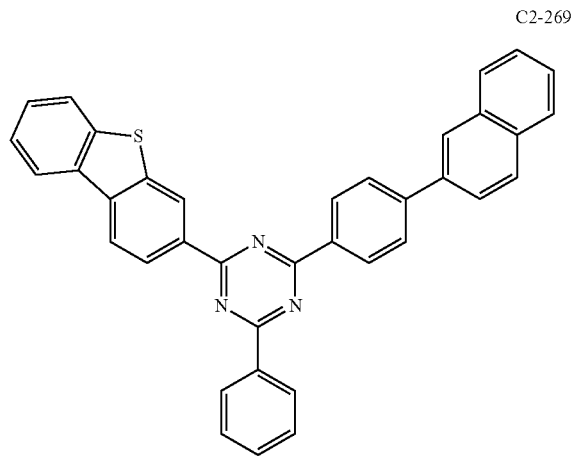
C2-270
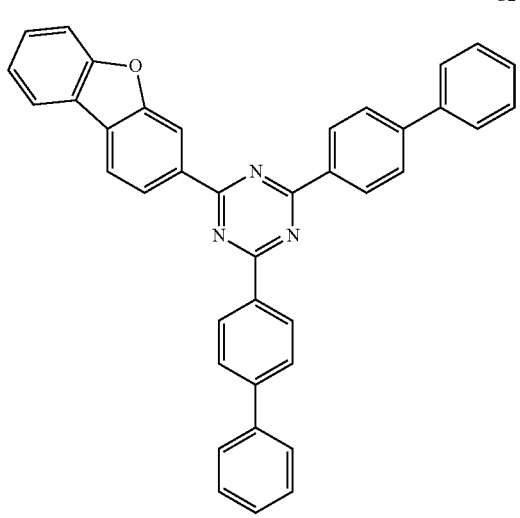
C2-271
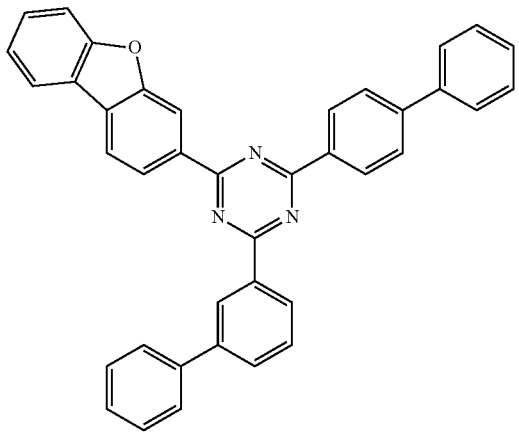
C2-272
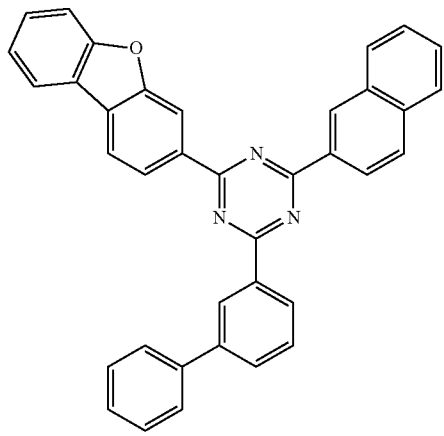
C2-273
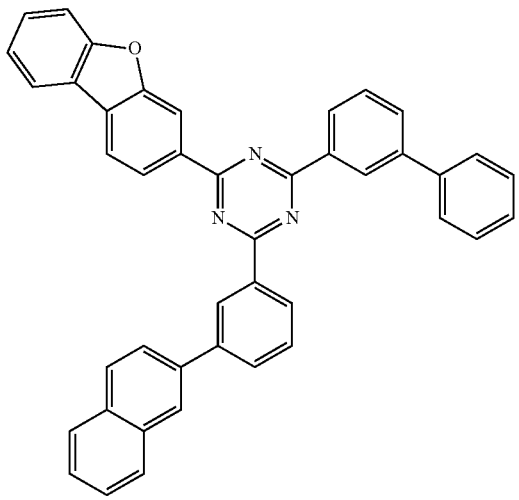

-continued

C2-274

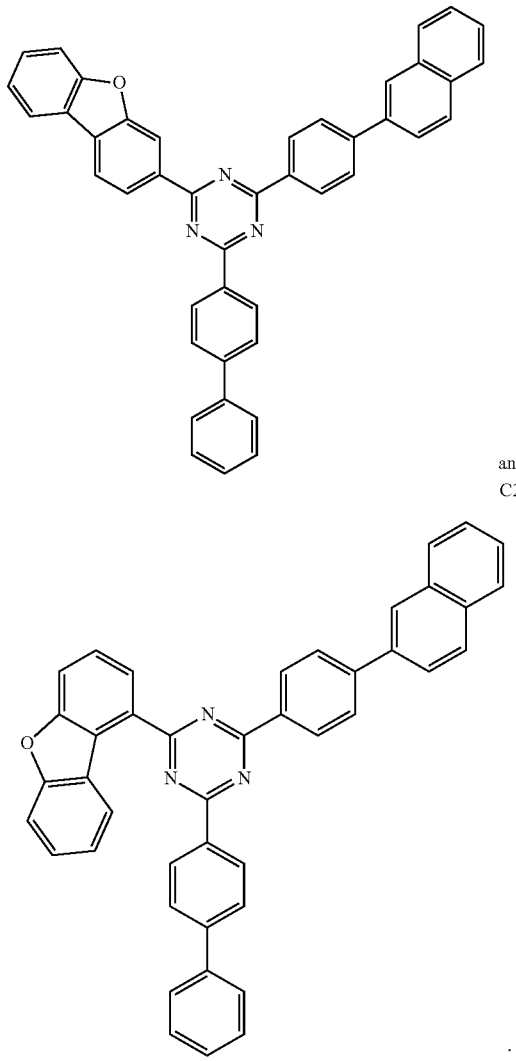

and
C2-275

8. An organic electroluminescent device comprising: an anode; a cathode; and at least one light-emitting layer between the anode and the cathode, wherein the at least one light-emitting layer(s) comprises the plurality of host materials according to claim 1.

9. An organic electroluminescent compound represented by the following formula 1-1-1:

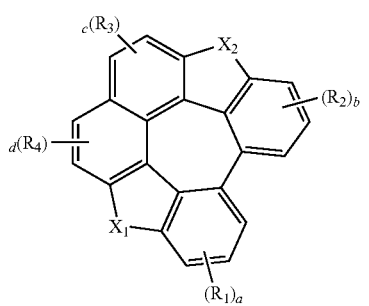

(1-1-1)

wherein $X_1$ and $X_2$ each independently represent $NR_5$, $CR_6R_7$, O, or S;

$R_1$ to $R_4$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30) alkenylamino, a substituted or unsubstituted mono- or di- (C6-C30)arylamino, a substituted or unsubstituted (C1-C30)alkyl(C6-C30)arylamino, a substituted or unsubstituted mono- or di- (3- to 30-membered)heteroarylamino, a substituted or unsubstituted (C1-C30) alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, or a substituted or unsubstituted (C6-C30)aryl(3- to 30-membered)heteroarylamino;

$R_5$ to $R_7$ each independently represent a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted fused ring of (C3-C30) aliphatic ring and (C6-C30) aromatic ring, a substituted or unsubstituted mono- or di- (C1-C30)alkylamino, a substituted or unsubstituted mono- or di- (C2-C30)alkenylamino, a substituted or unsubstituted (C1-C30)alkyl(C2-C30)alkenylamino, a substituted or unsubstituted mono- or di- (C6-C30) arylamino, a substituted or unsubstituted (C1-C30) alkyl(C6-C30)arylamino, a substituted or unsubstituted mono- or di- (3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino;

provided that at least one of $R_1$ to $R_5$ represent(s) -$(L_1)_m$-$(Ar_1)_n$;

$L_1$ represents a single bond, a substituted or unsubstituted fused ring of (C3-C30) aliphatic ring and (C6-C30) aromatic ring, or a substituted or unsubstituted (C6-C30)arylene;

$Ar_1$ represents a substituted or unsubstituted (C6-C30) aryl, a substituted or unsubstituted fused ring of (C3-C30) aliphatic ring and (C6-C30) aromatic ring, a substituted or unsubstituted (3- to 30-membered)heteroaryl, or —N—$(Ar_2)(Ar_3)$;

Ar₂ and Ar₃ each independently represent a substituted or unsubstituted (C1-C30)alkyl, a substituted or unsubstituted (C2-C30)alkenyl, a substituted or unsubstituted fused ring of (C3-C30) aliphatic ring and (C6-C30) aromatic ring, a substituted or unsubstituted (C6-C30) aryl, or a substituted or unsubstituted (3- to 30-membered)heteroaryl;

a and b each independently represent an integer of 1 to 3, and c, d, m, and n each independently represent an integer of 1 or 2; and when a to d, m, and n each independently are an integer of 2 or more, each of $R_1$ to $R_4$, each of $L_1$, and each of $Ar_1$ may be the same or different;

provided that, the compound in which $L_1$ represents a single bond and Ar represents a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted benzofuropyrimidinyl, or a substituted or unsubstituted benzothienopyrimidinyl, is excluded from formula 1-1-1.

10. The organic electroluminescent compound according to claim 9, wherein the compound represented by formula 1-1-1 is selected from the following compounds:

C1-1
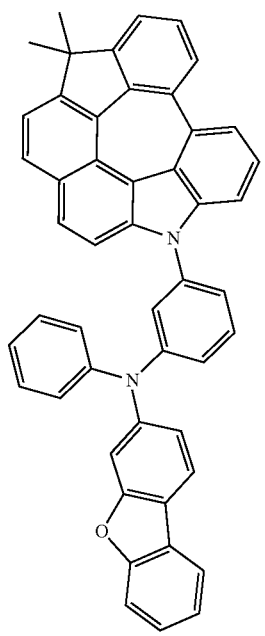

C1-2
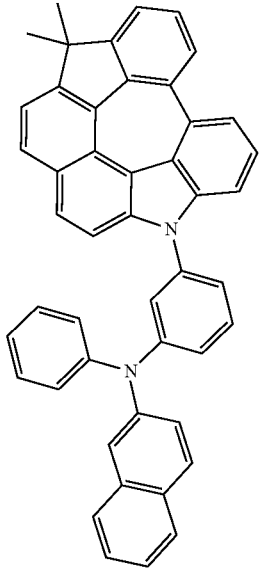

C1-3
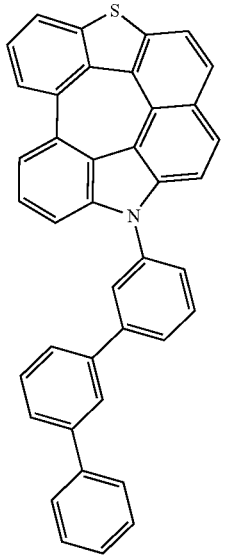

C1-4
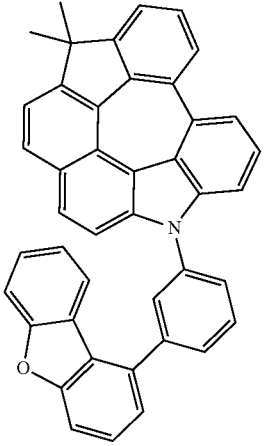

C1-5
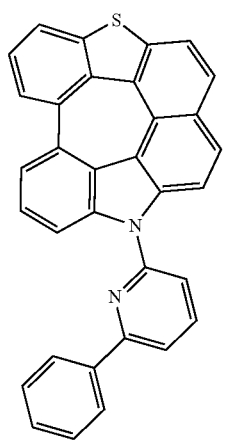
C1-6
C1-8
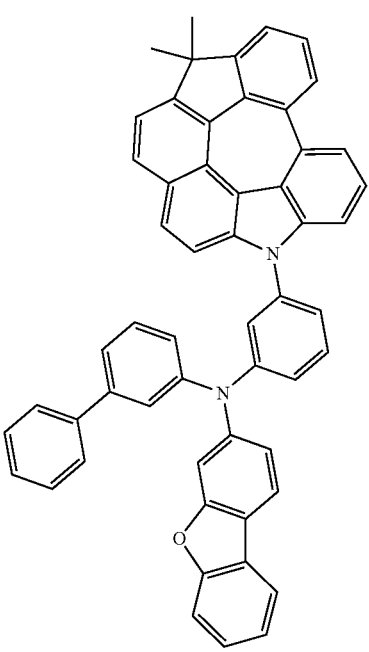
C1-7
C1-9
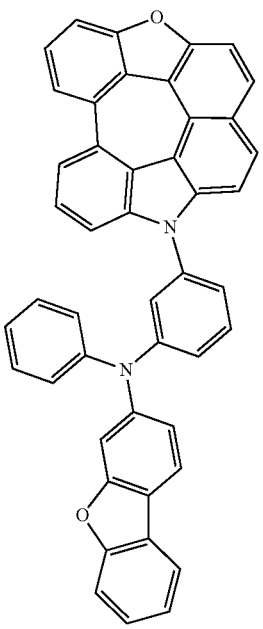

-continued
C1-10
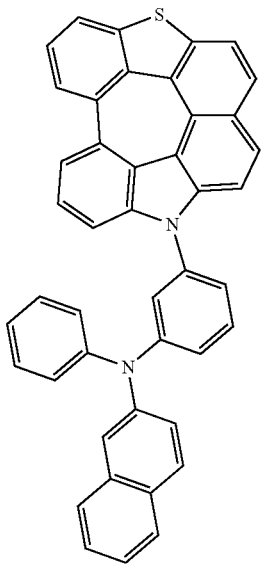
C1-11
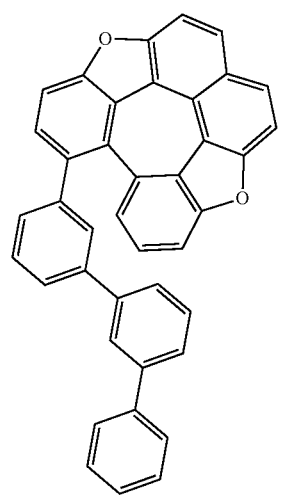
C1-12
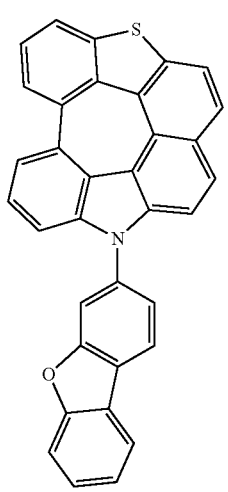
-continued
C1-13
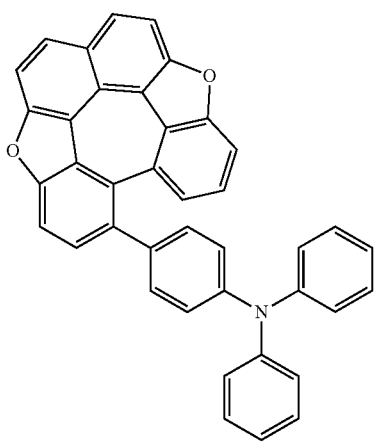
C1-14
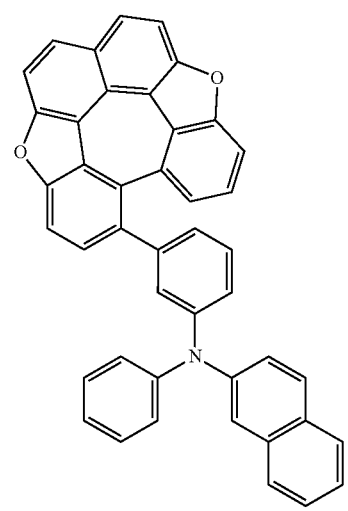
C1-15
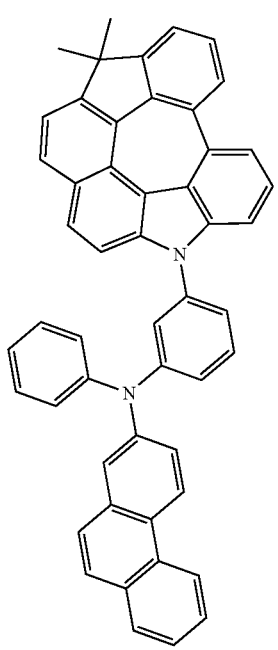

-continued
C1-16
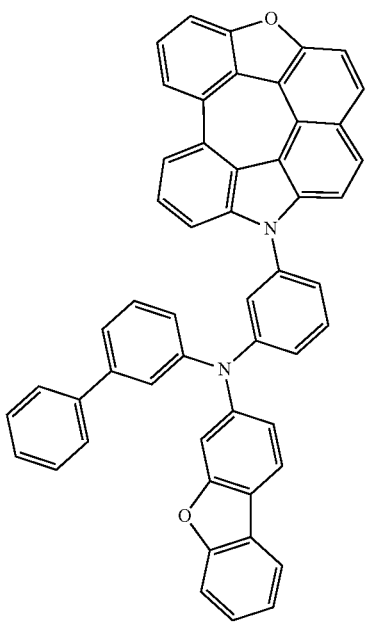
C1-17
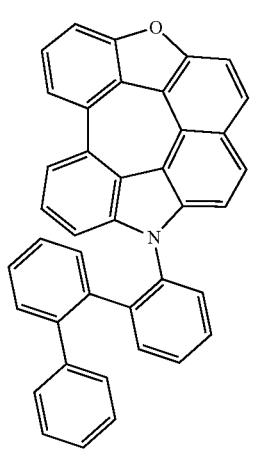
C1-18
-continued
C1-19
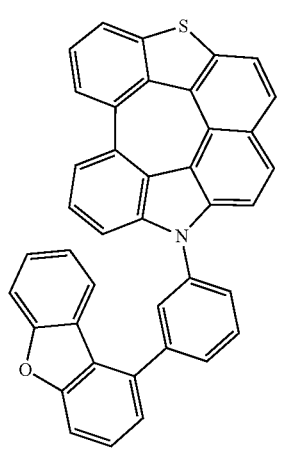
C1-20
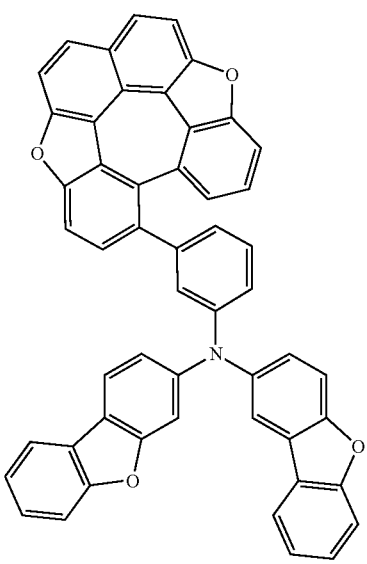
C1-21
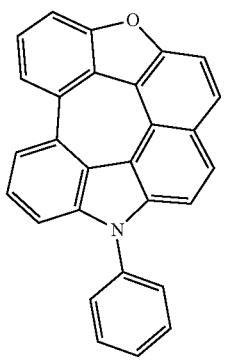

C1-22
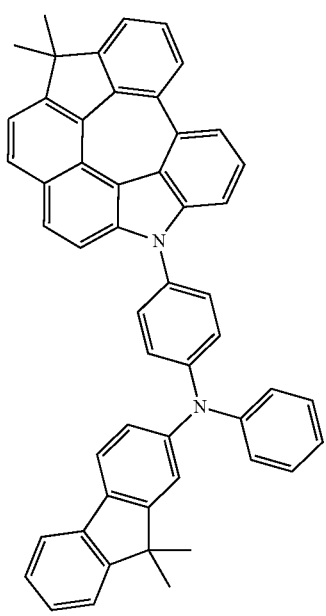
C1-23
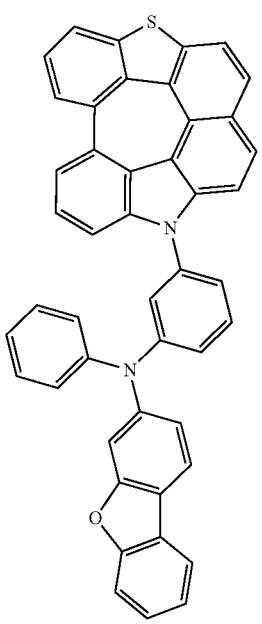
C1-24
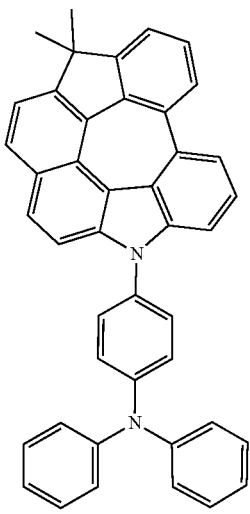
C1-25
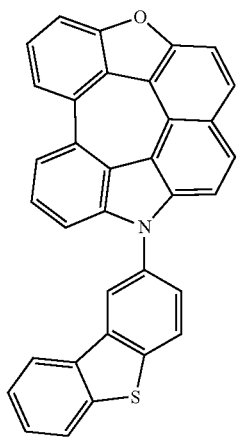
C1-26
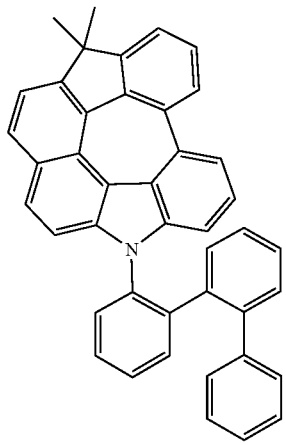

C1-27
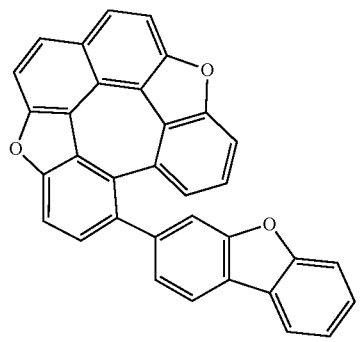
C1-28
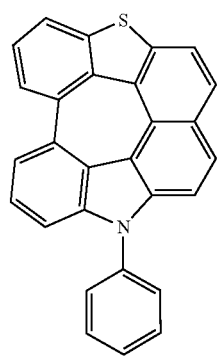
C1-29
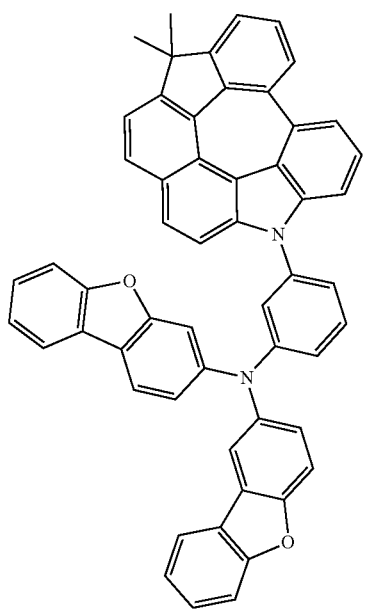
C1-30
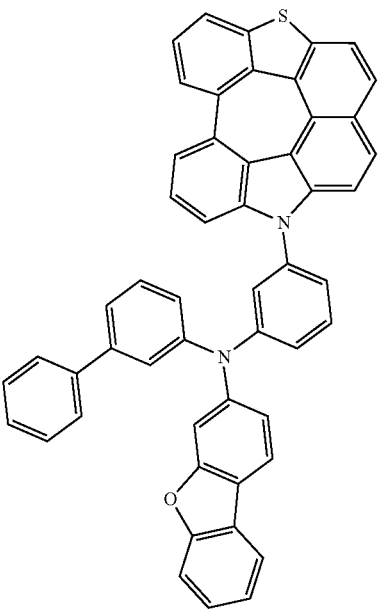
C1-31
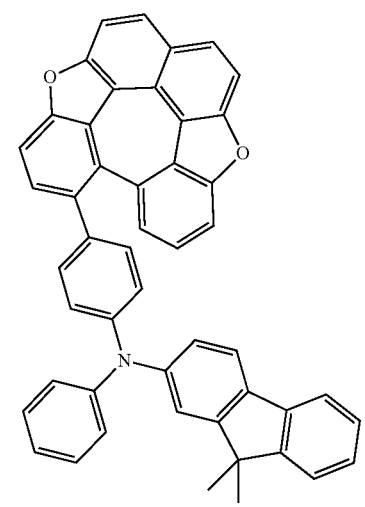
C1-32
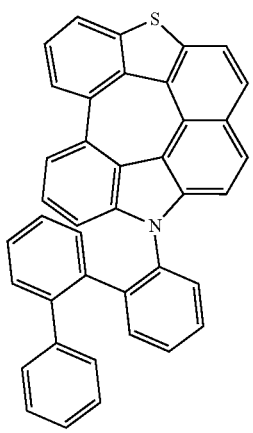

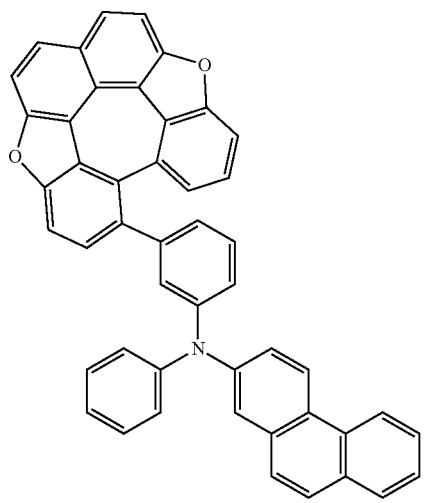
C1-33
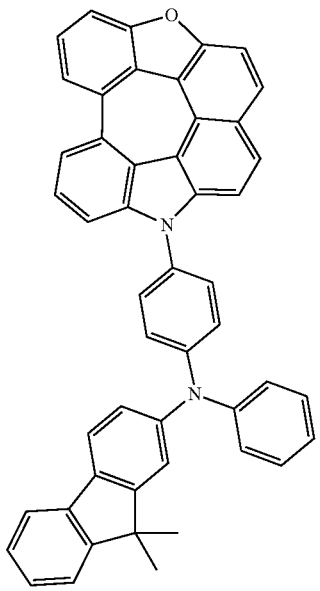
C1-36
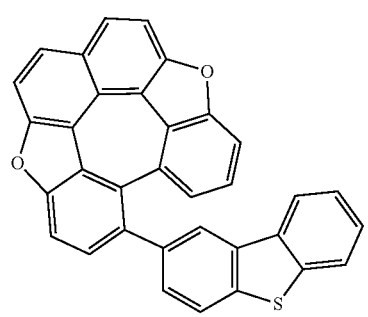
C1-34
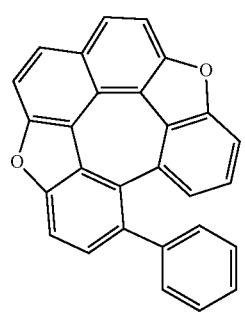
C1-35
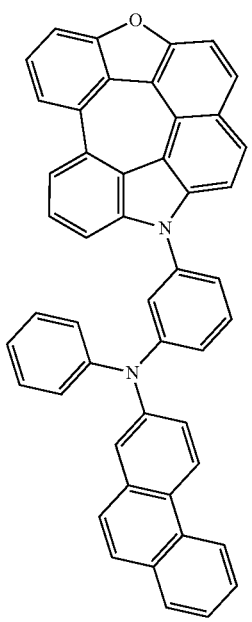
C1-37

C1-38
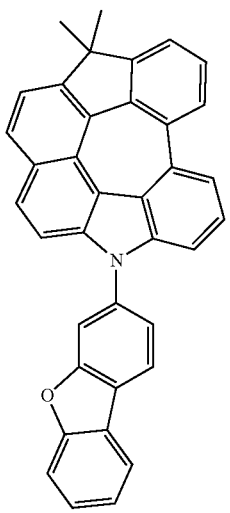
C1-39
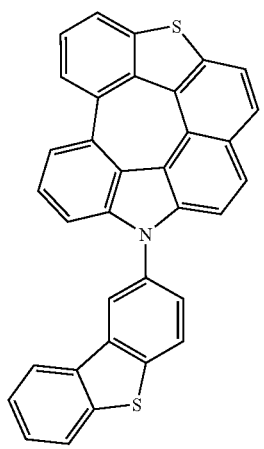
C1-40
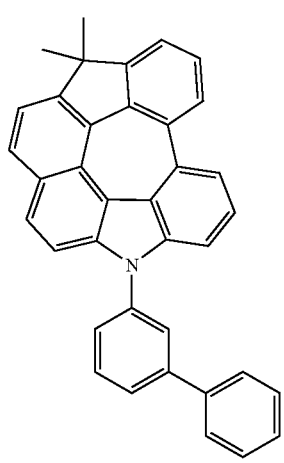
C1-41
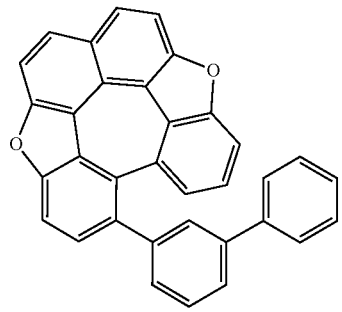
C1-42
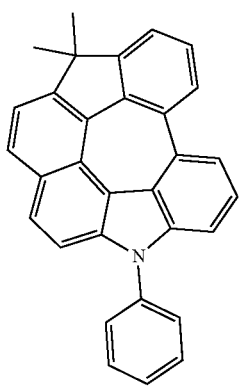
C1-43
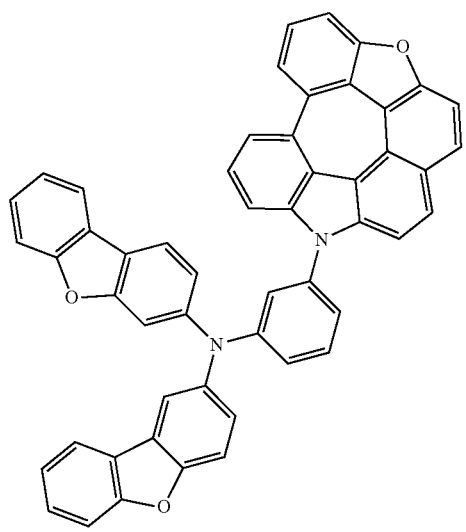

C1-44
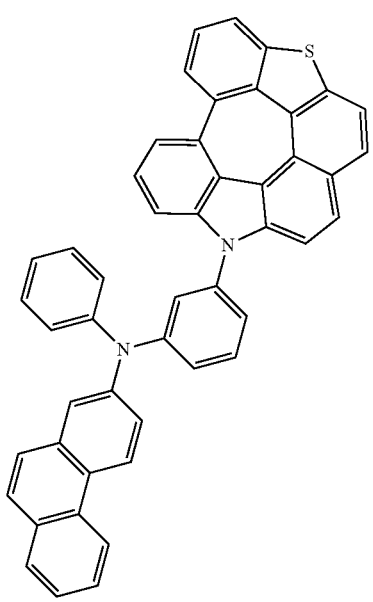
C1-45
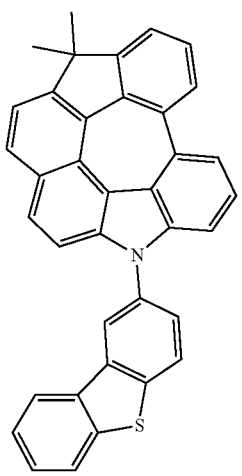
C1-46
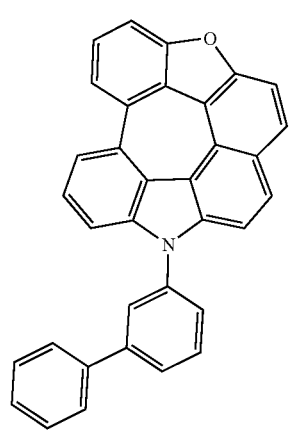
C1-47
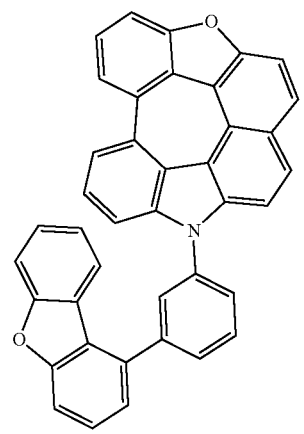
C1-48
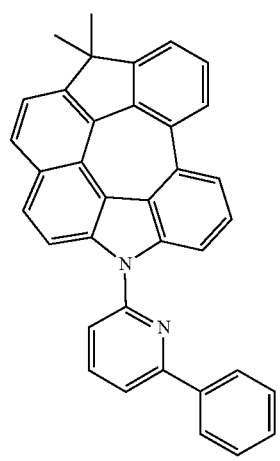
C1-49
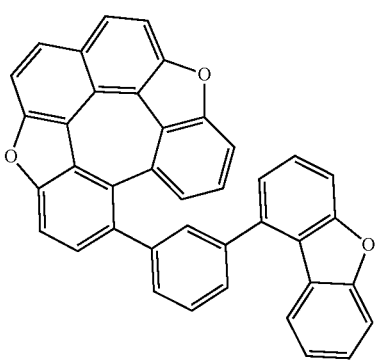

C1-50
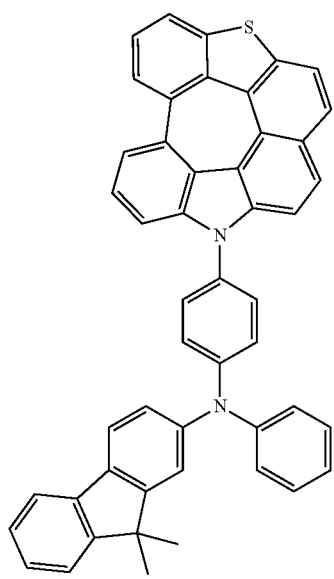
C1-51
C1-52
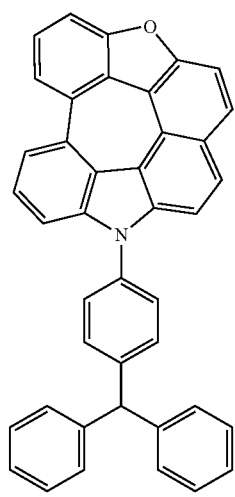
C1-53
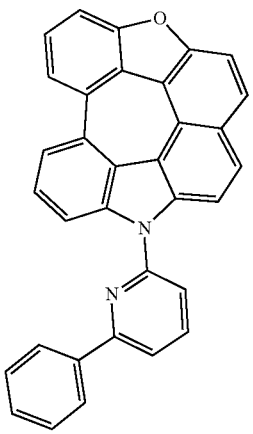
C1-54
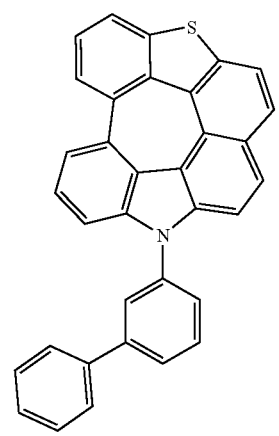
C1-55
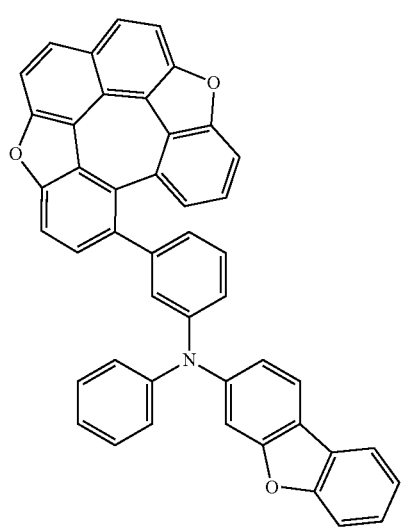

C1-56
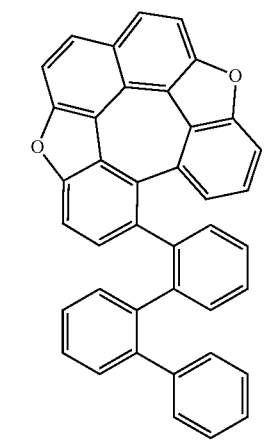
C1-57
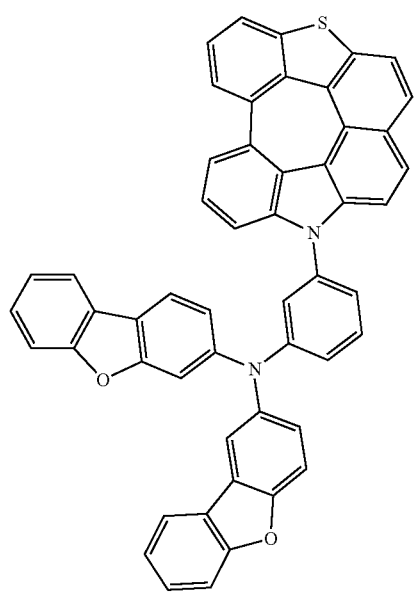
C1-58
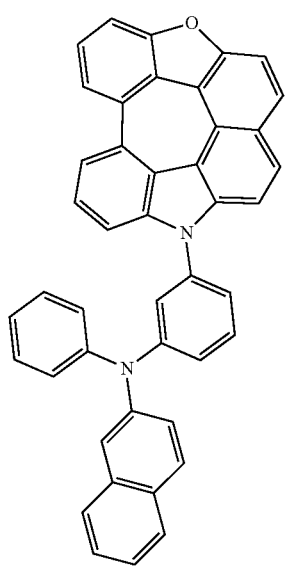
C1-59
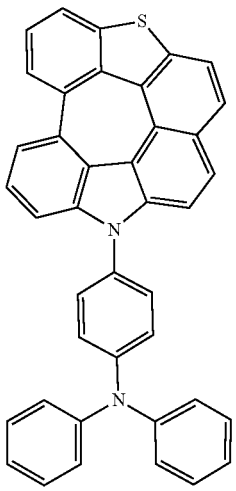
C1-60
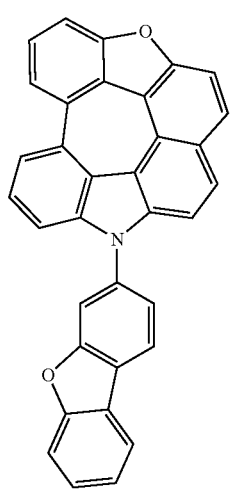
C1-61
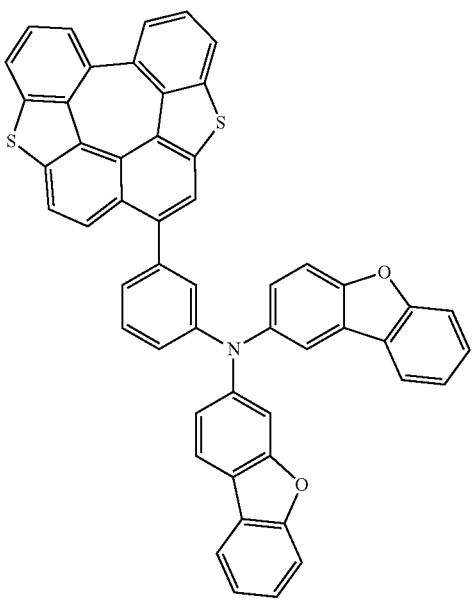

C1-62
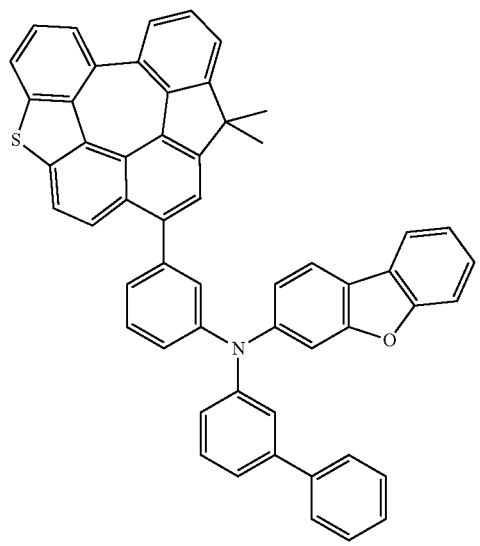
C1-63
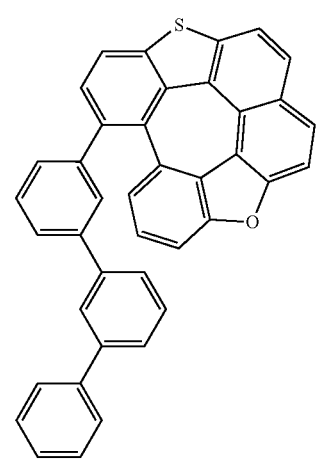
C1-64
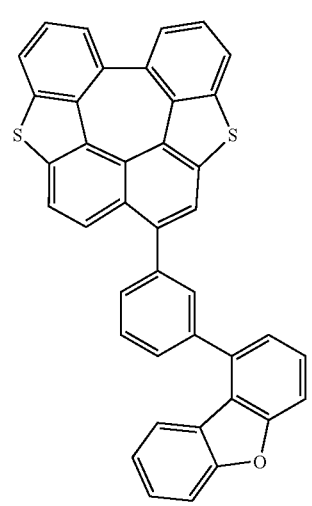
C1-65
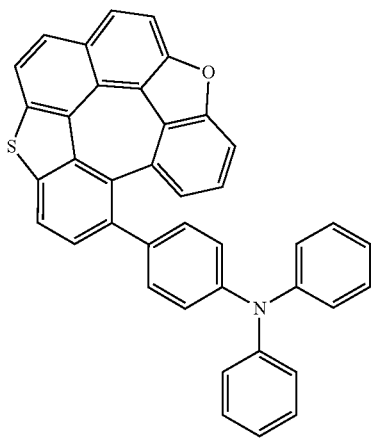
C1-66
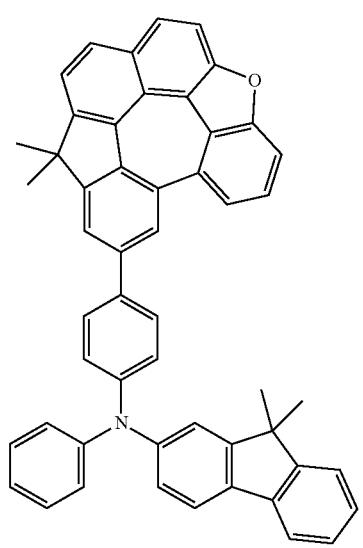
C1-67
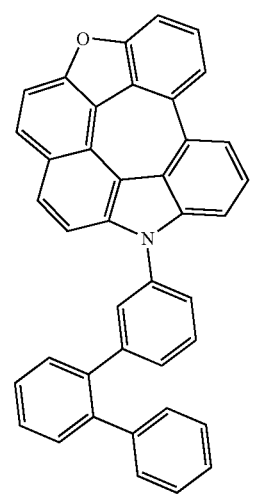

-continued
C1-68
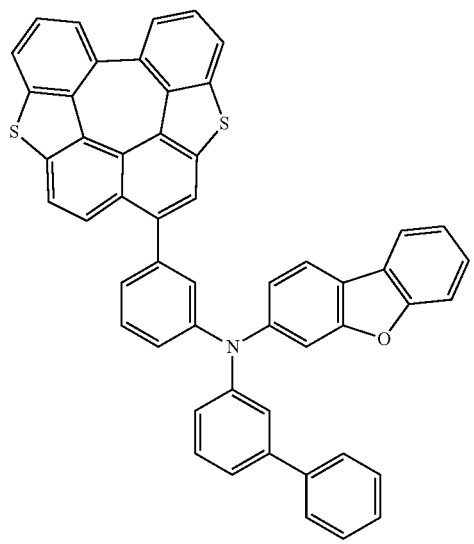
C1-69
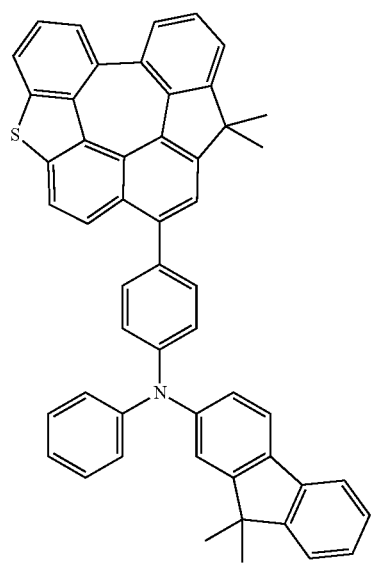
C1-70
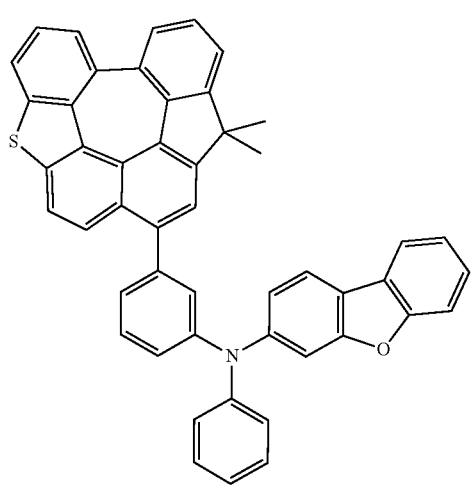
-continued
C1-71
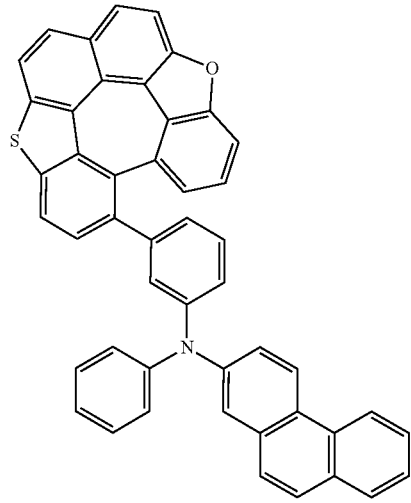
C1-72
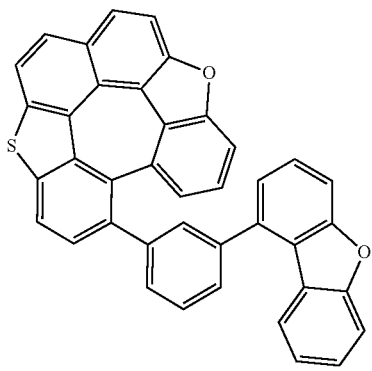
C1-73
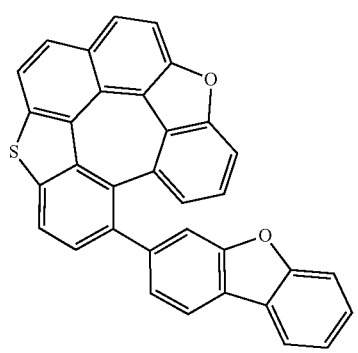

-continued
C1-74
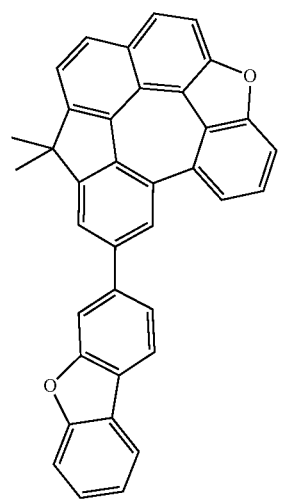
C1-75
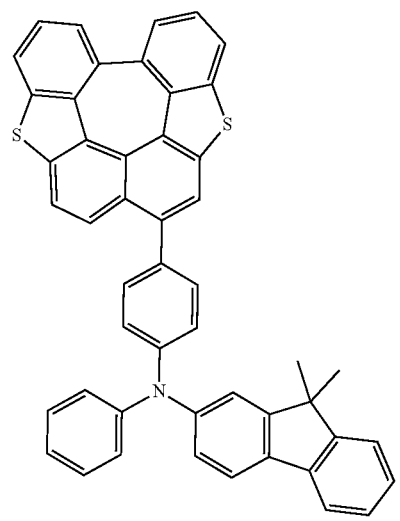
C1-76
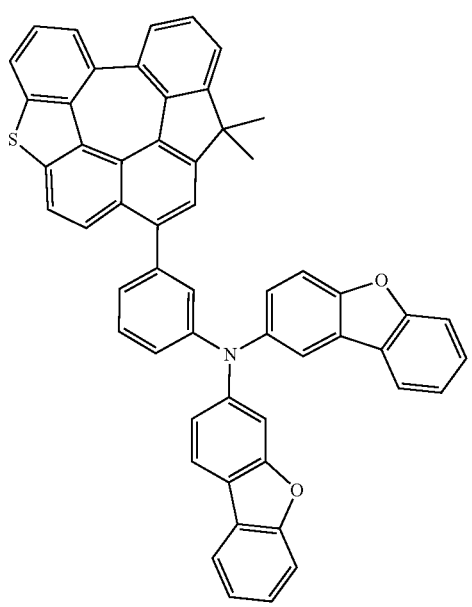
-continued
C1-77
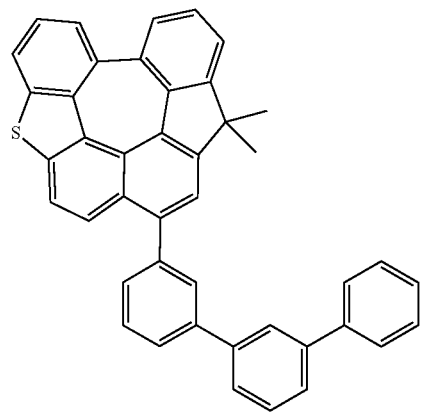
C1-78
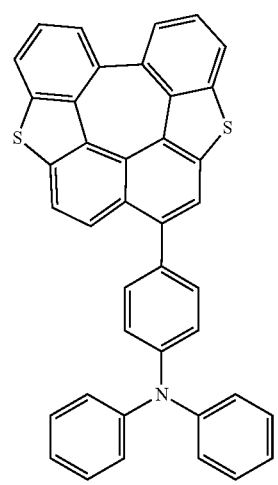
C1-79
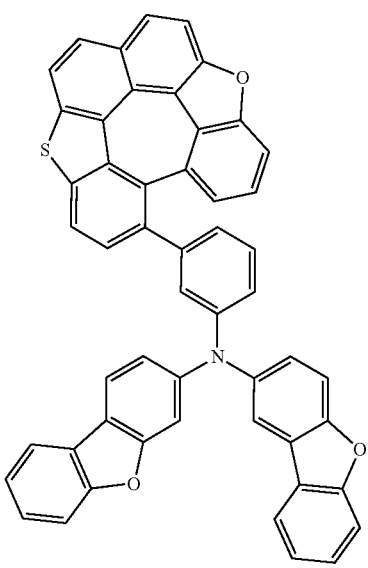

-continued
C1-80
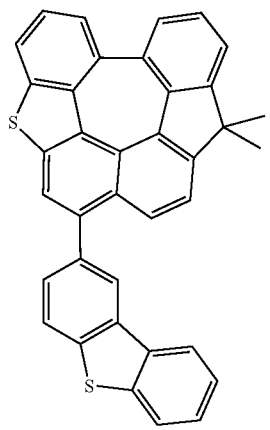
C1-81
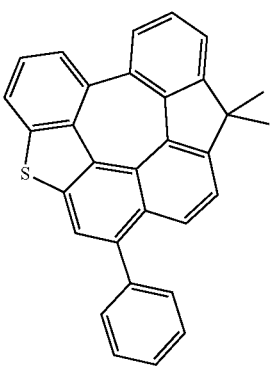
C1-82
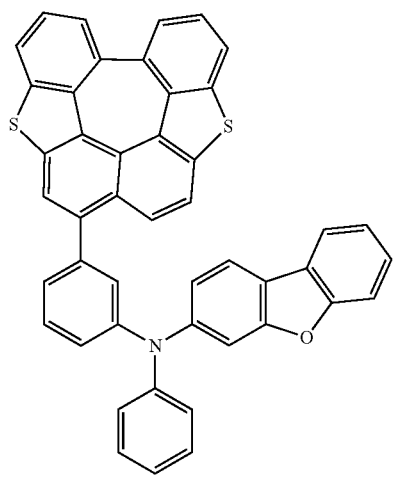
-continued
C1-83
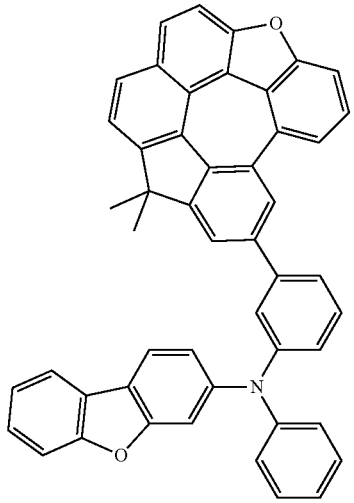
C1-84
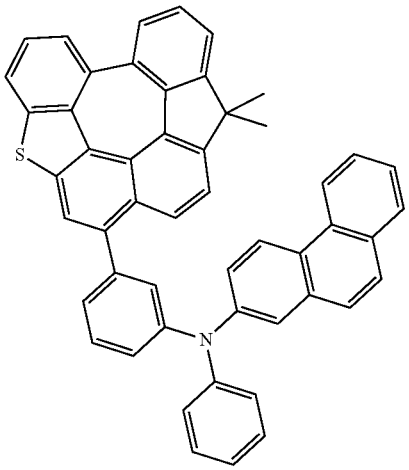
C1-85
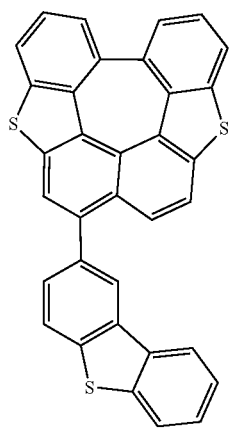

C1-86
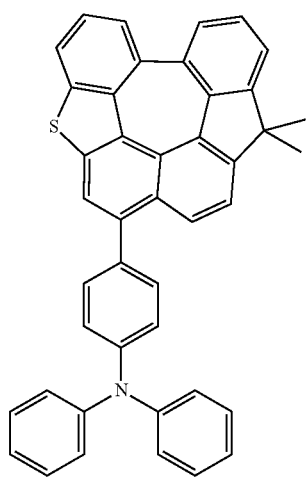
C1-89
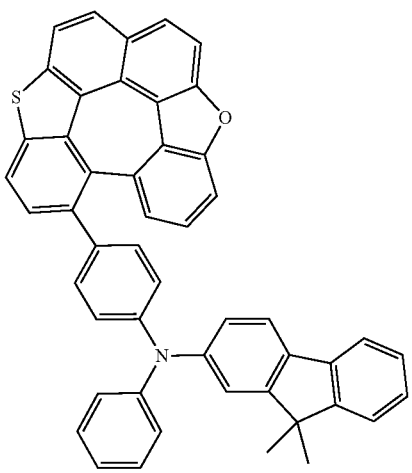
C1-87
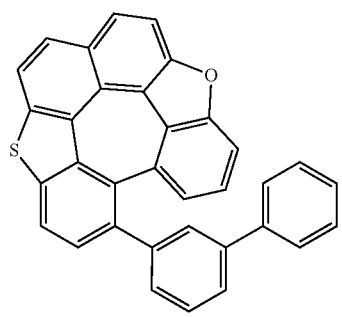
C1-90
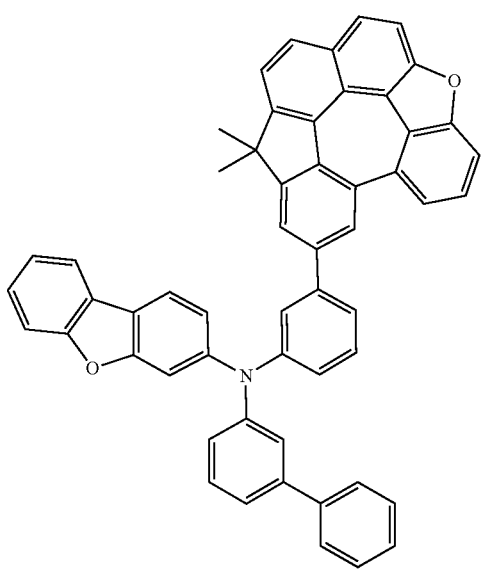
C1-88
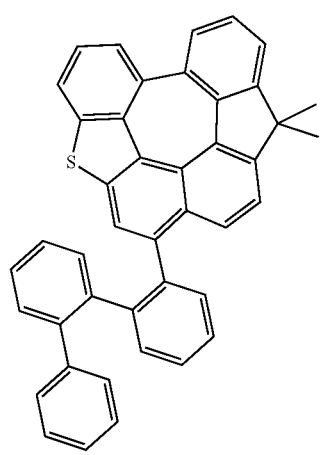
C1-91
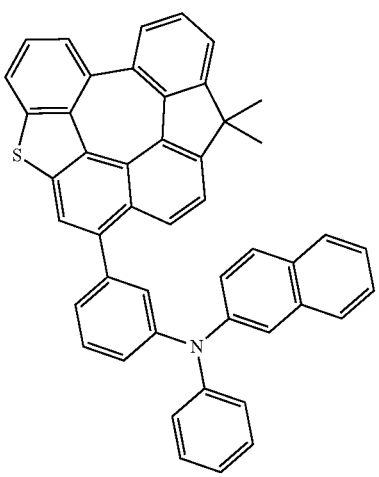

C1-92
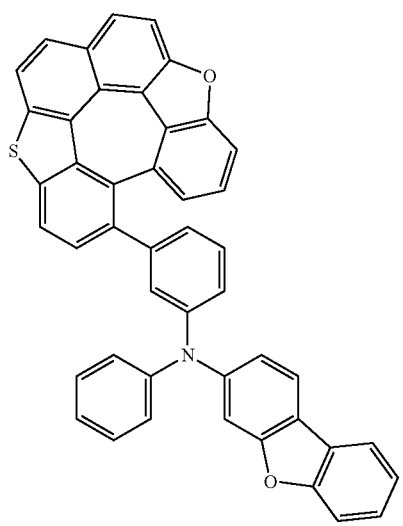
C1-93
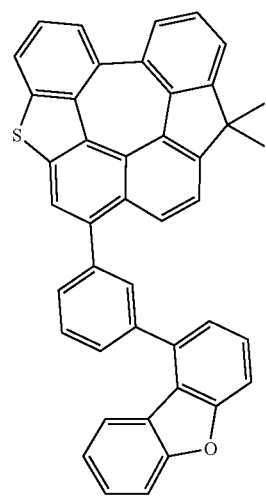
C1-94
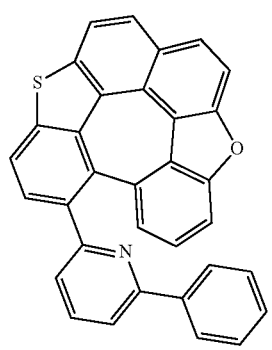
C1-95
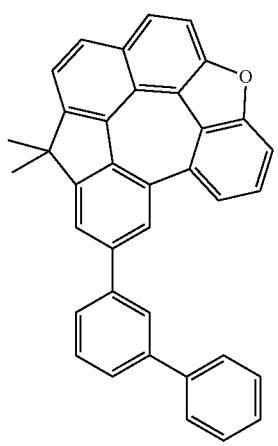
C1-96
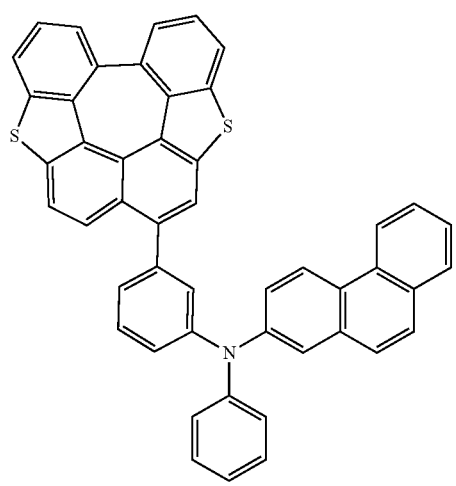
C1-97

C1-98
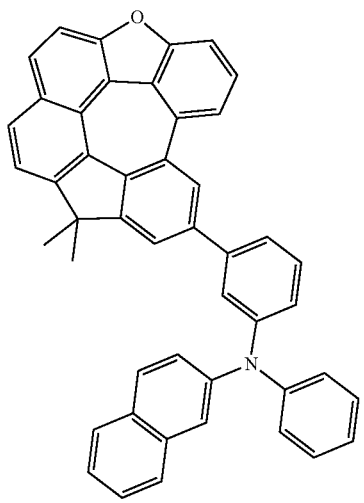
C1-99
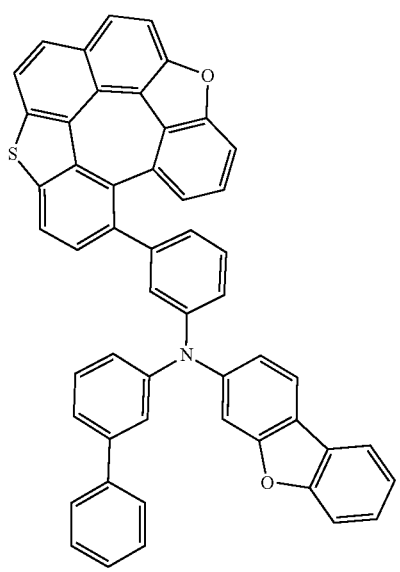
C1-100
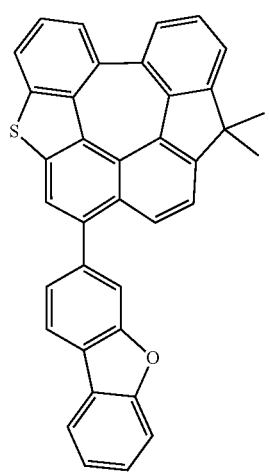
C1-101
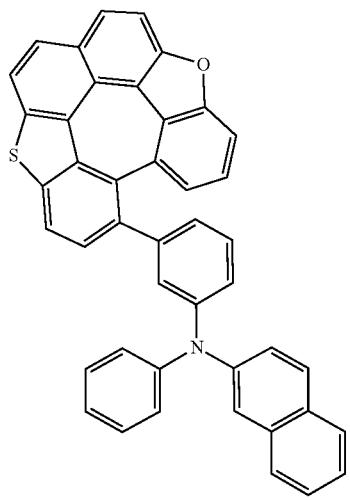
C1-102
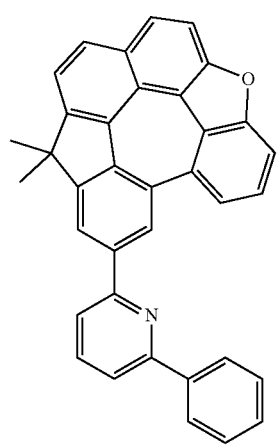
C1-103
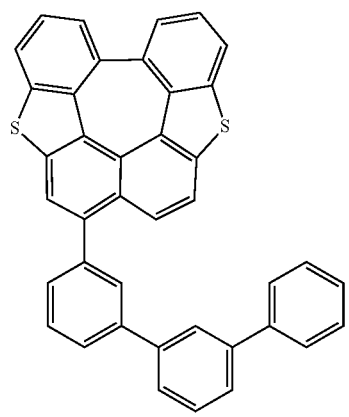

-continued
C1-104
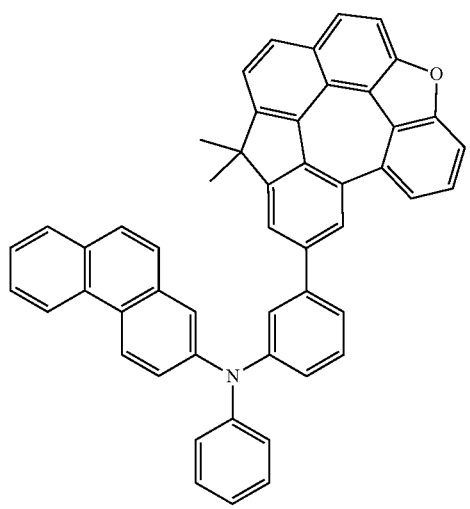
C1-105
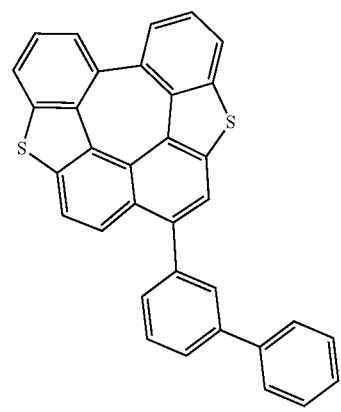
C1-106
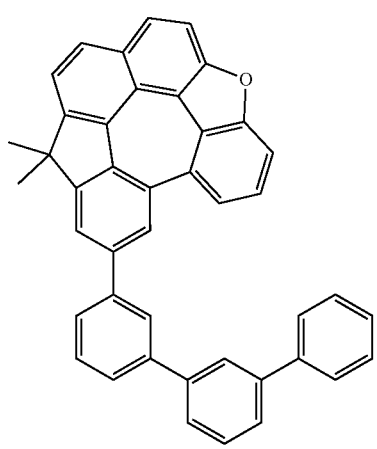
-continued
C1-107
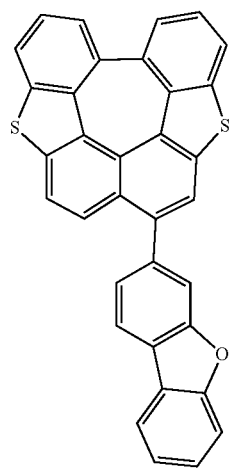
C1-108
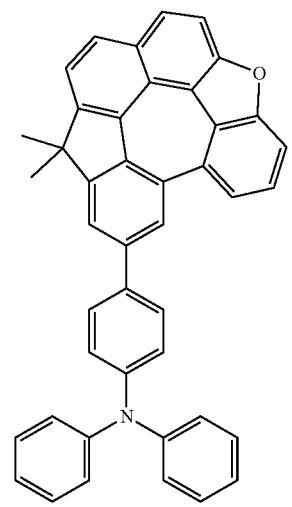
C1-109
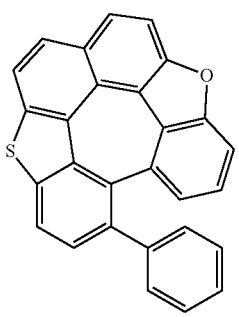

C1-110
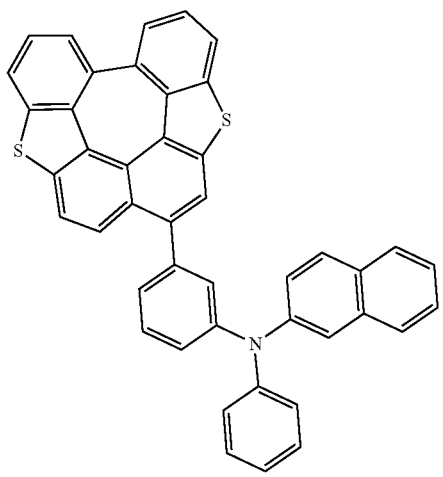
C1-111
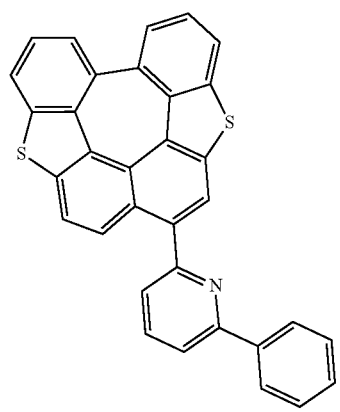
C1-112
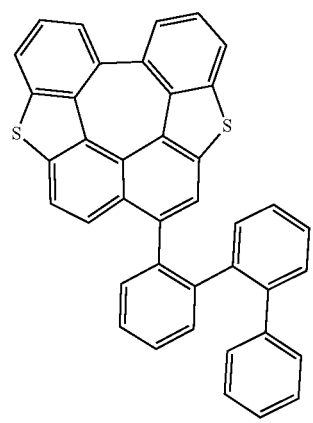
C1-113
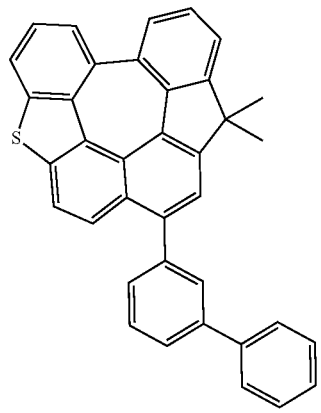
C1-114
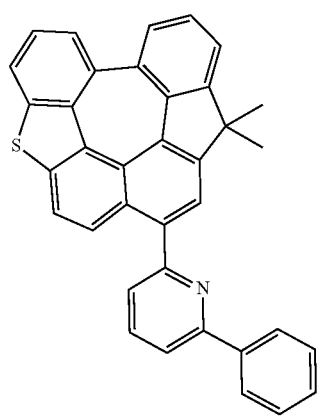
C1-115
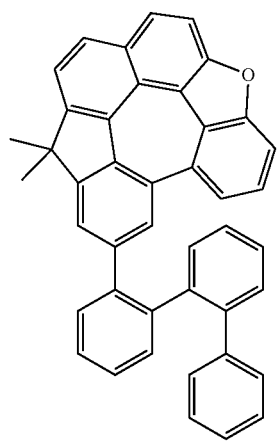

C1-116
C1-117
C1-118
C1-119
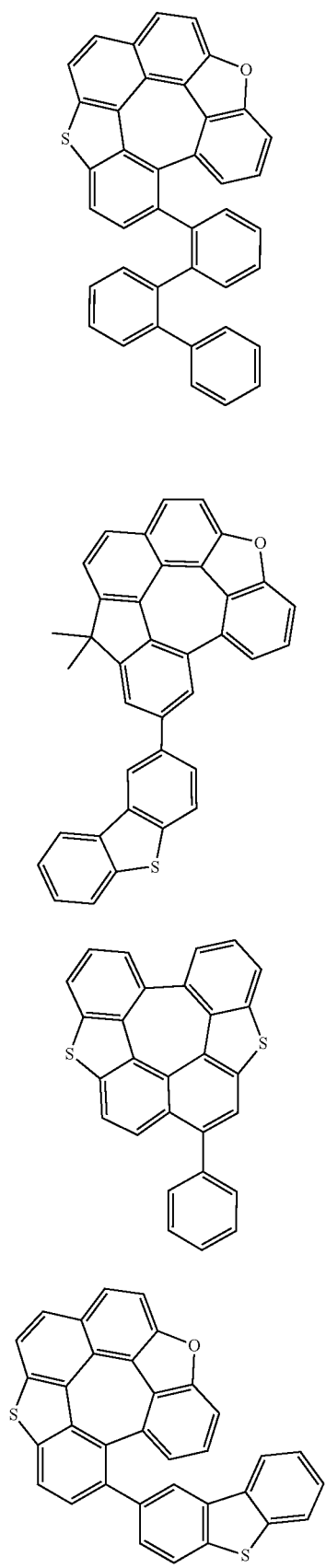
C1-120
H-1
H-2
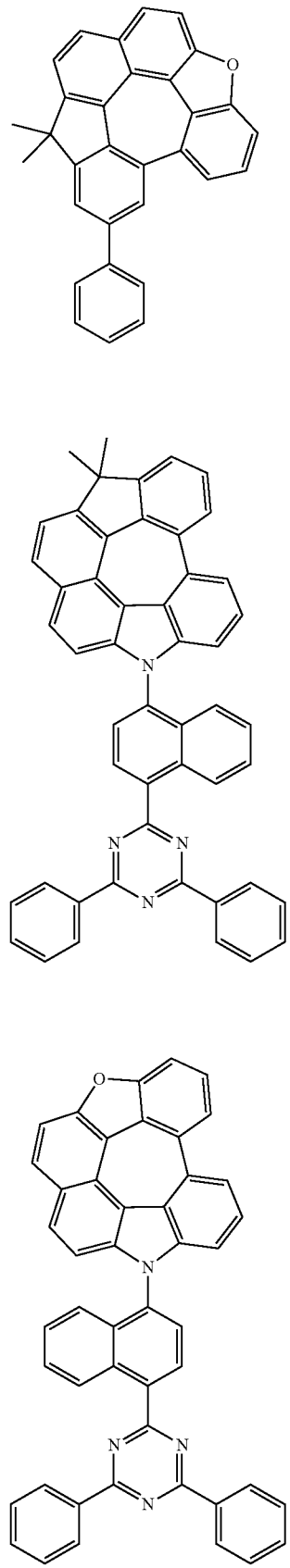

H-3
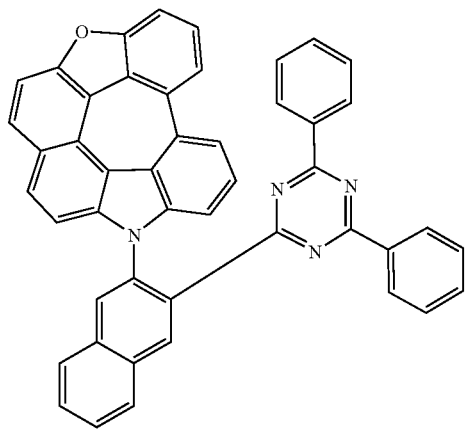
H-4
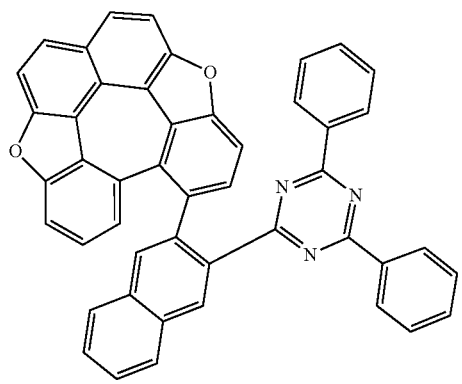
H-5
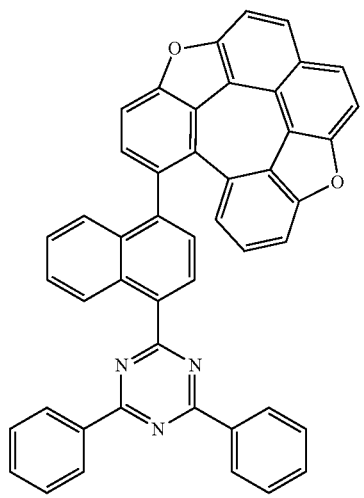
H-6
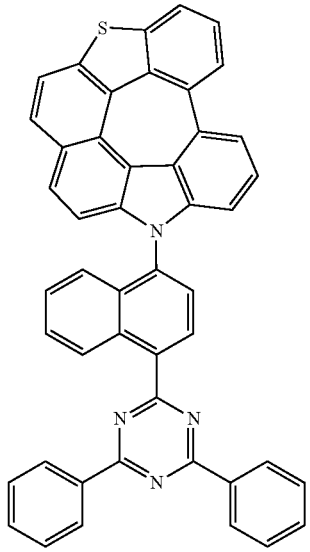
H-7
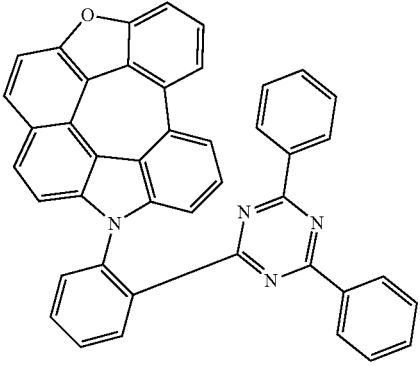
H-8
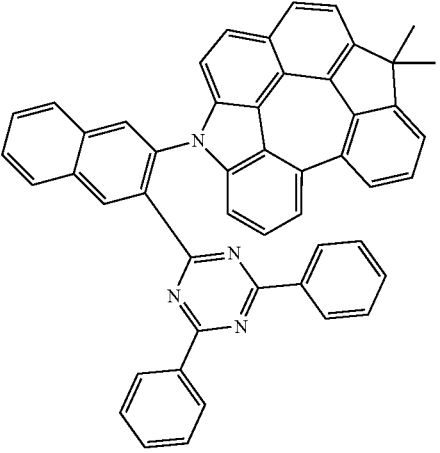

| 441 -continued | 442 -continued |
|---|---|
| 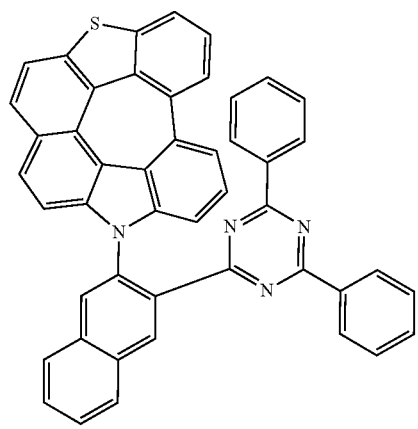 H-9 | 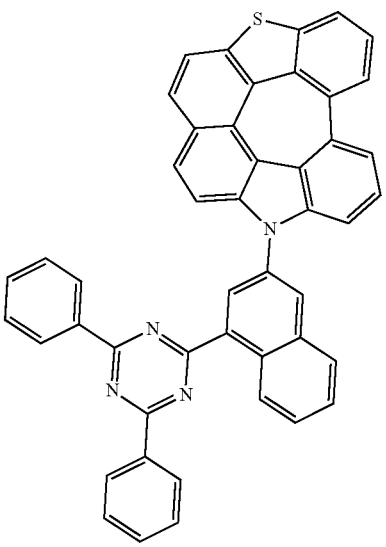 H-12 |
| 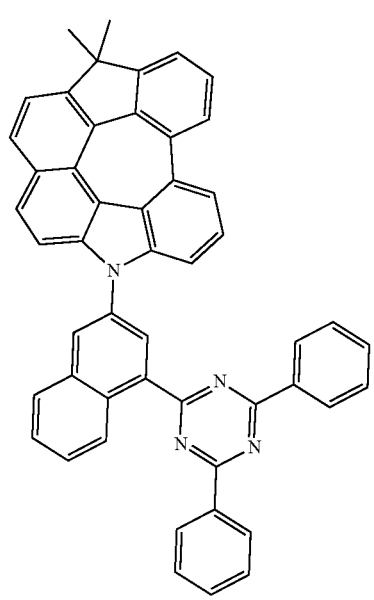 H-10 | 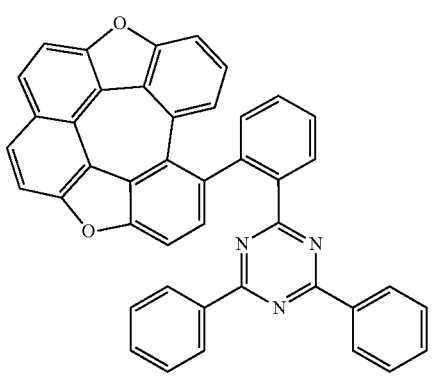 H-13 |
| 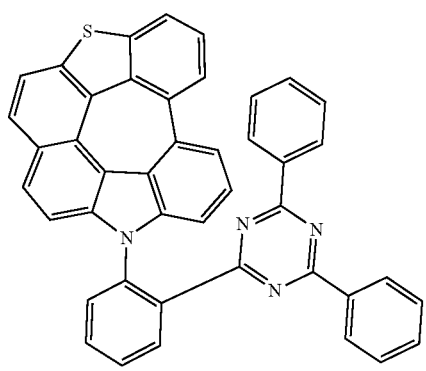 H-11 | 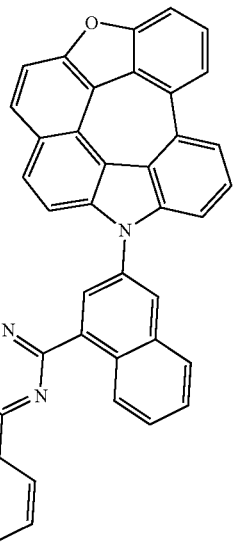 H-14 |

H-15
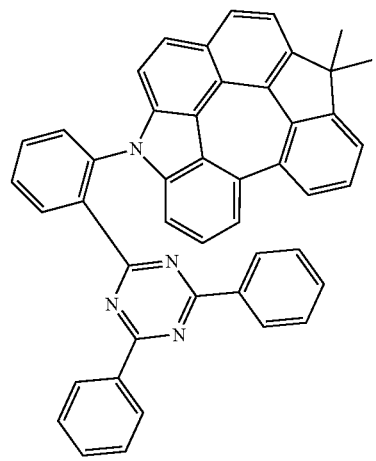
H-16
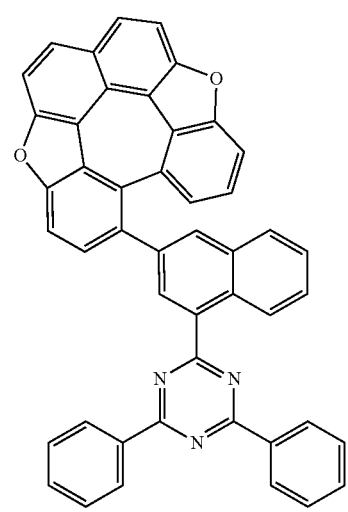
H-17
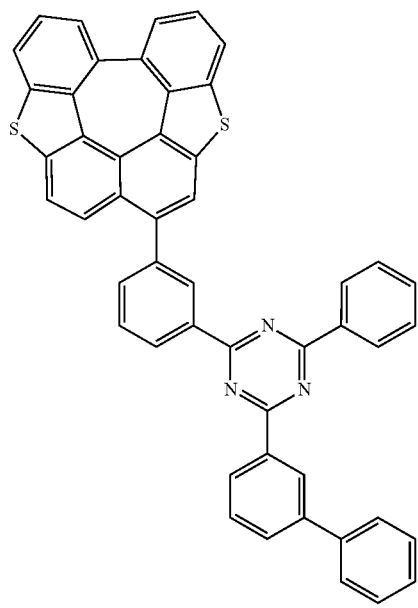
H-18
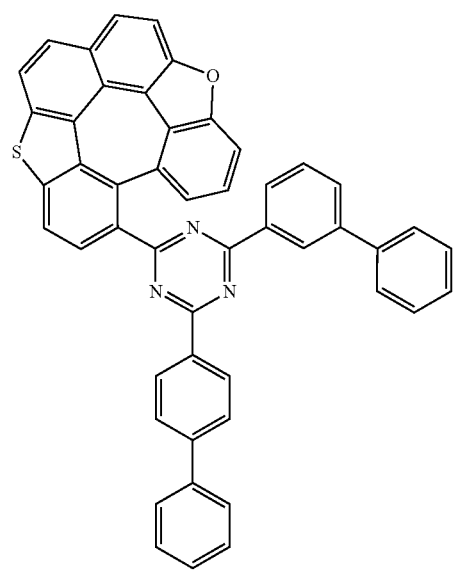
H-19
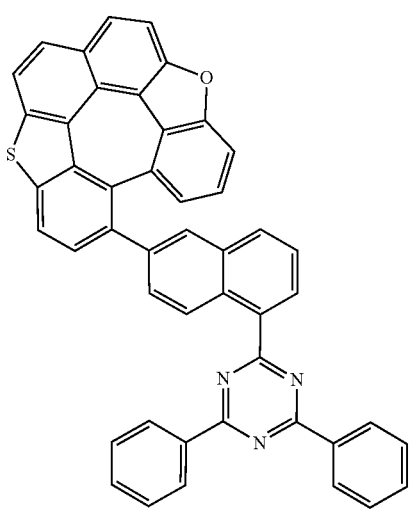
H-20
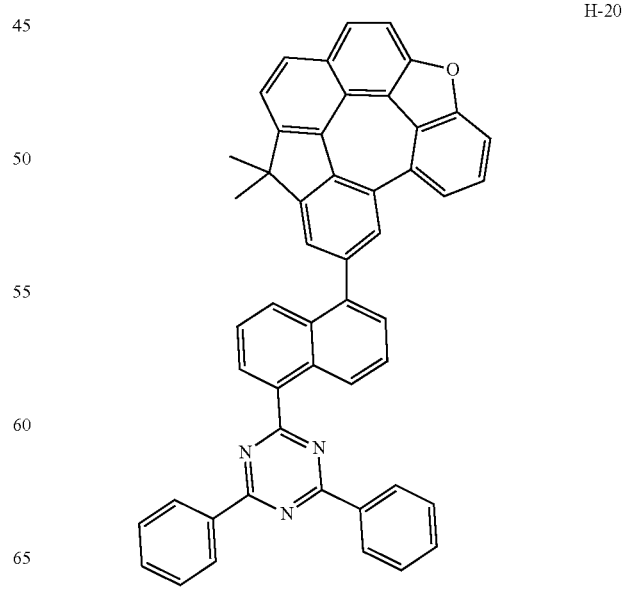

H-21
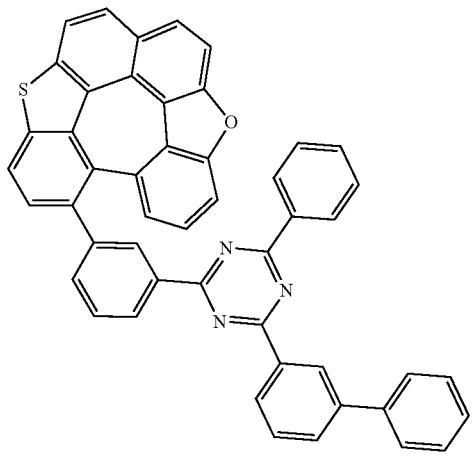
H-22
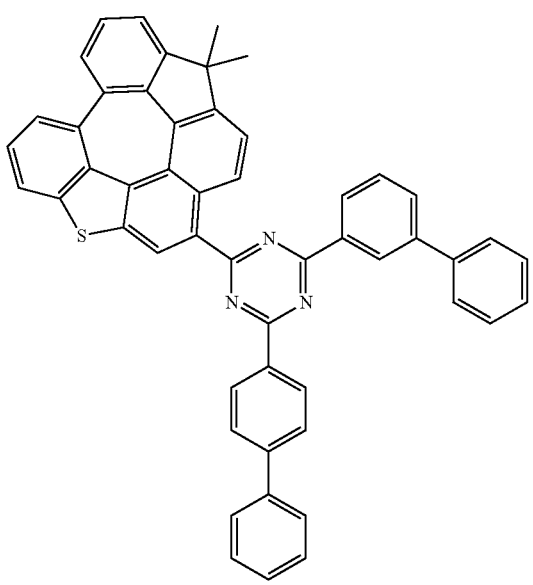
H-23
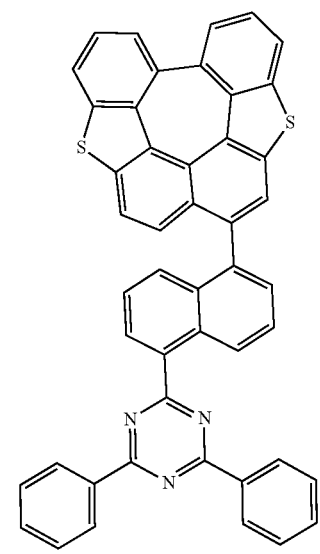
H-24
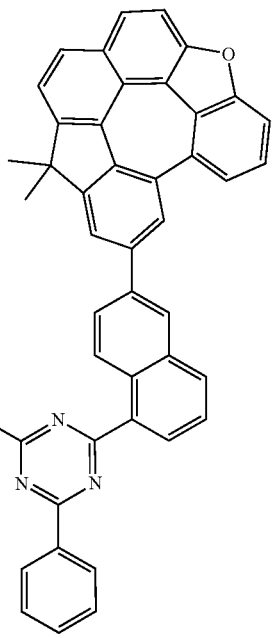
H-25
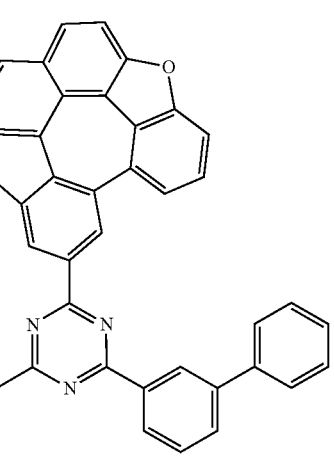
H-26
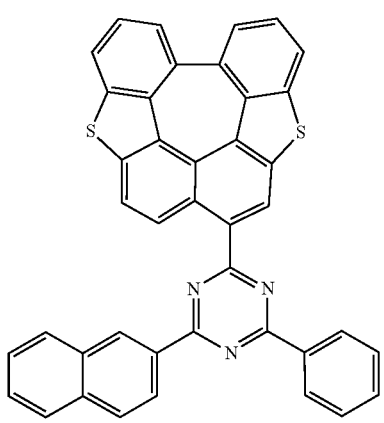

H-27
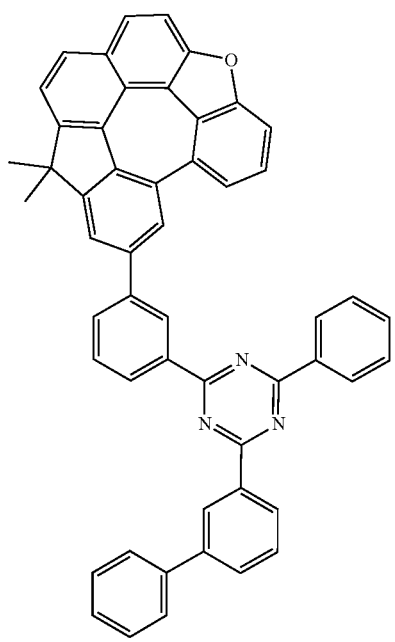
H-28
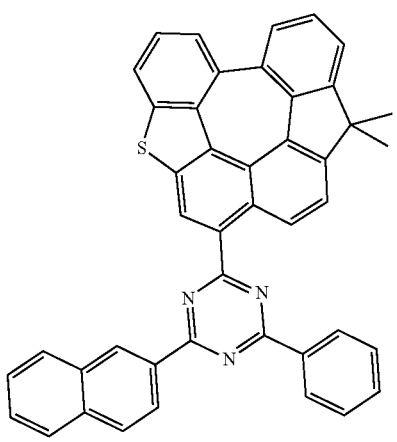
H-29
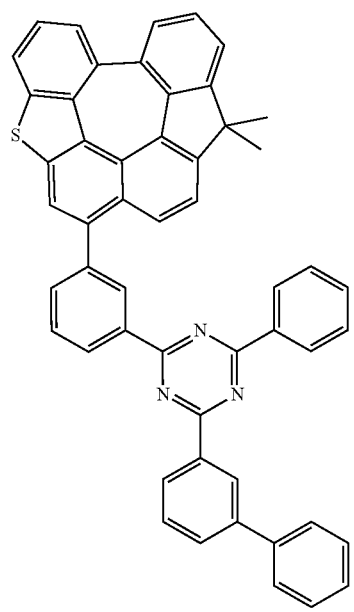
H-30
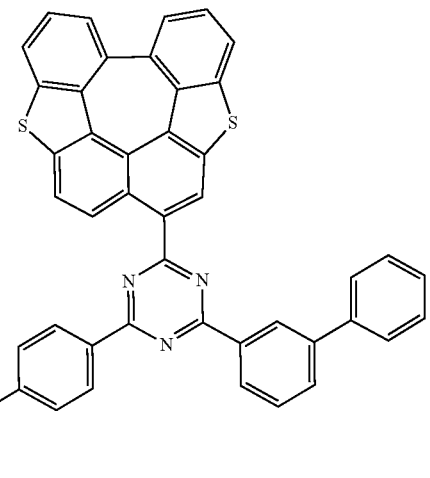
H-31
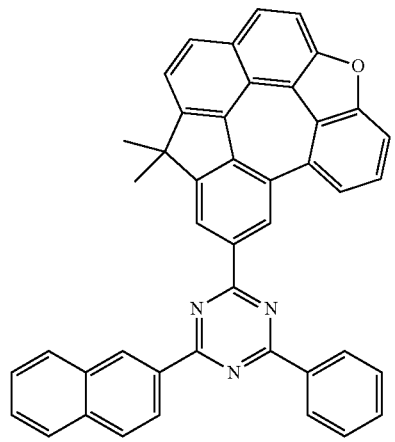
H-32

449
-continued
450
-continued
H-33
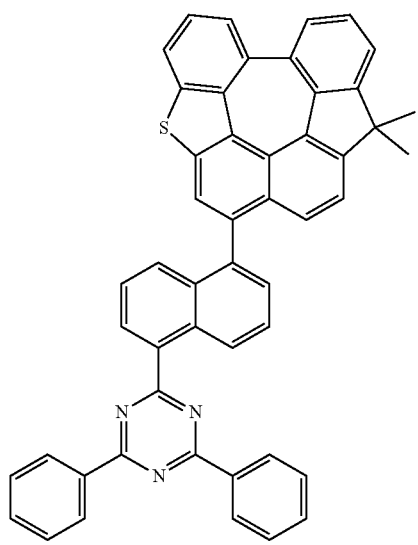
H-35
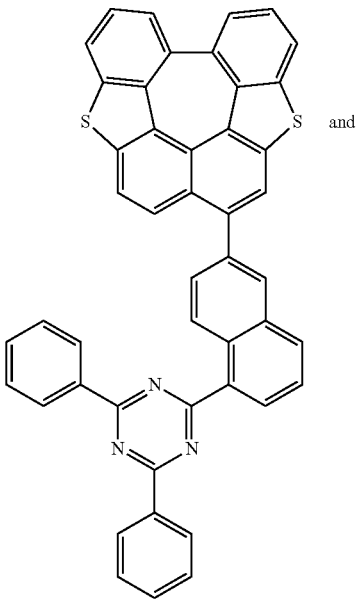
and
H-34
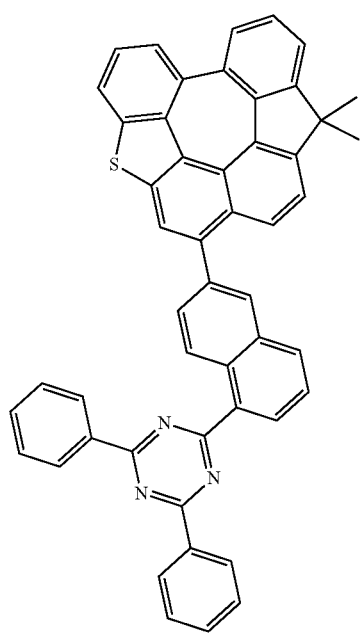
H-36
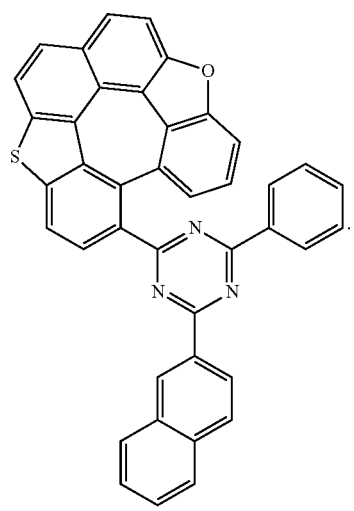
11. An organic electroluminescent material comprising an organic electroluminescent compound according to claim 9.
12. An organic electroluminescent device comprising an organic electroluminescent material according to claim 11.
* * * * *